US008603808B2

(12) United States Patent
Fischer et al.

(10) Patent No.: US 8,603,808 B2
(45) Date of Patent: Dec. 10, 2013

(54) LEISHMANIA VACCINE USING SAND FLY SALIVARY IMMUNOGEN

(75) Inventors: Laurent Bernard Fischer, Sainte Foy les Lyon (FR); Jesus G. Valenzuela, Gaithersburg, MD (US); Jose Ribeiro, Rockville, MD (US); Shaden Kamhawi, Rockville, MD (US)

(73) Assignees: Merial Limited, Duluth, GA (US); The United States of America As Represented by The Secretary of the Department of Health and Human Services, Rockville, MD (US)

( * ) Notice: Subject to any disclaimer, the term of this patent is extended or adjusted under 35 U.S.C. 154(b) by 956 days.

(21) Appl. No.: 12/436,398

(22) Filed: May 6, 2009

(65) Prior Publication Data

US 2009/0324649 A1  Dec. 31, 2009

Related U.S. Application Data

(60) Provisional application No. 61/051,635, filed on May 8, 2008, provisional application No. 61/101,345, filed on Sep. 30, 2008.

(51) Int. Cl.
*C12N 15/00* (2006.01)
*C12N 15/74* (2006.01)
*C07H 21/02* (2006.01)
*C07H 21/04* (2006.01)

(52) U.S. Cl.
USPC ....... 435/320.1; 435/476; 536/23.1; 536/23.6

(58) Field of Classification Search
None
See application file for complete search history.

(56) References Cited

U.S. PATENT DOCUMENTS

| 5,756,103 A * | 5/1998 | Paoletti et al. ............ 424/199.1 |
| 7,485,306 B2 * | 2/2009 | Valenzuela et al. ........ 424/190.1 |
| 7,794,736 B2 * | 9/2010 | Fischer ...................... 424/269.1 |
| 8,343,499 B2 * | 1/2013 | Valenzuela et al. ........ 424/184.1 |
| 8,414,882 B2 * | 4/2013 | Valenzuela et al. ........ 424/269.1 |
| 2006/0051364 A1 * | 3/2006 | Valenzuela et al. ........ 424/190.1 |
| 2008/0241193 A1 * | 10/2008 | Fischer ...................... 424/269.1 |
| 2009/0117139 A1 * | 5/2009 | Valenzuela et al. ........ 424/185.1 |
| 2009/0324649 A1 * | 12/2009 | Fischer et al. ............. 424/269.1 |
| 2010/0278752 A1 * | 11/2010 | Kotsyfakis et al. .......... 424/9.81 |
| 2010/0285066 A1 * | 11/2010 | Fischer ...................... 424/232.1 |

FOREIGN PATENT DOCUMENTS

| EP | 1572968 | * | 4/2009 |
| EP | 2085467 A2 | * | 8/2009 |
| JP | 2006516187 A8 | * | 6/2006 |
| JP | 2010142226 A8 | * | 7/2010 |
| WO | WO 2009/137577 A2 | * | 11/2009 |
| WO | WO 2010/078469 A2 | * | 7/2010 |
| WO | WO 2010/078466 A2 | * | 8/2010 |

OTHER PUBLICATIONS

Evans et al, J. Tropical Medicine, 2012, Article ID 892817, 14 pages.*
da Silva et al, Acta Tropica, 2011, 120:185-190.*
de Oliveira et al, Parasitology International, 2009, 58:319-324.*
Tavares et al, PLoS, May 2011, 5/5: e1169, 11 pages.*
Valenzuela et al, J. Exp. Biol., 2004, 207:3717-3729.*
Collin et al, PLoS, May 2009, 5/5:e1000441, 11 pages.*
Coutinho et al, Veterinary Parasitology, 2005, 128:149-155.*
Dunning, BioscienceHorizons, Mar. 2009, 2/1:73-82.*
Oliveira et al, Parasitology International, 2009, 58:1-5.*
Teixeira et al, PLoS, Mar. 2010, 4/3: e639, 10 pages.*
Valenzuela et al, J. Exp. Med., Aug. 6, 2001, 198/3:331-342.*
Doug Carithers, Merial Literature Update ©2004 Merial Limited, Duluth, GA All rights reserved. Bulletin No. TSB-4-0019-FTB.*
Taylor et al, Vaccine, 1995, 13/6:539-549.*
Mazloumi Gavgani et al., Effect of Insecticide-Impregnated Dog Collars on Incidence of Zoonotic Visceral Leishmaniasis in Iranian Children . . . Lancet, 2002, 360: 374-9.
Dietze et al., Effect of Eliminating Seropositive Canines on the Transmission of Visceral Leishmaniasis in Brazil. Clin. Infect. Dis., 1997, 25: 1240-2.
Moreira et al., Assessment of an optimized dog-culling program in the dynamics of canine *Leishmania* transmission. Vet. Parasitol., 2004, 122: 245-52.
Gradoni et al.,Failure of a multi-subunit recombinant leishmanial vaccine(MML) to protect dogs from *Leishmania infantum* infection and toprevent . . . Vaccine, 2005, 23: 5245-51.
Guo et al. J. Virol., Expression in Recombinant Vaccinia Virus of the *Equine herpesvirus* 1 Gene Encoding Glycoprotein gp13 and Protection.1989, 63, 4189-4198.
Taylor et al. Recombinant fowlpox virus inducing protective immunity in non-avian species. Vaccine. 6: 497-503, 1988.
Oliveira et al., From transcriptome to immunome: Identification of DTH inducing proteins from a *Phlebotomus ariasi* salivary gland cDNA library. Vaccine (2006) 24: 374-90.
Panicali et al., Construction of poxviruses as cloning vectors: Insertion of the thymidine kinase gene from herpes simplex . . . Proc. Natl Acad Sci USA, 1982, 79: 4927-4931.
Piccini et al., Vaccinia Virus as an Expression Vector. Methods Enzymol., 1987, 153: 545-563.
Anderson et al., (2006). Comparative salivary gland transcriptomics of sandfly vectors of visceral leishmaniasis. BMC Genomics. 7:52.
Sutter et al., Nonreplicating vaccinia vector efficiently expresses recombinant genes. Proc. Natl. Acad. Sci. U.S.A., 1992, 89, 10847-10851.
Meyer et al., Mapping of deletions in the genome of the highly attenuated vaccinia virus MVA and their influence on virulence. 1991, J. Gen. Virol. 72, 1031-1038.

(Continued)

*Primary Examiner* — Nita M Minnifield
(74) *Attorney, Agent, or Firm* — Judy Jarecki-Black; Ruoying Chen; Merial Limited

(57) ABSTRACT

The present invention provides vectors that contain and express in vivo or in vitro sand fly *Lu. longipalpis* salivary antigens that elicit an immune response in animal or human against *Leishmania*, vaccine compositions comprising said vectors and/or *Lu. longipalpis* salivary polypeptides, methods of vaccination against *Leishmania*, and kits for use with such methods and compositions.

12 Claims, 43 Drawing Sheets

(56) References Cited

OTHER PUBLICATIONS

Staib et al., Biotechniques, 2000, 28(6): 1137-42, 1144-6, 1148.

Gomes et al.,(2008). Immunity to a salivary protein of a sand fly vector protects against the fatal outcome of visceral leishmaniasis in a hamster model. PNAS 105:7845-50.

Oliveira et al.,(2008) Immunity to distinct sand fly salivary proteins primes the anti-*Leishmania* immune response . . . PLoS Negl Trop Dis, 2(4):e226.

Collin Nicolas et al: "Sand Fly Salivary Proteins Induce Strong Cellular Immunity in a Natural Reservoir of Visceral Leishmaniasis with Adverse Consequences for *Leishmania*" PLOS Pathogens, vol. 5, No. 5, May 2009.

Desjeux, The Increase in Risk Factors for Leishmaniasis Worldwide. Trans. R. Soc. Trop. Med. Hyg., 2001, 95: 239-43.

McConkey et al., *Leishmanial* polyarthritis in a dog. Canine Vet J 43:607-609, 2002.

Slappendel et al., Infectious Diseases of the Dog and Cat. WB Saunders Co, Philadelphia, 1998, pp. 450-458.

Grosjean et al., Serum concentrations of acute phase proteins in dogs with leishmaniasis. Vet Rec 150:241-244, 2002.

Lindsay et al., Leishmaniasis in American Foxhounds: An Emerging Zoonosis? Compend Cont Educ Pract Vet 24:304-312, 2002.

Martinez-Subiela et al., Serum concentrations of acute phase proteins in dogs with leishmaniasis. Vet Rec 150:241-244, 2002.

Valenzuela et al., (2004). Identification of the most abundant secreted proteins from the salivary glands of the sand fly *Lutzomyia* . . . J Exp Biol, 207:3717-29.

Molina et al., Infectivity of Dogs Naturally Infected with *Leishmania* Infanturn to Colonized *Phlebotomus perniciosus*.Trans. R. Soc. Trop. Med. Hyg., 1994, 88: 491-3.

Courtenay et al., Infectiousness in a Cohort of Brazilian Dogs: Why Culling Fails to Control Visceral Leishmaniasis in Areas of High . . . J. Infect. Dis., 2002, 186: 1314-20.

Maroli et al., Evidence for an Impact on the Incidence of Canine Leishmaniasis by the Mass Use of Deltamethrin-Impregnated Dog . . . Med. Vet. Entomol., 2001, 15: 358-63.

\* cited by examiner

FIGURE 1

(pVR2001 LJM17: SEQ ID NO:9)

```
aagggatccagatctgctgtgccttctagttgccagccatctgttgtttgcccctccccgtgccttccttgaccct
ggaaggtgccactcccactgtccttccctaataaaatgaggaaattgcatcgcattgtctgagtaggtgtcattcta
ttctgggggtggggtggggcagcacagcaagggggaggattgggaagacaatagcaggcatgctgggatgcggtg
ggctctatgggtacccaggtgctgaagaattgacccggttcctcctgggccagaaagaagcaggcacatcccttct
ctgtgacacaccctgtccacgccctggttcttagttccagccccactcataggacactcatagctcaggagggctc
cgccttcaatcccaccgctaaagtacttggagcggtctctccctccctcatcagcccaccaaaccaaacctagcct
ccaagagtgggaagaaattaaagcaagataggctattaagtgcagagggagagaaaatgcctccaacatgtgaggaa
gtaatgagagaaatcatagaatttcttccgcttcctcgctcactgactcgctgcgctcggtcgttcggctgcggcga
gcggtatcagctcactcaaaggcggtaatacggttatccacagaatcaggggataacgcaggaaagaacatgtgagc
aaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccct
ggaagctccctcgtgcgctctcctgttccgaccctgccgcttaccggatacctgtccgcctttctcccttcgggaag
cgtggcgctttctcaatgctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaa
gtggtggcctaactacggctacactagaaggacagtatttggtatctgcgctctgctgaagccagttaccttcggaa
aaagagttggtagctcttgatccggcaaacaaaccaccgctggtagcggtggtttttttgtttgcaagcagcagatt
acgcgcagaaaaaaggatctcaagaagatcctttgatcttttctacggggtctgacgctcagtggaacgaaaactc
acgttaagggattttggtcatgagattatcaaaaggatcttcacctagatccttttaaattaaaaatgaagtttta
aatcaatctaaagtatatatgagtaaacttggtctgacagttaccaatgcttaatcagtgaggcacctatctcagcg
atctgtctatttcgttcatccatagttgcctgactccccgtcgtgtagataactacgatacgggagggcttaccatctggccccagtgctgcaatgataccgcgagacccacgctcaccggctccagatttatcagcaataaaccagccagccggaagggccgagcgcagaagtggtcctgcaactttatccgcctccatccagtctattaattgttgccgggaagctagagtaagtagttcgccagttaatagtttgcgcaacgttgttgccattgctacaggcatcgtggtgtcacgctcgtcgtttggtatggcttcattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatactcttcctttttcaatattattgaagcatttatcagggttattgtctcatga
gcggatacatatttgaatgtatttagaaaaataaacaatagggttccgcgcacatttccccgaaaagtgccacct
gacgtctaagaaaccattattatcatgacattaacctataaaaataggcgtatcacgaggccctttcgtctcgcgcg
tttcggtgatgacggtgaaaacctctgacacatgcagctcccggagacggtcacagcttgtctgtaagcggatgccg
ggagcagacaagcccgtcagggcgcgtcagcgggtgttggcgggtgtcggggctggcttaactatgcggcatcagag
cagattgtactgagagtgcaccatatgcggtgtgaaataccgcacagatgcgtaaggagaaaataccgcatcagatt
ggctattggccattgcatacgttgtatccatatcataatatgtacatttatattggctcatgtccaacattaccgcc
atgttgacattgattattgactagttattaatagtaatcaattacggggtcattagttcatagcccatatatggagt
tccgcgttacataacttacggtaaatggcccgcctggctgaccgcccaacgacccccgcccattgacgtcaataatg
acgtatgttcccatagtaacgccaatagggactttccattgacgtcaatgggtggagtatttacggtaaactgccca
cttggcagtacatcaagtgtatcatatgccaagtacgccccctattgacgtcaatgacggtaaatggcccgcctggc
attatgcccagtacatgaccttatgggactttcctacttggcagtacatctacgtattagtcatcgctattaccatg
gtgatgcggttttggcagtacatcaatgggcgtggatagcggtttgactcacggggatttccaagtctccaccccat
tgacgtcaatgggagtttgttttggcaccaaaatcaacgggactttccaaaatgtcgtaacaactccgccccattga
cgcaaatgggcggtaggcgtgtacggtgggaggtctatataagcagagctcgtttagtgaaccgtcagatcgcctgg
```

FIGURE 1 agacgccatccacgctgttttgacctccatagaagacaccgggaccgatccagcctccgcggccgggaacggtgcat
tggaacgcggattccccgtgccaagagtgacgtaagtaccgcctatagagtctataggcccaccccttggcttctt
atgcatgctatactgttttggcttggggtctatacaccccgcttcctcatgttataggtgatggtatagcttagc
ctataggtgtgggttattgaccattattgaccactccctattggtgacgatactttccattactaatccataacat
ggctctttgccacaactctctttattggctatatgccaatacactgtccttcagagactgacacggactctgtattt
ttacaggatggggtctcatttattatttacaaattcacatatacaacaccaccgtccccagtgccgcagttttat
taaacataacgtgggatctccacgcgaatctcgggtacgtgttccggacatgggctcttctccggtagcggcggagc
ttctacatccgagccctgctccatgcctccagcgactcatggtcgctcggcagctccttgctcctaacagtggagg
ccagacttaggcacagcacgatgcccaccaccaccagtgtgccgcacaaggccgtggcggtagggtatgtgtctgaa
aatgagctcggggagcgggcttgcaccgctgacgcatttggaagacttaagcgcagcggcagaagaagatgcaggcag
ctgagttgttgtgttctgataagagtcagaggtaactcccgttgcggtgctgttaacggtggagggcagtgtagtct
gagcagtactcgttgctgccgcgcgcgccaccagacataatagctgacagactaacagactgttcctttccatggt
cttttctcacgtcaccgtcgtcgaccagagctgagatcctacaggagtccagggctggagagaaaacctctgcgagg
aagggaaggagcaagccgtgaatttaaggagcgctgtgaagcaat*atggatgcaatgaagagagggctctgctgt*
*gtgctgctgctgtgtggagcagtcttcgtttcgcccagcggtaccggatccacccttGCTTATGTGGAAATAGGATA
TTCTCTGAGAAATATTACATTCGATGGATTGGATACAGATGACTACAATCCAAAGTTCAACATTCCAACGGGTTTGG
CAGTTGATCCCGAAGGATATAGGCTCTTCATAGCCATCCCAAGGAGAAAGCCAAAGGTTCCCTACACTGTGGCTGAA
CTGAATATGGTCATGAATCCCGGATTTCCCGTCGAGAGAGCTCCGAGCTTTGAGAAATTCAAAAAATTCAATGGCGA
GGGCAAAAAGGATCTTGTTAATGTGTATCAGCCAGTCATTGATGATTGTCGTCGTCTTTGGGTGCTTGACATTGGGA
AGGTGGAATACACCGGTGGTGATGCTGATCAATATCCCAAAGGAAAGCCTACCCTAATTGCCTACGACCTCAAGAAG
GATCATACTCCGGAAATTCATCGATTTGAAATTCCAGACGATCTCTATAGCTCACAAGTTGAATTTGGTGGATTTGC
CGTTGATGTTGTTAACACGAAAGGAGACTGTACGGAGTCATTTGTCTACCTGACCAATTTCAAGGATAACTCTCTAA
TTGTCTACGATGAGACACAAAAGAAAGCTTGGAAATTCACAGATAAAACATTTGAAGCTGATAAGGAATCCACGTTC
TCCTACTCGGGAGAGGAACAAATGAAGTACAAAGTCGGTCTTTTTGGGATAGCTCTGGGTGATAGGGATGAAATGGG
GCATCGTCCTGCCTGCTACATCGCTGGGAGTAGCACCAAAGTCTACAGTGTTAACACTAAAGAACTCAAAACAGAGA
ATGGTCAGTTAAATCCTCAGCTTCACGGTGATCGTGGAAAGTACACAGATGCAATTGCCCTAGCCTACGATCCTGAG
CATAAAGTCCTCTACTTTGCTGAATCCGACAGCAGGCAGGTGTCCTGTTGGAATGTAAATATGGAGCTAAAACCAGA
CAATACGGATGTGATCTTCTCTAGTGCCCGTTTTACTTTTGGAACGGATATTTTGGTTGATAGCAAGGGAATGCTGT
GGATAATGGCTAATGGACATCCACCAGTAGAGGATCAAGAGAAGATTTGGAAGATGAGATTCGTAAACCGGAAGATC
CGTATTATGAAAGTGGATACGGAACGTGTTTTCAAATATTCACGCTGCAATCCAAATTATAAGCCCCCAAAGGAAAT
TGAAGTTTGA

FIGURE 2

(pVR2001 LJL143: SEQ ID NO:10)

```
aagggatccagatctgctgtgccttctagttgccagccatctgttgtttgccctccccgtgccttccttgaccct
ggaaggtgccactcccactgtcctttcctaataaaatgaggaaattgcatcgcattgtctgagtaggtgtcattcta
ttctggggggtggggtggggcagcacagcaaggggggaggattgggaagacaatagcaggcatgctggggatgcggtg
ggctctatgggtacccaggtgctgaagaattgacccggttcctcctgggccagaaagaagcaggcacatcccttct
ctgtgacacaccctgtccacgccctggttcttagttccagcccactcataggacactcatagctcaggagggctc
cgccttcaatcccaccgctaaagtacttggagcggtctctccctcctcatcagcccaccaaaccaaacctagcct
ccaagagtgggaagaaattaaagcaagataggctattaagtgcagaggggagagaaaatgcctccaacatgtgaggaa
gtaatgagagaaatcatagaatttcttccgcttcctcgctcactgactcgctgcgctcggtcgttcggctgcggcga
gcggtatcagctcactcaaaggcggtaatacggttatccacagaatcaggggataacgcaggaaagaacatgtgagc
aaaaggccagcaaaaggccaggaaccgtaaaaaggccgcgttgctggcgtttttccataggctccgcccccctgacg
agcatcacaaaaatcgacgctcaagtcagaggtggcgaaacccgacaggactataaagataccaggcgtttccccct
ggaagctccctcgtgcgctctcctgttccgaccctgccgcttaccggatacctgtccgcctttctcccttcgggaag
cgtggcgctttctcaatgctcacgctgtaggtatctcagttcggtgtaggtcgttcgctccaagctgggctgtgtgc
acgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagttcttgaa
gtggtggcctaactacggctacactagaaggacagtatttggtatctgcgctctgctgaagccagttaccttcggaa
aaagagttggtagctcttgatccggcaaacaaaccaccgctggtagcggtggtttttttgtttgcaagcagcagatt
acgcgcagaaaaaaggatctcaagaagatcctttgatcttttctacggggtctgacgctcagtggaacgaaaactc
acgttaagggattttggtcatgagattatcaaaaggatcttcacctagatccttttaaattaaaaatgaagtttta
aatcaatctaaagtatatatgagtaaacttggtctgacagttaccaatgcttaatcagtgaggcacctatctcagcg
atctgtctatttcgttcatccatagttgcctgactccccgtcgtggggggggggcgctgaggtctgcctcgtgaagaagtg
ttgctgactcataccaggcctgaatcgccccatcatccagccagaaagtgagggagccacggttgatgagagctttg
ttgtaggtggaccagttggtgattttgaacttttgctttgccacggaacggtctgcgttgtcgggaagatgcgtgat
ctgatccttcaactcagcaaaagttcgatttattcaacaaagccgccgtcccgtcaagtcagcgtaatgctctgcca
gtgttacaaccaattaaccaattctgattagaaaaactcatcgagcatcaaatgaaactgcaatttattcatatcag
gattatcaataccatattttgaaaaagccgtttctgtaatgaaggagaaaactcaccgaggcagttccataggatg
gcaagatcctggtatcggtctgcgattccgactcgtccaacatcaatacaacctattaatttccctcgtcaaaaat
aaggttatcaagtgagaaatcaccatgagtgacgactgaatccggtgagaatggcaaaagcttatgcatttctttcc
agacttgttcaacaggccagccattacgctcgtcatcaaaatcactcgcatcaaccaaaccgttattcattcgtgat
tgcgcctgagcgagacgaaatacgcgatcgctgttaaaaggacaattacaaacaggaatcgaatgcaaccggcgcag
gaacactgccagcgcatcaacaatattttcacctgaatcaggatattcttctaatacctggaatgctgtttttccgg
ggatcgcagtggtgagtaaccatgcatcatcaggagtaacatggataaaatgcttgatggtcggaagaggcataaattcc
gtcagccagtttagtctgaccatctcatctgtaacatcattggcaacgctacctttgccatgtttcagaaacaactc
tggcgcatcgggcttcccatacaatcgatagattgtcgcacctgattgcccgacattatcgcgagcccatttatacc
catataaatcagcatccatgttggaatttaatcgcggcctcgagcaagacgtttcccgttgaatatggctcataaca
cccccttgtattactgtttatgtaagcagacagttttattgttcatgatgatatatttttatcttgtgcaatgtaaca
tcagagattttgagacacaacgtggctttccccccccccccattattgaagcatttatcagggttattgtctcatga
gcggatacatatttgaatgtatttagaaaaataaacaatagggggttccgcgcacatttccccgaaaagtgccacct
gacgtctaagaaaccattattatcatgacattaacctataaaaataggcgtatcacgaggccctttcgtctcgcgcg
tttcggtgatgacggtgaaaacctctgacacatgcagctcccggagacggtcacagcttgtctgtaagcggatgccg
ggagcagacaagcccgtcagggcgcgtcagcgggtgttggcgggtgtcggggctggcttaactatgcggcatcagag
cagattgtactgagagtgcaccatatgcggtgtgaaataccgcacagatgcgtaaggagaaaataccgcatcagatt
ggctattggccattgcatacgttgtatccatatcataatatgtacatttatattggctcatgtccaacattaccgcc
atgttgacattgattattgactagttattaatagtaatcaattacggggtcattagttcatagcccatatatggagt
tccgcgttacataacttacggtaaatggcccgcctggctgaccgcccaacgacccccgcccattgacgtcaataatg
acgtatgttcccatagtaacgccaatagggactttccattgacgtcaatgggtggagtatttacggtaaactgccca
cttggcagtacatcaagtgtatcatatgccaagtacgccccctattgacgtcaatgacggtaaatggcccgcctggc
attatgcccagtacatgaccttatgggactttcctacttggcagtacatctacgtattagtcatcgctattaccatg
gtgatgcggttttggcagtacatcaatgggcgtggatagcggtttgactcacggggatttccaagtctccaccccat
tgacgtcaatgggagtttgttttggcaccaaaatcaacgggactttccaaaatgtcgtaacaactccgccccattga
cgcaaatgggcggtaggcgtgtacggtgggaggtctatataagcagagctcgtttagtgaaccgtcagatcgcctgg
```

FIGURE 2

```
agacgccatccacgctgttttgacctccatagaagacaccgggaccgatccagcctccgcggccgggaacggtgcat
tggaacgcggattccccgtgccaagagtgacgtaagtaccgcctatagagtctataggcccaccccttggcttctt
atgcatgctatactgttttggcttggggtctatacaccccgcttcctcatgttataggtgatggtatagcttagc
ctataggtgtgggttattgaccattattgaccactccctattggtgacgatactttccattactaatccataacat
ggctctttgccacaactctctttattggctatatgccaatacactgtccttcagagactgacacggactctgtattt
ttacaggatggggtctcatttattatttacaaattcacatatacaacaccaccgtccccagtgccgcagttttat
taaacataacgtgggatctccacgcgaatctcgggtacgtgttccggacatgggctcttctccggtagcggcggagc
ttctacatccgagccctgctcccatgcctccagcgactcatggtcgctcggcagctccttgctcctaacagtggagg
ccagacttaggcacagcacgatgccaccaccaccagtgtgccgcacaaggccgtggcggtagggtatgtgtctgaa
aatgagctcggggagcgggcttgcaccgctgacgcatttggaagacttaaggcagcggcagaagaagatgcaggcag
ctgagttgttgtgttctgataagagtcagaggtaactcccgttgcggtgctgttaacggtggagggcagtgtagtct
gagcagtactcgttgctgccgcgcgcgccaccagacataatagctgacagactaacagactgttcctttccatgggt
cttttctcacgtcaccgtcgtcgaccagagctgagatcctacaggagtccagggctggagagaaaacctctgcgagg
aaagggaaggagcaagccgtgaatttaagggacgctgtgaagcaatcatggatgcaatgaagagagggctctgctgt
gtgctgctgctgtgtggagcagtcttcgtttcgcccagcggtaccggatccacccttGATGGTGATGAATATTTCAT
TGGAAAATACAAAGAAAAAGATGAGACACTGTTTTTTGCAAGCTACGGCCTAAAGAGGGATCCTTGCCAAATTGTCT
TAGGCTACAAATGCTCAAACAATCAAACCCACTTTGTGCTTAATTTTAAAACCAATAAGAAATCCTGCATATCAGCA
ATTAAGCTGACTTCTTACCCAAAAATCAATCAAAACTCGGATTTAACTAAAAATCTCTACTGCCAAACTGGAGGAAT
AGGAACAGATAACTGCAAACTTGTCTTCAAGAAACGTAAAAGACAAATAGCAGCTAATATTGAAATCTACGGCATTC
CAGCGAAGAAATGTTCCTTCAAGGATCGTTACATTGGAGCTGATCCACTCCACGTCGATTCCTATGGGCTTCCGTAT
CAGTTTGATCAGGAACATGGATGGAATGTGGAACGATATAACATTTTCAAAGACACAAGATTTTCCACAGAAGTTTT
CTACCACAAAAATGGTTTATTTAACACCCAAATAACTTATTTGGCTGAAGAAGATTCCTTCTCTGAAGCTCGAGAGA
TTACTGCGAAGGATATTAAGAAGAAGTTTTCAATTATTTTGCCCAATGAAGAGTATAAGAGGATTAGTTTCTTGGAC
GTTTATTGGTTCCAGGAGACTATGCGAAAAAAGCCTAAATATCCCTACATTCACTACAATGGAGAATGCAGCAATGA
GAATAAAACTTGTGAACTTGTCTTTGACACCGATGAACTAATGACCTACGCCCTTGTTAAAGTCTTTACTAATCCTG
AGAGTGATGGATCTAGGCTCAAAGAAGAGGATTTGGGAAGAGGATAA
```

FIGURE 4 vCP2390 (ALVAC C3 H6p-synthetic Leishmania LJM17) (SEQ ID NO:92)

[1-940]: C3 left arm
[2224-2409]: H6 promoter
[982-2223]: Leishmania LJM17
[2433-4995]: C3 right arm

```
   1  TCAGATATATTAGATGCATTGTTAGTTCTGTAGATCAGTAACGTATAGCATACGAGTATA
  61  ATTATCGTAGGTAGTAGGTATCCTAAAATAAATCTGATACAGATAATAACTTTGTAAATC
 121  AATTCAGCAATTTCTCTATTATCATGATAATGATTAATACACAGCGTGTCGTTATTTTTT
 181  GTTACGATAGTATTTCTAAAGTAAAGAGCAGGAATCCCTAGTATAATAGAAATAATCCAT
 241  ATGAAAAATATAGTAATGTACATATTTCTAATGTTAACATATTTATAGGTAAATCCAGGA
 301  AGGGTAATTTTTACATATCTATATACGCTTATTACAGTTATTAAAAATATACTTGCAAAC
 361  ATGTTAGAAGTAAAAAAGAAAGAACTAATTTTACAAAGTGCTTTACCAAAATGCCAATGG
 421  AAATTACTTAGTATGTATATAATGTATAAAGGTATGAATATCACAAACAGCAAATCGGCT
 481  ATTCCCAAGTTGAGAAACGGTATAATAGATATATTTCTAGATACCATTAATAACCTTATA
 541  AGCTTGACGTTTCCTATAATGCCTACTAAGAAAACTAGAAGATACATACATACTAACGCC
 601  ATACGAGAGTAACTACTCATCGTATAACTACTGTTGCTAACAGTGACACTGATGTTATAA
 661  CTCATCTTTGATGTGGTATAAATGTATAATAACTATATTACACTGGTATTTTATTTCAGT
 721  TATATACTATATAGTATTAAAAATTATATTTGTATAATTATATTATTATATTCAGTGTAG
 781  AAAGTAAAATACTATAAATATGTATCTCTTATTTATAACTTATTAGTAAAGTATGTACTA
 841  TTCAGTTATATTGTTTTATAAAAGCTAAATGCTACTAGATTGATATAAATGAATATGTAA
 901  TAAATTAGTAATGTAGTATACTAATATTAACTCACATTTACTAATTAGCTATAAAAACC
 961  CCTAGTCAATAAAAACTCGAGTCATCACACTTCGATTTCTTTGGGGGGCTTGTAGTTGGG
1021  GTTGCACCGGCTGTACTTGAACACCCGCTCGGTGTCCACCTTCATGATCCGGATCTTCCG
1081  GTTCACGAACCGCATCTTCCAGATCTTTTCCTGGTCCTCCACGGGGGGTGGCCGTTGGC
1141  CATGATCCACAGCATGCCCTTGCTGTCCACCAGGATGTCGGTGCCGAAGGTGAACCGGGC
1201  GCTGCTGAAGATCACGTCGGTGTTGTCGGGCTTCAGTTCCATGTTCACGTTCCAGCAGGA
1261  CACCTGCCGGCTGTCGCTCTCGGCGAAGTACAGCACCTTGTGCTCGGGGTCGTAGGCCAG
1321  GGCAATGGCGTCGGTGTACTTGCCCCGGTCGCCGTGCAGCTGGGGGTTCAGCTGGCCGTT
1381  CTCGGTTTTCAGCTCTTTGGTATTCACGCTGTACACCTTGGTGCTGCTGCCGGCGATGTA
1441  GCAGGCGGGCCTGTGGCCCATCTCGTCCCGGTCGCCCAGGGCGATGCCGAACAGGCCCAC
1501  TTTGTACTTCATCTGTTCCTCGCCGCTGTAGCTGAAGGTGCTCTCTTTGTCGGCCTCGAA
1561  GGTCTTGTCGGTGAACTTCCAGGCCTTCTTCTGGGTCTCGTCGTACACGATCAGGCTGTT
1621  GTCCTTGAAGTTGGTCAGGTACACGAAGCTCTCGGTGCAGTCGCCCTTGGTGTTCACCAC
1681  GTCCACGGCAAAGCCGCCGAACTCCACCTGGCTGCTGTACAGGTCGTCGGGGATCTCGAA
1741  CCGGTGGATCTCGGGGGTGTGGTCCTTCTTCAGGTCGTAGGCGATCAGGGTGGGCTTGCC
1801  CTTGGGGTACTGGTCGGCGTCGCCGCCTGTGTACTCCACCTTGCCGATGTCCAGCACCCA
1861  CAGCCGCCTGCAGTCGTCGATCACGGGCTGGTACACGTTCACCAGGTCTTTCTTGCCCTC
1921  GCCGTTAAACTTCTTGAACTTCTCGAAGCTGGGGCCCTCTCCACGGGGAAGCCGGGGTT
1981  CATCACCATGTTCAGCTCGGCCACGGTGTAGGGCACCTTGGGCTTCCGCCTGGGGATGGC
2041  GATGAACAGCCGGTAGCCCTCGGGGTCCACGGCCAGGCCGGTGGGGATGTTGAACTTGGG
2101  GTTGTAGTCGTCGGTGTCCAGGCCGTCGAAGGTGATGTTCCGCAGGCTGTAGCCGATCTC
2161  CACGTAGGCGCCGTGGATGCCCTGGAACAGCACGATGGCCAGGAACACGAAGAAGAACCG
2221  CATTACGATACAAACTTAACGGATATCGCGATAATGAAATAATTTATGATTATTTCTCGC
2281  TTTCAATTTAACACAACCCTCAAGAACCTTTGTATTTATTTTCACTTTTTAAGTATAGAA
2341  TAAAGAAGCTCTAATTAATTAACGAGCAGATAGTCTCGTTCTCGCCCTGCCTGATGACTA
2401  ATTAATTAACCCCTAGTTAATCAAATAAAAAGCATACAAGCTATTGCTTCGCTATCGTTA
2461  CAAAATGGCAGGAATTTTGTGTAAACTAAGCCACATACTTGCCAATGAAAAAAATAGTAG
2521  AAAGGATACTATTTTAATGGGATTAGATGTTAAGGTTCCTTGGGATTATAGTAACTGGGC
2581  ATCTGTTAACTTTTACGACGTTAGGTTAGATACTGATGTTACAGATTATAATAATGTTAC
2641  AATAAAATACATGACAGGATGTGATATTTTTCCTCATATAACTCTTGGAATAGCAAATAT
2701  GGATCAATGTGATAGATTTGAAAATTTCAAAAAGCAAATAACTGATCAAGATTTACAGAC
```

FIGURE 4

```
2761  TATTTCTATAGTCTGTAAAGAAGAGATGTGTTTTCCTCAGAGTAACGCCTCTAAACAGTT
2821  GGGAGCGAAAGGATGCGCTGTAGTTATGAAACTGGAGGTATCTGATGAACTTAGAGCCCT
2881  AAGAAATGTTCTGCTGAATGCGGTACCCTGTTCGAAGGACGTGTTTGGTGATATCACAGT
2941  AGATAATCCGTGGAATCCTCACATAACAGTAGGATATGTTAAGGAGGACGATGTCGAAAA
3001  CAAGAAACGCCTAATGGAGTGCATGTCCAAGTTTAGGGGGCAAGAAATACAAGTTCTAGG
3061  ATGGTATTAATAAGTATCTAAGTATTTGGTATAATTTATTAAATAGTATAATTATAACAA
3121  ATAATAAATAACATGATAACGGTTTTTATTAGAATAAAATAGAGATAATATCATAATGAT
3181  ATATAATACTTCATTACCAGAAATGAGTAATGGAAGACTTATAAATGAACTGCATAAAGC
3241  TATAAGGTATAGAGATATAAATTTAGTAAGGTATATACTTAAAAAATGCAAATACAATAA
3301  CGTAAATATACTATCAACGTCTTTGTATTTAGCCGTAAGTATTTCTGATATAGAAATGGT
3361  AAAATTATTACTAGAACACGGTGCCGATATTTTAAAATGTAAAAATCCTCCTCTTCATAA
3421  AGCTGCTAGTTTAGATAATACAGAAATTGCTAAACTACTAATAGATTCTGGCGCTGACAT
3481  AGAACAGATACATTCTGGAAATAGTCCGTTATATATTTCTGTATATAGAAACAATAAGTC
3541  ATTAACTAGATATTTATTAAAAAAGGTGTTAATTGTAATAGATTCTTTCTAAATTATTA
3601  CGATGTACTGTATGATAAGATATCTGATGATATGTATAAAATATTTATAGATTTTAATAT
3661  TGATCTTAATATACAAACTAGAAATTTTGAAACTCCGTTACATTACGCTATAAAGTATAA
3721  GAATATAGATTTAATTAGGATATTGTTAGATAATAGTATTAAAATAGATAAAAGTTTATT
3781  TTTGCATAAACAGTATCTCATAAAGGCACTTAAAAATAATTGTAGTTACGATATAATAGC
3841  GTTACTTATAAATCACGGAGTGCCTATAAACGAACAAGATGATTTAGGTAAAACCCCATT
3901  ACATCATTCGGTAATTAATAGAAGAAAAGATGTAACAGCACTTCTGTTAAATCTAGGAGC
3961  TGATATAAACGTAATAGATGACTGTATGGGCAGTCCCTTACATTACGCTGTTTCACGTAA
4021  CGATATCGAAACAACAAAGACACTTTTAGAAAGAGGATCTAATGTTAATGTGGTTAATAA
4081  TCATATAGATACCGTTCTAAATATAGCTGTTGCATCTAAAAACAAAACTATAGTAAACTT
4141  ATTACTGAAGTACGGTACTGATACAAAGTTGGTAGGATTAGATAAACATGTTATTCACAT
4201  AGCTATAGAAATGAAAGATATTAATATACTGAATGCGATCTTATTATATGGTTGCTATGT
4261  AAACGTCTATAATCATAAAGGTTTCACTCCTCTATACATGGCAGTTAGTTCTATGAAAAC
4321  AGAATTTGTTAAACTCTTACTTGACCACGGTGCTTACGTAAATGCTAAAGCTAAGTTATC
4381  TGGAAATACTCCTTTACATAAAGCTATGTTATCTAATAGTTTTAATAATATAAAATTACT
4441  TTTATCTTATAACGCCGACTATAATTCTCTAAATAATCACGGTAATACGCCTCTAACTTG
4501  TGTTAGCTTTTTAGATGACAAGATAGCTATTATGATAATATCTAAAATGATGTTAGAAAT
4561  ATCTAAAAATCCTGAAATAGCTAATTCAGAAGGTTTTATAGTAAACATGGAACATATAAA
4621  CAGTAATAAAAGACTACTATCTATAAAAGAATCATGCGAAAAAGAACTAGATGTTATAAC
4681  ACATATAAAGTTAAATTCTATATATTCTTTTAATATCTTTCTTGACAATAACATAGATCT
4741  TATGGTAAAGTTCGTAACTAATCCTAGAGTTAATAAGATACCTGCATGTATACGTATATA
4801  TAGGGAATTAATACGGAAAAATAAATCATTAGCTTTTCATAGACATCAGCTAATAGTTAA
4861  AGCTGTAAAAGAGAGTAAGAATCTAGGAATAATAGGTAGGTTACCTATAGATATCAAACA
4921  TATAATAATGGAACTATTAAGTAATAATGATTTACATTCTGTTATCACCAGCTGTTGTAA
4981  CCCAGTAGTATAAAG
```

FIGURE 4 vCP2390 (ALVAC C3 H6p-synthetic (coding) Leishmania LJM17) (SEQ ID NO:93)

```
   1 ctttatacta ctgggttaca acagctggtg ataacagaat gtaaatcatt attacttaat
  61 agttccatta ttatatgttt gatatctata ggtaacctac ctattattcc tagattctta
 121 ctctctttta cagctttaac tattagctga tgtctatgaa aagctaatga tttatttttc
 181 cgtattaatt ccctatatat acgtatacat gcaggtatct tattaactct aggattagtt
 241 acgaacttta ccataagatc tatgttattg tcaagaaaga tattaaaaga atatatagaa
 301 tttaacttta tatgtgttat aacatctagt tcttttttcgc atgattcttt tatagatagt
 361 agtcttttat tactgtttat atgttccatg tttactataa aaccttctga attagctatt
 421 tcaggatttt tagatatttc taacatcatt ttagatatta tcataatagc tatcttgtca
 481 tctaaaaagc taacacaagt tagaggcgta ttaccgtgat tatttagaga attatagtcg
 541 gcgttataag ataaaagtaa tttatatta ttaaaactat tagataacat agctttatgt
 601 aaaggagtat ttccagataa cttagcttta gcatttacgt aagcaccgtg gtcaagtaag
 661 agtttaacaa attctgtttt catagaacta actgccatgt atagaggagt gaaaccttta
 721 tgattataga cgttacata gcaaccatat aataagatcg cattcagtat attaatatct
 781 ttcatttcta tagctatgtg aataacatgt ttatctaatc ctaccaactt tgtatcagta
 841 ccgtacttca gtaataagtt tactatagtt ttgttttag atgcaacagc tatatttaga
 901 acggtatcta tatgattatt aaccacatta acattagatc ctctttctaa aagtgtcttt
 961 gttgtttcga tatcgttacg tgaaacagcg taatgtaagg gactgcccat acagtcatct
1021 attacgttta tatcagctcc tagatttaac agaagtgctg ttacatcttt tcttctatta
1081 attaccgaat gatgtaatgg ggttttacct aaatcatctt gttcgtttat aggcactccg
1141 tgatttataa gtaacgctat tatatcgtaa ctacaattat tttaagtgc ctttatgaga
1201 tactgtttat gcaaaaataa acttttatct attttaatac tattatctaa caatatccta
1261 attaaatcta tattcttata ctttatagcg taatgtaacg gagtttcaaa atttctagtt
1321 tgtatattaa gatcaatatt aaaatctata aatatttat acatatcatc agatatctta
1381 tcatacagta catcgtaata atttagaaag aatctattac aattaacacc ttttttaat
1441 aaatatctag ttaatgactt attgtttcta tatacagaaa tatataacgg actatttcca
1501 gaatgtatct gttctatgtc agcgccagaa tctattagta gtttagcaat ttctgtatta
1561 tctaaactag cagctttatg aagaggagga tttttacatt ttaaaatatc ggcaccgtgt
1621 tctagtaata atttaccat ttctatatca gaaatactta cggctaaata caagacgtt
1681 gatagtatat ttacgttatt gtatttgcat ttttaagta tacccttac taaatttata
1741 tctctatacc ttatagcttt atgcagttca tttataagtc ttccattact catttctggt
1801 aatgaagtat tatatatcat tatgatatta tctctatttt attctaataa aaaccgttat
1861 catgttattt attatttgtt ataattatac tatttaataa attataccaa atacttagat
1921 acttattaat accatcctag aacttgtatt tcttgccccc taaacttgga catgcactcc
1981 attaggcgtt tcttgttttc gacatcgtcc tccttaacat atcctactgt tatgtgagga
2041 ttccacggat tatctactgt gatatcacca aacacgtcct tgaacaggg taccgcattc
2101 agcagaacat ttcttagggc tctaagttca tcagatacct ccagtttcat aactacagcg
2161 catcctttcg ctcccaactg tttagaggcg ttactctgag gaaacacat ctcttcttta
2221 cagactatag aaatagtctg taaatcttga tcagttattt gcttttgaa attttcaaat
2281 ctatcacatt gatccatatt tgctattcca agagttatat gaggaaaaat atcacatcct
2341 gtcatgtatt ttattgtaac attattataa tctgtaacat cagtatctaa cctaacgtcg
2401 taaagttaa cagatgccca gttactataa tcccaaggaa ccttaacatc taatcccatt
2461 aaaatagtat cctttctact atttttttca ttggcaagta tgtggcttag tttacacaaa
2521 attcctgcca ttttgtaacg atagcgaagc aatagcttgt atgcttttta tttgattaac
2581 tagggttaa ttaattagtc atcaggcagg gcgagaacga gactatctgc tgttaatta
2641 attagagctt ctttattcta tacttaaaaa gtgaaaataa atacaaaggt tcttgagggt
2701 tgtgttaaat tgaaagcgag aaataatcat aaattatttc attatcgcga tatccgttaa
2761 gtttgtatcg taatgcggtt cttcttcgtg ttcctggcca tcgtgctgtt ccagggcatc
2821 cacggcgcct acgtggagat cggctacagc ctgcggaaca tcacttcga cggcctggac
2881 accgacgact acaaccccaa gttcaacatc cccaccggcc tggccgtgga ccccgagggc
2941 taccggctgt tcatcgccat ccccaggcgg aagcccaagg tgccctacac cgtggccgag
```

FIGURE 4

```
3001 ctgaacatgg tgatgaaccc cggcttcccc gtggagaggg cccccagctt cgagaagttc
3061 aagaagttta acggcgaggg caagaaagac ctggtgaacg tgtaccagcc cgtgatcgac
3121 gactgcaggc ggctgtgggt gctggacatc ggcaaggtgg agtacacagg cggcgacgcc
3181 gaccagtacc ccaagggcaa gcccaccctg atcgcctacg acctgaagaa ggaccacacc
3241 cccgagatcc accggttcga gatccccgac gacctgtaca gcagccaggt ggagttcggc
3301 ggctttgccg tggacgtggt gaacaccaag ggcgactgca ccgagagctt cgtgtacctg
3361 accaacttca aggacaacag cctgatcgtg tacgacgaga cccagaagaa ggcctggaag
3421 ttcaccgaca agaccttcga ggccgacaaa gagagcacct cagctacag cggcgaggaa
3481 cagatgaagt acaaagtggg cctgttcggc atcgccctgg gcgaccggga cgagatgggc
3541 cacaggcccg cctgctacat cgccggcagc agcaccaagg tgtacagcgt gaataccaaa
3601 gagctgaaaa ccgagaacgg ccagctgaac ccccagctgc acggcgaccg gggcaagtac
3661 accgacgcca ttgccctggc ctacgacccc gagcacaagg tgctgtactt cgccgagagc
3721 gacagccggc aggtgtcctg ctggaacgtg aacatggaac tgaagcccga caacaccgac
3781 gtgatcttca gcagcgcccg gttcaccttc ggcaccgaca tcctggtgga cagcaagggc
3841 atgctgtgga tcatggccaa cggccacccc cccgtggagg accaggaaaa gatctggaag
3901 atgcggttcg tgaaccggaa gatccggatc atgaaggtgg acaccgagcg ggtgttcaag
3961 tacagccggt gcaaccccaa ctacaagccc cccaaagaaa tcgaagtgtg atgactcgag
4021 tttttattga ctagggtttt ttatagctaa ttagtcaaat gtgagttaat attagtatac
4081 tacattacta atttattaca tattcattta tatcaatcta gtagcattta gcttttataa
4141 aacaatataa ctgaatagta catactttac taataagtta taaataagag atacatattt
4201 atagtatttt actttctaca ctgaatataa taatataatt atacaaatat aatttttaat
4261 actatatagt atataactga aataaaatac cagtgtaata tagttattat acatttatac
4321 cacatcaaag atgagttata acatcagtgt cactgttagc aacagtagtt atacgatgag
4381 tagttactct cgtatggcgt tagtatgtat gtatcttcta gttttcttag taggcattat
4441 aggaaacgtc aagcttataa ggttattaat ggtatctaga aatatatcta ttataccgtt
4501 tctcaacttg gaatagccg atttgctgtt tgtgatattc atacctttat acattatata
4561 catactaagt aatttccatt ggcattttgg taaagcactt tgtaaaatta gttctttctt
4621 ttttacttct aacatgtttg caagtatatt tttaataact gtaataagcg tatatagata
4681 tgtaaaaatt accttcctg gattaccta taaatatgtt aacattagaa atatgtacat
4741 tactatattt ttcatatgga ttatttctat tatactaggg attcctgctc tttactttag
4801 aaatactatc gtaacaaaaa ataacgacac gctgtgtatt aatcattatc atgataatag
4861 agaaattgct gaattgattt acaaagttat tatctgtatc agatttattt taggatacct
4921 actacctacg ataattatac tcgtatgcta tacgttactg atctacagaa ctaacaatgc
4981 atctaatata tctga
```

FIGURE 6 vCP2389 (ALVAC C3 H6p-synthetic Leishmania LJL143) (SEQ ID NO:94)

[336-1275]: C3 left arm
[1300-1485]: H6 promoter
[1486-2388]: Leishmania LJL143
[2422-4993]: C3 right arm

```
   1  CGAGTCCTTCTAACACTGTGGTTTATTGGCTGGAATAAAAGGATAAAGACACCTATACTG
  61  ATTCATTTTCATCTGTCAACGTTTCTCTAAGAGATTCATAGGTATTATTATTACATCGAT
 121  CTAGAAGTCTAATAACTGCTAAGTATATTATTGGATTTAACGCGCTATAAACGCATCCAA
 181  AACCTACAAATATAGGAGAAGCTTCTCTTATGAAACTTCTTAAAGCTTTACTCTTACTAT
 241  TACTACTCAAAAGAGATATTACATTAATTATGTGATGAGGCATCCAACATATAAAGAAGA
 301  CTAAAGCTGTAGAAGCTGTTATGAAGAATATCTTATCAGATATATTAGATGCATTGTTAG
 361  TTCTGTAGATCAGTAACGTATAGCATACGAGTATAATTATCGTAGGTAGTAGGTATCCTA
 421  AAATAAATCTGATACAGATAATAACTTTGTAAATCAATTCAGCAATTCTCTATTATCAT
 481  GATAATGATTAATACACAGCGTGTCGTTATTTTTTGTTACGATAGTATTTCTAAAGTAAA
 541  GAGCAGGAATCCCTAGTATAATAGAAATAATCCATATGAAAAATATAGTAATGTACATAT
 601  TTCTAATGTTAACATATTTATAGGTAAATCCAGGAAGGGTAATTTTTACATATCTATATA
 661  CGCTTATTACAGTTATTAAAAATATACTTGCAAACATGTTAGAAGTAAAAAAGAAAGAAC
 721  TAATTTTACAAAGTGCTTTACCAAAATGCCAATGGAAATTACTTAGTATGTATATAATGT
 781  ATAAAGGTATGAATATCACAAACAGCAAATCGGCTATTCCCAAGTTGAGAAACGGTATAA
 841  TAGATATATTTCTAGATACCATTAATAACCTTATAAGCTTGACGTTTCCTATAATGCCTA
 901  CTAAGAAAACTAGAAGATACATACATACTAACGCCATACGAGAGTAACTACTCATCGTAT
 961  AACTACTGTTGCTAACAGTGACACTGATGTTATAACTCATCTTTGATGTGGTATAAATGT
1021  ATAATAACTATATTACACTGGTATTTTATTTCAGTTATATACTATATAGTATTAAAAATT
1081  ATATTTGTATAATTATATTATTATATTCAGTGTAGAAAGTAAAATACTATAAATATGTAT
1141  CTCTTATTTATAACTTATTAGTAAAGTATGTACTATTCAGTTATATTGTTTTATAAAAGC
1201  TAAATGCTACTAGATTGATATAAATGAATATGTAATAAATTAGTAATGTAGTATACTAAT
1261  ATTAACTCACATTTGACTAATTAGCTATAAAAACCCGGGTTAATTAATTAGTCATCAGGC
1321  AGGGCGAGAACGAGACTATCTGCTCGTTAATTAATTAGAGCTTCTTTATTCTATACTTAA
1381  AAAGTGAAAATAAATACAAAGGTTCTTGAGGGTTGTGTTAAATTGAAAGCGAGAAATAAT
1441  CATAAATTATTTCATTATCGCGATATCCGTTAAGTTTGTATCGTAATGAACAGCATCAAC
1501  TTTCTGAGCATCGTGGGCCTGATCAGCTTCGGCTTCATCGTGGCCGTGAAGTGCGACGGC
1561  GACGAGTACTTCATCGGCAAGTACAAAGAGAAGGACGAGACCCTGTTCTTCGCCAGCTAC
1621  GGCCTGAAGCGGGACCCCTGCCAGATCGTGCTGGGCTACAAGTGCAGCAACAACCAGACC
1681  CACTTCGTGCTGAACTTCAAGACCAACAAGAAGAGCTGCATCAGCGCCATCAAGCTGACC
1741  AGCTACCCCAAGATCAACCAGAACAGCGACCTGACCAAGAACCTGTACTGCCAGACCGGC
1801  GGCATCGGCACCGACAACTGCAAGCTGGTGTTCAAGAAGCGGAAGCGGCAGATCGCCGCC
1861  AACATCGAGATCTACGGCATCCCCGCCAAGAAGTGCAGCTTCAAGGACCGGTACATCGGC
1921  GCCGACCCCCTGCACGTGGACTCCTACGCCCTGCCCTACCAGTTCGACCAGGAACACGGC
1981  TGGAACGTCGAGCGGTACAACATCTTCAAGGACACCCGGTTCAGCACCGAGGTGTTCTAC
2041  CACAAGAACGGCCTGTTCAACACCCAGATCACCTACCTGGCCGAAGAGGACAGCTTCAGC
2101  GAGGCCCGGGAGATCACCGCCAAGGACATCAAGAAGAAGTTCAGCATCATCCTGCCCAAC
2161  GAGGAATACAAGCGGATCAGCTTCCTGGACGTGTACTGGTTCCAGGAAACCATGCGGAAG
2221  AAGCCCAAGTACCCCTACATCCACTACAACGGCGAGTGCTCCAACGAGAACAAGACCTGC
2281  GAACTGGTGTTCGACACCGACGAGCTGATGACCTACGCCCTGGTGAAGGTGTTCACCAAC
2341  CCCGAGAGCGACGGCAGCCGGCTGAAGAAGAGGACCTGGGCAGGGGCTGATGACTCGAG
2401  TTTTTATTGACTAGTTAATCAAATAAAAAGCATACAAGCTATTGCTTCGCTATCGTTACA
2461  AAATGCAGGAATTTTGTGTAAACTAAGCCACATACTTGCCAATGAAAAAAATAGTAGAA
2521  AGGATACTATTTTAATGGGATTAGATGTTAAGGTTCCTTGGGATTATAGTAACTGGGCAT
2581  CTGTTAACTTTTACGACGTTAGGTTAGATACTGATGTTACAGATTATAATAATGTTACAA
2641  TAAAATACATGACAGGATGTGATATTTTTCCTCATATAACTCTTGAATAGCAAATATGG
2701  ATCAATGTGATAGATTTGAAAATTTCAAAAAGCAAATAACTGATCAAGATTTACAGACTA
2761  TTTCTATAGTCTGTAAAGAAGAGATGTGTTTCCTCAGAGTAACGCCTCTAAACAGTTGG
```

FIGURE 6

```
2821  GAGCGAAAGGATGCGCTGTAGTTATGAAACTGGAGGTATCTGATGAACTTAGAGCCCTAA
2881  GAAATGTTCTGCTGAATGCGGTACCCTGTTCGAAGGACGTGTTTGGTGATATCACAGTAG
2941  ATAATCCGTGGAATCCTCACATAACAGTAGGATATGTTAAGGAGGACGATGTCGAAAACA
3001  AGAAACGCCTAATGGAGTGCATGTCCAAGTTTAGGGGGCAAGAAATACAAGTTCTAGGAT
3061  GGTATTAATAAGTATCTAAGTATTTGGTATAATTTATTAAATAGTATAATTATAACAAAT
3121  AATAAATAACATGATAACGGTTTTTATTAGAATAAAATAGAGATAATATCATAATGATAT
3181  ATAATACTTCATTACCAGAAATGAGTAATGGAAGACTTATAAATGAACTGCATAAAGCTA
3241  TAAGGTATAGAGATATAAATTTAGTAAGGTATATACTTAAAAAATGCAAATACAATAACG
3301  TAAATATACTATCAACGTCTTTGTATTTAGCCGTAAGTATTTCTGATATAGAAATGGTAA
3361  AATTATTACTAGAACACGGTGCCGATATTTTAAAATGTAAAAATCCTCCTCTTCATAAAG
3421  CTGCTAGTTTAGATAATACAGAAATTGCTAAACTACTAATAGATTCTGGCGCTGACATAG
3481  AACAGATACATTCTGGAAATAGTCCGTTATATATTTCTGTATATAGAAACAATAAGTCAT
3541  TAACTAGATATTTATTAAAAAAGGTGTTAATTGTAATAGATTCTTTCTAAATTATTACG
3601  ATGTACTGTATGATAAGATATCTGATGATATGTATAAAATATTTATAGATTTTAATATTG
3661  ATCTTAATATACAAACTAGAAATTTTGAAACTCCGTTACATTACGCTATAAAGTATAAGA
3721  ATATAGATTTAATTAGGATATTGTTAGATAATAGTATTAAAATAGATAAAAGTTTATTTT
3781  TGCATAAACAGTATCTCATAAAGGCACTTAAAAATAATTGTAGTTACGATATAATAGCGT
3841  TACTTATAAATCACGGAGTGCCTATAAACGAACAAGATGATTTAGGTAAAACCCCATTAC
3901  ATCATTCGGTAATTAATAGAAGAAAAGATGTAACAGCACTTCTGTTAAATCTAGGAGCTG
3961  ATATAAACGTAATAGATGACTGTATGGGCAGTCCCTTACATTACGCTGTTTCACGTAACG
4021  ATATCGAAACAACAAAGACACTTTTAGAAAGAGGATCTAATGTTAATGTGGTTAATAATC
4081  ATATAGATACCGTTCTAAATATAGCTGTTGCATCTAAAAACAAAACTATAGTAAACTTAT
4141  TACTGAAGTACGGTACTGATACAAAGTTGGTAGGATTAGATAAACATGTTATTCACATAG
4201  CTATAGAAATGAAAGATATTAATATACTGAATGCGATCTTATTATATGGTTGCTATGTAA
4261  ACGTCTATAATCATAAAGGTTTCACTCCTCTATACATGGCAGTTAGTTCTATGAAAACAG
4321  AATTTGTTAAACTCTTACTTGACCACGGTGCTTACGTAAATGCTAAAGCTAAGTTATCTG
4381  GAAATACTCCTTTACATAAAGCTATGTTATCTAATAGTTTTAATAATATAAAATTACTTT
4441  TATCTTATAACGCCGACTATAATTCTCTAAATAATCACGGTAATACGCCTCTAACTTGTG
4501  TTAGCTTTTTAGATGACAAGATAGCTATTATGATAATATCTAAAATGATGTTAGAAATAT
4561  CTAAAAATCCTGAAATAGCTAATTCAGAAGGTTTTATAGTAAACATGGAACATATAAACA
4621  GTAATAAAAGACTACTATCTATAAAAGAATCATGCGAAAAAGAACTAGATGTTATAACAC
4681  ATATAAAGTTAAATTCTATATATTCTTTTAATATCTTTCTTGACAATAACATAGATCTTA
4741  TGGTAAAGTTCGTAACTAATCCTAGAGTTAATAAGATACCTGCATGTATACGTATATATA
4801  GGGAATTAATACGGAAAATAAATCATTAGCTTTTCATAGACATCAGCTAATAGTTAAAG
4861  CTGTAAAAGAGAGTAAGAATCTAGGAATAATAGGTAGGTTACCTATAGATATCAAACATA
4921  TAATAATGGAACTATTAAGTAATAATGATTTACATTCTGTTATCACCAGCTGTTGTAACC
4981  CAGTAGTATAAAGTGATTTTATTCAATTACGAAGATAAACATTAAATTTGTTAACAGATA
```

FIGURE 9
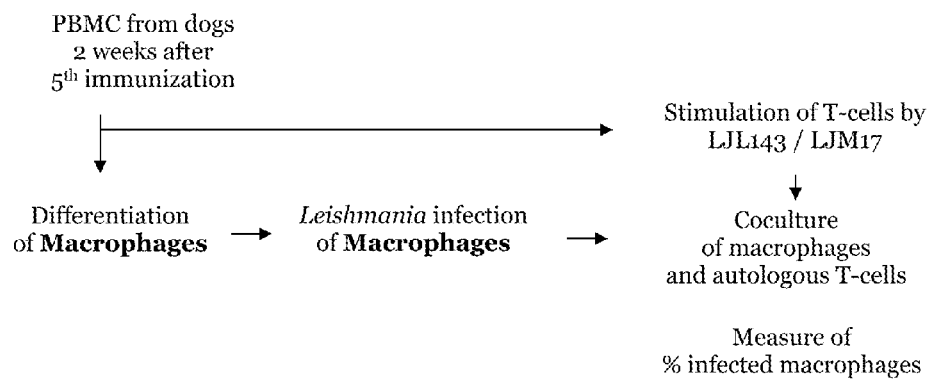
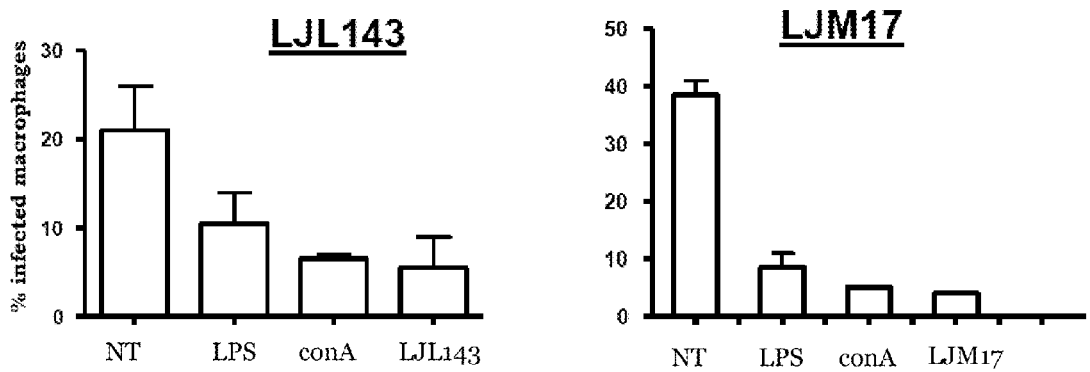

FIGURE 11

(pNBO002 : SEQ ID NO :19)

ttggctattggccattgcatacgttgtatccatatcataatatgtacatttatattggctcatgtccaacattaccg
ccatgttgacattgattattgactagttattaatagtaatcaattacggggtcattagttcatagcccatatatgga
gttccgcgttacataacttacggtaaatggcccgcctggctgaccgcccaacgaccccgccattgacgtcaataa
tgacgtatgttcccatagtaacgccaataggggactttccattgacgtcaatgggtggagtatttacggtaaactgcc
cacttggcagtacatcaagtgtatcatatgccaagtacgccccctattgacgtcaatgacggtaaatggcccgcctg
gcattatgcccagtacatgaccttatgggactttcctacttggcagtacatctacgtattagtcatcgctattacca
tggtgatgcggttttggcagtacatcaatgggcgtggatagcggtttgactcacggggatttccaagtctccaccc
attgacgtcaatgggagtttgttttggcaccaaaatcaacgggactttccaaaatgtcgtaacaactccgccccatt
gacgcaaatgggcggtaggcgtgtacggtgggaggtctatataagcagagctcgtttagtgaaccgtcagatcgcct
ggagacgccatccacgctgttttgacctccatagaagacaccgggaccgatccagcctccgcggccgggaacggtgc
attggaacgcggattcccgtgccaagagtgacgtaagtacgcctatagagtctataggcccacccccttggcttc
ttatgcatgctatactgtttttggcttgggtctatacaccccgcttcctcatgttataggtgatggtatagctta
gcctataggtgtgggttattgaccattattgaccactccctattggtgacgatacttccattactaatccataac
atggctctttgccacaactctctttattggctatatgccaatacactgtccttcagagactgacacggactctgtat
ttttacaggatggggtctcatttattattacaaattcacatatcacaaccaccgtccccagtgcccgcagttttt
attaaacataacgtgggatctccacgcgaatctcgggtacgtgttccggacatgggctcttctccggtagcggcgga
gcttctacatccgagccctgctcccatgcctccagcgactcatggtcgctcggcagctccttgctcctaacagtgga
ggccagacttaggcacagcacgatgcccaccaccaccagtgtgccgcacaaggccgtggcggtagggtatgtgtctg
aaaatgagctcggggagcgggcttgcaccgctgacgcatttggaagacttaaggcagcggcagaagaagatgcaggc
agctgagttgttgtgttctgataagagtcagaggtaactcccgttgcggtgctgttaacggtggagggcagtgtagt
ctgagcagtactcgttgctgccgcgcgcgccaccagacataatagctgacagactaacagactgttcctttccatgg
gtcttttctcacgtcaccgtcgtcgaccagagctgagatcctacaggagtccagggctggagagaaaacctctgcga
ggaaagggaaggagcaagccgtgaatttaagggacgctgtgaagcaatcatggatgcaatgaagagaggg ctctgct
gtgtgctgctgctgtgtggagcagtcttcgtttcgcccagcggtaccggatccacccttGCTTATGTGGAAATAGGA
TATTCTCTGAGAAATATTACATTCGATGGATTGGATACAGATGACTACAATCCAAAGTTCAACATTCCAACGGGTTT
GGCAGTTGATCCCGAAGGATATAGGCTCTTCATAGCCATCCCAAGGAGAAAGCCAAAGGTTCCCTACACTGTGGCTG
AACTGAATATGGTCATGAATCCCGGATTTCCCGTCGAGAGAGCTCCGAGCTTTGAGAAATTCAAAAAATTCAATGGC
GAGGGCAAAAAGGATCTTGTTAATGTGTATCAGCCAGTCATTGATGATTGTCGTCGTCTTTGGGTGCTTGACATTGG
GAAGGTGGAATACACCGGTGGTGATGCTGATCAATATCCCAAAGGAAAGCCTACCCTAATTGCCTACGACCTCAAGA
AGGATCATACTCCGGAAATTCATCGATTTGAAATTCCAGACGATCTCTATAGCTCACAAGTTGAATTTGGTGGATTT
GCCGTTGATGTTGTTAACACGAAAGGAGACTGTACGGAGTCATTTGTCTACCTGACCAATTTCAAGGATAACTCTCT
AATTGTCTACGATGAGACACAAAAGAAAGCTTGGAAATTTACAGATAAAACATTTGAAGCTGATAAGGAATCCACGT
TCTCCTACTCGGGAGAGGAACAAATGAAGTACAAAGTTGGTCTTTTTGGGATAGCTCTGGGTGATAGGGATGAAATG
GGGCATCGTCCTGCCTACTATATCGCTGGGAGTAGCACCAAAGTCTACAGTGTTAACACTAAAGAACTCAAAACAGA
GAATGGTCAGTTAAATCCTCAGCTTCACGGTGATCGTGGAAAGTACACGGATGCAATTGCCCTAGCCCACGATCCTG
AGCATAAAGTCCTCTACTTTGCTGAATCCGACAGCAGGCAGGTGTCCTGTTGGAATGTAGATATGGAGCTAAAACCA
GACAATACGGATGTGATCTTCTCTAGTCCCGTTTTACTTTTGGAACGGATATTTTGGTTGATAGCAAGGGAATGCT
GTGGATAATGGCTAATGGACATCCACCAGTAGAGGATCAAGAGAAGATTTGGAAGATGAGATTCGTAAACCGGAAGA
TCAGTATTATGAAAGTGGATACGGAACGTGTATTCAAATATTCACGCTGCAATCCAAATTATAAGCCCCGAAAGAA
ATTGAAGTTTGAaagggatccagatctgctgtgccttctagttgccagccatctgttgtttgccctccccgtgcc
ttccttgaccctggaaggtgccactcccactgtcctttcctaataaaatgaggaaattgcatcgcattgtctgagta
ggtgtcattctattctgggggtggggtgggcagcacgacaaggggaggattgggaagacaatagcaggcatgct
ggggatgcggtgggctctatgggtacccagtgctgaagaattgacccggttcctcctgggccagaaagaagcaggc
acatcccttctctgtgacacaccctgtccacgcccctggttcttagttccagccccactcataggacactcatagc
tcaggagggctccgccttcaatcccacccgctaaagtacttggagcggtctctccctccctcatcagcccaccaaac
caaacctagcctccaagagtgggaagaaattaaagcaagataggctattaagtgcagagggagagaaaatgcctcca
acatgtgaggaagtaatgagagaaatcatagaatttcttccgcttcctcgctcactgactcgctgcgctcggtcgtt
cggctgcggcgagcggtatcagctcactcaaaggcggtaatacggttatccacagaatcaggggataacgcaggaaa
gaacatgtgagcaaaaggccagcaaaaggccaggaaccgtaaaaaggccgcgttgctggcgttttccataggctcc
gcccccctgacgagcatcacaaaaatcgacgctcaagtcagaggtggcgaaacccgacaggactataaagataccag
gcgtttccccctggaagctccctcgtgcgctctcctgttccgaccctgccgcttaccggatacctgtccgcctttct

FIGURE 11

```
cccttcgggaagcgtggcgctttctcaatgctcacgctgtaggtatctcagttcggtgtaggtcgttcgctccaagc
tgggctgtgtgcacgaaccccccgttcagcccgaccgctgcgccttatccggtaactatcgtcttgagtccaacccg
gtaagacacgacttatcgccactggcagcagccactggtaacaggattagcagagcgaggtatgtaggcggtgctac
agagttcttgaagtggtggcctaactacggctacactagaaggacagtatttggtatctgcgctctgctgaagccag
ttaccttcggaaaaagagttggtagctcttgatccggcaaacaaaccacgctggtagcggtggttttttttgtttgc
aagcagcagattacgcgcagaaaaaaaggatctcaagaagatcctttgatcttttctacggggtctgacgctcagtg
gaacgaaaactcacgttaagggattttggtcatgagattatcaaaaaggatcttcacctagatccttttaaattaaa
aatgaagttttaaatcaatctaaagtatatatgagtaaacttggtctgacagttaccaatgcttaatcagtgaggca
cctatctcagcgatctgtctatttcgttcatccatagttgcctgactccggggggggggggcgctgaggtctgcctc
gtgaagaaggtgttgctgactcataccaggcctgaatcgccccatcatccagccagaaagtgagggagccacggttg
atgagagctttgttgtaggtggaccagttggtgattttgaacttttgctttgccacggaacggtctgcgttgtcggg
aagatgcgtgatctgatccttcaactcagcaaaagttcgatttattcaacaaagccgccgtcccgtcaagtcagcgt
aatgctctgccagtgttacaaccaattaaccaattctgattagaaaaactcatcgagcatcaaatgaaactgcaatt
tattcatatcaggattatcaataccatattttgaaaaagccgtttctgtaatgaaggagaaaactcaccgaggcag
ttccataggatggcaagatcctggtatcggtctgcgattccgactcgtccaacatcaatacaacctattaatttccc
ctcgtcaaaaataaggttatcaagtgagaaatcaccatgagtgacgactgaatccggtgagaatggcaaaagcttat
gcatttctttccagacttgttcaacaggccagccattacgctcgtcatcaaaatcactcgcatcaaccaaaccgtta
ttcattcgtgattgcgcctgagcgagacgaaatacgcgatcgctgttaaaaggacaattacaaacaggaatcgaatg
caaccggcgcaggaacactgccagcgcatcaacaatattttcacctgaatcaggatattcttctaatacctggaatg
ctgtttccgggatcgcagtggtgagtaaccatgcatcatcaggagtacggataaaatgcttgatggtcggaaga
ggcataaattccgtcagccagtttagtctgaccatctcatctgtaacatcattggcaacgctacctttgccatgttt
cagaaacaactctggcgcatcgggcttcccatacaatcgatagattgtcgcacctgattgcccgacattatcgcgag
cccatttataccatataaatcagcatccatgttggaatttaatcgcggcctcgagcaagacgtttcccgttgaata
tggctcataacaccccttgtattactgtttatgtaagcagacagttttattgttcatgatgatatattttatcttg
tgcaatgtaacatcagagattttgagacacaacgtggctttcccccccccccattattgaagcatttatcagggtt
attgtctcatgagcggatacatatttgaatgtatttagaaaaataaacaatagggggttccgcgcacatttccccga
aaagtgccacctgacgtctaagaaaccattattatcatgacattaacctataaaaataggcgtatcacgaggccctt
tcgtctcgcgcgtttcggtgatgacggtgaaaacctctgacacatgcagctcccggagacggtcacagcttgtctgt
aagcggatgccgggagcagacaagcccgtcagggcgcgtcagcgggtgttggcgggtgtcggggctggcttaactat
gcggcatcagagcagattgtactgagagtgcaccatatgcggtgtgaaataccgcacagatgcgtaaggagaaaata
ccgcatcaga
```

FIGURE 13

( pNBO003: SEQ ID NO:20)

ttggctattggccattgcatacgttgtatccatatcataatatgtacatttatattggctcatgtccaacattaccg
ccatgttgacattgattattgactagttattaatagtaatcaattacggggtcattagttcatagcccatatatgga
gttccgcgttacataacttacggtaaatggcccgcctggctgaccgcccaacgaccccgcccattgacgtcaataa
tgacgtatgttcccatagtaacgccaataggggactttccattgacgtcaatgggtggagtatttacggtaaactgcc
cacttggcagtacatcaagtgtatcatatgccaagtacgccccctattgacgtcaatgacggtaaatggcccgcctg
gcattatgcccagtacatgaccttatgggactttcctacttggcagtacatctacgtattagtcatcgctattacca
tggtgatgcggttttggcagtacatcaatgggcgtggatagcggtttgactcacggggatttccaagtctccacccc
attgacgtcaatgggagtttgttttggcaccaaaatcaacgggactttccaaaatgtcgtaacaactccgccccatt
gacgcaaatgggcggtaggcgtgtacggtgggaggtctatataagcagagctcgtttagtgaaccgtcagatcgcct
ggagacgccatccacgctgttttgacctccatagaagacaccgggaccgatccagcctccgcggccgggaacggtgc
attggaacgcggattccccgtgccaagagtgacgtaagtaccgcctatagagtctataggcccacccccttggcttc
ttatgcatgctatactgttttggcttggggtctatacaccccgcttcctcatgttataggtgatggtatagctta
gcctataggtgtgggttattgaccattattgaccactcccctattggtgacgatactttccattactaatccataac
atggctctttgccacaactctctttattggctatatgccaatacactgtccttcagagactgacacggactctgtat
ttttacaggatggggtctcatttatttattacaaattcacatatacaacaccaccgtccccagtgcccgcagttttt
attaaacataacgtgggatctccacgcgaatctcgggtacgtgttccggacatgggctcttctccggtagcggcgga
gcttctacatccgagccctgctcccatgcctccagcgactcatggtcgctcggcagctccttgctcctaacagtgga
ggccagacttaggcacagcacgatgcccaccaccaccagtgtgccgcacaaggccgtggcggtagggtatgtgtctg
aaaatgagctcggggagcgggcttgcaccgctgacgcatttggaagacttaaggcagcggcagaagaagatgcaggc
agctgagttgttgtgttctgataagagtcagaggtaactcccgttgcggtgctgttaacggtggagggcagtgtagt
ctgagcagtactcgttgctgccgcgcgcgccaccagacataatagctgacagactaacagactgttccttccatgg
gtcttttctcacgtcaccgtcgtcgaccagagctgagatcctacaggagtccagggctggagagaaaacctctgcga
ggaaagggaaggagcaagccgtgaatttaagggacgctgtgaagcaat<u>atggatgcaatgaagagagggctctgct</u>
<u>gtgtgctgctgctgtgtggagcagtcttcgtttcgcccagcggtaccggatccacccttGATGGTGATGAATATTTC</u>
ATTGGAAAATACAAAGAAAAAGATGAGACACTGTTTTTTGCAAGCTACGGCCTAAAGAGGGATCCTTGCCAGATTGT
CTTAGGCTACAAATGCTCAAACAATCAAACCCACTTTGTGCTTAATTTTAAAACCAATAAGAAATCCTGCATATCAG
CAATTAAGCTGACTTCTTACCCAAAAATCAATCAAAACTCGGATTTAACTAGAAATCTCTACTGCCAAACTGGAGGA
ATAGGAACAGATAACTGCAAACTTGTCTTCAAGAAACGTAAAAGACAAATAGCAGCTAATATTGAAATCTACGGCAT
TCCAGCGAAGAAATGTTCCTTCAAGGATCGTTACATTGGAGCTGATCCACTCCACGTCGATTCCTATGGGCTTTCGT
ATCAGTTTGATCAGGAACATGGATGGAATTTGGAACGAAATAACATTTTCAAAGACACAAGATTTTCCACAGAAGTT
TTCTACCACAAAAATGGTTTATTTAACACCCAAATAACTTATTTGGCTGAAGAAGATTCCTTCTCTGAAGCTCGAGA
GATTACTGCGAAGGATATTAAGAAGAAGTTTTCAATTATTTTGCCCAATGAAGAGTATAAGAGGATTAGTTTCTTGG
ACGTTTATTGGTTCCAGGAGACTATGCGAAAAAAGCCTAAATATCCCTACATTCACTACAATGGAGAATGCAGCAAT
GAGAATAAAACTTGTGAACTTGTCTTTGACACCGATGAACTAATGACCTACGCCCTTGTTAAAGTCTTTACTAATCC
TGAGAGTGATGGATCTAGGCTCAAAGAAGAGGATTTGGGAAGAGGATAAaagggatccagatctgctgtgccttcta
gttgccagccatctgttgtttgccctcccccgtgccttccttgaccctggaaggtgccactcccactgtcctttcc
taataaaatgaggaaattgcatcgcattgtctgagtaggtgtcattctattctgggggtggggtggggcagcacag
caaggggggaggattgggaagacaatagcaggcatgctgggatgcggtgggctctatgggtacccaggtgctgaaga
attgacccggttcctcctgggccagaaagaagcaggcacatcccctctctgtgacacccctgtccacgccctgg
ttcttagttccagccccactcataggacactcatagctcaggagggctccgccttcaatccccaccgctaaagtact
tggagcggtctctccctccctcatcagcccaccaaaccaaacctagcctccaagagtgggaagaaattaaagcaaga
taggctattaagtgcagagggagagaaaatgcctccaacatgtgaggaagtaatgagagaaatcatagaatttcttc
cgcttcctcgctcactgactcgctgcgctcggtcgttcggctgcggcgagcggtatcagctcactcaaaggcggtaa
tacggttatccacagaatcaggggataacgcaggaaagaacatgtgagcaaaaggccagcaaaaggccaggaaccgt
aaaaaggccgcgttgctggcgtttttccataggctccgcccccctgacgagcatcacaaaaatcgacgctcaagtca
gaggtggcgaaacccgacaggactataaagataccaggcgtttccccctggaagctccctcgtgcgctctcctgttc
cgaccctgccgcttaccggatacctgtccgcctttctcccttcgggaagcgtggcgctttctcaatgctcacgctgt
aggtatctcagttcggtgtaggtcgttcgctccaagctgggctgtgtgcacgaaccccccgttcagcccgaccgctg
cgccttatccggtaactatcgtcttgagtccaacccggtaagacacgacttatcgccactggcagcagccactggta
acaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaa

FIGURE 13 acaaaccaccgctggtagcggtggttttttttgtttgcaagcagcagattacgcgcagaaaaaaaggatctcaagaag
atcctttgatcttttctacggggtctgacgctcagtggaacgaaaactcacgttaagggattttggtcatgagatta
tcaaaaaggatcttcacctagatccttttaaattaaaaatgaagttttaaatcaatctaaagtatatatgagtaaac
ttggtctgacagttaccaatgcttaatcagtgaggcacctatctcagcgatctgtctatttcgttcatccatagttg
cctgactccggggggggggggcgctgaggtctgcctcgtgaagaaggtgttgctgactcataccaggcctgaatcgc
cccatcatccagccagaaagtgagggagccacggttgatgagagctttgttgtaggtggaccagttggtgattttga
actttttgctttgccacggaacggtctgcgttgtcgggaagatgcgtgatctgatccttcaactcagcaaaagttcga
tttattcaacaaagccgccgtcccgtcaagtcagcgtaatgctctgccagtgttacaaccaattaaccaattctgat
tagaaaaactcatcgagcatcaaatgaaactgcaatttattcatatcaggattatcaataccatatttttgaaaaag
ccgtttctgtaatgaaggagaaaactcaccgaggcagttccataggatggcaagatcctggtatcggtctgcgattc
cgactcgtccaacatcaatacaacctattaatttccctcgtcaaaaataaggttatcaagtgagaaatcaccatga
gtgacgactgaatccggtgagaatggcaaaagcttatgcatttctttccagacttgttcaacaggccagccattacg
ctcgtcatcaaaatcactcgcatcaaccaaaccgttattcattcgtgattgcgcctgagcgagacgaaatacgcgat
cgctgttaaaaggacaattacaaacaggaatcgaatgcaaccggcgcaggaacactgccagcgcatcaacaatattt
tcacctgaatcaggatattcttctaatacctggaatgctgtttcccggggatcgcagtggtgagtaaccatgcatc
atcaggagtacggataaaatgcttgatggtcggaagaggcataaaattccgtcagccagtttagtctgaccatctcat
ctgtaacatcattggcaacgctacctttgccatgtttcagaaacaactctggcgcatcgggcttcccatacaatcga
tagattgtcgcacctgattgcccgacattatcgcgagcccatttatacccatataaatcagcatccatgttggaatt
taatcgcggcctcgagcaagacgtttcccgttgaatatggctcataacacccttgtattactgtttatgtaagcag
acagttttattgttcatgatgatatattttatcttgtgcaatgtaacatcagagattttgagacacaacgtggctt
tccccccccccccattattgaagcatttatcagggttattgtctcatgagcggatacatatttgaatgtatttagaa
aaataaacaataggggttccgcgcacatttccccgaaaagtgccacctgacgtctaagaaaccattattatcatga
cattaacctataaaaataggcgtatcacgaggccctttcgtctcgcgcgtttcggtgatgacggtgaaaacctctga
cacatgcagctcccggagacggtcacagcttgtctgtaagcggatgccgggagcagacaagcccgtcagggcgcgtc
agcgggtgttggcgggtgtcggggctggcttaactatgcggcatcagagcagattgtactgagagtgcaccatatgc
ggtgtgaaataccgcacagatgcgtaaggagaaaataccgcatcaga

FIGURE 15

Unprocessed protein LJL143 (SEQ ID NO: 1)

MNSINFLSIVGLISFGFIVAVKCDGDEYFIGKYKEKDETLFFASYGLKRDPCQIVLGYKCSNNQTHFVLNFKTNKKS
CISAIKLTSYPKINQNSDLTKNLYCQTGGIGTDNCKLVFKKRKRQIAANIEIYGIPAKKCSFKDRYIGADPLHVDSY
GLPYQFDQEHGWNVERYNIFKDTRFSTEVFYHKNGLFNTQITYLAEEDSFSEAREITAKDIKKKFSIILPNEEYKRI
SFLDVYWFQETMRKKPKYPYIHYNGECSNENKTCELVFDTDELMTYALVKVFTNPESDGSRLKEEDLGRG

Mature protein LJL143 (SEQ ID NO: 3)

DGDEYFIGKYKEKDETLFFASYGLKRDPCQIVLGYKCSNNQTHFVLNFKTNKKSCISAIKLTSYPKINQNSDLTKNL
YCQTGGIGTDNCKLVFKKRKRQIAANIEIYGIPAKKCSFKDRYIGADPLHVDSYGLPYQFDQEHGWNVERYNIFKDT
RFSTEVFYHKNGLFNTQITYLAEEDSFSEAREITAKDIKKKFSIILPNEEYKRISFLDVYWFQETMRKKPKYPYIHY
NGECSNENKTCELVFDTDELMTYALVKVFTNPESDGSRLKEEDLGRG

Unprocessed protein LJM17 (SEQ ID NO: 5)

MRFFFVFLAIVLFQGIHGAYVEIGYSLRNITFDGLDTDDYNPKFNIPTGLAVDPEGYRLFIAIPRRKPKVPYTVAEL
NMVMNPGFPVERAPSFEKFKKFNGEGKKDLVNVYQPVIDDCRRLWVLDIGKVEYTGGDADQYPKGKPTLIAYDLKKD
HTPEIHRFEIPDDLYSSQVEFGGFAVDVVNTKGDCTESFVYLTNFKDNSLIVYDETQKKAWKFTDKTFEADKESTFS
YSGEEQMKYKVGLFGIALGDRDEMGHRPACYIAGSSTKVYSVNTKELKTENGQLNPQLHGDRGKYTDAIALAYDPEH
KVLYFAESDSRQVSCWNVNMELKPDNTDVIFSSARFTFGTDILVDSKGMLWIMANGHPPVEDQEKIWKMRFVNRKIR
IMKVDTERVFKYSRCNPNYKPPKEIEV

Mature protein LJM17 (SEQ ID NO: 7)

AYVEIGYSLRNITFDGLDTDDYNPKFNIPTGLAVDPEGYRLFIAIPRRKPKVPYTVAELNMVMNPGFPVERAPSFEK
FKKFNGEGKKDLVNVYQPVIDDCRRLWVLDIGKVEYTGGDADQYPKGKPTLIAYDLKKDHTPEIHRFEIPDDLYSSQ
VEFGGFAVDVVNTKGDCTESFVYLTNFKDNSLIVYDETQKKAWKFTDKTFEADKESTFSYSGEEQMKYKVGLFGIAL
GDRDEMGHRPACYIAGSSTKVYSVNTKELKTENCQLNPQLHGDRGKYTDAIALAYDPEHKVLYFAESDSRQVSCWNV
NMELKPDNTDVIFSSARFTFGTDILVDSKGMLWIMANGHPPVEDQEKIWKMRFVNRKIRIMKVDTERVFKYSRCNPN
YKPPKEIEV

Unprocessed protein LJL143 (SEQ ID NO: 11)

MNSINFLSIVGLISFGFIVAVKCDGDEYFIGKYKEKDETLFFASYGLKRDPCQIVLGYKCSNNQTHFVLNFKTNKKS
CISAIKLTSYPKINQNSDLTRNLYCQTGGIGTDNCKLVFKKRKRQIAANIEIYGIPAKKCSFKDRYIGADPLHVDSY
GLSYQFDQEHGWNLERNNIFKDTRFSTEVFYHKNGLFNTQITYLAEEDSFSEAREITAKDIKKKFSIILPNEEYKRI
SFLDVYWFQETMRKKPKYPYIHYNGECSNENKTCELVFDTDELMTYALVKVFTNPESDGSRLKEEDLGRG

FIGURE 15

Mature protein LJL143 (SEQ ID NO: 13)

DGDEYFIGKYKEKDETLFFASYGLKRDPCQIVLGYKCSNNQTHFVLNFKTNKKSCISAIKLTSYPKINQNSDLTRNL
YCQTGGIGTDNCKLVFKKRKRQIAANIEIYGIPAKKCSFKDRYIGADPLHVDSYGLSYQFDQEHGWNLERNNIFKDT
RFSTEVFYHKNGLFNTQITYLAEEDSFSEAREITAKDIKKKFSIILPNEEYKRISFLDVYWFQETMRKKPKYPYIHY
NGECSNENKTCELVFDTDELMTYALVKVFTNPESDGSRLKEEDLGRG

Unprocessed protein LJM17 (SEQ ID NO: 15)

MRFFFVFLAIVLFQGIHGAYVEIGYSLRNITFDGLDTDDYNPKFNIPTGLAVDPEGYRLFIAIPRRKPKVPYTVAEL
NMVMNPGFPVERAPSFEKFKKFNGEGKKDLVNVYQPVIDDCRRLWVLDIGKVEYTGGDADQYPKGKPTLIAYDLKKD
HTPEIHRFEIPDDLYSSQVEFGGFAVDVVNTKGDCTESFVYLTNFKDNSLIVYDETQKKAWKFTDKTFEADKESTFS
YSGEEQMKYKVGLFGIALGDRDEMGHRPAYYIAGSSTKVYSVNTKELKTENGQLNPQLHGDRGKYTDAIALAHDPEH
KVLYFAESDSRQVSCWNVDMELKPDNTDVIFSSARFTFGTDILVDSKGMLWIMANGHPPVEDQEKIWKMRFVNRKIS
IMKVDTERVFKYSRCNPNYKPPKEIEV

Mature protein LJM17 (SEQ ID NO: 17)

AYVEIGYSLRNITFDGLDTDDYNPKFNIPTGLAVDPEGYRLFIAIPRRKPKVPYTVAELNMVMNPGFPVERAPSFEK
FKKFNGEGKKDLVNVYQPVIDDCRRLWVLDIGKVEYTGGDADQYPKGKPTLIAYDLKKDHTPEIHRFEIPDDLYSSQ
VEFGGFAVDVVNTKGDCTESFVYLTNFKDNSLIVYDETQKKAWKFTDKTFEADKESTFSYSGEEQMKYKVGLFGIAL
GDRDEMGHRPAYYIAGSSTKVYSVNTKELKTENGQLNPQLHGDRGKYTDAIALAHDPEHKVLYFAESDSRQVSCWNV
DMELKPDNTDVIFSSARFTFGTDILVDSKGMLWIMANGHPPVEDQEKIWKMRFVNRKISIMKVDTERVFKYSRCPN
YKPPKEIEV

FIGURE 16

Polynucleotide encoding unprocessed protein LJL143 (SEQ ID NO: 2)

ATGAATTCGATTAATTTCCTATCAATAGTTGGTTTAATCAGTTTTGGATTCATTGTTGCAGTAAAGTGTGATGGTGAT
GAATATTTCATTGGAAAATACAAAGAAAAAGATGAGACACTGTTTTTTGCAAGCTACGGCCTAAAGAGGGATCCTTGC
CAAATTGTCTTAGGCTACAAATGCTCAAACAATCAAACCCACTTTGTGCTTAATTTTAAAACCAATAAGAAATCCTGC
ATATCAGCAATTAAGCTGACTTCTTACCCAAAAATCAATCAAAACTCGGATTTAACTAAAAATCTCTACTGCCAAACT
GGAGGAATAGGAACAGATAACTGCAAACTTGTCTTCAAGAAACGTAAAAGACAAATAGCAGCTAATATTGAAATCTAC
GGCATTCCAGCGAAGAAATGTTCCTTCAAGGATCGTTACATTGGAGCTGATCCACTCCACGTCGATTCCTATGGGCTT
CCGTATCAGTTTGATCAGGAACATGGATGGAATGTGGAACGATATAACATTTTCAAAGACACAAGATTTTCCACAGAA
GTTTTCTACCACAAAAATGGTTTATTTAACACCCAAATAACTTATTTGGCTGAAGAAGATTCCTTCTCTGAAGCTCGA
GAGATTACTGCGAAGGATATTAAGAAGAAGTTTTCAATTATTTTGCCCAATGAAGAGTATAAGAGGATTAGTTTCTTG
GACGTTTATTGGTTCCAGGAGACTATGCGAAAAAAGCCTAAATATCCCTACATTCACTACAATGGACAATGCAGCAAT
GAGAATAAAACTTGTGAACTTGTCTTTGACACCGATGAACTAATGACCTACGCCCTTGTTAAAGTCTTTACTAATCCT
GAGAGTGATGGATCTAGGCTCAAAGAAGAGGATTTGGGAAGAGGATAA

Polynucleotide encoding mature protein LJL143 (SEQ ID NO: 4)

GATGGTGATGAATATTTCATTGGAAAATACAAAGAAAAAGATGAGACACTGTTTTTTGCAAGCTACGGCCTAAAGAG
GGATCCTTGCCAAATTGTCTTAGGCTACAAATGCTCAAACAATCAAACCCACTTTGTGCTTAATTTTAAAACCAATA
AGAAATCCTGCATATCAGCAATTAAGCTGACTTCTTACCCAAAAATCAATCAAAACTCGGATTTAACTAAAAATCTC
TACTGCCAAACTGGAGGAATAGGAACAGATAACTGCAAACTTGTCTTCAAGAAACGTAAAAGACAAATAGCAGCTAA
TATTGAAATCTACGGCATTCCAGCGAAGAAATGTTCCTTCAAGGATCGTTACATTGGAGCTGATCCACTCCACGTCG
ATTCCTATGGGCTTCCGTATCAGTTTGATCAGGAACATGGATGGAATGTGGAACGATATAACATTTTCAAAGACACA
AGATTTTCCACAGAAGTTTTCTACCACAAAAATGGTTTATTTAACACCCAAATAACTTATTTGGCTGAAGAAGATTC
CTTCTCTGAAGCTCGAGAGATTACTGCGAAGGATATTAAGAAGAAGTTTTCAATTATTTTGCCCAATGAAGAGTATA
AGAGGATTAGTTTCTTGGACGTTTATTGGTTCCAGGAGACTATGCGAAAAAAGCCTAAATATCCCTACATTCACTAC
AATGGAGAATGCAGCAATGAGAATAAAACTTGTGAACTTGTCTTTGACACCGATGAACTAATGACCTACGCCCTTGT
TAAAGTCTTTACTAATCCTGAGAGTGATGGATCTAGGCTCAAAGAAGAGGATTTGGGAAGAGGATAA

FIGURE 16

Polynucleotide encoding unprocessed protein LJM17 (SEQ ID NO: 6)

ATGAGGTTCTTCTTTGTTTTCCTTGCCATCGTCCTTTTTCAAGGGATCCACGGAGCTTATGTGGAAATAGGATATTC
TCTGAGAAATATTACATTCGATGGATTGGATACAGATGACTACAATCCAAAGTTCAACATTCCAACGGGTTTGGCAG
TTGATCCCGAAGGATATAGGCTCTTCATAGCCATCCCAAGGAGAAAGCCAAAGGTTCCCTACACTGTGGCTGAACTG
AATATGGTCATGAATCCCGGATTTCCCGTCGAGAGAGCTCCGAGCTTTGAGAAATTCAAAAAATTCAATGGCGAGGG
CAAAAAGGATCTTGTTAATGTGTATCAGCCAGTCATTGATGATTGTCGTCGTCTTTGGGTGCTTGACATTGGGAAGG
TGGAATACACCGGTGGTGATGCTGATCAATATCCCAAAGGAAAGCCTACCCTAATTGCCTACGACCTCAAGAAGGAT
CATACTCCGGAAATTCATCGATTTGAAATTCCAGACGATCTCTATAGCTCACAAGTTGAATTTGGTGGATTTGCCGT
TGATGTTGTTAACACGAAAGGAGACTGTACGGAGTCATTTGTCTACCTGACCAATTTCAAGGATAACTCTCTAATTG
TCTACGATGAGACACAAAAGAAAGCTTGGAAATTCACAGATAAAACATTTGAAGCTGATAAGGAATCCACGTTCTCC
TACTCGGGAGAGGAACAAATGAAGTACAAAGTCGGTCTTTTTGGGATAGCTCTGGGTGATAGGGATGAAATGGGGCA
TCGTCCTGCCTGCTACATCGCTGGGAGTAGCACCAAAGTCTACAGTGTTAACACTAAAGAACTCAAAACAGAGAATG
GTCAGTTAAATCCTCAGCTTCACGGTGATCGTGGAAAGTACACAGATGCAATTGCCCTAGCCTACGATCCTGAGCAT
AAAGTCCTCTACTTTGCTGAATCCGACAGCAGGCAGGTGTCCTGTTGGAATGTAAATATGGAGCTAAAACCAGACAA
TACGGATGTGATCTTCTCTAGTGCCCGTTTTACTTTTGGAACGGATATTTTGGTTGATAGCAAGGGAATGCTGTGGA
TAATGGCTAATGGACATCCACCAGTAGAGGATCAAGAGAAGATTTGGAAGATGAGATTCGTAAACCGGAAGATCCGT
ATTATGAAAGTGGATACGGAACGTGTTTTCAAATATTCACGCTGCAATCCAAATTATAAGCCCCCAAAGGAAATTGA
AGTTTGA

Polynucleotide encoding mature protein LJM17 (SEQ ID NO: 8)

GCTTATGTGGAAATAGGATATTCTCTGAGAAATATTACATTCGATGGATTGGATACAGATGACTACAATCCAAAGTT
CAACATTCCAACGGGTTTGGCAGTTGATCCCGAAGGATATAGGCTCTTCATAGCCATCCCAAGGAGAAAGCCAAAGG
TTCCCTACACTGTGGCTGAACTGAATATGGTCATGAATCCCGGATTTCCCGTCGAGAGAGCTCCGAGCTTTGAGAAA
TTCAAAAAATTCAATGGCGAGGGCAAAAAGGATCTTGTTAATGTGTATCAGCCAGTCATTGATGATTGTCGTCGTCT
TTGGGTGCTTGACATTGGGAAGGTGGAATACACCGGTGGTGATGCTGATCAATATCCCAAAGGAAAGCCTACCCTAA
TTGCCTACGACCTCAAGAAGGATCATACTCCGGAAATTCATCGATTTGAAATTCCAGACGATCTCTATAGCTCACAA
GTTGAATTTGGTGGATTTGCCGTTGATGTTGTTAACACGAAAGGAGACTGTACGGAGTCATTTGTCTACCTGACCAA
TTTCAAGGATAACTCTCTAATTGTCTACGATGAGACACAAAAGAAAGCTTGGAAATTCACAGATAAAACATTTGAAG
CTGATAAGGAATCCACGTTCTCCTACTCGGGAGAGGAACAAATGAAGTACAAAGTCGGTCTTTTTGGGATAGCTCTG
GGTGATAGGGATGAAATGGGGCATCGTCCTGCCTGCTACATCGCTGGGAGTAGCACCAAAGTCTACAGTGTTAACAC
TAAAGAACTCAAAACAGAGAATGGTCAGTTAAATCCTCAGCTTCACGGTGATCGTGGAAAGTACACAGATGCAATTG
CCCTAGCCTACGATCCTGAGCATAAAGTCCTCTACTTTGCTGAATCCGACAGCAGGCAGGTGTCCTGTTGGAATGTA
AATATGGAGCTAAAACCAGACAATACGGATGTGATCTTCTCTAGTGCCCGTTTTACTTTTGGAACGGATATTTTGGT
TGATAGCAAGGGAATGCTGTGGATAATGGCTAATGGACATCCACCAGTAGAGGATCAAGAGAAGATTTGGAAGATGA
GATTCGTAAACCGGAAGATCCGTATTATGAAAGTGGATACGGAACGTGTTTTCAAATATTCACGCTGCAATCCAAAT
TATAAGCCCCCAAAGGAAATTGAAGTTTGA

FIGURE 16

Polynucleotide encoding unprocessed protein LJL143 (SEQ ID NO: 12)

ATGAATTCGATTAATTTCCTATCAATAGTTGGTTTAATCAGTTTTGGATTCATTGTTGCAGTAAAGTGTGATGGTGA
TGAATATTTCATTGGAAAATACAAAGAAAAAGATGAGACACTGTTTTTTGCAAGCTACGGCCTAAAGAGGGATCCTT
GCCAGATTGTCTTAGGCTACAAATGCTCAAACAATCAAACCCACTTTGTGCTTAATTTTAAAACCAATAAGAAATCC
TGCATATCAGCAATTAAGCTGACTTCTTACCCAAAAATCAATCAAAACTCGGATTTAACTAGAAATCTCTACTGCCA
AACTGGAGGAATAGGAACAGATAACTGCAAACTTGTCTTCAAGAAACGTAAAAGACAAATAGCAGCTAATATTGAAA
TCTACGGCATTCCAGCGAAGAAATGTTCCTTCAAGGATCGTTACATTGGAGCTGATCCACTCCACGTCGATTCCTAT
GGGCTTTCGTATCAGTTTGATCAGGAACATGGATGGAATTTGGAACGAAATAACATTTTCAAAGACACAAGATTTTC
CACAGAAGTTTTCTACCACAAAAATGGTTTATTTAACACCCAAATAACTTATTTGGCTGAAGAAGATTCCTTCTCTG
AAGCTCGAGAGATTACTGCGAAGGATATTAAGAAGAAGTTTTCAATTATTTTGCCCAATGAAGAGTATAAGAGGATT
AGTTTCTTGGACGTTTATTGGTTCCAGGAGACTATGCGAAAAAAGCCTAAATATCCCTACATTCACTACAATGGAGA
ATGCAGCAATGAGAATAAAACTTGTGAACTTGTCTTTGACACCGATGAACTAATGACCTACGCCCTTGTTAAAGTCT
TTACTAATCCTGAGAGTGATGGATCTAGGCTCAAAGAAGAGGATTTGGGAAGAGGATAA

Polynucleotide encoding mature protein LJL143 (SEQ ID NO: 14)

GATGGTGATGAATATTTCATTGGAAAATACAAAGAAAAAGATGAGACACTGTTTTTTGCAAGCTACGGCCTAAAGAG
GGATCCTTGCCAGATTGTCTTAGGCTACAAATGCTCAAACAATCAAACCCACTTTGTGCTTAATTTTAAAACCAATA
AGAAATCCTGCATATCAGCAATTAAGCTGACTTCTTACCCAAAAATCAATCAAAACTCGGATTTAACTAGAAATCTC
TACTGCCAAACTGGAGGAATAGGAACAGATAACTGCAAACTTGTCTTCAAGAAACGTAAAAGACAAATAGCAGCTAA
TATTGAAATCTACGGCATTCCAGCGAAGAAATGTTCCTTCAAGGATCGTTACATTGGAGCTGATCCACTCCACGTCG
ATTCCTATGGGCTTTCGTATCAGTTTGATCAGGAACATGGATGGAATTTGGAACGAAATAACATTTTCAAAGACACA
AGATTTTCCACAGAAGTTTTCTACCACAAAAATGGTTTATTTAACACCCAAATAACTTATTTGGCTGAAGAAGATTC
CTTCTCTGAAGCTCGAGAGATTACTGCGAAGGATATTAAGAAGAAGTTTTCAATTATTTTGCCCAATGAAGAGTATA
AGAGGATTAGTTTCTTGGACGTTTATTGGTTCCAGGAGACTATGCGAAAAAAGCCTAAATATCCCTACATTCACTAC
AATGGAGAATGCAGCAATGAGAATAAAACTTGTGAACTTGTCTTTGACACCGATGAACTAATGACCTACGCCCTTGT
TAAAGTCTTTACTAATCCTGAGAGTGATGGATCTAGGCTCAAAGAAGAGGATTTGGGAAGAGGATAA

FIGURE 16

Polynucleotide encoding unprocessed protein LJM17 (SEQ ID NO: 16)

ATGAGGTTCTTCTTTGTTTTCCTTGCCATCGTCCTTTTTCAAGGGATCCACGGAGCTTATGTGGAAATAGGATATTC
TCTGAGAAATATTACATTCGATGGATTGGATACAGATGACTACAATCCAAAGTTCAACATTCCAACGGGTTTGGCAG
TTGATCCCGAAGGATATAGGCTCTTCATAGCCATCCCAAGGAGAAAGCCAAAGGTTCCCTACACTGTGGCTGAACTG
AATATGGTCATGAATCCCGGATTTCCCGTCGAGAGAGCTCCGAGCTTTGAGAAATTCAAAAAATTCAATGGCGAGGG
CAAAAAGGATCTTGTTAATGTGTATCAGCCAGTCATTGATGATTGTCGTCGTCTTTGGGTGCTTGACATTGGGAAGG
TGGAATACACCGGTGGTGATGCTGATCAATATCCCAAAGGAAAGCCTACCCTAATTGCCTACGACCTCAAGAAGGAT
CATACTCCGGAAATTCATCGATTTGAAATTCCAGACGATCTCTATAGCTCACAAGTTGAATTTGGTGGATTTGCCGT
TGATGTTGTTAACACGAAAGGAGACTGTACGGAGTCATTTGTCTACCTGACCAATTTCAAGGATAACTCTCTAATTG
TCTACGATGAGACACAAAAGAAAGCTTGGAAATTTACAGATAAAACATTTGAAGCTGATAAGGAATCCACGTTCTCC
TACTCGGGAGAGGAACAAATGAAGTACAAAGTTGGTCTTTTTGGGATAGCTCTGGGTGATAGGGATGAAATGGGGCA
TCGTCCTGCCTACTATATCGCTGGGAGTAGCACCAAAGTCTACAGTGTTAACACTAAAGAACTCAAAACAGAGAATG
GTCAGTTAAATCCTCAGCTTCACGGTGATCGTGGAAAGTACACGGATGCAATTGCCCTAGCCCACGATCCTGAGCAT
AAAGTCCTCTACTTTGCTGAATCCGACAGCAGGCAGGTGTCCTGTTGGAATGTAGATATGGAGCTAAAACCAGACAA
TACGGATGTGATCTTCTCTAGTGCCCGTTTTACTTTTGGAACGGATATTTTGGTTGATAGCAAGGGAATGCTGTGGA
TAATGGCTAATGGACATCCACCAGTAGAGGATCAAGAGAAGATTTGGAAGATGAGATTCGTAAACCGGAAGATCAGT
ATTATGAAAGTGGATACGGAACGTGTATTCAAATATTCACGCTGCAATCCAAATTATAAGCCCCCGAAAGAAATTGA
AGTTTGA

Polynucleotide encoding mature protein LJM17 (SEQ ID NO: 18)

GCTTATGTGGAAATAGGATATTCTCTGAGAAATATTACATTCGATGGATTGGATACAGATGACTACAATCCAAAGTT
CAACATTCCAACGGGTTTGGCAGTTGATCCCGAAGGATATAGGCTCTTCATAGCCATCCCAAGGAGAAAGCCAAAGG
TTCCCTACACTGTGGCTGAACTGAATATGGTCATGAATCCCGGATTTCCCGTCGAGAGAGCTCCGAGCTTTGAGAAA
TTCAAAAAATTCAATGGCGAGGGCAAAAAGGATCTTGTTAATGTGTATCAGCCAGTCATTGATGATTGTCGTCGTCT
TTGGGTGCTTGACATTGGGAAGGTGGAATACACCGGTGGTGATGCTGATCAATATCCCAAAGGAAAGCCTACCCTAA
TTGCCTACGACCTCAAGAAGGATCATACTCCGGAAATTCATCGATTTGAAATTCCAGACGATCTCTATAGCTCACAA
GTTGAATTTGGTGGATTTGCCGTTGATGTTGTTAACACGAAAGGAGACTGTACGGAGTCATTTGTCTACCTGACCAA
TTTCAAGGATAACTCTCTAATTGTCTACGATGAGACACAAAAGAAAGCTTGGAAATTTACAGATAAAACATTTGAAG
CTGATAAGGAATCCACGTTCTCCTACTCGGGAGAGGAACAAATGAAGTACAAAGTTGGTCTTTTTGGGATAGCTCTG
GGTGATAGGGATGAAATGGGGCATCGTCCTGCCTACTATATCGCTGGGAGTAGCACCAAAGTCTACAGTGTTAACAC
TAAAGAACTCAAAACAGAGAATGGTCAGTTAAATCCTCAGCTTCACGGTGATCGTGGAAAGTACACGGATGCAATTG
CCCTAGCCCACGATCCTGAGCATAAAGTCCTCTACTTTGCTGAATCCGACAGCAGGCAGGTGTCCTGTTGGAATGTA
GATATGGAGCTAAAACCAGACAATACGGATGTGATCTTCTCTAGTGCCCGTTTTACTTTTGGAACGGATATTTTGGT
TGATAGCAAGGGAATGCTGTGGATAATGGCTAATGGACATCCACCAGTAGAGGATCAAGAGAAGATTTGGAAGATGA
GATTCGTAAACCGGAAGATCAGTATTATGAAAGTGGATACGGAACGTGTATTCAAATATTCACGCTGCAATCCAAAT
TATAAGCCCCCGAAAGAAATTGAAGTTTGA

FIGURE 16

Codon optimzed unprocessed LJM17 DNA sequence (SEQ ID NO :91)
atgcggttcttcttcgtgttcctggccatcgtgctgttccagggcatccacggcgcctacgtggagatcggctacag
cctgcggaacatcaccttcgacggcctggacaccgacgactacaaccccaagttcaacatccccacggcctggccg
tggaccccgagggctaccggctgttcatcgccatccccaggcggaagcccaaggtgccctacaccgtggccgagctg
aacatggtgatgaaccccggcttccccgtggagagggcccccagcttcgagaagttcaagaagtttaacggcgaggg
caagaaagacctggtgaacgtgtaccagcccgtgatcgacgactgcaggcggctgtgggtgctggacatcggcaagg
tggagtacacaggcggcgacgccgaccagtaccccaagggcaagcccaccctgatcgcctacgacctgaagaaggac
cacacccccgagatccaccggttcgagatccccgacgacctgtacagcagccaggtggagttcggcggctttgccgt
ggacgtggtgaacaccaagggcgactgcaccgagagcttcgtgtacctgaccaacttcaaggacaacagcctgatcg
tgtacgacgagacccagaagaaggcctggaagttcaccgacaagaccttcgaggccgacaagagagcaccttcagc
tacagcggcgaggaacagatgaagtacaaagtgggcctgttcggcatcgccctgggcgaccgggacgagatgggcca
caggcccgcctgctacatcgccggcagcagcaccaaggtgtacagcgtgaataccaaagagctgaaaaccgagaacg
gccagctgaaccccagctgcacggcgaccggggcaagtacaccgacgccattgccctggcctacgaccccgagcac
aaggtgctgtacttcgccgagagcgacagccggcaggtgtcctgctggaacgtgaacatggaactgaagcccgacaa
caccgacgtgatcttcagcagcgcccggttcaccttcggcaccgacatcctggtggacagcaagggcatgctgtgga
tcatggccaacggccaccccccgtggaggaccaggaaaagatctggaagatgcggttcgtgaaccggaagatccgg
atcatgaaggtggacaccgagcgggtgttcaagtacagccggtgcaaccccaactacaagccccccaaagaaatcga
agtgtga

FIGURE 17

Table 1. Global amino acid sequence identity percentage between mature LJL143 and LJM17

|  | SEQ ID NO:3 (LJL143) | SEQ ID NO:7 (LJM17) | SEQ ID NO:13 (LJL143) | SEQ ID NO:17 (LJM17) |
|---|---|---|---|---|
| SEQ ID NO:3 | 100 | 20 | 98 | 20 |
| SEQ ID NO:7 |  | 100 | 20 | 99 |
| SEQ ID NO:13 |  |  | 100 | 20 |
| SEQ ID NO:17 |  |  |  | 100 |

Table 2. Global amino acid sequence identity percentage between unprocessed LJL143 and LJM17

|  | SEQ ID NO:1 (LJL143) | SEQ ID NO:5 (LJM17) | SEQ ID NO:11 (LJL143) | SEQ ID NO:15 (LJM17) |
|---|---|---|---|---|
| SEQ ID NO:1 | 100 | 19 | 98 | 19 |
| SEQ ID NO:5 |  | 100 | 19 | 99 |
| SEQ ID NO:11 |  |  | 100 | 19 |
| SEQ ID NO:15 |  |  |  | 100 |

Table 3. Global nucleic acid sequence identity percentage between polynucleotides encoding mature LJL143 and LJM17

| SEQ ID NO: | 4 (LJL143) | 8 (LJM17) | 14 (LJL143) | 18 (LJM17) | 22 (LJL143) | 91 (LJM17) |
|---|---|---|---|---|---|---|
| 4 | 100 | 36 | 99 | 47 | 74 | 43 |
| 8 |  | 100 | 47 | 99 | 44 | 76 |
| 14 |  |  | 100 | 47 | 78 | 43 |
| 18 |  |  |  | 100 | 44 | 75 |
| 22 |  |  |  |  | 100 | 51 |
| 91 |  |  |  |  |  | 100 |

Table 4. Global nucleic acid sequence identity percentage between polynucleotides encoding unprocessed LJL143 and LJM17

| SEQ ID NO: | 2 (LJL143) | 6 (LJM17) | 12 (LJL143) | 16 (LJM17) | 89 (LJL143) | 90 (LJM17) | 91 (codon optimized LJM17) | 22 (codon optimized LJL143) |
|---|---|---|---|---|---|---|---|---|
| 2 | 100 | 46 | 99 | 46 | 100 | 47 | 43 | 73 |
| 6 |  | 100 | 47 | 99 | 45 | 100 | 76 | 46 |
| 12 |  |  | 100 | 46 | 99 | 48 | 43 | 73 |
| 16 |  |  |  | 100 | 45 | 99 | 76 | 45 |
| 89 |  |  |  |  | 100 | 47 | 43 | 73 |
| 90 |  |  |  |  |  | 100 | 76 | 46 |
| 21 |  |  |  |  |  |  | 100 | 48 |
| 22 |  |  |  |  |  |  |  | 100 |

The percent sequence identity between two nucleic acid or polypeptide sequences is determined using Vector NTI 11.0 (PC) software package (Invitrogen, 1600 Faraday Ave., Carlsbad, CA). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. The percent identity was calculated based on the shorter sequence.

FIGURE 18

| SEQ ID NO | type | name | Corresponding SEQ ID NO in 61/101,345 | Corresponding SEQ ID NO in 61/051,635 |
|---|---|---|---|---|
| 1 | PRT | Unprocessed LJL143 protein | 1 | 15 |
| 2 | DNA | Unprocessed LJL143 DNA | 2 | |
| 3 | PRT | Mature LJL143 protein | 3 | |
| 4 | DNA | Mature LJL143 DNA | 4 | |
| 5 | PRT | Unprocessed LJM17 protein | 5 | 23 |
| 6 | DNA | Unprocessed LJM17 DNA | 6 | |
| 7 | PRT | Mature LJM17 protein | 7 | |
| 8 | DNA | Mature LJM17 DNA | 8 | |
| 9 | DNA | Plasmid pVR2001 LJM17 | 9 | |
| 10 | DNA | Plasmid pVR2001 LJL143 | 10 | |
| 11 | PRT | Unprocessed LJL143 protein | 11 | |
| 12 | DNA | Unprocessed LJL143 DNA | 12 | |
| 13 | PRT | Mature LJL143 protein | 13 | |
| 14 | DNA | Mature LJL143 DNA | 14 | |
| 15 | PRT | Unprocessed LJM17 protein | 15 | |
| 16 | DNA | Unprocessed LJM17 DNA | 16 | |
| 17 | PRT | Mature LJM17 protein | 17 | |
| 18 | DNA | Mature LJM17 DNA | 18 | |
| 19 | DNA | Plasmid pNBO002 | 19 | |
| 20 | DNA | Plasmid pNBO003 | 20 | |
| 21 | DNA | Codon-optimized unprocessed LJM17 DNA (reverse complementary strand) | 21 | |
| 22 | DNA | Codon-optimized unprocessed LJL143 DNA | 22 | |
| 23 | PRT | LJL34 protein | | 1 |
| 24 | DNA | LJL34 DNA | | 2 |
| 25 | PRT | LJL18 protein | | 3 |
| 26 | DNA | LJL18 DNA | | 4 |
| 27 | PRT | LJS193 protein | | 5 |
| 28 | DNA | LJS193 DNA | | 6 |
| 29 | PRT | LJS201 protein | | 7 |
| 30 | DNA | LJS201 DNA | | 8 |
| 31 | PRT | LJL13 protein | | 9 |
| 32 | DNA | LJL13 DNA | | 10 |
| 33 | PRT | LJL23 protein | | 11 |
| 34 | DNA | LJL23 DNA | | 12 |
| 35 | PRT | LJM10 protein | | 13 |
| 36 | DNA | LJM10 DNA | | 14 |
| 37 | PRT | LJS142 protein | | 17 |
| 38 | DNA | LJS142 DNA | | 18 |
| 39 | PRT | LJL17 protein | | 19 |
| 40 | DNA | LJL17 DNA | | 20 |
| 41 | PRT | LJM06 protein | | 21 |
| 42 | DNA | LJM06 DNA | | 22 |
| 43 | PRT | LJL04 protein | | 25 |
| 44 | DNA | LJL04 DNA | | 26 |
| 45 | PRT | LJM114 protein | | 27 |
| 46 | DNA | LJM114 DNA | | 28 |
| 47 | PRT | LJM111 protein | | 29 |
| 48 | DNA | LJM111 DNA | | 30 |
| 49 | PRT | LJM78 protein | | 31 |

Figure 18

| | | | | |
|---|---|---|---|---|
| 50 | DNA | LJM78 DNA | | 32 |
| 51 | PRT | LJS238 protein | | 33 |
| 52 | DNA | LJS238 DNA | | 34 |
| 53 | PRT | LJS169 protein | | 35 |
| 54 | DNA | LJS169 DNA | | 36 |
| 55 | PRT | LJL11 protein | | 37 |
| 56 | DNA | LJL11 DNA | | 38 |
| 57 | PRT | LJL08 protein | | 39 |
| 58 | DNA | LJL08 DNA | | 40 |
| 59 | PRT | LJS105 protein | | 41 |
| 60 | DNA | LJS105 DNA | | 42 |
| 61 | PRT | LJL09 protein | | 43 |
| 62 | DNA | LJL09 DNA | | 44 |
| 63 | PRT | LJL38 protein | | 45 |
| 64 | DNA | LJL38 DNA | | 46 |
| 65 | PRT | LJM04 protein | | 47 |
| 66 | DNA | LJM04 DNA | | 48 |
| 67 | PRT | LJM26 protein | | 49 |
| 68 | DNA | LJM26 DNA | | 50 |
| 69 | PRT | LJS03 protein | | 51 |
| 70 | DNA | LJS03 DNA | | 52 |
| 71 | PRT | LJS192 protein | | 53 |
| 72 | DNA | LJS192 DNA | | 54 |
| 73 | PRT | LJM19 protein | | 55 |
| 74 | DNA | LJM19 DNA | | 56 |
| 75 | PRT | LJL138 protein | | 57 |
| 76 | DNA | LJL138 DNA | | 58 |
| 77 | PRT | LJL15 protein | | 59 |
| 78 | DNA | LJL15 DNA | | 60 |
| 79 | PRT | LJL91 protein | | 61 |
| 80 | DNA | LJL91 DNA | | 62 |
| 81 | PRT | LJM11 protein | | 63 |
| 82 | DNA | LJM11 DNA | | 64 |
| 83 | PRT | LJS138 protein | | 65 |
| 84 | DNA | LJS138 DNA | | 66 |
| 85 | PRT | LJL124 protein | | 67 |
| 86 | DNA | LJL124 DNA | | 68 |
| 87 | PRT | LJL35 protein | | 69 |
| 88 | DNA | LJL35 DNA | | 70 |
| 89 | DNA | LJL143 DNA | | 16 |
| 90 | DNA | LJM17 DNA | | 24 |
| 91 | DNA | Codon-optimized unprocessed LJM17 DNA | | |
| 92 | DNA | vCP2390 | | |
| 93 | DNA | vCP2390 (containing LJM17 in coding direction) | | |
| 94 | DNA | vCP2389 | | |

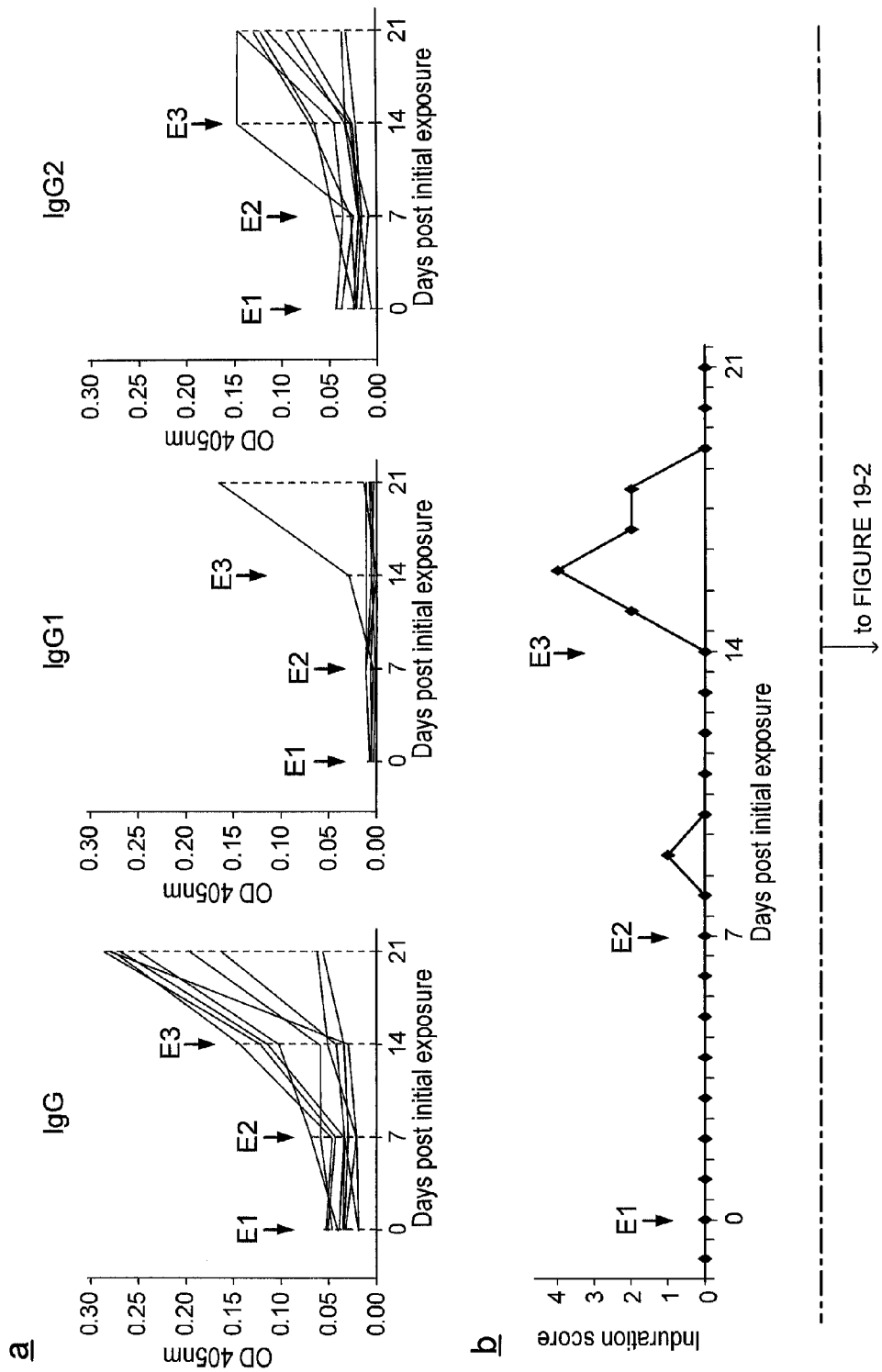

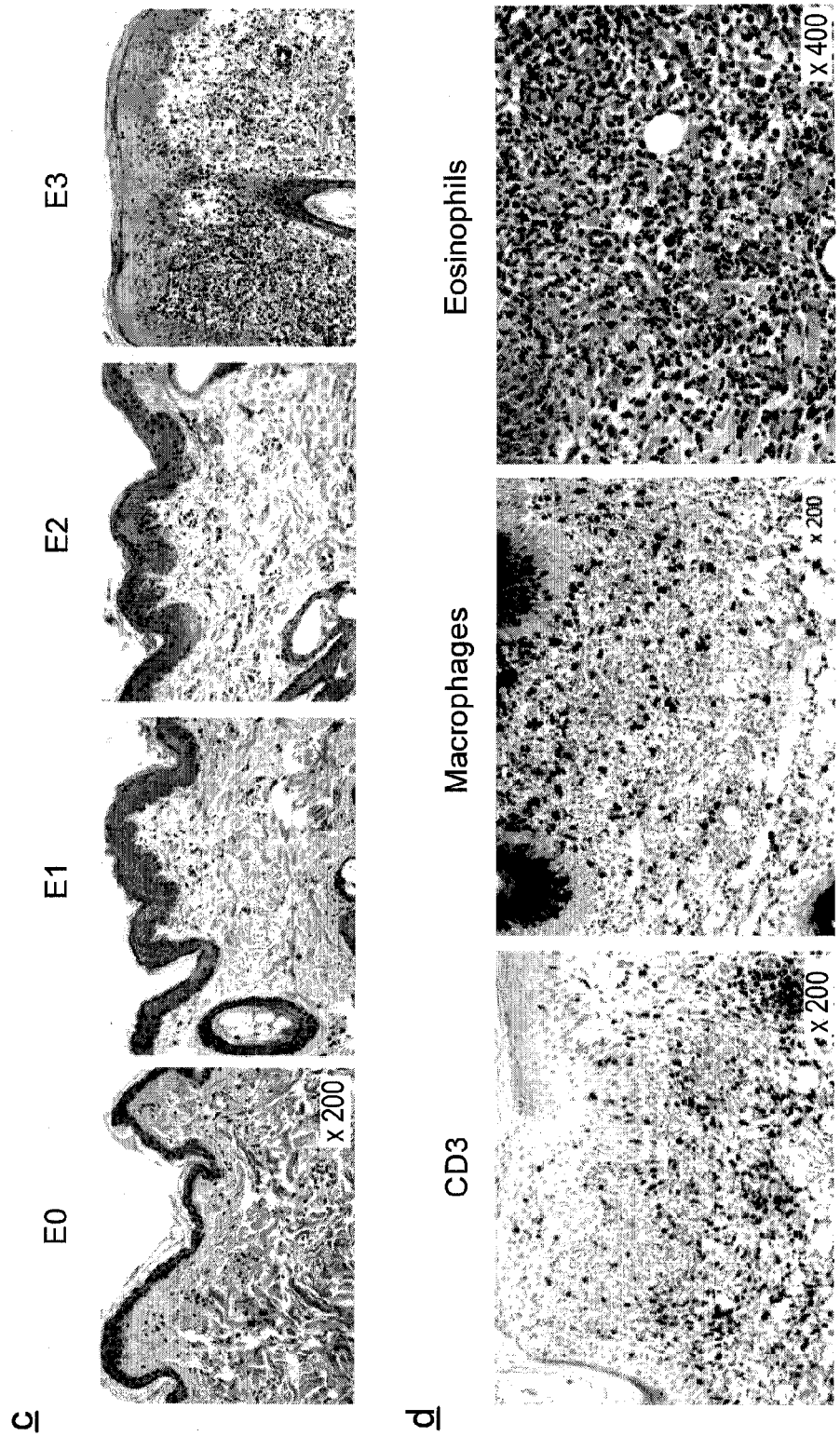

to FIGURE 21-2

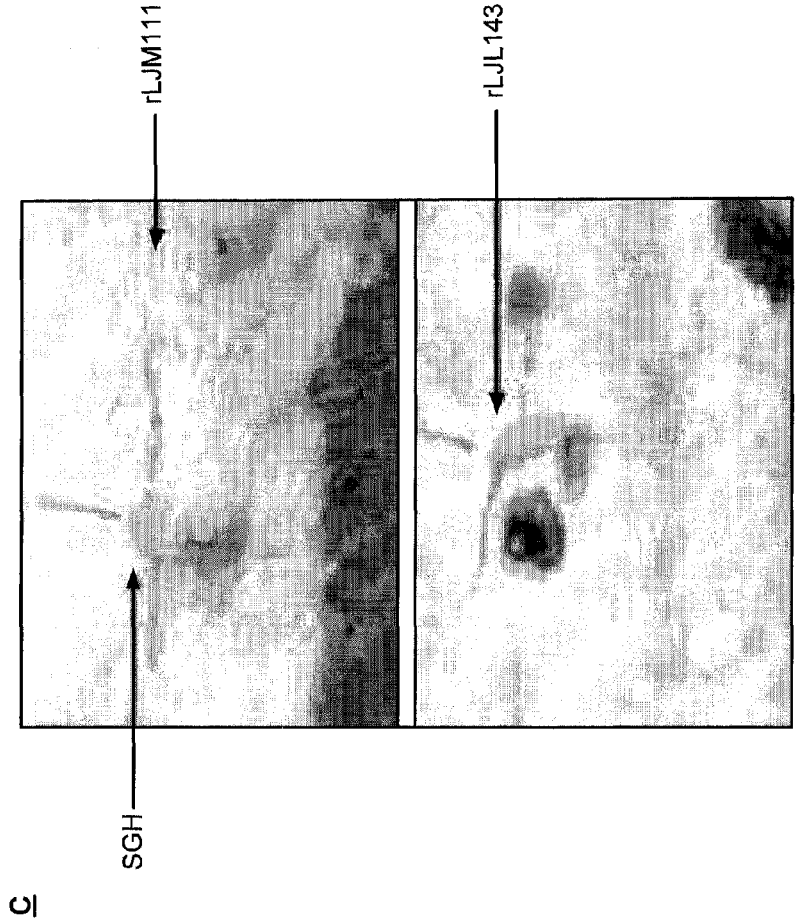

SEQUENCE LISTING

```
<160> NUMBER OF SEQ ID NOS: 94

<210> SEQ ID NO 1
<211> LENGTH: 301
<212> TYPE: PRT
<213> ORGANISM: Lutzomyia longipalpis

<400> SEQUENCE: 1

Met Asn Ser Ile Asn Phe Leu Ser Ile Val Gly Leu Ile Ser Phe Gly
1               5                   10                  15

Phe Ile Val Ala Val Lys Cys Asp Gly Asp Glu Tyr Phe Ile Gly Lys
            20                  25                  30

Tyr Lys Glu Lys Asp Glu Thr Leu Phe Phe Ala Ser Tyr Gly Leu Lys
        35                  40                  45

Arg Asp Pro Cys Gln Ile Val Leu Gly Tyr Lys Cys Ser Asn Asn Gln
```

```
                50                  55                  60
Thr His Phe Val Leu Asn Phe Lys Thr Asn Lys Ser Cys Ile Ser
 65                  70                  75                  80

Ala Ile Lys Leu Thr Ser Tyr Pro Lys Ile Asn Gln Asn Ser Asp Leu
                 85                  90                  95

Thr Lys Asn Leu Tyr Cys Gln Thr Gly Gly Ile Gly Thr Asp Asn Cys
            100                 105                 110

Lys Leu Val Phe Lys Lys Arg Lys Arg Gln Ile Ala Ala Asn Ile Glu
        115                 120                 125

Ile Tyr Gly Ile Pro Ala Lys Lys Cys Ser Phe Lys Asp Arg Tyr Ile
    130                 135                 140

Gly Ala Asp Pro Leu His Val Asp Ser Tyr Gly Leu Pro Tyr Gln Phe
145                 150                 155                 160

Asp Gln Glu His Gly Trp Asn Val Glu Arg Tyr Asn Ile Phe Lys Asp
                165                 170                 175

Thr Arg Phe Ser Thr Glu Val Phe Tyr His Lys Asn Gly Leu Phe Asn
            180                 185                 190

Thr Gln Ile Thr Tyr Leu Ala Glu Glu Asp Ser Phe Ser Glu Ala Arg
        195                 200                 205

Glu Ile Thr Ala Lys Asp Ile Lys Lys Phe Ser Ile Ile Leu Pro
    210                 215                 220

Asn Glu Glu Tyr Lys Arg Ile Ser Phe Leu Asp Val Tyr Trp Phe Gln
225                 230                 235                 240

Glu Thr Met Arg Lys Lys Pro Lys Tyr Pro Tyr Ile His Tyr Asn Gly
                245                 250                 255

Glu Cys Ser Asn Glu Asn Lys Thr Cys Glu Leu Val Phe Asp Thr Asp
            260                 265                 270

Glu Leu Met Thr Tyr Ala Leu Val Lys Val Phe Thr Asn Pro Glu Ser
        275                 280                 285

Asp Gly Ser Arg Leu Lys Glu Glu Asp Leu Gly Arg Gly
    290                 295                 300

<210> SEQ ID NO 2
<211> LENGTH: 906
<212> TYPE: DNA
<213> ORGANISM: Lutzomyia longipalpis

<400> SEQUENCE: 2
atgaattcga ttaatttcct atcaatagtt ggtttaatca gttttggatt cattgttgca      60
gtaaagtgtg atggtgatga atatttcatt ggaaaataca agaaaaaga tgagacactg      120 ttttttgcaa gctacggcct aaagagggat ccttgccaaa ttgtcttagg ctacaaatgc      180
tcaaacaatc aaacccactt tgtgcttaat tttaaaacca taagaaatc ctgcatatca      240 gcaattaagc tgacttctta cccaaaaatc aatcaaaact cggatttaac taaaaatctc      300
tactgccaaa ctggaggaat aggaacagat aactgcaaac ttgtcttcaa gaaacgtaaa      360
agacaaatag cagctaatat tgaaatctac ggcattccag cgaagaaatg ttccttcaag      420
gatcgttaca ttggagctga tccactccac gtcgattcct atgggcttcc gtatcagttt      480
gatcaggaac atggatggaa tgtggaacga tataacattt tcaaagacac aagattttcc      540
acagaagttt tctaccacaa aaatggttta tttaacaccc aaataactta tttggctgaa      600
gaagattcct tctctgaagc tcgagagatt actgcgaagg atattaagaa gaagtttttca     660 attattttgc ccaatgaaga gtaagagg attagttttct tggacgttta ttggttccag      720
gagactatgc gaaaaaagcc taaatatccc tacattcact acaatggaga atgcagcaat      780
```

```
gagaataaaa cttgtgaact tgtctttgac accgatgaac taatgaccta cgcccttgtt      840
aaagtcttta ctaatcctga gagtgatgga tctaggctca agaagagga tttgggaaga       900 ggataa                                                                 906
```

<210> SEQ ID NO 3
<211> LENGTH: 278
<212> TYPE: PRT
<213> ORGANISM: Lutzomyia longipalpis

<400> SEQUENCE: 3

```
Asp Gly Asp Glu Tyr Phe Ile Gly Lys Tyr Lys Glu Lys Asp Glu Thr
1               5                   10                  15

Leu Phe Phe Ala Ser Tyr Gly Leu Lys Arg Asp Pro Cys Gln Ile Val
            20                  25                  30

Leu Gly Tyr Lys Cys Ser Asn Asn Gln Thr His Phe Val Leu Asn Phe
        35                  40                  45

Lys Thr Asn Lys Lys Ser Cys Ile Ser Ala Ile Lys Leu Thr Ser Tyr
    50                  55                  60

Pro Lys Ile Asn Gln Asn Ser Asp Leu Thr Lys Asn Leu Tyr Cys Gln
65                  70                  75                  80

Thr Gly Gly Ile Gly Thr Asp Asn Cys Lys Leu Val Phe Lys Lys Arg
                85                  90                  95

Lys Arg Gln Ile Ala Ala Asn Ile Glu Ile Tyr Gly Ile Pro Ala Lys
            100                 105                 110

Lys Cys Ser Phe Lys Asp Arg Tyr Ile Gly Ala Asp Pro Leu His Val
        115                 120                 125

Asp Ser Tyr Gly Leu Pro Tyr Gln Phe Asp Gln Glu His Gly Trp Asn
    130                 135                 140

Val Glu Arg Tyr Asn Ile Phe Lys Asp Thr Arg Phe Ser Thr Glu Val
145                 150                 155                 160

Phe Tyr His Lys Asn Gly Leu Phe Asn Thr Gln Ile Thr Tyr Leu Ala
                165                 170                 175

Glu Glu Asp Ser Phe Ser Glu Ala Arg Glu Ile Thr Ala Lys Asp Ile
            180                 185                 190

Lys Lys Lys Phe Ser Ile Ile Leu Pro Asn Glu Glu Tyr Lys Arg Ile
        195                 200                 205

Ser Phe Leu Asp Val Tyr Trp Phe Gln Glu Thr Met Arg Lys Lys Pro
    210                 215                 220

Lys Tyr Pro Tyr Ile His Tyr Asn Gly Cys Ser Asn Glu Asn Lys
225                 230                 235                 240

Thr Cys Glu Leu Val Phe Asp Thr Asp Glu Leu Met Thr Tyr Ala Leu
                245                 250                 255

Val Lys Val Phe Thr Asn Pro Glu Ser Asp Gly Ser Arg Leu Lys Glu
            260                 265                 270

Glu Asp Leu Gly Arg Gly
        275
```

<210> SEQ ID NO 4
<211> LENGTH: 837
<212> TYPE: DNA
<213> ORGANISM: Lutzomyia longipalpis

<400> SEQUENCE: 4

```
gatggtgatg aatatttcat tggaaaatac aaagaaaaag atgagacact gttttttgca      60
agctacggcc ta

```
caaacccact tgtgcttaa ttttaaaacc aataagaaat cctgcatatc agcaattaag     180
ctgacttctt acccaaaaat caatcaaaac tcggatttaa ctaaaaatct ctactgccaa     240
actggaggaa taggaacaga taactgcaaa cttgtcttca agaaacgtaa aagacaaata     300
gcagctaata ttgaaatcta cggcattcca gcgaagaaat gttccttcaa ggatcgttac     360
attggagctg atccactcca cgtcgattcc tatgggcttc cgtatcagtt tgatcaggaa     420
catggatgga atgtggaacg atataacatt ttcaaagaca caagattttc cacagaagtt     480
ttctaccaca aaatggtttt atttaacacc caaataactt atttggctga agaagattcc     540
ttctctgaag ctcgagagat tactgcgaag gatattaaga agaagtttc aattattttg     600 cccaatgaag agtataagag gattagtttc ttggacgttt attggttcca ggagactatg     660
cgaaaaaagc ctaaatatcc ctacattcac tacaatggag aatgcagcaa tgagaataaa     720
acttgtgaac ttgtctttga caccgatgaa ctaatgacct acgcccttgt taaagtcttt     780
actaatcctg agagtgatgg atctaggctc aaagaagagg atttgggaag aggataa     837

<210> SEQ ID NO 5
<211> LENGTH: 412
<212> TYPE: PRT
<213> ORGANISM: Lutzomyia longipalpis

<400> SEQUENCE: 5

Met Arg Phe Phe Phe Val Phe Leu Ala Ile Val Leu Phe Gln Gly Ile
1               5                   10                  15

His Gly Ala Tyr Val Glu Ile Gly Tyr Ser Leu Arg Asn Ile Thr Phe
            20                  25                  30

Asp Gly Leu Asp Thr Asp Asp Tyr Asn Pro Lys Phe Asn Ile Pro Thr
        35                  40                  45

Gly Leu Ala Val Asp Pro Glu Gly Tyr Arg Leu Phe Ile Ala Ile Pro
    50                  55                  60

Arg Arg Lys Pro Lys Val Pro Tyr Thr Val Ala Glu Leu Asn Met Val
65                  70                  75                  80

Met Asn Pro Gly Phe Pro Val Glu Arg Ala Pro Ser Phe Glu Lys Phe
                85                  90                  95

Lys Lys Phe Asn Gly Glu Gly Lys Lys Asp Leu Val Asn Val Tyr Gln
            100                 105                 110

Pro Val Ile Asp Asp Cys Arg Arg Leu Trp Val Leu Asp Ile Gly Lys
        115                 120                 125

Val Glu Tyr Thr Gly Gly Asp Ala Asp Gln Tyr Pro Lys Gly Lys Pro
    130                 135                 140

Thr Leu Ile Ala Tyr Asp Leu Lys Lys Asp His Thr Pro Glu Ile His
145                 150                 155                 160

Arg Phe Glu Ile Pro Asp Asp Leu Tyr Ser Ser Gln Val Glu Phe Gly
                165                 170                 175

Gly Phe Ala Val Asp Val Val Asn Thr Lys Gly Asp Cys Thr Glu Ser
            180                 185                 190

Phe Val Tyr Leu Thr Asn Phe Lys Asp Asn Ser Leu Ile Val Tyr Asp
        195                 200                 205

Glu Thr Gln Lys Lys Ala Trp Lys Phe Thr Lys Thr Phe Glu Ala
    210                 215                 220

Asp Lys Glu Ser Thr Phe Ser Tyr Ser Gly Glu Glu Gln Met Lys Tyr
225                 230                 235                 240

Lys Val Gly Leu Phe Gly Ile Ala Leu Gly Asp Arg Asp Glu Met Gly
                245                 250                 255
```

His Arg Pro Ala Cys Tyr Ile Ala Gly Ser Ser Thr Lys Val Tyr Ser
            260                 265                 270

Val Asn Thr Lys Glu Leu Lys Thr Glu Asn Gly Gln Leu Asn Pro Gln
        275                 280                 285

Leu His Gly Asp Arg Gly Lys Tyr Thr Asp Ala Ile Ala Leu Ala Tyr
    290                 295                 300

Asp Pro Glu His Lys Val Leu Tyr Phe Ala Glu Ser Asp Ser Arg Gln
305                 310                 315                 320

Val Ser Cys Trp Asn Val Asn Met Glu Leu Lys Pro Asp Asn Thr Asp
                325                 330                 335

Val Ile Phe Ser Ser Ala Arg Phe Thr Phe Gly Thr Asp Ile Leu Val
            340                 345                 350

Asp Ser Lys Gly Met Leu Trp Ile Met Ala Asn Gly His Pro Pro Val
        355                 360                 365

Glu Asp Gln Glu Lys Ile Trp Lys Met Arg Phe Val Asn Arg Lys Ile
    370                 375                 380

Arg Ile Met Lys Val Asp Thr Glu Arg Val Phe Lys Tyr Ser Arg Cys
385                 390                 395                 400

Asn Pro Asn Tyr Lys Pro Pro Lys Glu Ile Glu Val
                405                 410

```
<210> SEQ ID NO 6
<211> LENGTH: 1239
<212> TYPE: DNA
<213> ORGANISM: Lutzomyia longipalpis

<400> SEQUENCE: 6
atgaggttct tctttgtttt ccttgccatc gtcctttttc aagggatcca cggagcttat      60
gtggaaatag atattctct gagaaatatt acattcgatg gattggatac agatgactac     120
aatccaaagt tcaacattcc aacgggtttg gcagttgatc ccgaaggata taggctcttc     180
atagccatcc aaggagaaa gccaaaggtt ccctacactg tggctgaact gaatatggtc     240
atgaatcccg gatttcccgt cgagagagct ccgagctttg agaaattcaa aaaattcaat     300
ggcgagggca aaaggatct tgttaatgtg tatcagccag tcattgatga ttgtcgtcgt     360
ctttgggtgc ttgacattgg aaggtggaa tacaccggtg tgatgctga tcaatatccc     420 aaaggaaagc ctaccctaat tgcctacgac ctcaagaagg atcatactcc ggaaattcat     480
cgatttgaaa ttccagacga tctctatagc tcacaagttg aatttggtgg atttgccgtt     540
gatgttgtta acacgaaagg agactgtacg gagtcatttg tctacctgac caatttcaag     600
gataactctc taattgtcta cgatgagaca caaaagaaag cttggaaatt cacagataaa     660
acatttgaag ctgataagga tccacgttc tcctactcgg gagaggaaca aatgaagtac     720
aaagtcggtc tttttgggat agctctgggt gatagggatg aaatggggca tcgtcctgcc     780
tgctacatcg ctgggagtag caccaaagtc tacagtgtta acactaaaga actcaaaaca     840
gagaatggtc agttaaatcc tcagcttcac ggtgatcgtg gaaagtacac agatgcaatt     900
gccctagcct acgatcctga gcataaagtc ctctactttg ctgaatccga cagcaggcag     960
gtgtcctgtt ggaatgtaaa tatggagcta aaaccagaca atacggatgt gatcttctct    1020
agtgcccgtt ttactttgg aacggatatt tggttgata gcaagggaat gctgtggata    1080
atggctaatg gacatccacc agtagaggat caagagaaga tttggaagat gagattcgta    1140
aaccggaaga tccgtattat gaaagtggat acgaacgtg tttttcaaata ttcacgctgc    1200 aatccaaatt ataagccccc aaaggaaatt gaagtttga                          1239
```

<210> SEQ ID NO 7
<211> LENGTH: 394
<212> TYPE: PRT
<213> ORGANISM: Lutzomyia longipalpis

<400> SEQUENCE: 7

```
Ala Tyr Val Glu Ile Gly Tyr Ser Leu Arg Asn Ile Thr Phe Asp Gly
1               5                   10                  15

Leu Asp Thr Asp Asp Tyr Asn Pro Lys Phe Asn Ile Pro Thr Gly Leu
            20                  25                  30

Ala Val Asp Pro Glu Gly Tyr Arg Leu Phe Ile Ala Ile Pro Arg Arg
        35                  40                  45

Lys Pro Lys Val Pro Tyr Thr Val Ala Glu Leu Asn Met Val Met Asn
50                  55                  60

Pro Gly Phe Pro Val Glu Arg Ala Pro Ser Phe Glu Lys Phe Lys Lys
65                  70                  75                  80

Phe Asn Gly Glu Gly Lys Lys Asp Leu Val Asn Val Tyr Gln Pro Val
            85                  90                  95

Ile Asp Asp Cys Arg Arg Leu Trp Val Leu Asp Ile Gly Lys Val Glu
        100                 105                 110

Tyr Thr Gly Gly Asp Ala Asp Gln Tyr Pro Lys Gly Lys Pro Thr Leu
    115                 120                 125

Ile Ala Tyr Asp Leu Lys Lys Asp His Thr Pro Glu Ile His Arg Phe
130                 135                 140

Glu Ile Pro Asp Asp Leu Tyr Ser Ser Gln Val Glu Phe Gly Gly Phe
145                 150                 155                 160

Ala Val Asp Val Val Asn Thr Lys Gly Asp Cys Thr Glu Ser Phe Val
            165                 170                 175

Tyr Leu Thr Asn Phe Lys Asp Asn Ser Leu Ile Val Tyr Asp Glu Thr
        180                 185                 190

Gln Lys Lys Ala Trp Lys Phe Thr Asp Lys Thr Phe Glu Ala Asp Lys
    195                 200                 205

Glu Ser Thr Phe Ser Tyr Ser Gly Glu Glu Met Lys Tyr Lys Val
210                 215                 220

Gly Leu Phe Gly Ile Ala Leu Gly Asp Arg Asp Glu Met Gly His Arg
225                 230                 235                 240

Pro Ala Cys Tyr Ile Ala Gly Ser Ser Thr Lys Val Tyr Ser Val Asn
            245                 250                 255

Thr Lys Glu Leu Lys Thr Glu Asn Gly Gln Leu Asn Pro Gln Leu His
        260                 265                 270

Gly Asp Arg Gly Lys Tyr Thr Asp Ala Ile Ala Leu Ala Tyr Asp Pro
    275                 280                 285

Glu His Lys Val Leu Tyr Phe Ala Glu Ser Asp Ser Arg Gln Val Ser
290                 295                 300

Cys Trp Asn Val Asn Met Glu Leu Lys Pro Asp Asn Thr Asp Val Ile
305                 310                 315                 320

Phe Ser Ser Ala Arg Phe Thr Phe Gly Thr Asp Ile Leu Val Asp Ser
            325                 330                 335

Lys Gly Met Leu Trp Ile Met Ala Asn Gly His Pro Val Glu Asp
        340                 345                 350

Gln Glu Lys Ile Trp Lys Met Arg Phe Val Asn Arg Lys Ile Arg Ile
    355                 360                 365

Met Lys Val Asp Thr Glu Arg Val Phe Lys Tyr Ser Arg Cys Asn Pro
370                 375                 380
```

Asn Tyr Lys Pro Pro Lys Glu Ile Glu Val
385                 390

<210> SEQ ID NO 8
<211> LENGTH: 1185
<212> TYPE: DNA
<213> ORGANISM: Lutzomyia longipalpis

<400> SEQUENCE: 8

```
gcttatgtgg aaataggata ttctctgaga aatattacat tcgatggatt ggatacagat      60
gactacaatc caaagttcaa cattccaacg ggtttggcag ttgatcccga aggatatagg     120
ctcttcatag ccatcccaag gagaaagcca aaggttccct acactgtggc tgaactgaat     180
atggtcatga atcccggatt tcccgtcgag agagctccga gctttgagaa attcaaaaaa     240
ttcaatggcg agggcaaaaa ggatcttgtt aatgtgtatc agccagtcat tgatgattgt     300
cgtcgtcttt gggtgcttga cattgggaag gtggaataca ccggtggtga tgctgatcaa     360
tatcccaaag gaaagcctac cctaattgcc tacgacctca agaaggatca tactccggaa     420
attcatcgat ttgaaattcc agacgatctc tatagctcac aagttgaatt tggtggattt     480
gccgttgatg ttgttaacac gaaaggagac tgtacggagt catttgtcta cctgaccaat     540
ttcaaggata actctctaat tgtctacgat gagacacaaa agaaagcttg gaaattcaca     600
gataaaacat ttgaagctga taaggaatcc acgttctcct actcgggaga ggaacaaatg     660
aagtacaaag tcggtctttt tgggatagct ctgggtgata gggatgaaat ggggcatcgt     720
cctgcctgct acatcgctgg gagtagcacc aaagtctaca gtgttaacac taagaactc      780
aaaacagaga atggtcagtt aaatcctcag cttcacggtg atcgtggaaa gtacacagat     840
gcaattgccc tagcctacga tcctgagcat aaagtcctct actttgctga atccgacagc     900
aggcaggtgt cctgttggaa tgtaaatatg gagctaaaac cagacaatac ggatgtgatc     960
ttctctagtg cccgttttac ttttggaacg gatattttgg ttgatagcaa gggaatgctg    1020
tggataatgg ctaatggaca tccaccagta gaggatcaag agaagatttg gaagatgaga    1080
ttcgtaaacc ggaagatccg tattatgaaa gtggatacgg aacgtgtttt caaatattca    1140
cgctgcaatc caaattataa gcccccaaag gaaattgaag tttga                    1185
```

<210> SEQ ID NO 9
<211> LENGTH: 6247
<212> TYPE: DNA
<213> ORGANISM: artificial
<220> FEATURE:
<223> OTHER INFORMATION: nucleic acid sequence of one strand of the plasmid pVR2001 LJM17

<400> SEQUENCE: 9

```
aagggatcca gatctgctgt gccttctagt tgccagccat ctgttgtttg cccctcccc       60
gtgccttcct tgaccctgga aggtgccact cccactgtcc tttcctaata aaatgaggaa    120
attgcatcgc attgtctgag taggtgtcat tctattctgg ggggtggggt ggggcagcac    180
agcaaggggg aggattggga agacaatagc aggcatgctg gggatgcggt gggctctatg    240
ggtacccagg tgctgaagaa ttgacccggt tcctcctggg ccagaaagaa gcaggcacat    300
ccccttctct gtgacacacc ctgtccacgc ccctggttct tagttccagc ccactcata     360
ggacactcat agctcaggag ggctccgcct tcaatcccac ccgctaaagt acttggagcg    420
gtctctccct ccctcatcag cccaccaaac caaacctagc ctccaagagt gggaagaaat    480
taaagcaaga taggctatta agtgcagagg gagagaaaat gcctccaaca tgtgaggaag    540
```

```
taatgagaga aatcatagaa tttcttccgc ttcctcgctc actgactcgc tgcgctcggt    600
cgttcggctg cggcgagcgg tatcagctca ctcaaaggcg gtaatacggt tatccacaga    660
atcaggggat aacgcaggaa agaacatgtg agcaaaaggc cagcaaaagg ccaggaaccg    720
taaaaaggcc gcgttgctgg cgttttttcca taggctccgc cccctgacg agcatcacaa     780
aaatcgacgc tcaagtcaga ggtggcgaaa cccgacagga ctataaagat accaggcgtt    840
tccccctgga agctccctcg tgcgctctcc tgttccgacc ctgccgctta ccggatacct    900
gtccgccttt ctcccttcgg gaagcgtggc gctttctcaa tgctcacgct gtaggtatct    960
cagttcggtg taggtcgttc gctccaagct gggctgtgtg cacgaacccc ccgttcagcc   1020
cgaccgctgc gccttatccg gtaactatcg tcttgagtcc aacccggtaa gacacgactt   1080
atcgccactg gcagcagcca ctggtaacag gattagcaga gcgaggtatg taggcggtgc   1140
tacagagttc ttgaagtggt ggcctaacta cggctacact agaaggacag tatttggtat   1200
ctgcgctctg ctgaagccag ttaccttcgg aaaaagagtt ggtagctctt gatccggcaa   1260
acaaaccacc gctggtagcg gtggtttttt tgtttgcaag cagcagatta cgcgcagaaa   1320
aaaaggatct caagaagatc ctttgatctt ttctacgggg tctgacgctc agtggaacga   1380
aaactcacgt taagggattt tggtcatgag attatcaaaa aggatcttca cctagatcct   1440
tttaaattaa aaatgaagtt ttaaatcaat ctaaagtata tatgagtaaa cttggtctga   1500
cagttaccaa tgcttaatca gtgaggcacc tatctcagcg atctgtctat ttcgttcatc   1560
catagttgcc tgactccggg ggggggggc gctgaggtct gcctcgtgaa gaaggtgttg   1620
ctgactcata ccaggcctga atcgccccat catccagcca gaaagtgagg gagccacggt   1680
tgatgagagc tttgttgtag gtggaccagt tggtgatttt gaacttttgc tttgccacgg   1740
aacggtctgc gttgtcggga agatgcgtga tctgatcctt caactcagca aaagttcgat   1800
ttattcaaca aagccgccgt cccgtcaagt cagcgtaatg ctctgccagt gttacaacca   1860
attaaccaat tctgattaga aaaactcatc gagcatcaaa tgaaactgca atttattcat   1920
atcaggatta tcaataccat attttgaaa aagccgtttc tgtaatgaag gagaaaactc   1980
accgaggcag ttccatagga tggcaagatc ctggtatcgg tctgcgattc cgactcgtcc   2040
aacatcaata caacctatta atttcccctc gtcaaaaata aggttatcaa gtgagaaatc   2100
accatgagtg acgactgaat ccggtgagaa tggcaaaagc ttatgcattt ctttccagac   2160
ttgttcaaca ggccagccat tacgctcgtc atcaaaatca ctcgcatcaa ccaaaccgtt   2220
attcattcgt gattgcgcct gagcgagacg aaatacgcga tcgctgttaa aaggacaatt   2280
acaaacagga tcgaatgcaa ccggcgcag gaacactgcc agcgcatcaa caatatttc   2340
acctgaatca ggatattctt ctaatacctg gaatgctgtt ttcccgggga tcgcagtggt   2400
gagtaaccat gcatcatcag gagtacggat aaaatgcttg atggtcggaa gaggcataaa   2460
ttccgtcagc cagtttagtc tgaccatctc atctgtaaca tcattggcaa cgctacctt   2520
gccatgtttc agaaacaact ctggcgcatc gggcttccca tacaatcgat agattgtcgc   2580
acctgattgc ccgacattat cgcgagccca tttataccca tataaatcag catccatgtt   2640
ggaatttaat cgcggcctcg agcaagacgt ttcccgttga atatggctca taacacccct   2700
tgtattactg tttatgtaag cagacagttt tattgttcat gatgatatat ttttatcttg   2760
tgcaatgtaa catcagagat tttgagacac aacgtggctt tccccccccc cccattattg   2820
aagcatttat caggggttatt gtctcatgag cggatacata tttgaatgta tttagaaaaa   2880
taaacaaata ggggttccgc gcacatttcc ccgaaaagtg ccacctgacg tctaagaaac   2940
```

```
cattattatc atgacattaa cctataaaaa taggcgtatc acgaggccct ttcgtctcgc   3000
gcgtttcggt gatgacggtg aaaacctctg acacatgcag ctcccggaga cggtcacagc   3060
ttgtctgtaa gcggatgccg ggagcagaca agcccgtcag ggcgcgtcag cgggtgttgg   3120
cgggtgtcgg ggctggctta actatgcggc atcagagcag attgtactga gagtgcacca   3180
tatgcggtgt gaaataccgc acagatgcgt aaggagaaaa taccgcatca gattggctat   3240
tggccattgc atacgttgta tccatatcat aatatgtaca tttatattgg ctcatgtcca   3300
acattaccgc catgttgaca ttgattattg actagttatt aatagtaatc aattacgggg   3360
tcattagttc atagcccata tatggagttc cgcgttacat aacttacggt aaatggcccg   3420
cctggctgac cgcccaacga cccccgccca ttgacgtcaa taatgacgta tgttcccata   3480
gtaacgccaa tagggacttt ccattgacgt caatgggtgg agtatttacg gtaaactgcc   3540
cacttggcag tacatcaagt gtatcatatg ccaagtacgc cccctattga cgtcaatgac   3600
ggtaaatggc ccgcctggca ttatgcccag tacatgacct tatgggactt tcctacttgg   3660
cagtacatct acgtattagt catcgctatt accatggtga tgcggttttg gcagtacatc   3720
aatgggcgtg gatagcggtt tgactcacgg ggatttccaa gtctccaccc cattgacgtc   3780
aatgggagtt tgttttggca ccaaaatcaa cgggactttc caaaatgtcg taacaactcc   3840
gccccattga cgcaaatggg cggtaggcgt gtacggtggg aggtctatat aagcagagct   3900
cgtttagtga accgtcagat cgcctggaga cgccatccac gctgttttga cctccataga   3960
agacaccggg accgatccag cctccgcggc cgggaacggt gcattggaac gcggattccc   4020
cgtgccaaga gtgacgtaag taccgcctat agagtctata ggcccacccc cttggcttct   4080
tatgcatgct atactgtttt tggcttgggg tctatacacc cccgcttcct catgttatag   4140
gtgatggtat agcttagcct ataggtgtgg gttattgacc attattgacc actcccctat   4200
tggtgacgat actttccatt actaatccat aacatggctc tttgccacaa ctctctttat   4260
tggctatatg ccaatacact gtccttcaga gactgacacg gactctgtat ttttacagga   4320
tggggtctca tttattattt acaaattcac atatacaaca ccaccgtccc cagtgccgc    4380 agtttttatt aaacataacg tgggatctcc acgcgaatct cgggtacgtg ttccggacat   4440
gggctcttct ccggtagcgg cggagcttct acatccgagc cctgctccca tgcctccagc   4500
gactcatggt cgctcggcag ctccttgctc ctaacagtgg aggccagact taggcacagc   4560
acgatgccca ccaccaccag tgtgccgcac aaggccgtgg cggtagggta tgtgtctgaa   4620
aatgagctcg gggagcgggc ttgcaccgct gacgcatttg gaagacttaa ggcagcggca   4680
gaagaagatg caggcagctg agttgttgtg ttctgataag agtcagaggt aactcccgtt   4740
gcggtgctgt taacggtgga gggcagtgta gtctgagcag tactcgttgc tgccgcgcgc   4800
gccaccagac ataatagctg acagactaac agactgttcc tttccatggg tcttttctca   4860
cgtcaccgtc gtcgaccaga gctgagatcc tacaggagtc cagggctgga gagaaaacct   4920
ctgcgaggaa agggaaggag caagccgtga atttaaggga cgctgtgaag caatcatgga   4980
tgcaatgaag agagggctct gctgtgtgct gctgctgtgt ggagcagtct tcgtttcgcc   5040
cagcggtacc ggatccaccc ttgcttatgt ggaaatagga tattctctga gaaatattac   5100
attcgatgga ttggatacag atgactacaa tccaaagttc aacattccaa cgggtttggc   5160
agttgatccc gaaggatata ggctcttcat agccatccca aggagaaagc caaaggttcc   5220
ctacactgtg gctgaactga atatggtcat gaatcccgga tttcccgtcg agagagctcc   5280
gagctttgag aaattcaaaa aattcaatgg cgagggcaaa aaggatcttg ttaatgtgta   5340
```

```
tcagccagtc attgatgatt gtcgtcgtct ttgggtgctt gacattggga aggtggaata    5400
caccggtggt gatgctgatc aatatcccaa aggaaagcct accctaattg cctacgacct    5460
caagaaggat catactccgg aaattcatcg atttgaaatt ccagacgatc tctatagctc    5520
acaagttgaa tttggtggat tgccgttgat tgttgttaac acgaaaggag actgtacgga    5580
```
(Note: verify line 5580 — reading as shown)
```
gtcatttgtc tacctgacca atttcaagga taactctcta attgtctacg atgagacaca    5640
aaagaaagct tggaaattca cagataaaac atttgaagct gataaggaat ccacgttctc    5700
ctactcggga gaggaacaaa tgaagtacaa agtcggtctt tttgggatag ctctgggtga    5760
tagggatgaa atggggcatc gtcctgcctg ctacatcgct gggagtagca ccaaagtcta    5820
cagtgttaac actaaagaac tcaaaacaga gaatggtcag ttaaatcctc agcttcacgg    5880
tgatcgtgga aagtacacag atgcaattgc cctagcctac gatcctgagc ataaagtcct    5940
ctactttgct gaatccgaca gcaggcaggt gtcctgttgg aatgtaaata tggagctaaa    6000
accagacaat acgatgtga tcttctctag tgcccgtttt acttttggaa cggatatttt     6060
```
(verify: "acgatgtga" may be "acgatgtgat")
```
ggttgatagc aagggaatgc tgtggataat ggctaatgga catccaccag tagaggatca    6120
agagaagatt tggaagatga gattcgtaaa ccggaagatc cgtattatga agtggatac     6180 ggaacgtgtt ttcaaatatt cacgctgcaa tccaaattat aagcccccaa aggaaattga    6240
agtttga                                                              6247
```

<210> SEQ ID NO 10
<211> LENGTH: 5899
<212> TYPE: DNA
<213> ORGANISM: artificial
<220> FEATURE:
<223> OTHER INFORMATION: nucleic acid sequence of one strand of the
      plasmid pVR2001 LJL143

<400> SEQUENCE: 10

```
aagggatcca gatctgctgt gccttctagt tgccagccat ctgttgtttg cccctccccc      60
gtgccttcct tgaccctgga aggtgccact cccactgtcc tttcctaata aaatgaggaa     120
attgcatcgc attgtctgag taggtgtcat tctattctgg ggggtggggt ggggcagcac     180
agcaaggggg aggattggga agacaatagc aggcatgctg gggatgcggt gggctctatg     240
ggtacccagg tgctgaagaa ttgacccggt tcctcctggg ccagaaagaa gcaggcacat     300 cccettctct gtgacacacc ctgtccacgc cctggttct tagttccagc cccactcata      360
ggacactcat agctcaggag ggctccgcct tcaatcccac ccgctaaagt acttggagcg     420
gtctctccct ccctcatcag cccaccaaac caaacctagc ctccaagagt gggaagaaat     480
taaagcaaga taggctatta agtgcagagg gagagaaaat gcctccaaca tgtgaggaag     540
taatgagaga atcatagaa tttcttccgc ttcctcgctc actgactcgc tgcgctcggt      600
cgttcggctg cggcgagcgg tatcagctca ctcaaaggcg gtaatacggt tatccacaga     660
atcaggggat aacgcaggaa agaacatgtg agcaaaaggc cagcaaaagg ccaggaaccg     720
taaaaaggcc gcgttgctgg cgttttccca taggctccgc cccctgacg agcatcacaa      780 aaatcgacgc tcaagtcaga ggtggcgaaa cccgacagga ctataaagat accaggcgtt     840
tcccctggaa gctccctcg tgcgctctcc tgttccgacc ctgccgctta ccggatacct      900
gtccgccttt ctccctcgg gaagcgtggc gctttctcaa tgctcacgct gtaggtatct     960
cagttcggtg taggtcgttc gctccaagct gggctgtgtg cacgaacccc ccgttcagcc    1020
cgaccgctgc gccttatccg gtaactatcg tcttgagtcc aacccggtaa gacacgactt    1080
```

```
atcgccactg gcagcagcca ctggtaacag gattagcaga gcgaggtatg taggcggtgc    1140
tacagagttc ttgaagtggt ggcctaacta cggctacact agaaggacag tatttggtat    1200
ctgcgctctg ctgaagccag ttaccttcgg aaaaagagtt ggtagctctt gatccggcaa    1260
acaaaccacc gctggtagcg gtggtttttt tgtttgcaag cagcagatta cgcgcagaaa    1320
aaaaggatct caagaagatc ctttgatctt ttctacgggg tctgacgctc agtggaacga    1380
aaactcacgt taagggattt tggtcatgag attatcaaaa aggatcttca cctagatcct    1440
tttaaattaa aaatgaagtt ttaaatcaat ctaaagtata tatgagtaaa cttggtctga    1500
cagttaccaa tgcttaatca gtgaggcacc tatctcagcg atctgtctat ttcgttcatc    1560
catagttgcc tgactccggg ggggggggc gctgaggtct gcctcgtgaa gaaggtgttg    1620
ctgactcata ccaggcctga atcgccccat catccagcca gaaagtgagg gagccacggt    1680
tgatgagagc tttgttgtag gtggaccagt tggtgatttt gaacttttgc tttgccacgg    1740
aacggtctgc gttgtcggga agatgcgtga tctgatcctt caactcagca aaagttcgat    1800
ttattcaaca aagccgccgt cccgtcaagt cagcgtaatg ctctgccagt gttacaacca    1860
attaaccaat tctgattaga aaactcatcg agcatcaaa tgaaactgca atttattcat    1920
atcaggatta tcaataccat attttttgaaa aagccgtttc tgtaatgaag gagaaaactc    1980
accgaggcag ttccatagga tggcaagatc ctggtatcgg tctgcgattc cgactcgtcc    2040
aacatcaata caacctatta atttcccctc gtcaaaaata aggttatcaa gtgagaaatc    2100
accatgagtg acgactgaat ccggtgagaa tggcaaaagc ttatgcattt ctttccagac    2160
ttgttcaaca ggccagccat tacgctcgtc atcaaaatca ctcgcatcaa ccaaaccgtt    2220
attcattcgt gattgcgcct gagcgagacg aaatacgcga tcgctgttaa aggacaatt    2280 acaaacagga atcgaatgca accggcgcag gaacactgcc agcgcatcaa caatattttc    2340
acctgaatca ggatattctt ctaataccty gaatgctgtt ttcccgggga tcgcagtggt    2400
gagtaaccat gcatcatcag gagtacggat aaaatgcttg atggtcggaa gaggcataaa    2460
ttccgtcagc cagtttagtc tgaccatctc atctgtaaca tcattggcaa cgctacccttt   2520 gccatgtttc agaaacaact ctggcgcatc gggcttccca tacaatcgat agattgtcgc    2580
acctgattgc ccgacattat cgcgagccca tttatcccca tataaatcag catccatgtt    2640
ggaatttaat cgcggcctcg agcaagacgt ttcccgttga atatggctca taacaccccct  2700 tgtattactg tttatgtaag cagacagttt tattgttcat gatgatatat ttttatcttg    2760
tgcaatgtaa catcagagat tttgagacac aacgtggctt ccccccccc cccattattg    2820 aagcatttat cagggttatt gtctcatgag cggatacata tttgaatgta tttagaaaaa    2880
taaacaaata ggggttccgc gcacatttcc ccgaaaagtg ccacctgacg tctaagaaac    2940
cattattatc atgacattaa cctataaaaa taggcgtatc acgaggccct ttcgtctcgc    3000
gcgtttcggt gatgacggtg aaaacctctg acacatgcag ctcccggaga cggtcacagc    3060
ttgtctgtaa gcggatgccg ggagcagaca agcccgtcag ggcgcgtcag cgggtgttgg    3120
cgggtgtcgg gctggctta actatgcggc atcagagcag attgtactga gagtgcacca    3180
tatgcggtgt gaaataccgc acagatgcgt aaggagaaaa taccgcatca gattggctat    3240
tggccattgc atacgttgta tccatatcat aatatgtaca tttatattgg ctcatgtcca    3300
acattaccgc catgttgaca ttgattattg actagttatt aatagtaatc aattacgggg    3360
tcattagttc atagcccata tatggagttc cgcgttacat aacttacggt aaatggcccg    3420
cctggctgac cgcccaacga ccccgccca ttgacgtcaa taatgacgta tgttcccata    3480
```

-continued

```
gtaacgccaa tagggacttt ccattgacgt caatgggtgg agtatttacg gtaaactgcc    3540
cacttggcag tacatcaagt gtatcatatg ccaagtacgc cccctattga cgtcaatgac    3600
ggtaaatggc ccgcctggca ttatgcccag tacatgacct tatgggactt tcctacttgg    3660
cagtacatct acgtattagt catcgctatt accatggtga tgcggttttg gcagtacatc    3720
aatgggcgtg gatagcggtt tgactcacgg ggatttccaa gtctccaccc cattgacgtc    3780
aatgggagtt tgttttggca ccaaaatcaa cgggactttc caaaatgtcg taacaactcc    3840
gccccattga cgcaaatggg cggtaggcgt gtacggtggg aggtctatat aagcagagct    3900
cgtttagtga accgtcagat cgcctggaga cgccatccac gctgttttga cctccataga    3960
agacaccggg accgatccag cctccgcggc cgggaacggt gcattggaac gcggattccc    4020
cgtgccaaga gtgacgtaag taccgcctat agagtctata ggcccacccc cttggcttct    4080
tatgcatgct atactgtttt tggcttgggg tctatacacc cccgcttcct catgttatag    4140
gtgatggtat agcttagcct ataggtgtgg gttattgacc attattgacc actcccctat    4200
tggtgacgat actttccatt actaatccat aacatggctc tttgccacaa ctctctttat    4260
tggctatatg ccaatacact gtccttcaga gactgacacg gactctgtat ttttacagga    4320
tggggtctca tttattattt acaaattcac atatacaaca ccaccgtccc cagtgcccgc    4380
agttttatt aaacataacg tgggatctcc acgcgaatct cgggtacgtg ttccggacat    4440
gggctcttct ccggtagcgg cggagcttct acatccgagc cctgctccca tgcctccagc    4500
gactcatggt cgctcggcag ctccttgctc ctaacagtgg aggccagact taggcacagc    4560
acgatgccca ccaccaccag tgtgccgcac aaggccgtgg cggtagggta tgtgtctgaa    4620
aatgagctcg gggagcgggc ttgcaccgct gacgcatttg gaagacttaa ggcagcggca    4680
gaagaagatg caggcagctg agttgttgtg ttctgataag agtcagaggt aactcccgtt    4740
gcggtgctgt taacggtgga gggcagtgta gtctgagcag tactcgttgc tgccgcgcgc    4800
gccaccagac ataatagctg acagactaac agactgttcc tttccatggg tctttctca    4860
cgtcaccgtc gtcgaccaga gctgagatcc tacaggagtc cagggctgga gagaaaacct    4920
ctgcgaggaa agggaaggag caagccgtga atttaaggga cgctgtgaag caatcatgga    4980
tgcaatgaag agagggctct gctgtgtgct gctgctgtgt ggagcagtct tcgtttcgcc    5040
cagcggtacc ggatccaccc ttgatggtga tgaatatttc attggaaaat acaaagaaaa    5100
agatgagaca ctgttttttg caagctacgg cctaaagagg gatccttgcc aaattgtctt    5160
aggctacaaa tgctcaaaca atcaaaccca ctttgtgctt aattttaaaa ccaataagaa    5220
atcctgcata tcagcaatta agctgacttc ttacccaaaa atcaatcaaa actcggattt    5280
aactaaaaat ctctactgcc aaactggagg aataggaaca gataactgca aacttgtctt    5340
caagaaacgt aaaagacaaa tagcagctaa tattgaaatc tacggcattc cagcgaagaa    5400
atgttccttc aaggatcgtt acattggagc tgatccactc cacgtcgatt cctatgggct    5460
tccgtatcag tttgatcagg aacatggatg gaatgtggaa cgatataaca ttttcaaaga    5520
cacaagattt tccacagaag ttttctacca caaaaatggt ttatttaaca cccaaataac    5580
ttatttggct gaagaagatt ccttctctga agctcgagag attactgcga aggatattaa    5640
gaagaagttt tcaattattt tgcccaatga agagtataag aggattagtt tcttggacgt    5700
ttattggttc caggagacta tgcgaaaaaa gcctaaatat ccctacattc actacaatgg    5760
agaatgcagc aatgagaata aaacttgtga acttgtcttt gacaccgatg aactaatgac    5820
ctacgccctt gttaaagtct ttactaatcc tgagagtgat ggatctaggc tcaaagaaga    5880
```

-continued ggatttggga agaggataa 5899

<210> SEQ ID NO 11
<211> LENGTH: 301
<212> TYPE: PRT
<213> ORGANISM: Lutzomyia longipalpis

<400> SEQUENCE: 11

Met Asn Ser Ile Asn Phe Leu Ser Ile Val Gly Leu Ile Ser Phe Gly
1 5 10 15

Phe Ile Val Ala Val Lys Cys Asp Gly Asp Glu Tyr Phe Ile Gly Lys
20 25 30

Tyr Lys Glu Lys Asp Glu Thr Leu Phe Phe Ala Ser Tyr Gly Leu Lys
35 40 45

Arg Asp Pro Cys Gln Ile Val Leu Gly Tyr Lys Cys Ser Asn Asn Gln
50 55 60

Thr His Phe Val Leu Asn Phe Lys Thr Asn Lys Lys Ser Cys Ile Ser
65 70 75 80

Ala Ile Lys Leu Thr Ser Tyr Pro Lys Ile Asn Gln Asn Ser Asp Leu
85 90 95

Thr Arg Asn Leu Tyr Cys Gln Thr Gly Gly Ile Gly Thr Asp Asn Cys
100 105 110

Lys Leu Val Phe Lys Lys Arg Lys Arg Gln Ile Ala Ala Asn Ile Glu
115 120 125

Ile Tyr Gly Ile Pro Ala Lys Lys Cys Ser Phe Lys Asp Arg Tyr Ile
130 135 140

Gly Ala Asp Pro Leu His Val Asp Ser Tyr Gly Leu Ser Tyr Gln Phe
145 150 155 160

Asp Gln Glu His Gly Trp Asn Leu Glu Arg Asn Asn Ile Phe Lys Asp
165 170 175

Thr Arg Phe Ser Thr Glu Val Phe Tyr His Lys Asn Gly Leu Phe Asn
180 185 190

Thr Gln Ile Thr Tyr Leu Ala Glu Glu Asp Ser Phe Ser Glu Ala Arg
195 200 205

Glu Ile Thr Ala Lys Asp Ile Lys Lys Lys Phe Ser Ile Ile Leu Pro
210 215 220

Asn Glu Glu Tyr Lys Arg Ile Ser Phe Leu Asp Val Tyr Trp Phe Gln
225 230 235 240

Glu Thr Met Arg Lys Lys Pro Lys Tyr Pro Tyr Ile His Tyr Asn Gly
245 250 255

Glu Cys Ser Asn Glu Asn Lys Thr Cys Glu Leu Val Phe Asp Thr Asp
260 265 270

Glu Leu Met Thr Tyr Ala Leu Val Lys Val Phe Thr Asn Pro Glu Ser
275 280 285

Asp Gly Ser Arg Leu Lys Glu Glu Asp Leu Gly Arg Gly
290 295 300

<210> SEQ ID NO 12
<211> LENGTH: 906
<212> TYPE: DNA
<213> ORGANISM: Lutzomyia longipalpis

<400> SEQUENCE: 12
atgaattcga ttaatttcct atcaatagtt ggtttaatca gttttggatt cattgttgca 60
gtaaagtgtg atggtgatga atatttcatt ggaaaataca aagaaaaaga tgagacactg 120
ttttttgcaa gctacggcct aaagagggat ccttgccaga ttgtcttagg ctacaaatgc 180

-continued

```
tcaaacaatc aaacccactt tgtgcttaat tttaaaacca ataagaaatc ctgcatatca      240
gcaattaagc tgacttctta cccaaaaatc aatcaaaact cggatttaac tagaaatctc      300
tactgccaaa ctggaggaat aggaacagat aactgcaaac ttgtcttcaa gaaacgtaaa      360
agacaaatag cagctaatat tgaaatctac ggcattccag cgaagaaatg ttccttcaag      420
gatcgttaca ttggagctga tccactccac gtcgattcct atgggctttc gtatcagttt      480
gatcaggaac atggatggaa tttggaacga ataacatttt caaagacac aagattttcc      540 acagaagttt tctaccacaa aaatggttta tttaacaccc aaataactta tttggctgaa      600
gaagattcct tctctgaagc tcgagagatt actgcgaagg atattaagaa gaagttttca      660
attattttgc ccaatgaaga gtaagagg attagtttct tggacgttta ttggttccag       720
gagactatgc gaaaaagcc taaatatccc tacattcact acaatggaga atgcagcaat      780
gagaataaaa cttgtgaact tgtctttgac accgatgaac taatgaccta cgcccttgtt      840
aaagtcttta ctaatcctga gagtgatgga tctaggctca agaagagga tttgggaaga      900 ggataa                                                                906
```

<210> SEQ ID NO 13
<211> LENGTH: 278
<212> TYPE: PRT
<213> ORGANISM: Lutzomyia longipalpis

<400> SEQUENCE: 13

Asp Gly Asp Glu Tyr Phe Ile Gly Lys Tyr Lys Glu Lys Asp Glu Thr
1               5                   10                  15

Leu Phe Phe Ala Ser Tyr Gly Leu Lys Arg Asp Pro Cys Gln Ile Val
            20                  25                  30

Leu Gly Tyr Lys Cys Ser Asn Asn Gln Thr His Phe Val Leu Asn Phe
        35                  40                  45

Lys Thr Asn Lys Lys Ser Cys Ile Ser Ala Ile Lys Leu Thr Ser Tyr
    50                  55                  60

Pro Lys Ile Asn Gln Asn Ser Asp Leu Thr Arg Asn Leu Tyr Cys Gln
65                  70                  75                  80

Thr Gly Gly Ile Gly Thr Asp Asn Cys Lys Leu Val Phe Lys Lys Arg
                85                  90                  95

Lys Arg Gln Ile Ala Ala Asn Ile Glu Ile Tyr Gly Ile Pro Ala Lys
            100                 105                 110

Lys Cys Ser Phe Lys Asp Arg Tyr Ile Gly Ala Asp Pro Leu His Val
        115                 120                 125

Asp Ser Tyr Gly Leu Ser Tyr Gln Phe Asp Gln Glu His Gly Trp Asn
    130                 135                 140

Leu Glu Arg Asn Asn Ile Phe Lys Asp Thr Arg Phe Ser Thr Glu Val
145                 150                 155                 160

Phe Tyr His Lys Asn Gly Leu Phe Asn Thr Gln Ile Thr Tyr Leu Ala
                165                 170                 175

Glu Glu Asp Ser Phe Ser Glu Ala Arg Glu Ile Thr Ala Lys Asp Ile
            180                 185                 190

Lys Lys Lys Phe Ser Ile Ile Leu Pro Asn Glu Glu Tyr Lys Arg Ile
        195                 200                 205

Ser Phe Leu Asp Val Tyr Trp Phe Gln Glu Thr Met Arg Lys Lys Pro
    210                 215                 220

Lys Tyr Pro Tyr Ile His Tyr Asn Gly Glu Cys Ser Asn Glu Asn Lys
225                 230                 235                 240

```
Thr Cys Glu Leu Val Phe Asp Thr Asp Glu Leu Met Thr Tyr Ala Leu
            245                 250                 255
Val Lys Val Phe Thr Asn Pro Glu Ser Asp Gly Ser Arg Leu Lys Glu
            260                 265                 270
Glu Asp Leu Gly Arg Gly
        275
```

<210> SEQ ID NO 14
<211> LENGTH: 837
<212> TYPE: DNA
<213> ORGANISM: Lutzomyia longipalpis

<400> SEQUENCE: 14

```
gatggtgatg aatatttcat tggaaaatac aaagaaaaag atgagacact gttttttgca      60
agctacggcc taaagaggga tccttgccag attgtcttag ctacaaatg ctcaaacaat     120
caaacccact ttgtgcttaa ttttaaaacc aataagaaat cctgcatatc agcaattaag    180
ctgacttctt acccaaaaat caatcaaaac tcggatttaa ctagaaatct ctactgccaa    240
actggaggaa taggaacaga taactgcaaa cttgtcttca agaaacgtaa aagacaaata    300
gcagctaata ttgaaatcta cggcattcca gcgaagaaat gttccttcaa ggatcgttac    360
attggagctg atccactcca cgtcgattcc tatgggcttt cgtatcagtt tgatcaggaa    420
catggatgga atttggaacg aaataacatt ttcaaagaca caagattttc cacagaagtt    480
ttctaccaca aaaatggttt atttaacacc caaataactt atttggctga agaagattcc    540
ttctctgaag ctcgagagat tactgcgaag gatattaaga agaagttttc aattattttg    600
cccaatgaag agtataagag gattagtttc ttggacgttt attggttcca ggagactatg    660
cgaaaaaagc ctaaatatcc ctacattcac tacaatggag aatgcagcaa tgagaataaa    720
acttgtgaac ttgtctttga caccgatgaa ctaatgacct acgcccttgt taaagtcttt    780
actaatcctg agagtgatgg atctaggctc aaagaagagg atttgggaag aggataa      837
```

<210> SEQ ID NO 15
<211> LENGTH: 412
<212> TYPE: PRT
<213> ORGANISM: Lutzomyia longipalpis

<400> SEQUENCE: 15

```
Met Arg Phe Phe Phe Val Phe Leu Ala Ile Val Leu Phe Gln Gly Ile
1               5                   10                  15

His Gly Ala Tyr Val Glu Ile Gly Tyr Ser Leu Arg Asn Ile Thr Phe
            20                  25                  30

Asp Gly Leu Asp Thr Asp Asp Tyr Asn Pro Lys Phe Asn Ile Pro Thr
        35                  40                  45

Gly Leu Ala Val Asp Pro Glu Gly Tyr Arg Leu Phe Ile Ala Ile Pro
    50                  55                  60

Arg Arg Lys Pro Lys Val Pro Tyr Thr Val Ala Glu Leu Asn Met Val
65                  70                  75                  80

Met Asn Pro Gly Phe Pro Val Glu Arg Ala Pro Ser Phe Glu Lys Phe
                85                  90                  95

Lys Lys Phe Asn Gly Glu Gly Lys Lys Asp Leu Val Asn Val Tyr Gln
            100                 105                 110

Pro Val Ile Asp Asp Cys Arg Arg Leu Trp Val Leu Asp Ile Gly Lys
        115                 120                 125

Val Glu Tyr Thr Gly Gly Asp Ala Asp Gln Tyr Pro Lys Gly Lys Pro
    130                 135                 140
```

```
Thr Leu Ile Ala Tyr Asp Leu Lys Lys Asp His Thr Pro Glu Ile His
145                 150                 155                 160

Arg Phe Glu Ile Pro Asp Asp Leu Tyr Ser Gln Val Glu Phe Gly
            165                 170                 175

Gly Phe Ala Val Asp Val Val Asn Thr Lys Gly Asp Cys Thr Glu Ser
        180                 185                 190

Phe Val Tyr Leu Thr Asn Phe Lys Asp Asn Ser Leu Ile Val Tyr Asp
    195                 200                 205

Glu Thr Gln Lys Lys Ala Trp Lys Phe Thr Asp Lys Thr Phe Glu Ala
210                 215                 220

Asp Lys Glu Ser Thr Phe Ser Tyr Ser Gly Glu Gln Met Lys Tyr
225                 230                 235                 240

Lys Val Gly Leu Phe Gly Ile Ala Leu Gly Asp Arg Asp Glu Met Gly
                245                 250                 255

His Arg Pro Ala Tyr Tyr Ile Ala Gly Ser Ser Thr Lys Val Tyr Ser
            260                 265                 270

Val Asn Thr Lys Glu Leu Lys Thr Glu Asn Gly Gln Leu Asn Pro Gln
        275                 280                 285

Leu His Gly Asp Arg Gly Lys Tyr Thr Asp Ala Ile Ala Leu Ala His
    290                 295                 300

Asp Pro Glu His Lys Val Leu Tyr Phe Ala Glu Ser Asp Ser Arg Gln
305                 310                 315                 320

Val Ser Cys Trp Asn Val Asp Met Glu Leu Lys Pro Asp Asn Thr Asp
                325                 330                 335

Val Ile Phe Ser Ser Ala Arg Phe Thr Phe Gly Thr Asp Ile Leu Val
            340                 345                 350

Asp Ser Lys Gly Met Leu Trp Ile Met Ala Asn Gly His Pro Pro Val
        355                 360                 365

Glu Asp Gln Glu Lys Ile Trp Lys Met Arg Phe Val Asn Arg Lys Ile
    370                 375                 380

Ser Ile Met Lys Val Asp Thr Glu Arg Val Phe Lys Tyr Ser Arg Cys
385                 390                 395                 400

Asn Pro Asn Tyr Lys Pro Pro Lys Glu Ile Glu Val
                405                 410

<210> SEQ ID NO 16
<211> LENGTH: 1239
<212> TYPE: DNA
<213> ORGANISM: Lutzomyia longipalpis

<400> SEQUENCE: 16
atgaggttct tctttgtttt ccttgccatc gtcctttttc aagggatcca cggagcttat      60
gtggaaatag atattctct gagaaatatt acattcgatg gattggatac agatgactac     120
aatccaaagt tcaacattcc aacgggtttg gcagttgatc ccgaaggata taggctcttc     180
atagccatcc aaggagaaa gccaaaggtt ccctacactg tggctgaact gaatatggtc     240
atgaatcccg gatttcccgt cgagagagct ccgagctttg agaaattcaa aaaattcaat     300
ggcgagggca aaaggatct tgttaatgtg tatcagccag tcattgatga ttgtcgtcgt     360
ctttgggtgc ttgacattgg aaggtggaa tacaccggtg gtgatgctga tcaatatccc     420
aaaggaaagc ctaccctaat tgcctacgac ctcaagaagg atcatactcc ggaaattcat     480
cgatttgaaa ttccagacga tctctatagc tcacaagttg aatttggtgg atttgccgtt     540
gatgttgtta acacgaaagg agactgtacg gagtcatttg tctacctgac caatttcaag     600
gataactctc taattgtcta cgatgagaca caaaagaaag cttggaaatt tacagataaa     660
```

```
acatttgaag ctgataagga atccacgttc tcctactcgg gagaggaaca aatgaagtac      720
aaagttggtc ttttgggat agctctgggt gatagggatg aaatggggca tcgtcctgcc       780
tactatatcg ctgggagtag caccaaagtc tacagtgtta acactaaaga actcaaaaca      840
gagaatggtc agttaaatcc tcagcttcac ggtgatcgtg gaaagtacac ggatgcaatt     900
gccctagccc acgatcctga gcataaagtc ctctactttg ctgaatccga cagcaggcag     960
gtgtcctgtt ggaatgtaga tatggagcta aaaccagaca atacggatgt gatcttctct    1020
agtgcccgtt ttacttttgg aacggatatt ttggttgata gcaagggaat gctgtggata    1080
atggctaatg gacatccacc agtagaggat caagagaaga tttggaagat gagattcgta    1140
aaccggaaga tcagtattat gaaagtggat acggaacgtg tattcaaata ttcacgctgc    1200
aatccaaatt ataagccccc gaaagaaatt gaagtttga                          1239
```

<210> SEQ ID NO 17
<211> LENGTH: 394
<212> TYPE: PRT
<213> ORGANISM: Lutzomyia longipalpis

<400> SEQUENCE: 17

```
Ala Tyr Val Glu Ile Gly Tyr Ser Leu Arg Asn Ile Thr Phe Asp Gly
1               5                   10                  15

Leu Asp Thr Asp Asp Tyr Asn Pro Lys Phe Asn Ile Pro Thr Gly Leu
            20                  25                  30

Ala Val Asp Pro Glu Gly Tyr Arg Leu Phe Ile Ala Ile Pro Arg Arg
        35                  40                  45

Lys Pro Lys Val Pro Tyr Thr Val Ala Glu Leu Asn Met Val Met Asn
    50                  55                  60

Pro Gly Phe Pro Val Glu Arg Ala Pro Ser Phe Lys Phe Lys Lys
65                  70                  75                  80

Phe Asn Gly Glu Gly Lys Lys Asp Leu Val Asn Val Tyr Gln Pro Val
                85                  90                  95

Ile Asp Asp Cys Arg Arg Leu Trp Val Leu Asp Ile Gly Lys Val Glu
            100                 105                 110

Tyr Thr Gly Gly Asp Ala Asp Gln Tyr Pro Lys Gly Lys Pro Thr Leu
        115                 120                 125

Ile Ala Tyr Asp Leu Lys Lys Asp His Thr Pro Glu Ile His Arg Phe
    130                 135                 140

Glu Ile Pro Asp Asp Leu Tyr Ser Ser Gln Val Glu Phe Gly Gly Phe
145                 150                 155                 160

Ala Val Asp Val Val Asn Thr Lys Gly Asp Cys Thr Glu Ser Phe Val
                165                 170                 175

Tyr Leu Thr Asn Phe Lys Asp Asn Ser Leu Ile Val Tyr Asp Glu Thr
            180                 185                 190

Gln Lys Lys Ala Trp Lys Phe Thr Asp Lys Thr Phe Glu Ala Asp Lys
        195                 200                 205

Glu Ser Thr Phe Ser Tyr Ser Gly Glu Glu Gln Met Lys Tyr Lys Val
    210                 215                 220

Gly Leu Phe Gly Ile Ala Leu Gly Asp Arg Asp Glu Met Gly His Arg
225                 230                 235                 240

Pro Ala Tyr Tyr Ile Ala Gly Ser Ser Thr Lys Val Tyr Ser Val Asn
                245                 250                 255

Thr Lys Glu Leu Lys Thr Glu Asn Gly Gln Leu Asn Pro Gln Leu His
            260                 265                 270
```

-continued

```
Gly Asp Arg Gly Lys Tyr Thr Asp Ala Ile Ala Leu Ala His Asp Pro
        275                 280                 285

Glu His Lys Val Leu Tyr Phe Ala Glu Ser Asp Ser Arg Gln Val Ser
    290                 295                 300

Cys Trp Asn Val Asp Met Glu Leu Lys Pro Asp Asn Thr Asp Val Ile
305                 310                 315                 320

Phe Ser Ser Ala Arg Phe Thr Phe Gly Thr Asp Ile Leu Val Asp Ser
                325                 330                 335

Lys Gly Met Leu Trp Ile Met Ala Asn Gly His Pro Pro Val Glu Asp
            340                 345                 350

Gln Glu Lys Ile Trp Lys Met Arg Phe Val Asn Arg Lys Ile Ser Ile
        355                 360                 365

Met Lys Val Asp Thr Glu Arg Val Phe Lys Tyr Ser Arg Cys Asn Pro
    370                 375                 380

Asn Tyr Lys Pro Pro Lys Glu Ile Glu Val
385                 390

<210> SEQ ID NO 18
<211> LENGTH: 1185
<212> TYPE: DNA
<213> ORGANISM: Lutzomyia longipalpis

<400> SEQUENCE: 18
gcttatgtgg aaataggata ttctctgaga aatattacat tcgatggatt ggatacagat      60
gactacaatc caaagttcaa cattccaacg ggtttggcag ttgatcccga aggatatagg     120
ctcttcatag ccatcccaag gagaaagcca aaggttccct acactgtggc tgaactgaat     180
atggtcatga atcccggatt tcccgtcgag agagctccga gctttgagaa attcaaaaaa     240
ttcaatggcg agggcaaaaa ggatcttgtt aatgtgtatc agccagtcat tgatgattgt     300
cgtcgtcttt gggtgcttga cattgggaag gtggaataca ccggtggtga tgctgatcaa     360
tatcccaaag gaaagcctac cctaattgcc tacgacctca agaaggatca tactccggaa     420
attcatcgat ttgaaattcc agacgatctc tatagctcac aagttgaatt tggtggattt     480
gccgttgatg ttgttaacac gaaaggagac tgtacggagt catttgtcta cctgaccaat     540
ttcaaggata actctctaat tgtctacgat gagacacaaa agaaagcttg gaaatttaca     600
gataaaacat ttgaagctga taaggaatcc acgttctcct actcgggaga ggaacaaatg     660
aagtacaaag ttggtctttt tgggatagct ctgggtgata gggatgaaat ggggcatcgt     720
cctgcctact atatcgctgg gagtagcacc aaagtctaca gtgttaacac taaagaactc     780
aaaacagaga atggtcagtt aaatcctcag cttcacggtg atcgtggaaa gtacacggat     840
gcaattgccc tagcccacga tcctgagcat aaagtcctct actttgctga atccgacagc     900
aggcaggtgt cctgttggaa tgtagatatg gagctaaaac cagacaatac ggatgtgatc     960
ttctctagtg cccgttttac ttttggaacg gatattttgg ttgatagcaa gggaatgctg    1020
tggataatgg ctaatggaca tccaccagta gaggatcaag agaagatttg gaagatgaga    1080
ttcgtaaacc ggaagatcag tattatgaaa gtggatacgg aacgtgtatt caaatattca    1140
cgctgcaatc caaattataa gcccccgaaa gaaattgaag tttga                    1185

<210> SEQ ID NO 19
<211> LENGTH: 6247
<212> TYPE: DNA
<213> ORGANISM: Artificial
<220> FEATURE:
<223> OTHER INFORMATION: nucleic acid sequence of one strand of the
      plasmid pNBO002
```

<400> SEQUENCE: 19

```
ttggctattg gccattgcat acgttgtatc catatcataa tatgtacatt tatattggct      60
catgtccaac attaccgcca tgttgacatt gattattgac tagttattaa tagtaatcaa     120
ttacggggtc attagttcat agcccatata tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtgatg cggttttggc     480
agtacatcaa tgggcgtgga tagcggtttg actcacgggg atttccaagt ctccacccca     540
ttgacgtcaa tgggagtttg ttttggcacc aaaatcaacg ggactttcca aaatgtcgta     600
acaactccgc cccattgacg caaatgggcg gtaggcgtgt acggtgggag gtctatataa     660
gcagagctcg tttagtgaac cgtcagatcg cctggagacg ccatccacgc tgttttgacc     720
tccatagaag acaccgggac cgatccagcc tccgcggccg gaacggtgc attggaacgc      780
ggattccccg tgccaagagt gacgtaagta ccgcctatag agtctatagg cccacccct      840
tggcttctta tgcatgctat actgttttg gcttggggtc tatacacccc cgcttcctca      900
tgttataggt gatggtatag cttagcctat aggtgtgggt tattgaccat tattgaccac     960
tccctattg gtgacgatac tttccattac taatccataa catggctctt tgccacaact    1020
ctctttattg gctatatgcc aatacactgt ccttcagaga ctgacacgga ctctgtattt    1080
ttacaggatg gggtctcatt tattattac aaattcacat atacaacacc accgtcccca    1140
gtgcccgcag tttttattaa acataacgtg ggatctccac gcgaatctcg ggtacgtgtt    1200
ccggacatgg gctcttctcc ggtagcggcg gagcttctac atccgagccc tgctcccatg    1260
cctccagcga ctcatggtcg ctcggcagct ccttgctcct aacagtggag gccagactta    1320
ggcacagcac gatgcccacc accaccagtg tgccgcacaa ggccgtggcg gtagggtatg    1380
tgtctgaaaa tgagctcggg gagcgggctt gcaccgctga cgcatttgga agacttaagg    1440
cagcggcaga agaagatgca ggcagctgag ttgttgtgtt ctgataagag tcagaggtaa    1500
ctcccgttgc ggtgctgtta acggtggagg gcagtgtagt ctgagcagta ctcgttgctg    1560
ccgcgcgcgc caccagacat aatagctgac agactaacag actgttcctt tccatgggtc    1620
ttttctcacg tcaccgtcgt cgaccagagc tgagatccta caggagtcca gggctggaga    1680
gaaaacctct gcgaggaaag ggaaggagca agccgtgaat ttaagggacg ctgtgaagca    1740
atcatggatg caatgaagag agggctctgc tgtgtgctgc tgctgtgtgg agcagtcttc    1800
gtttcgccca gcggtaccgg atccacccctt gcttatgtgg aaataggata ttctctgaga    1860
aatattacat tcgatggatt ggatacagat gactacaatc caaagttcaa cattccaacg    1920
ggtttggcag ttgatcccga aggatatagg ctcttcatag ccatcccaag gagaaagcca    1980
aaggttccct acactgtggc tgaactgaat atggtcatga atcccggatt tcccgtcgag    2040
agagctccga gctttgagaa attcaaaaaa ttcaatggcg agggcaaaaa ggatcttgtt    2100
aatgtgtatc agccagtcat tgatgattgt cgtcgtcttt gggtgcttga cattgggaag    2160
gtggaataca ccggtggtga tgctgatcaa tatcccaaag gaaagcctac cctaattgcc    2220
tacgacctca agaaggatca tactccggaa attcatcgat ttgaaattcc agacgatctc    2280
tatagctcac aagttgaatt tggtggattt gccgttgatg ttgttaacac gaaaggagac    2340
```

```
tgtacggagt catttgtcta cctgaccaat ttcaaggata actctctaat tgtctacgat    2400
gagacacaaa agaaagcttg gaaatttaca gataaaacat ttgaagctga taaggaatcc    2460
acgttctcct actcgggaga ggaacaaatg aagtacaaag ttggtctttt tgggatagct    2520
ctgggtgata gggatgaaat ggggcatcgt cctgcctact atatcgctgg gagtagcacc    2580
aaagtctaca gtgttaacac taaagaactc aaaacagaga atggtcagtt aaatcctcag    2640
cttcacggtg atcgtggaaa gtacacggat gcaattgccc tagcccacga tcctgagcat    2700
aaagtcctct actttgctga atccgacagc aggcaggtgt cctgttggaa tgtagatatg    2760
gagctaaaac cagacaatac ggatgtgatc ttctctagtg cccgttttac ttttggaacg    2820
gatattttgg ttgatagcaa gggaatgctg tggataatgg ctaatggaca tccaccagta    2880
gaggatcaag agaagatttg gaagatgaga ttcgtaaacc ggaagatcag tattatgaaa    2940
gtggatacgg aacgtgtatt caaatattca cgctgcaatc caaattataa gcccccgaaa    3000
gaaattgaag tttgaaaggg atccagatct gctgtgcctt ctagttgcca gccatctgtt    3060
gtttgcccct cccccgtgcc ttccttgacc ctggaaggtg ccactcccac tgtcctttcc    3120
taataaaatg aggaaattgc atcgcattgt ctgagtaggt gtcattctat tctgggggt     3180 ggggtggggc agcacagcaa gggggaggat tgggaagaca atagcaggca tgctggggat    3240
gcggtgggct ctatgggtac ccaggtgctg aagaattgac ccggttcctc ctgggccaga    3300
aagaagcagg cacatcccct tctctgtgac acaccctgtc cacgcccctg gttcttagtt    3360
ccagccccac tcataggaca ctcatagctc aggagggctc cgccttcaat cccacccgct    3420
aaagtacttg gagcggtctc tccctccctc atcagcccac caaaccaaac ctagcctcca    3480
agagtgggaa gaaattaaag caagataggc tattaagtgc agagggagag aaaatgcctc    3540
caacatgtga ggaagtaatg agagaaatca tagaatttct tccgcttcct cgctcactga    3600
ctcgctgcgc tcggtcgttc ggctgcggcg agcggtatca gctcactcaa aggcggtaat    3660
acggttatcc acagaatcag gggataacgc aggaaagaac atgtgagcaa aaggccagca    3720
aaaggccagg aaccgtaaaa aggccgcgtt gctggcgttt ttccataggc tccgcccccc    3780
tgacgagcat cacaaaaatc gacgctcaag tcagaggtgg cgaaacccga caggactata    3840
aagataccag gcgtttcccc ctggaagctc cctcgtgcgc tctcctgttc cgaccctgcc    3900
gcttaccgga tacctgtccg cctttctccc ttcgggaagc gtggcgcttt ctcaatgctc    3960
acgctgtagg tatctcagtt cggtgtaggt cgttcgctcc aagctgggct gtgtgcacga    4020
accccccgtt cagcccgacc gctgcgcctt atccggtaac tatcgtcttg agtccaaccc    4080
ggtaagacac gacttatcgc cactggcagc agccactggt aacaggatta gcagagcgag    4140
gtatgtaggc ggtgctacag agttcttgaa gtggtggcct aactacggct acactagaag    4200
gacagtattt ggtatctgcg ctctgctgaa gccagttacc ttcggaaaaa gagttggtag    4260
ctcttgatcc ggcaaacaaa ccaccgctgg tagcggtggt ttttttgttt gcaagcagca    4320
gattacgcgc agaaaaaaag gatctcaaga agatcctttg atcttttcta cggggtctga    4380
cgctcagtgg aacgaaaact cacgttaagg gattttggtc atgagattat caaaaaggat    4440
cttcacctag atccttttaa attaaaaatg aagttttaaa tcaatctaaa gtatatatga    4500
gtaaacttgg tctgacagtt accaatgctt aatcagtgag gcacctatct cagcgatctg    4560
tctatttcgt tcatccatag ttgcctgact ccggggggg gggcgctga ggtctgcctc     4620 gtgaagaagg tgttgctgac tcataccagg cctgaatcgc cccatcatcc agccagaaag    4680
tgagggagcc acggttgatg agagctttgt tgtaggtgga ccagttggtg attttgaact    4740
```

```
tttgctttgc cacggaacgg tctgcgttgt cgggaagatg cgtgatctga tccttcaact    4800
cagcaaaagt tcgatttatt caacaaagcc gccgtcccgt caagtcagcg taatgctctg    4860
ccagtgttac aaccaattaa ccaattctga ttagaaaaac tcatcgagca tcaaatgaaa    4920
ctgcaattta ttcatatcag gattatcaat accatatttt tgaaaagcc gtttctgtaa     4980 tgaaggagaa aactcaccga ggcagttcca taggatggca agatcctggt atcggtctgc    5040
gattccgact cgtccaacat caatacaacc tattaatttc ccctcgtcaa aaataaggtt    5100
atcaagtgag aaatcaccat gagtgacgac tgaatccggt gagaatggca aaagcttatg    5160
catttctttc cagacttgtt caacaggcca gccattacgc tcgtcatcaa aatcactcgc    5220
atcaaccaaa ccgttattca ttcgtgattg cgcctgagcg agacgaaata cgcgatcgct    5280
gttaaaagga caattacaaa caggaatcga atgcaaccgg cgcaggaaca ctgccagcgc    5340
atcaacaata ttttcacctg aatcaggata ttcttctaat acctggaatg ctgttttccc    5400
ggggatcgca gtggtgagta accatgcatc atcaggagta cggataaaat gcttgatggt    5460
cggaagaggc ataaattccg tcagccagtt tagtctgacc atctcatctg taacatcatt    5520
ggcaacgcta cctttgccat gtttcagaaa caactctggc gcatcgggct tcccatacaa    5580
tcgatagatt gtcgcacctg attgcccgac attatcgcga gcccatttat acccatataa    5640
atcagcatcc atgttggaat ttaatcgcgg cctcgagcaa gacgtttccc gttgaatatg    5700
gctcataaca ccccttgtat tactgtttat gtaagcagac agttttattg ttcatgatga    5760 tatatttta tcttgtgcaa tgtaacatca gagattttga gacacaacgt ggctttcccc    5820 cccccccat tattgaagca tttatcaggg ttattgtctc atgagcggat acatatttga    5880
atgtatttag aaaaataaac aaataggggt tccgcgcaca tttcccgaa aagtgccacc    5940 tgacgtctaa gaaaccatta ttatcatgac attaacctat aaaaataggc gtatcacgag    6000 gcccttcgt ctcgcgcgtt tcggtgatga cggtgaaaac ctctgacaca tgcagctccc    6060
ggagacggtc acagcttgtc tgtaagcgga tgccgggagc agacaagccc gtcagggcgc    6120
gtcagcgggt gttggcgggt gtcggggctg gcttaactat gcggcatcag agcagattgt    6180
actgagagtg caccatatgc ggtgtgaaat accgcacaga tgcgtaagga gaaaataccg    6240
catcaga                                                              6247
```

<210> SEQ ID NO 20
<211> LENGTH: 5899
<212> TYPE: DNA
<213> ORGANISM: Artificial
<220> FEATURE:
<223> OTHER INFORMATION: nucleic acid sequence of one strand of the
      plasmid pNBO003

<400> SEQUENCE: 20

```
ttggctattg gccattgcat acgttgtatc catatcataa tatgtacatt tatattggct      60
catgtccaac attaccgcca tgttgacatt gattattgac tagttattaa tagtaatcaa     120
ttacggggtc attagttcat agcccatata tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtgatg cggttttggc     480
```

```
agtacatcaa tgggcgtgga tagcggtttg actcacgggg atttccaagt ctccacccca    540
ttgacgtcaa tgggagtttg ttttggcacc aaaatcaacg ggactttcca aaatgtcgta    600
acaactccgc cccattgacg caaatgggcg gtaggcgtgt acggtgggag gtctatataa    660
gcagagctcg tttagtgaac cgtcagatcg cctggagacg ccatccacgc tgttttgacc    720
tccatagaag acaccgggac cgatccagcc tccgcggccg ggaacggtgc attggaacgc    780
ggattccccg tgccaagagt gacgtaagta ccgcctatag agtctatagg cccaccccct    840
tggcttctta tgcatgctat actgtttttg gcttggggtc tatacacccc cgcttcctca    900
tgttataggt gatggtatag cttagcctat aggtgtgggt tattgaccat tattgaccac    960
tcccctattg gtgacgatac tttccattac taatccataa catggctctt gccacaact    1020
ctctttattg gctatatgcc aatacactgt ccttcagaga ctgacacgga ctctgtattt   1080
ttacaggatg gggtctcatt tattatttac aaattcacat atacaacacc accgtcccca   1140
gtgcccgcag ttttattaa acataacgtg ggatctccac gcgaatctcg ggtacgtgtt    1200
ccggacatgg gctcttctcc ggtagcggcg gagcttctac atccgagccc tgctcccatg   1260
cctccagcga ctcatggtcg ctcggcagct ccttgctcct aacagtggag gccagactta   1320
ggcacagcac gatgcccacc accaccagtg tgccgcacaa ggccgtggcg gtagggtatg   1380
tgtctgaaaa tgagctcggg gagcgggctt gcaccgctga cgcatttgga agacttaagg   1440
cagcggcaga agaagatgca ggcagctgag ttgttgtgtt ctgataagag tcagaggtaa   1500
ctcccgttgc ggtgctgtta acggtggagg cagtgtagt ctgagcagta ctcgttgctg    1560
ccgcgcgcgc caccagacat aatagctgac agactaacag actgttcctt tccatgggtc   1620
ttttctcacg tcaccgtcgt cgaccagagc tgagatccta caggagtcca gggctggaga   1680
gaaaacctct gcgaggaaag ggaaggagca agccgtgaat ttaagggacg ctgtgaagca   1740
atcatggatg caatgaagag agggctctgc tgtgtgctgc tgctgtgtgg agcagtcttc   1800
gtttcgccca gcggtaccgg atccaccctt gatggtgatg aatatttcat tggaaaatac   1860
aaagaaaaag atgagacact gttttttgca agctacggcc taaagaggga tccttgccag   1920
attgtcttag gctacaaatg ctcaaacaat caaacccact tgtgcttaa ttttaaaacc     1980
aataagaaat cctgcatatc agcaattaag ctgacttctt acccaaaaat caatcaaaac   2040
tcggatttaa ctagaaatct ctactgccaa actggaggaa taggaacaga taactgcaaa   2100
cttgtcttca agaaacgtaa aagacaaata gcagctaata ttgaaatcta cggcattcca   2160
gcgaagaaat gttccttcaa ggatcgttac attggagctg atcccactcca cgtcgattcc   2220
tatgggcttt cgtatcagtt tgatcaggaa catggatgga atttggaacg aaataacatt   2280
ttcaaagaca caagattttc cacagaagtt ttctaccaca aaaatggttt atttaacacc   2340
caaataactt atttggctga agaagattcc ttctctgaag ctcgagagat tactgcgaag   2400
gatattaaga agaagttttc aattattttg cccaatgaag agtataagag gattagtttc   2460
ttggacgttt attggttcca ggagactatg cgaaaaagc ctaaatatcc ctacattcac    2520
tacaatggag aatgcagcaa tgagaataaa acttgtgaac ttgtctttga caccgatgaa   2580
ctaatgacct acgcccttgt taaagtcttt actaatcctg agagtgatgg atctaggctc   2640
aaagaagagg atttgggaag aggataaaag ggatccagat ctgctgtgcc ttctagttgc   2700
cagccatctg ttgtttgccc ctccccgtg ccttccttga ccctggaagg tgccactccc    2760
actgtccttt cctaataaaa tgaggaaatt gcatcgcatt gtctgagtag gtgtcattct   2820
attctggggg gtggggtggg gcagcacagc aagggggagg attgggaaga caatagcagg   2880
```

```
catgctgggg atgcggtggg ctctatgggt acccaggtgc tgaagaattg acccggttcc    2940
tcctgggcca gaaagaagca ggcacatccc cttctctgtg acacaccctg tccacgcccc    3000
tggttcttag ttccagcccc actcatagga cactcatagc tcaggagggc tccgccttca    3060
atcccacccg ctaaagtact tggagcggtc tctccctccc tcatcagccc accaaaccaa    3120
acctagcctc caagagtggg aagaaattaa agcaagatag gctattaagt gcagagggag    3180
agaaaatgcc tccaacatgt gaggaagtaa tgagagaaat catagaattt cttccgcttc    3240
ctcgctcact gactcgctgc gctcggtcgt tcggctgcgg cgagcggtat cagctcactc    3300
aaaggcggta atacggttat ccacagaatc agggggataac gcaggaaaga acatgtgagc    3360
aaaaggccag caaaaggcca ggaaccgtaa aaaggccgcg ttgctggcgt ttttccatag    3420
gctccgcccc cctgacgagc atcacaaaaa tcgacgctca agtcagaggt ggcgaaaccc    3480
gacaggacta taaagatacc aggcgtttcc ccctggaagc tccctcgtgc gctctcctgt    3540
tccgaccctg ccgcttaccg gatacctgtc cgcctttctc ccttcgggaa gcgtggcgct    3600
ttctcaatgc tcacgctgta ggtatctcag ttcggtgtag gtcgttcgct ccaagctggg    3660
ctgtgtgcac gaaccccccg ttcagcccga ccgctgcgcc ttatccggta actatcgtct    3720
tgagtccaac ccggtaagac acgacttatc gccactggca gcagccactg gtaacaggat    3780
tagcagagcg aggtatgtag gcggtgctac agagttcttg aagtggtggc ctaactacgg    3840
ctacactaga aggacagtat ttggtatctg cgctctgctg aagccagtta ccttcggaaa    3900
aagagttggt agctcttgat ccggcaaaca aaccaccgct ggtagcggtg gtttttttgt    3960
ttgcaagcag cagattacgc gcagaaaaaa aggatctcaa gaagatcctt tgatcttttc    4020
tacggggtct gacgctcagt ggaacgaaaa ctcacgttaa gggattttgg tcatgagatt    4080
atcaaaaagg atcttcacct agatcctttt aaattaaaaa tgaagtttta atcaatcta    4140 aagtatatat gagtaaactt ggtctgacag ttaccaatgc ttaatcagtg aggcacctat    4200
ctcagcgatc tgtctatttc gttcatccat agttgcctga ctccgggggg gggggcgct    4260 gaggtctgcc tcgtgaagaa ggtgttgctg actcatacca ggcctgaatc gccccatcat    4320
ccagccagaa agtgagggag ccacggttga tgagagcttt gttgtaggtg gaccagttgg    4380
tgattttgaa cttttgcttt gccacggaac ggtctgcgtt gtcgggaaga tgcgtgatct    4440
gatccttcaa ctcagcaaaa gttcgattta ttcaacaaag ccgccgtccc gtcaagtcag    4500
cgtaatgctc tgccagtgtt acaaccaatt aaccaattct gattagaaaa actcatcgag    4560
catcaaatga aactgcaatt tattcatatc aggattatca ataccatatt tttgaaaaag    4620
ccgtttctgt aatgaaggag aaaactcacc gaggcagttc cataggatgg caagatcctg    4680
gtatcggtct gcgattccga ctcgtccaac atcaatacaa cctattaatt tcccctcgtc    4740
aaaaataagg ttatcaagtg agaaatcacc atgagtgacg actgaatccg gtgagaatgg    4800
caaaagctta tgcatttctt tccagacttg ttcaacaggc cagccattac gctcgtcatc    4860
aaaatcactc gcatcaacca accgttatt cattcgtgat tgcgcctgag cgagacgaaa    4920
tacgcgatcg ctgttaaaag gacaattaca acaggaatc gaatgcaacc ggcgcaggaa    4980
cactgccagc gcatcaacaa tattttcacc tgaatcagga tattcttcta atacctggaa    5040
tgctgttttc ccggggatcg cagtggtgag taaccatgca tcatcaggag tacggataaa    5100
atgcttgatg gtcggaagag gcataaattc cgtcagccag tttagtctga ccatctcatc    5160
tgtaacatca ttggcaacgc tacctttgcc atgtttcaga aacaactctg gcgcatcggg    5220
cttcccatac aatcgataga ttgtcgcacc tgattgcccg acattatcgc gagcccattt    5280
```

-continued

```
atacccatat aaatcagcat ccatgttgga atttaatcgc ggcctcgagc aagacgtttc   5340
ccgttgaata tggctcataa caccccttgt attactgttt atgtaagcag acagttttat   5400
tgttcatgat gatatatttt tatcttgtgc aatgtaacat cagagatttt gagacacaac   5460
gtggctttcc cccccccccc attattgaag catttatcag ggttattgtc tcatgagcgg   5520
atacatattt gaatgtattt agaaaaataa acaaataggg gttccgcgca catttccccg   5580
aaaagtgcca cctgacgtct aagaaaccat tattatcatg acattaacct ataaaaatag   5640
gcgtatcacg aggccctttc gtctcgcgcg tttcggtgat gacggtgaaa acctctgaca   5700
catgcagctc ccggagacgg tcacagcttg tctgtaagcg gatgccggga gcagacaagc   5760
ccgtcagggc gcgtcagcgg gtgttggcgg gtgtcggggc tggcttaact atgcggcatc   5820
agagcagatt gtactgagag tgcaccatat gcggtgtgaa ataccgcaca gatgcgtaag   5880
gagaaaatac cgcatcaga                                                 5899
```

<210> SEQ ID NO 21
<211> LENGTH: 1239
<212> TYPE: DNA
<213> ORGANISM: Artificial
<220> FEATURE:
<223> OTHER INFORMATION: codon-optimized nucleic acid sequence for mammalian expression (unprocessed LJM17 protein from Lutzomyia longipalpis)

<400> SEQUENCE: 21

```
tcacacttcg atttctttgg ggggcttgta gttggggttg caccggctgt acttgaacac     60
ccgctcggtg tccaccttca tgatccggat cttccggttc acgaaccgca tcttccagat    120
cttttcctgg tcctccacgg gggggtggcc gttggccatg atccacagca tgcccttgct    180
gtccaccagg atgtcggtgc cgaaggtgaa ccgggcgctg ctgaagatca cgtcggtgtt    240
gtcgggcttc agttccatgt tcacgttcca gcaggacacc tgccggctgt cgctctcggc    300
gaagtacagc accttgtgct cggggtcgta ggccagggca atggcgtcgg tgtacttgcc    360
ccggtcgccg tgcagctggg ggttcagctg gccgttctcg gttttcagct ctttggtatt    420
cacgctgtac accttggtgc tgctgccggc gatgtagcag gcgggcctgt ggcccatctc    480
gtcccggtcg cccagggcga tgccgaacag gcccactttg tacttcatct gttcctcgcc    540
gctgtagctg aaggtgctct ctttgtcggc ctcgaaggtc ttgtcggtga acttccaggc    600
cttcttctgg gtctcgtcgt acacgatcag gctgttgtcc ttgaagttgg tcaggtacac    660
gaagctctcg gtgcagtcgc ccttggtgtt caccacgtcc acggcaaagc cgccgaactc    720
cacctggctg ctgtacaggt cgtcggggat ctcgaaccgg tggatctcgg gggtgtggtc    780
cttcttcagg tcgtaggcga tcagggtggg cttgcccttg gggtactggt cggcgtcgcc    840
gcctgtgtac tccaccttgc cgatgtccag cacccacagc cgcctgcagt cgtcgatcac    900
gggctggtac acgttcacca ggtctttctt gccctcgccg ttaaacttct tgaacttctc    960
gaagctgggg gccctctcca cggggaagcc ggggttcatc accatgttca gctcggccac   1020
ggtgtagggc accttgggct tccgcctggg gatggcgatg aacagccggt agccctcggg   1080
gtccacggcc aggccggtgg ggatgttgaa cttggggttg tagtcgtcgg tgtccaggcc   1140
gtcgaaggtg atgttccgca ggctgtagcc gatctccacg taggcgccgt ggatgccctg   1200
gaacagcacg atggccagga acacgaagaa gaaccgcat                          1239
```

<210> SEQ ID NO 22
<211> LENGTH: 906
<212> TYPE: DNA

<213> ORGANISM: Artificial
<220> FEATURE:
<223> OTHER INFORMATION: codon-optimized nucleic acid sequence for
      mammalian expression (unprocessed LJL143 protein from Lutzomyia
      longipalpis)

<400> SEQUENCE: 22

```
atgaacagca tcaactttct gagcatcgtg ggcctgatca gcttcggctt catcgtggcc    60
gtgaagtgcg acggcgacga gtacttcatc ggcaagtaca agagaagga cgagaccctg   120
ttcttcgcca gctacggcct gaagcgggac ccctgccaga tcgtgctggg ctacaagtgc   180
agcaacaacc agacccactt cgtgctgaac ttcaagacca caagaagag ctgcatcagc   240
gccatcaagc tgaccagcta ccccaagatc aaccagaaca gcgacctgac caagaacctg   300
tactgccaga ccggcggcat cggcaccgac aactgcaagc tggtgttcaa gaagcggaag   360
cggcagatcg ccgccaacat cgagatctac ggcatccccg ccaagaagtg cagcttcaag   420
gaccggtaca tcggcgccga ccccctgcac gtggactcct acggcctgcc ctaccagttc   480
gaccaggaac acggctggaa cgtcgagcgg tacaacatct tcaaggacac ccggttcagc   540
accgaggtgt tctaccacaa gaacggcctg ttcaacaccc agatcaccta cctggccgaa   600
gaggacagct tcagcgaggc ccgggagatc accgccaagg acatcaagaa gaagttcagc   660
atcatcctgc ccaacgagga atacaagcgg atcagcttcc tggacgtgta ctggttccag   720
gaaaccatgc ggaagaagcc caagtacccc tacatccact acaacggcga gtgctccaac   780
gagaacaaga cctgcgaact ggtgttcgac accgacgagc tgatgaccta cgccctggtg   840
aaggtgttca ccaaccccga gagcgacggc agccggctga agaagagga cctgggcagg   900
ggctga                                                             906
```

<210> SEQ ID NO 23
<211> LENGTH: 271
<212> TYPE: PRT
<213> ORGANISM: Lutzomyia longipalpis

<400> SEQUENCE: 23

```
Met Leu Gln Ile Lys His Leu Leu Ile Phe Val Gly Leu Leu Val Val
1               5                   10                  15

Val Asn Ala Gln Ser Asn Tyr Cys Lys Gln Glu Ser Cys Ser Ser Gly
            20                  25                  30

Gly Val Glu Arg Pro His Ile Gly Cys Lys Asn Ser Gly Asp Phe Ser
        35                  40                  45

Glu Thr Cys Ser Gly Asp Ala Glu Ile Val Lys Met Asp Lys Lys
    50                  55                  60

Gln Asn Leu Leu Val Lys Met His Asn Arg Leu Arg Asp Arg Phe Ala
65                  70                  75                  80

Arg Gly Ala Val Pro Gly Phe Ala Pro Ala Ala Lys Met Pro Met Leu
                85                  90                  95

Lys Trp Asn Asp Glu Leu Ala Lys Leu Ala Glu Tyr Asn Val Arg Thr
            100                 105                 110

Cys Lys Phe Ala His Asp Lys Cys Arg Ala Ile Asp Val Cys Pro Tyr
        115                 120                 125

Ala Gly Gln Asn Leu Ala Gln Met Met Ser Tyr Pro Thr His Arg Asp
    130                 135                 140

Leu Asn Tyr Val Leu Lys Asn Leu Thr Arg Glu Trp Phe Trp Glu Tyr
145                 150                 155                 160

Arg Trp Ala Lys Gln Ser Gln Leu Asp Asn Tyr Val Gly Gly Pro Gly
                165                 170                 175
```

```
Lys Asp Asn Lys Gln Ile Gly His Phe Thr Ala Phe Val His Glu Lys
            180                 185                 190
Thr Asp Lys Val Gly Cys Ala Ile Ala Arg Phe Thr Asn Glu His Asn
        195                 200                 205
Phe Lys Glu Thr Leu Leu Ala Cys Asn Tyr Cys Tyr Thr Asn Met Met
    210                 215                 220
Lys Glu Arg Ile Tyr Thr Gln Gly Lys Pro Cys Ser Gln Cys Gln Ser
225                 230                 235                 240
Lys Lys Cys Gly Pro Val Tyr Lys Asn Leu Cys Asp Pro Ser Glu Lys
                245                 250                 255
Val Asp Pro Thr Pro Asp Val Leu Lys Gln Trp Lys His Gly Lys
            260                 265                 270

<210> SEQ ID NO 24
<211> LENGTH: 905
<212> TYPE: DNA
<213> ORGANISM: Lutzomyia longipalpis

<400> SEQUENCE: 24
agttgtggag cttttggtca ttttacgtga tgttgcaaat taaacatctt ctgattttttg      60
tgggattgct cgtggttgtt aatgcacaga gcaattactg caaacaggaa tcgtgctcat     120
cgggaggtgt tgagagaccc catattgggt gcaaaaactc tggagatttt ccgaaacttt     180
gctccggaga tgcagaaatt gttaagatgg acaagaagaa gcagaaccttc cttgtgaaaa     240
tgcacaatcg cctgagagat agatttgctc gtggtgcagt gccaggtttt gcaccagctg     300
cgaaaatgcc aatgcttaaa tggaacgatg aactggccaa attggcagag tacaacgtga     360
gaacgtgcaa atttgcccac gataaatgcc gcgcaattga tgtctgcccc tatgctggac     420
agaatctagc tcaaatgatg tcctatccta cccatcgaga tctaaactat gttcttaaga     480
atctcacaag ggaatggttc tgggagtaca gatgggctaa gcaatctcag cttgataatt     540
acgtgggtgg tcctgggaaa gacaacaaac aaattggaca tttcacagct tttgtgcatg     600
agaaaacaga caaagttgga tgcgctatag ctcgatttac aaatgagcac aattttaagg     660
agaccctcct agcttgcaac tactgctaca cgaatatgat gaaggagagg atctacacgc     720
agggaaaacc ttgttcacag tgtcagagca aaaagtgtgg gccagtctac aagaaccctgt     780
gtgatccttc ggagaaggtt gatccaactc ctgatgtcct taagcaatgg aagcatggaa     840
aatgattatt aagctcactt caaatgtttc caatccaaaa aaaaaaaaaa aaaaaaaaa     900
aaaaa                                                                905

<210> SEQ ID NO 25
<211> LENGTH: 159
<212> TYPE: PRT
<213> ORGANISM: Lutzomyia longipalpis

<400> SEQUENCE: 25

Met Leu Leu Arg Ser Leu Phe Val Leu Phe Leu Ile Phe Leu Thr Phe
1               5                   10                  15
Cys Asn Ala Glu Glu Glu Leu Ile Glu Arg Lys Leu Thr Gly Lys Thr
            20                  25                  30
Ile Tyr Ile Ser Thr Ile Lys Leu Pro Trp Phe Gln Ala Leu Asn His
        35                  40                  45
Cys Val Lys Asn Gly Tyr Thr Met Val Ser Ile Lys Thr Phe Glu Glu
    50                  55                  60
Asn Lys Glu Leu Leu Lys Glu Leu Lys Arg Val Ile Arg Thr Glu Asp
```

```
                 65                  70                  75                  80
Thr Gln Val Trp Ile Gly Gly Leu Lys His His Gln Phe Ala Asn Phe
                 85                  90                  95

Arg Trp Val Ser Asp Gly Ser His Val Ala Thr Ala Ser Gly Tyr Thr
                100                 105                 110

Asn Trp Ala Pro Gly Glu Pro Ala Asp Ser Phe Tyr Tyr Asp Gln Phe
                115                 120                 125

Cys Met Ala Met Leu Phe Arg Lys Asp Gly Ala Pro Trp Asp Asp Leu
            130                 135                 140

Asn Cys Trp Val Lys Asn Leu Phe Val Cys Glu Lys Arg Asp Asp
145                 150                 155

<210> SEQ ID NO 26
<211> LENGTH: 617
<212> TYPE: DNA
<213> ORGANISM: Lutzomyia longipalpis

<400> SEQUENCE: 26
ttttgagaaa aacatttcct tgtgagttaa atagttggta aattaaatca agagaatgtt      60
gcttcgttcc ttgtttgttc tttttctaat tttcttaaca ttctgcaacg ctgaggaaga     120
acttattgag agaaagttaa caggaaaaac gatctatatc tcaacaataa agcttccgtg     180
gttccaagct cttaatcatt gtgttaaaaa tggctacaca atggtgtcaa ttaagacatt     240
tgaagagaat aaagaactcc ttaaagaact caaagggtg attaggacag aagatacaca      300
agtttggatt ggaggcctca acatcatca atttgcaaac tttcgttggg taagcgatgg      360
aagccacgta gcaacagctt cagggtacac caattgggcc caggggagc cagctgattc      420 cttctattac gatcaattttt gcatggcgat gttgttcaga aaagacggcg ctccgtggga     480
tgatttgaat tgttgggtta agaatctttt tgtttgtgag aaacgagatg attgagaggc     540 tattttttgtt atctcaccgt tttgttgaat aaaaagaag aagaaagaca aaaaaaaaa      600 aaaaaaaaaa aaaaaaa                                                    617

<210> SEQ ID NO 27
<211> LENGTH: 304
<212> TYPE: PRT
<213> ORGANISM: Lutzomyia longipalpis

<400> SEQUENCE: 27

Met Lys Leu Leu Gln Ile Ile Phe Ser Leu Phe Leu Val Phe Phe Pro
1               5                  10                  15

Thr Ser Asn Gly Ala Leu Thr Gly Asn Glu Ser Ala Ala Asn Ala Ala
                20                  25                  30

Pro Leu Pro Val Val Leu Trp His Gly Met Gly Asp Ser Cys Cys Phe
            35                  40                  45

Pro Phe Ser Leu Gly Ser Ile Lys Lys Leu Ile Glu Gln Gln Ile Pro
        50                  55                  60

Gly Ile His Val Val Ser Leu Lys Ile Gly Lys Ser Leu Ile Glu Asp
65                  70                  75                  80

Tyr Glu Ser Gly Phe Phe Val His Pro Asp Lys Gln Ile Gln Glu Val
                85                  90                  95

Cys Glu Ser Leu Gln Asn Asp Leu Thr Leu Ala Asn Gly Phe Asn Ala
                100                 105                 110

Ile Gly Phe Ser Gln Gly Ser Gln Phe Leu Arg Gly Leu Val Gln Arg
            115                 120                 125

Cys Ser Ser Ile Gln Val Arg Asn Leu Ile Ser Ile Gly Gly Gln His
```

-continued

```
    130                 135                 140

Gln Gly Val Phe Gly Leu Pro Tyr Cys Pro Ser Leu Ser Arg Lys Thr
145                 150                 155                 160

Cys Glu Tyr Phe Arg Lys Leu Leu Asn Tyr Ala Ala Tyr Glu Lys Trp
                165                 170                 175

Val Gln Lys Leu Leu Val Gln Ala Thr Tyr Trp His Asp Pro Leu Asn
            180                 185                 190

Glu Asp Ala Tyr Arg Thr Gly Ser Thr Phe Leu Ala Asp Ile Asn Asn
        195                 200                 205

Glu Arg Gln Ile Asn Asn Asp Tyr Ile Asn Asn Ile Arg Lys Leu Asn
    210                 215                 220

Arg Phe Val Met Val Lys Phe Leu Asn Asp Ser Met Val Gln Pro Ile
225                 230                 235                 240

Glu Ser Ser Phe Phe Gly Phe Tyr Ala Pro Gly Thr Asp Thr Glu Val
                245                 250                 255

Leu Pro Leu Lys Gln Ser Lys Ile Tyr Leu Glu Asp Arg Leu Gly Leu
            260                 265                 270

Gln Ser Val Pro Ile Asp Tyr Leu Glu Cys Gly Gly Asp His Leu Gln
        275                 280                 285

Phe Thr Lys Glu Trp Phe Ile Lys Phe Ile Ile Pro Tyr Leu Lys Gln
    290                 295                 300

<210> SEQ ID NO 28
<211> LENGTH: 1273
<212> TYPE: DNA
<213> ORGANISM: Lutzomyia longipalpis

<400> SEQUENCE: 28
tacttcgtac tctcagaatt tcttacaagt tcctttttct cttaactttt aaagttttat      60
ttaacaaaat tgctccattt tttcgttttc tgaatattct gttgaaattt tgattaatct     120
attttatgtg cagtttttac taaaaatccc ttatcagcaa cccggtgtct acagttttgt     180
cacgctcagt agcatcttca aggtggtaag aaaaaatgaa actcctgcaa atcatcttct     240
ctctcttcct ggtctttttc ccgacctcaa atggggccct gaccggaaat gaaagtgcag     300
caaatgcagc tcccttgcct gtcgtcctgt ggcacgggat gggcgattct tgctgctttc     360
ccttcagttt gggaagcata aaaaaattaa ttgaacaaca aattcctggg attcatgttg     420
ttagcctgaa aattggaaag tctctcattg aggactatga aagtggattt tttgttcatc     480
cagacaagca aattcaggaa gtttgtgagt cacttcagaa cgatctaaca ctcgcaaatg     540
gattcaatgc aattggattt tctcagggta gtcagttcct gcgaggtctt gtgcaacgat     600
gttcttctat acaagtaagg aatctcattt ccattggagg acagcatcaa ggggtttttg     660
gtctgcccta ttgtccttcg ttgagcagaa agacttgcga atactttaga aagctcctga     720
attatgcagc ttatgaaaaa tggtacaga aactcctagt tcaagccacc tactggcatg      780
atcctctaaa tgaggatgca tatcggactg gaagcacttt ccttgctgat ataaataatg     840
agagacaaat caataatgac tatattaata atattcggaa gctaaatcgt tttgtgatgg     900
taaagttcct caacgacagc atggttcagc caattgaatc tagtttcttt ggattctacg     960
ctccaggaac tgatacagaa gttctcccat taaaacaaag caagatttat ttggaagatc    1020
gtttgggact tcaatcagta ccgatagatt atctagaatg cggaggagat catttgcaat    1080
ttacaaaaga atggttcata aagtttatca taccctatct gaagcaataa gagctgcaat    1140
gtaattgatt aaaaaatgtt aaccatttca ggatgattgg gtgacccctt aaaaatataa    1200
```

```
atgaaaaaat atacaaaaga aataaatttt tatattgatc ccacaaaaaa aaaaaaaaaa   1260
aaaaaaaaaa aaa                                                      1273
```

<210> SEQ ID NO 29
<211> LENGTH: 102
<212> TYPE: PRT
<213> ORGANISM: Lutzomyia longipalpis

<400> SEQUENCE: 29

```
Met Arg Asn Phe Ala Val Val Ser Leu Ala Val Ala Val Leu Leu Phe
1               5                   10                  15

Cys Ala Trp Pro Ile Asn Ala Glu Asp Asn Glu Glu Val Gly Lys Ala
            20                  25                  30

Arg Glu Lys Arg Gly Leu Lys Asp Ala Met Glu His Phe Lys Asn Gly
        35                  40                  45

Phe Lys Glu Leu Thr Lys Asp Phe Lys Leu Pro Ser Leu Pro Ser Leu
    50                  55                  60

Pro Gly Phe Gly Lys Lys Pro Glu Ser Gly Ser Ser Glu Asp Ser Gly
65                  70                  75                  80

Asp Lys Thr Glu Asp Thr Ser Gly Ser Lys Asp Gln Ser Lys Asp
                85                  90                  95

Asn Thr Val Glu Glu Ser
            100
```

<210> SEQ ID NO 30
<211> LENGTH: 466
<212> TYPE: DNA
<213> ORGANISM: Lutzomyia longipalpis

<400> SEQUENCE: 30

```
ggatcggcca ttatggccgg ggcagttaat cgccacaatt taataaaatg aggaactttg    60
ctgtagtcag tttagccgtt gctgtcctgc tcttctgtgc atggcctata aatgcggaag   120
ataatgaaga agttggaaag gcgagagaaa aaagaggctt aaaagacgca atggaacact   180
tcaaaaatgg atttaaggag ctgacaaagg actttaaact tccaagcctt ccaagtcttc   240
ctggatttgg taaaaagcct gaatctggaa gttctgaaga ttctggagat aaaactgagg   300
ataccagtgg atctaaggac gaccaatcaa aggataatac ggtcgaagaa tcttaagaaa   360
ggcgcaaata gctattttca agtggcgaat gtttctttc tttatctgaa ataaatattt   420
ttaaaccttt cgaaaccaaa aaaaaaaaaa aaaaaaaaa aaaaaa               466
```

<210> SEQ ID NO 31
<211> LENGTH: 247
<212> TYPE: PRT
<213> ORGANISM: Lutzomyia longipalpis

<400> SEQUENCE: 31

```
Met Asn Phe Leu Leu Lys Ile Phe Ser Leu Cys Leu Cys Gly Leu
1               5                   10                  15

Gly Tyr Ser Trp Gln Asp Val Arg Asn Ala Asp Gln Thr Leu Trp Ala
            20                  25                  30

Tyr Arg Ser Cys Gln Lys Asn Pro Glu Asp Lys Asp His Val Pro Gln
        35                  40                  45

Trp Arg Lys Phe Glu Leu Pro Asp Asp Glu Lys Thr His Cys Tyr Val
    50                  55                  60

Lys Cys Val Trp Thr Arg Leu Gly Ala Tyr Asn Glu Asn Glu Asn Val
65                  70                  75                  80
```

```
Phe Lys Ile Asp Val Ile Thr Lys Gln Phe Asn Glu Arg Gly Leu Glu
             85                  90                  95
Val Pro Ala Gly Leu Asp Gln Glu Leu Gly Gly Ser Thr Asp Gly Thr
            100                 105                 110
Cys Lys Ala Val Tyr Asp Lys Ser Met Lys Phe Phe Lys Ser His Phe
            115                 120                 125
Met Asp Phe Arg Asn Ala Tyr Tyr Ala Thr Tyr Asp Gly Ser Asp Glu
            130                 135                 140
Trp Phe Ser Lys Asn Pro Asp Val Lys Pro Lys Gly Thr Lys Val Ser
145                 150                 155                 160
Glu Tyr Cys Lys Asn Lys Asp Asp Gly Asp Cys Lys His Ser Cys Ser
            165                 170                 175
Met Tyr Tyr Tyr Arg Leu Ile Asp Glu Asp Asn Leu Val Ile Pro Phe
            180                 185                 190
Ser Asn Leu Pro Asp Tyr Pro Glu Asp Lys Leu Glu Glu Cys Arg Asn
            195                 200                 205
Glu Ala Lys Ser Ala Asn Glu Cys Lys Ser Ser Val Ile Tyr Gln Cys
            210                 215                 220
Leu Glu Asn Ala Asp Lys Ser Ala Leu Asp Ala Ser Leu Asn Ile Leu
225                 230                 235                 240
Asp Glu Phe Ser Gly Arg Tyr
            245

<210> SEQ ID NO 32
<211> LENGTH: 955
<212> TYPE: DNA
<213> ORGANISM: Lutzomyia longipalpis

<400> SEQUENCE: 32
acttaaagat ttttgtttaa gcaaaatgaa cttcttgttg aaaattttct ctttgctctg      60
tctctgtgga ctggggtatt catggcagga tgtgagaaat gccgatcaaa ccctctgggc     120
gtatagatcg tgccaaaaga atcctgaaga taaggatcac gtacctcaat ggaggaagtt     180
cgaattaccc gacgatgaaa agactcattg ctacgtcaag tgcgtatgga cgcgtttggg     240
agcttacaat gaaaatgaaa atgttttcaa aattgatgtc attactaagc aatttaatga     300
acgtggccta agttccgg ctggacttga tcaagaattg ggtggttcta cagatggaac       360
ttgcaaagca gtttacgata atccatgaa gttcttcaaa tctcatttta tggactttag      420
gaatgcttac tacgcaactt atgacggttc tgatgaatgg tttagcaaga accctgatgt     480
aaaaccgaaa ggaacaaaag tttccgaata ctgcaaaaat aaagatgatg gagattgcaa     540
acattcctgc agtatgtact actaccgctt aatcgatgaa gacaacttag ttattccgtt     600
cagcaactta cctgactatc ccgaagataa gctcgaggaa tgcaggaatg aagccaagtc     660
cgcaaatgag tgcaaatcat ctgttatcta tcagtgtttg gaaaatgcgg ataagtcagc     720
tttagacgcg tctttgaata tactcgatga gttttctgga agatattaaa acaaactgga     780
taaaaaactt aggccaacct atgattcgaa cttacgattt tgaacttgaa attcatgtgc     840
tttaacctat tgtcccacta ggaagaaaaa tccatatttg gtgatgttaa actatttttg     900
aacctcttca aaataaacaa ttttcaaaaa aaaaaaaaaa aaaaaaaaaa aaaaa          955

<210> SEQ ID NO 33
<211> LENGTH: 325
<212> TYPE: PRT
<213> ORGANISM: Lutzomyia longipalpis

<400> SEQUENCE: 33
```

```
Met Phe Leu Lys Trp Val Val Cys Ala Phe Ala Thr Val Phe Leu Val
1               5                   10                  15

Gly Val Ser Gln Ala Ala Pro Pro Gly Val Glu Trp Tyr His Phe Gly
            20                  25                  30

Leu Ile Ala Asp Met Asp Lys Lys Ser Ile Ala Ser Asp Lys Thr Thr
        35                  40                  45

Phe Asn Ser Val Leu Lys Ile Asp Glu Leu Arg His Asn Thr Lys Thr
    50                  55                  60

Asp Gln Tyr Ile Tyr Val Arg Ser Arg Val Lys Lys Pro Val Ser Thr
65                  70                  75                  80

Arg Tyr Gly Phe Lys Gly Arg Gly Ala Glu Leu Ser Glu Ile Val Val
                85                  90                  95

Phe Asn Asn Lys Leu Tyr Thr Val Asp Asp Lys Ser Gly Ile Thr Phe
            100                 105                 110

Arg Ile Thr Lys Asp Gly Lys Leu Phe Pro Trp Val Ile Leu Ala Asp
        115                 120                 125

Ala Asp Gly Gln Arg Pro Asp Gly Phe Lys Gly Glu Trp Ala Thr Ile
    130                 135                 140

Lys Asp Asp Thr Ile Tyr Val Gly Ser Thr Gly Met Leu Lys Phe Thr
145                 150                 155                 160

Ser Ser Leu Trp Val Lys Lys Ile Thr Lys Asp Gly Val Val Thr Ser
                165                 170                 175

His Asp Trp Thr Asp Lys Tyr Arg Lys Ile Leu Lys Ala Leu Asn Met
            180                 185                 190

Pro Asn Gly Phe Val Trp His Glu Ala Val Thr Trp Ser Pro Phe Arg
        195                 200                 205

Lys Gln Trp Val Phe Met Pro Arg Lys Cys Ser Arg His Pro Phe Ser
    210                 215                 220

Gln Glu Leu Glu Glu Arg Thr Gly Cys Asn Lys Ile Val Thr Ala Asp
225                 230                 235                 240

Glu Asn Phe Asn Asp Ile Gln Val Ile His Ile Gln Asp Gln Pro Tyr
                245                 250                 255

Asn Leu Ala Ser Gly Phe Ser Ser Phe Arg Phe Ile Pro Gly Thr Lys
            260                 265                 270

Asn Glu Arg Leu Leu Ala Leu Arg Thr Val Glu Gln Glu Asp Gln Val
        275                 280                 285

Lys Thr Trp Ala Val Val Met Asp Met Lys Gly Thr Val Leu Met Tyr
    290                 295                 300

Glu Lys Glu Leu Tyr Asp Glu Lys Phe Glu Gly Leu Ala Phe Phe Gly
305                 310                 315                 320

Gly Ile Lys Lys Asn
                325
```

<210> SEQ ID NO 34
<211> LENGTH: 1071
<212> TYPE: DNA
<213> ORGANISM: Lutzomyia longipalpis

<400> SEQUENCE: 34

```
aaagagaagt agtgagaatg tttcttaagt gggttgtttg tgcttttgcg actgtcttcc      60
ttgttggggt gagtcaggca gccccaccgg gggttgaatg gtatcacttt ggtctgattg     120
ctgatatgga caaaaaatcc atcgcgagtg acaaaaccac ctttaacagc gtcctaaaga     180
tcgatgaatt gcgccacaac acaaaaacgg atcaatacat ttatgtgcgt agtcgagtga     240
```

-continued

```
agaagcccgt tccacgagg tatgggttca aggacgcgg tgcggaattg tcggaaattg      300
ttgtcttcaa caataaactt tacacagttg atgataaatc tggaattacg ttccgcataa      360
cgaaagacgg aaaactcttc ccgtgggtta ttctcgcaga tgccgatgga cagcgacccg      420
atggctttaa gggtgaatgg gctacaatta aggatgatac aatctatgtt ggatctacgg      480
ggatgctcaa gttcacttca tcccttttggg tgaagaagat cacgaaagat ggcgttgtta      540
cgagtcacga ttggactgat aaataccgaa agattctcaa agctctaaac atgccaaatg      600
gttttgtctg gcatgaggct gttacgtggt ctccattcag gaagcaatgg gtcttcatgc      660
cgagaaagtg ctcaaggcat cccttctcac aggaactcga agaacgcaca gggtgcaata      720
aaatagtgac ggcagatgag aatttcaacg acattcaagt tattcacatt caagatcagc      780
catataattt agcttctggt ttctcttcct tccgctttat tcctggtacg aaaaatgaaa      840
gacttctcgc cttgaggaca gtagagcagg aagatcaggt taaaacttgg gctgtggtca      900
tggatatgaa aggaacagtt ctgatgtacg aaaaggaact ttatgacgaa aaattcgaag      960
gtttagcatt ctttggtggt attaaaaaga attaatttgt tccagaagct tttagatgaa     1020
ataataaatt ttatttcatt ttaaaaaaaa aaaaaaaaa aaaaaaaaa a                1071
```

```
<210> SEQ ID NO 35
<211> LENGTH: 160
<212> TYPE: PRT
<213> ORGANISM: Lutzomyia longipalpis

<400> SEQUENCE: 35
```

```
Met Ala Leu Lys Phe Leu Pro Val Leu Leu Leu Ser Cys Phe Ala Met
1               5                   10                  15

Ser Thr Ala Leu Gln Val Thr Glu Lys Glu Leu Ser Asp Gly Lys Lys
            20                  25                  30

Ile Phe Ile Ser Lys Val Glu Leu Asn Trp Phe Glu Ala Leu Asp Phe
        35                  40                  45

Cys Ile His Arg Gly Leu Thr Leu Leu Ser Ile Lys Ser Ala Lys Glu
    50                  55                  60

Asn Val Asp Val Thr Lys Ala Ile Arg Ala Glu Leu Asn Phe Asp Ser
65                  70                  75                  80

Lys Lys Leu Ala His Val Trp Thr Gly Gly Ile Arg His Ser Gln Asp
                85                  90                  95

Lys Tyr Phe Arg Trp Ile Asn Asp Gly Thr Lys Val Val Lys Arg Val
            100                 105                 110

Tyr Thr Asn Trp Phe Thr Gly Glu Pro Asn Asn Gly Tyr Trp Lys Asp
        115                 120                 125

Glu Phe Cys Leu Glu Ile Tyr Tyr Lys Thr Glu Gly Lys Trp Asn
    130                 135                 140

Asp Asp Lys Cys His Val Lys His His Phe Val Cys Gln Glu Lys Lys
145                 150                 155                 160
```

```
<210> SEQ ID NO 36
<211> LENGTH: 648
<212> TYPE: DNA
<213> ORGANISM: Lutzomyia longipalpis

<400> SEQUENCE: 36
```

```
cgcggccgcg tcgaccgaca aaggggtag tttgtagaga actttgagtt ctaaaggaaa       60
ttctcaagaa gaaatattc aaagtaaag aatggcgttg aagtttcttc cggttctcct      120
tctaagctgc ttcgcaatga gcacggcact acaagttact gagaaggaac tttctgatgg      180
```

```
gaaaaagatc ttcatctcca aagttgagct aaactggttc gaagctcttg atttctgtat      240
ccatcgtggt cttacgttgc tctcaattaa atccgccaag gaaaatgtag acgtaacaaa      300
agcaattcgg gctgaattga attttgattc aaagaaattg gctcatgtgt ggactggagg      360
tattcgccat agtcaagata agtatttccg ttggataaat gatggaacta aagttgttaa      420
acgagtctac accaattggt tcactggaga accaaataat ggttactgga aggatgaatt      480
ttgtctggaa atttactata aaaccgaaga agggaagtgg aatgatgata atgtcacgt       540 gaagcatcat tttgtatgtc aagaaaagaa ataaattgat tgattttgtt tgctgatttg      600
cagttcagaa ttgaaaagcc aaaaaaaaaa aaaaaaaaa aaaaaaa                     648
```

```
<210> SEQ ID NO 37
<211> LENGTH: 161
<212> TYPE: PRT
<213> ORGANISM: Lutzomyia longipalpis

<400> SEQUENCE: 37

Met Ala Phe Ser Asn Thr Leu Phe Val Leu Phe Val Ser Phe Leu Thr
1               5                   10                  15

Phe Cys Gly Ala Asp Gln Thr Leu Ile Glu Lys Glu Leu Thr Gly Arg
            20                  25                  30

Thr Val Tyr Ile Ser Lys Ile Lys Leu Asn Trp Asn Asp Ala Phe Asp
        35                  40                  45

Tyr Cys Ile Arg Asn Gly Leu Thr Phe Ala Lys Ile Lys Ser Ala Glu
    50                  55                  60

Glu Asn Thr Glu Leu Ser Glu Lys Leu Lys Thr Val Ile Arg Thr Glu
65                  70                  75                  80

Glu Phe Gln Val Trp Ile Gly Gly Ile Glu His His Gln Asp Ser Ser
                85                  90                  95

Phe Arg Trp Val Ser Asp Ser Gln Pro Ile Thr Asn Lys Leu Gly Tyr
            100                 105                 110

Lys Tyr Thr Asn Trp Asn Thr Gly Glu Pro Thr Asn Tyr Gln Asn Asn
        115                 120                 125

Glu Tyr Cys Leu Glu Ile Leu Phe Arg Lys Glu Asp Gly Lys Trp Asn
    130                 135                 140

Asp Phe Pro Cys Ser Ala Arg His His Phe Val Cys Glu Lys Arg Thr
145                 150                 155                 160

Lys
```

```
<210> SEQ ID NO 38
<211> LENGTH: 586
<212> TYPE: DNA
<213> ORGANISM: Lutzomyia longipalpis

<400> SEQUENCE: 38
aatagatctt caaaacgtct aagaatggct ttcagcaaca ctttatttgt tcttttttgtg     60 agttttttaa cgttttgtgg cgctgatcag acacttattg agaaggaatt aaccggaaga     120 actgttttata tctccaaaat taagctaaat tggaacgatg ccttcgatta ctgcatccgc    180
aatggcctca cctttgctaa gattaaatca gctgaagaaa acaccgaact gagtgagaaa     240
ctcaagacag tcattcgtac ggaggagttt caagtttgga ttggaggcat tgaacatcat     300
caagacagtt ccttccgctg gtaagcgac tcccaaccaa taaccaacaa attgggctac      360
aaatacacaa actggaatac cggagagccc acaaattacc aaaacaacga atattgcttg    420
gaaatattat tccggaagga agatggaaaa tggaatgatt ttccctgcag tgcaagacat    480
```

```
cattttgttt gtgaaaaaag aacaaaataa aatgaagaaa atgtgatttt cctttggttg    540
aagaataaaa ttctgttgaa aaaaaaaaaa aaaaaaaaaa aaaaaa                  586
```

<210> SEQ ID NO 39
<211> LENGTH: 105
<212> TYPE: PRT
<213> ORGANISM: Lutzomyia longipalpis

<400> SEQUENCE: 39

```
Met Gln Asn Phe Leu Leu Val Ser Leu Ala Leu Ala Ala Leu Met Leu
1               5                   10                  15

Cys Ala Glu Ala Lys Pro Tyr Asp Phe Pro Leu Tyr Gln Asp Leu Ile
            20                  25                  30

Gln Gly Val Ile Gln Arg Glu Ser Gln Ala Glu Arg Glu Lys Arg Ser
        35                  40                  45

Pro Asn Glu Asp Tyr Glu Lys Gln Phe Gly Asp Ile Val Asp Gln Ile
    50                  55                  60

Lys Glu Ile Ser Phe Asn Val Met Lys Met Pro His Phe Gly Ser Ser
65                  70                  75                  80

Asp Asp Asn Arg Asp Asp Gly Glu Tyr Val Asp His Tyr Gly Asp
                85                  90                  95

Glu Asp Asp Arg Asp Tyr Asp His Tyr
            100                 105
```

<210> SEQ ID NO 40
<211> LENGTH: 457
<212> TYPE: DNA
<213> ORGANISM: Lutzomyia longipalpis

<400> SEQUENCE: 40

```
atttagtttg tgtttaacaa acaagaatg cagaacttcc ttttagtttc cttggcttta     60
gctgccttaa tgctatgtgc cgaagcaaag ccgtacgatt ttccgcttta tcaggactta   120
attcagggcg ttattcagcg cgaaagtcaa gctgagaggg agaagagaag ccccaatgag   180
gactatgaga agcaatttgg ggatattgtt gatcaaatta aggaaattag ttcaatgtc    240 atgaaaatgc cccattttgg aagctctgat gataatcgtg atgatggcga gtacgttgat   300
catcattatg gtgacgaaga tgatcgtgat tatgatcatt actaaatact acttgctcct   360
gctgaatgac ttgaaggaat catttttttg caaaaatatc catcaaatta ttgaattaat   420
aaagttgcaa aaaaaaaaaa aaaaaaaaaa aaaaaaa                            457
```

<210> SEQ ID NO 41
<211> LENGTH: 157
<212> TYPE: PRT
<213> ORGANISM: Lutzomyia longipalpis

<400> SEQUENCE: 41

```
Met Lys Phe Tyr Ile Phe Gly Val Phe Leu Val Ser Phe Leu Ala Leu
1               5                   10                  15

Cys Asn Ala Glu Asp Tyr Asp Lys Val Lys Leu Thr Gly Arg Thr Val
            20                  25                  30

Tyr Ile Ser Arg Ser Lys Ala Pro Trp Phe Thr Ala Leu Asp Asn Cys
        35                  40                  45

Asn Arg Arg Phe Thr Phe Ala Met Ile Lys Ser Gln Lys Glu Asn Glu
    50                  55                  60

Glu Leu Thr Asn Ala Leu Leu Ser Val Ile Lys Ser Asp Glu Glu Asn
65                  70                  75                  80
```

```
Val Trp Ile Gly Gly Leu Arg His Asp Leu Asp Asp Tyr Phe Arg Trp
                85                  90                  95

Ile Ser Phe Gly Thr Ala Leu Ser Lys Thr Ser Tyr Thr Asn Trp Ala
            100                 105                 110

Pro Lys Glu Pro Thr Gly Arg Pro His Arg Thr Gln Asn Asp Glu Phe
        115                 120                 125

Cys Met Gln Met Ser Phe Lys Asp Gly Gly Lys Trp Ser Asp Asn Thr
    130                 135                 140

Cys Trp Arg Lys Arg Leu Tyr Val Cys Glu Lys Arg Asp
145                 150                 155

<210> SEQ ID NO 42
<211> LENGTH: 596
<212> TYPE: DNA
<213> ORGANISM: Lutzomyia longipalpis

<400> SEQUENCE: 42
gtttaaggaa tttctttcat ctcagtcttc gattttcttt aaacaaataa tgaagtttta     60
tatttttgga gttttcctgg tgagctttct tgcattatgc aatgctgagg attatgataa    120
agtaaaactt actggaagaa ctgtttacat ctccagatca aaggctccgt ggttcacagc    180
tttagacaat tgtaatcgtt tacgcttcac cttcgccatg atcaagtctc agaaggagaa    240
tgaagagcta acaaatgcgc ttttaagtgt aattaaatct gacgaagaaa atgtttggat    300
tggaggtctt aggcacgatc tggatgacta cttccgttgg attagttttg aactgcatt     360 gtcaaagact tcgtacacca attgggcccc aaaggaaccc acaggaaggc cccatagaac    420
tcaaaatgat gaattctgca tgcaaatgtc tttcaaagat ggtggcaaat ggagtgataa    480
cacctgttgg cgtaaacgtt tgtacgtttg tgaaaagcgt gattaaataa aggaacactg    540
ccaatgaata ttgggcaatt tgagagaaat taaattaaaa aaaaaaaaaa aaaaaa        596

<210> SEQ ID NO 43
<211> LENGTH: 295
<212> TYPE: PRT
<213> ORGANISM: Lutzomyia longipalpis

<400> SEQUENCE: 43

Met Ile Lys Glu Val Phe Ser Leu Ala Leu Leu Val Ala Leu Ala Gln
1               5                   10                  15

Cys Ala Asn Glu Ile Pro Ile Asn Arg Gln Gly Lys Asp Tyr Pro Val
            20                  25                  30

Pro Ile Asp Pro Asn Lys Ser Ser Asp Tyr Phe Asp
        35                  40                  45

Arg Phe Tyr Pro Asp Ile Asp Asp Glu Gly Ile Ala Glu Ala Pro Lys
    50                  55                  60

Asp Asn Arg Gly Lys Ser Arg Gly Gly Ala Ala Gly Ala Arg Glu
65                  70                  75                  80

Gly Arg Leu Gly Thr Asn Gly Ala Lys Pro Gly Gln Gly Gly Thr Arg
                85                  90                  95

Pro Gly Gln Gly Gly Thr Arg Pro Gly Gln Gly Gly Thr Arg Pro Gly
            100                 105                 110

Gln Gly Gly Thr Arg Pro Gly Gln Gly Gly Thr Arg Pro Gly Gln Gly
        115                 120                 125

Arg Thr Lys Pro Ala Gln Gly Thr Thr Arg Pro Ala Gln Gly Thr Arg
    130                 135                 140

Asn Pro Gly Ser Val Gly Thr Lys Glu Ala Gln Asp Ala Ser Lys Gln
145                 150                 155                 160
```

Gly Gln Gly Lys Arg Arg Pro Gly Gln Val Gly Gly Lys Arg Pro Gly
                165                 170                 175
Gln Ala Asn Ala Pro Asn Ala Gly Thr Arg Lys Gln Gln Lys Gly Ser
            180                 185                 190
Arg Gly Val Gly Arg Pro Asp Leu Ser Arg Tyr Lys Asp Ala Pro Ala
        195                 200                 205
Lys Phe Val Phe Lys Ser Pro Asp Phe Ser Glu Gly Lys Thr Pro
    210                 215                 220
Thr Val Asn Tyr Phe Arg Thr Lys Lys Glu His Ile Val Thr Arg
225                 230                 235                 240
Gly Ser Pro Asn Asp Glu Phe Val Leu Glu Ile Leu Asp Gly Asp Pro
                245                 250                 255
Thr Gly Leu Gly Leu Lys Ser Glu Thr Ile Gly Lys Asp Thr Arg Leu
            260                 265                 270
Val Leu Glu Asn Pro Asn Gly Asn Ser Ile Val Ala Arg Val Lys Ile
        275                 280                 285
Tyr Lys Asn Gly Tyr Ser Gly
    290                 295

<210> SEQ ID NO 44
<211> LENGTH: 989
<212> TYPE: DNA
<213> ORGANISM: Lutzomyia longipalpis

<400> SEQUENCE: 44
actaaagcgt ctcaccgaaa tcagggaaaa tgattaagga agttttctct ctggctctac      60
ttgtggcctt ggcacagtgt gctaatgaaa tccctattaa tcgtcagggg aaagattatc     120
cagttccgat cattgatcca aataaatcat cttcggatga ttatttcgat gatcgcttct     180
accctgatat tgatgatgag ggcatagctg aggctcctaa ggataatagg ggaaaatccc     240
gtggtggtgg tgcggctggc gcaagagaag gtaggttagg tacgaatggg gctaaaccgg     300
gtcagggtgg aactagacca ggacagggtg gaactaggcc aggacagggt ggaactaggc     360
caggtcaggg tggaactagg ccaggtcagg gtggaactag acctgggcaa ggtagaacta     420
agcctgctca gggaactact aggccagctc agggaactag aaatccagga tcggttggta     480
cgaaagaagc ccaggatgcg tcaaaacaag gtcaaggtaa aagaaggcca gggcaagttg     540
gtggtaaaag accaggacaa gcaaatgctc ctaatgcagg cactagaaag caacagaaag     600
gcagtagagg cgttggaagg cctgatctat cgcgctacaa agatgcccct gctaaattcg     660 tttttcaaatc tcccgatttc agtggagaag gcaaaactcc aactgtaaat tactttagaa     720
cgaagaagaa ggagcacatt gtgacccgtg gtagtcctaa tgatgaattt gttctggaga     780
ttctcgatgg ggatccaact gggcttggac taaagagtga aaccataggc aaagatacgc     840
gtttagtgct ggagaatcct aatggaaatt ccatcgtggc tcgtgttaag atctacaaga     900
acggttattc aggatgaaga agaaatcctt tgatttcccc cccccctct tcctttaaaa     960 ttcaacataa taaaaaaaaa aaaaaaaaa                                        989

<210> SEQ ID NO 45
<211> LENGTH: 148
<212> TYPE: PRT
<213> ORGANISM: Lutzomyia longipalpis

<400> SEQUENCE: 45

Met Asn Ser Val Asn Thr Leu Ile Leu Thr Leu Leu Phe Ala Ile Phe
1               5                   10                  15

Leu Leu Val Lys Arg Ser Gln Ala Phe Leu Pro Ser Asp Pro Ser Ile
            20                  25                  30

Cys Val Lys Asn Leu Val Leu Asp Thr Gly Arg Thr Cys Glu Glu Ser
        35                  40                  45

Glu Tyr Phe Pro Asp Ile Lys Asn Val Lys Asn Gly Lys Arg Val Tyr
    50                  55                  60

Ile Val Cys Thr Asp Ser Asp Ala Val Asp Tyr Lys Phe Tyr Ile Cys
65                  70                  75                  80

Phe Asp Met Asn Arg Leu Ser Gly Pro Pro Tyr Pro Glu Glu Ile
            85                  90                  95

Leu Arg Glu Ser Thr Val Thr Tyr Ala Gln Ile Tyr Glu Leu Met Thr
            100                 105                 110

Thr Glu Thr Thr Glu Thr Lys Lys Pro Lys Lys Pro Lys Asn Ser
            115                 120                 125

Lys Thr Asp Asp Pro Pro Ala Ile Arg Pro Gly Phe Ser Phe Arg Asn
            130                 135                 140

Ser Ile Ser Val
145

<210> SEQ ID NO 46
<211> LENGTH: 826
<212> TYPE: DNA
<213> ORGANISM: Lutzomyia longipalpis

<400> SEQUENCE: 46 gtctttcct gagtgtttca ttaacaaaat gaattcagta aacactttaa ttttaactct     60
tctatttgca attttttat tagtgaaaag gtctcaggct tttcttccat ctgacccaag    120
tatctgtgtt aaaaatttag tattggatac aggaaggact tgtgaggaaa gtgaatattt    180
tccggatatc aagaacgtta aaaatggaaa aagagtttac attgtctgca ctgattcaga    240
tgcagttgat tataaatttt atatttgttt cgatatgaat cgtctttctg gaccaccgta    300
tcctgaggaa gaaatccttc gtgaatcaac ggtaacttat gcccaaattt atgagctgat    360
gactacggaa accactgaaa ccaaaaagcc aaaaagaaa ccaagaatt caaaacgga    420 cccagaccct ccagcaattc gtccaggatt tcatttaga aattcaattt ctgtttaatt    480
ttacaattta ttttgaaaga aaatgatat ttcgaaatat tctatacaaa aaacaacag    540 ttataaaacg aaaattcaat catttcaatg agaaaactta gtcttgagta aggtttattc    600
accacccgac gccacgctat ggtgaataat tttcttatt caccacatca aaatgacggc    660
ttataaactt caacaaatag tttggaaaat acatttctaa ctaatgcaat gtttacttaa    720 aatcactta caaattcacg catttgagat gcaacaaata tatacaattc aacgatataa    780
actttccaca aggaaaactt tcaaccaaa aaaaaaaaa aaaaaa                    826

<210> SEQ ID NO 47
<211> LENGTH: 397
<212> TYPE: PRT
<213> ORGANISM: Lutzomyia longipalpis

<400> SEQUENCE: 47

Met Lys Leu Phe Phe Phe Leu Tyr Thr Phe Gly Leu Val Gln Thr Ile
1               5                   10                  15

Phe Gly Val Glu Ile Lys Gln Gly Phe Lys Trp Asn Lys Ile Leu Tyr
            20                  25                  30

Glu Gly Asp Thr Ser Glu Asn Phe Asn Pro Asp Asn Asn Ile Leu Thr
        35                  40                  45

```
Ala Phe Ala Tyr Asp Pro Glu Ser Gln Lys Leu Phe Leu Thr Val Pro
         50                  55                  60

Arg Lys Tyr Pro Glu Thr Met Tyr Thr Leu Ala Glu Val Asp Thr Glu
 65                  70                  75                  80

Lys Asn Ser Phe Glu Ser Gly Asp Thr Ser Pro Leu Leu Gly Lys Phe
                 85                  90                  95

Ser Gly His Glu Thr Gly Lys Glu Leu Thr Ser Val Tyr Gln Pro Val
                100                 105                 110

Ile Asp Glu Cys His Arg Leu Trp Val Val Asp Val Gly Ser Val Glu
            115                 120                 125

Arg Asn Ser Asp Gly Thr Glu Gly Gln Pro Glu His Asn Pro Thr Leu
130                 135                 140

Val Ala Tyr Asp Leu Lys Glu Ala Asn Tyr Pro Glu Val Ile Arg Tyr
145                 150                 155                 160

Thr Phe Pro Asp Asn Ser Ile Glu Lys Pro Thr Phe Leu Gly Gly Phe
                165                 170                 175

Ala Val Asp Val Val Lys Pro Asp Glu Cys Ser Glu Thr Phe Val Tyr
            180                 185                 190

Ile Thr Asn Phe Leu Thr Asn Ala Leu Ile Val Tyr Asp His Lys Asn
            195                 200                 205

Lys Asp Ser Trp Thr Val Gln Asp Ser Thr Phe Gly Pro Asp Lys Lys
210                 215                 220

Ser Lys Phe Asp His Asp Gly Gln Gln Tyr Glu Tyr Glu Ala Gly Ile
225                 230                 235                 240

Phe Gly Ile Thr Leu Gly Glu Arg Asp Asn Glu Gly Asn Arg Gln Ala
                245                 250                 255

Tyr Tyr Leu Val Ala Ser Ser Thr Lys Leu His Ser Ile Asn Thr Lys
                260                 265                 270

Glu Leu Lys Gln Lys Gly Ser Lys Val Asn Ala Asn Tyr Leu Gly Asp
            275                 280                 285

Arg Gly Glu Ser Thr Asp Ala Ile Gly Leu Val Tyr Asp Pro Lys Thr
290                 295                 300

Lys Thr Ile Phe Phe Val Glu Ser Asn Ser Lys Arg Val Ser Cys Trp
305                 310                 315                 320

Asn Thr Gln Glu Thr Leu Asn Lys Asp Lys Ile Asp Val Ile Tyr His
                325                 330                 335

Asn Ala Asp Phe Ser Phe Gly Thr Asp Ile Ser Ile Asp Ser Gln Asp
            340                 345                 350

Asn Leu Trp Phe Leu Ala Asn Gly Leu Pro Pro Leu Glu Asn Ser Asp
            355                 360                 365

Lys Phe Val Phe Thr Lys Pro Arg Tyr Gln Ile Phe Lys Val Asn Ile
            370                 375                 380

Gln Glu Ala Ile Ala Gly Thr Lys Cys Glu Lys Asn Leu
385                 390                 395

<210> SEQ ID NO 48
<211> LENGTH: 1325
<212> TYPE: DNA
<213> ORGANISM: Lutzomyia longipalpis

<400> SEQUENCE: 48
atcattcaaa aggcagcagc acaatgaagt tatttttctt tctttacact tttggtctag      60
tccaaacgat ttttggagta gaaattaaac aaggatttaa atggaataaa atcctttatg     120
agggcgatac atcagaaaac ttcaatccag ataacaacat ccttacggct tttgcgtacg     180
```

```
atcctgagag tcagaaactc ttcctaactg tcccgaggaa atatcccgaa actatgtaca      240
ctttggcaga agttgatact gagaaaaatt cttttgaatc gggagatact tccccgctcc      300
ttggaaaatt cagtggtcat gaaactggga agaacttac atcagtttat cagccagtta       360
tcgatgaatg tcatcgtctt tgggttgttg atgttggatc agtagaacgt aactcagacg      420
gcacagaagg tcagccagaa cataatccta cccttgtggc gtacgatctc aaagaagcca      480
actatcctga agttattcgt tacacgtttc ccgataattc cattgagaag cccacatttc      540
tgggtggatt tgccgttgat gttgtaaagc cggatgaatg cagtgaaact tttgtctaca      600
tcacaaactt cctcaccaac gccctcatag tatacgatca taagaataag gactcctgga      660
cggtacaaga ttcaactttt ggaccagata aaaagtcaaa gtttgaccac gatggacaac      720
agtatgaata cgaagcagga atcttcggga ttacccttgg agagagagat aacgaaggaa      780
atcgtcaagc gtactattta gtagcaagta gtaccaaact tcacagcatc aacaccaaag      840
aactgaagca aaaggaagc aaagttaatg caaattattt gggagatcgt ggtgaatcca       900
ccgatgccat aggcttagtt tacgatccaa aaccaaaac tatcttcttc gttgagtcaa       960
atagcaaaag agtatcatgc tggaataccc aggaaacact aaacaaggat aaaattgatg      1020
taatctatca caatgcagac ttttcctttg aacagatat atcgattgat agtcaggata       1080
atttgtggtt cctagcaaat ggacttccac ctctggaaaa ttctgataaa tttgtctttta     1140 caaagccacg ttatcaaata ttcaaagtca acattcaaga agcaattgct ggaactaaat      1200
gtgaaaagaa tctttaacaa atgaaacttt gtagaaaaat acataatatc tgaataaaaa      1260
gtcataaatg taccataaaa aaaaaaaaaa aaaaaaaaaa aaaaaaaaaa aaaaaaaaaa      1320
aaaaa                                                                  1325
```

<210> SEQ ID NO 49
<211> LENGTH: 350
<212> TYPE: PRT
<213> ORGANISM: Lutzomyia longipalpis

<400> SEQUENCE: 49

```
Met Thr Phe Leu Ile Ile Leu Gly Ala Phe Leu Leu Val Gln Ile Ile
1               5                   10                  15

Thr Ala Ser Ala Leu Gly Leu Pro Glu Gln Phe Lys Gly Leu Glu Asp
            20                  25                  30

Leu Pro Lys Lys Pro Leu Ala Glu Thr Tyr Tyr His Glu Gly Leu Asn
        35                  40                  45

Asp Gly Lys Thr Asp Glu Met Val Asp Ile Phe Lys Ser Leu Ser Asp
    50                  55                  60

Glu Phe Lys Phe Ser Asp Glu Asn Leu Asp Val Gly Glu Glu Lys Asn
65                  70                  75                  80

Tyr Lys Lys Arg Asp Ile Thr Gln Asn Ser Val Ala Arg Asn Phe Leu
                85                  90                  95

Ser Asn Val Lys Gly Ile Pro Ser Met Pro Ser Leu Pro Ser Met Pro
            100                 105                 110

Ser Met Pro Ser Ile Pro Ser Leu Trp Ser Ser Gln Thr Gln Ala Ala
        115                 120                 125

Pro Asn Thr Ala Leu Ala Leu Pro Glu Ser Asp Tyr Ser Leu Leu Asp
    130                 135                 140

Met Pro Asn Ile Val Lys Asn Phe Leu Lys Glu Thr Arg Asp Leu Tyr
145                 150                 155                 160

Asn Asp Val Gly Ala Phe Leu Lys Ala Ile Thr Glu Ala Leu Thr Asn
```

```
                165                 170                 175
Arg Ser Ser Ser Ser Gln Leu Leu Ser Ser Pro Met Val Ser Thr Asn
            180                 185                 190
Lys Thr Lys Glu Phe Ile Arg Asn Glu Ile Gln Lys Val Arg Lys Val
        195                 200                 205
Arg Asn Phe Val Gln Glu Thr Leu Gln Lys Ile Arg Asp Ile Ser Ala
    210                 215                 220
Ala Ile Ala Lys Lys Val Lys Ser Ser Glu Cys Leu Ser Asn Leu Thr
225                 230                 235                 240
Asp Ile Lys Gly Leu Val Ser Asp Gly Ile Asn Cys Leu Lys Glu Lys
                245                 250                 255
Phe Asn Asp Gly Lys Arg Ile Ile Leu Gln Leu Tyr Asn Asn Leu Leu
            260                 265                 270
Lys Gly Leu Lys Ile Pro Asn Asp Leu Met Val Glu Leu Lys Lys Cys
        275                 280                 285
Asp Thr Asn Gln Asn Asn Thr Leu Gly Arg Ile Ile Cys Tyr Phe Leu
    290                 295                 300
Thr Pro Leu Gln Leu Glu Lys Glu Gln Ile Leu Leu Pro Val Glu Phe
305                 310                 315                 320
Ile Lys Arg Ile Leu Glu Leu Thr His Tyr Phe Ser Thr Met Lys Glu
                325                 330                 335
Asp Leu Ile Asn Cys Gly Ile Thr Thr Ile Ala Ser Ile Thr
            340                 345                 350

<210> SEQ ID NO 50
<211> LENGTH: 1275
<212> TYPE: DNA
<213> ORGANISM: Lutzomyia longipalpis

<400> SEQUENCE: 50
ctttaaagca aaattttgt gggaaaggaa gttacccgga gatgacgttt ctaattatac      60
ttggtgcatt tctccttgtt caaattatta cagcttcagc tttaggattg cctgaacagt     120
ttaaaggttt agaggattta cctaaaaaac ctttggcaga gacttattat cacgaaggat     180
tgaatgatgg aaaaacggat gaaatggtgg atattttaa aagtcttagc gatgaattta     240
aattcagtga tgaaaattta gatgttggtg aggagaaaaa ttacaagaaa cgtgatataa     300
cccaaaattc agtggcaagg aacttcctat caaacgtaaa gggaattcct tcaatgccat     360
cactcccttc aatgccttca atgccatcaa ttccttcact tggtcaagt cagacacagg      420 cggcaccaaa taccgcactt gcccttcctg aatctgatta ttcccttcta gatatgccga     480
atattgtgaa aaatttccta aaggaaacaa gagacctcta taacgatgtt ggagcttttc     540
ttaaggcaat tacagaagct ttaacaaata gatcttcatc atctcaactt ctttcctccc     600
caatggtgag cacgaataaa accaaagaat ttattcggaa tgaaatacaa aaagtccgaa     660
aagtgagaaa tttcgtccag gaaactcttc agaaaatccg agacatttct gctgctattg     720
ccaaaaaggt aaaatcatca gaatgtctgt ccaatcttac ggacatcaaa ggacttgtat     780
cagacggaat taattgttta aaggaaaaat tcaatgatgg aaaacgaatt atcctgcaat     840
tgtacaataa tttactaaaa ggactcaaaa ttccaaatga cctaatggtt gaattgaaga     900
aatgtgatac aaatcaaaac aatacttggg aagaataat ctgttatttt ttgcacaccat      960 tgcaactgga aaagaacaa attcttctac ctgtagaatt tataaagcgc attcttgaat    1020
taacccacta cttttccaca atgaaagaag atcttatcaa ctgtggcatc acaacgattg    1080
catccattac gtaaaaaatg gaaaaatgtg ccggtgaaat gcttgaaatc accaaagaaa    1140
```

```
tttcatcgca aataacagtt ccagaataac caaattttaa tgattacttc tcaaggaaaa    1200
tactaccaaa aggcattaat taaaacgatg ttttttataa acaatgtaag aaaaaaaaaa    1260
aaaaaaaaaa aaaaa                                                     1275
```

<210> SEQ ID NO 51
<211> LENGTH: 60
<212> TYPE: PRT
<213> ORGANISM: Lutzomyia longipalpis

<400> SEQUENCE: 51

```
Met Leu Lys Ile Val Leu Phe Leu Ser Val Leu Ala Val Leu Val Ile
1               5                   10                  15

Cys Val Ala Ala Met Pro Gly Ser Asn Val Pro Trp His Ile Ser Arg
            20                  25                  30

Glu Glu Leu Glu Lys Leu Arg Glu Ala Arg Lys Asn His Lys Ala Leu
        35                  40                  45

Glu Lys Ala Ile Asp Glu Leu Ile Asp Lys Tyr Leu
    50                  55                  60
```

<210> SEQ ID NO 52
<211> LENGTH: 413
<212> TYPE: DNA
<213> ORGANISM: Lutzomyia longipalpis

<400> SEQUENCE: 52

```
agttaatctt ctgtcaagct acaaaaatgc ttaaatcgt tttatttcta tcagttttgg      60
ctgtattagt gatttgtgta gcagcaatgc caggatccaa tgttccttgg cacatttcac    120
gagaagagct tgagaagctt cgtgaagctc gaaagaatca caaggcactc gagaaggcaa    180
ttgatgaatt aattgacaaa tatctctgat tttgaagagc aaggaagagg aaataaacgg    240
ccgaggaagg attttctta gagattcttc tttttattac ttcaaaccta acttcaaaat     300
cagtctgata tttttttaat ttgaaaaaaa tattgaaaat tttaactatt tgtgaaattt    360
aaataaataa agaatgtcag aagcaaaaaa aaaaaaaaaa aaaaaaaaaa aaa           413
```

<210> SEQ ID NO 53
<211> LENGTH: 120
<212> TYPE: PRT
<213> ORGANISM: Lutzomyia longipalpis

<400> SEQUENCE: 53

```
Met Lys Phe Ser Cys Pro Val Phe Val Ala Ile Phe Leu Leu Cys Gly
1               5                   10                  15

Phe Tyr Arg Val Glu Gly Ser Ser Gln Cys Glu Glu Asp Leu Lys Glu
            20                  25                  30

Glu Ala Glu Ala Phe Phe Lys Asp Cys Asn Glu Ala Lys Ala Asn Pro
        35                  40                  45

Gly Glu Tyr Glu Asn Leu Thr Lys Glu Glu Met Phe Glu Glu Leu Lys
    50                  55                  60

Glu Tyr Gly Val Ala Asp Thr Asp Met Glu Thr Val Tyr Lys Leu Val
65                  70                  75                  80

Glu Glu Cys Trp Asn Glu Leu Thr Thr Thr Asp Cys Lys Arg Phe Leu
                85                  90                  95

Glu Glu Ala Glu Cys Phe Lys Lys Lys Asn Ile Cys Lys Tyr Phe Pro
            100                 105                 110

Asp Glu Val Lys Leu Lys Lys Lys
        115                 120
```

<210> SEQ ID NO 54
<211> LENGTH: 428
<212> TYPE: DNA
<213> ORGANISM: Lutzomyia longipalpis

<400> SEQUENCE: 54

```
aattttcacc atgaagtttt cttgcccagt tttcgttgca attttccttt tgtgcggatt    60
ttatcgtgtt gagggtcat cacaatgtga agaagattta aagaagaag ctgaagcttt    120
ctttaaggat tgcaatgaag caaaagccaa tcctggtgaa tacgagaatc tcaccaaaga   180
agaaatgttt gaagaattga agaatatgg agttgctgac acagacatgg agacagttta   240
caaacttgtg gaagaatgtt ggaatgaatt aacaacaacg gattgtaaga gatttctcga   300
agaggctgaa tgcttcaaga agaagaatat ttgtaaatat ttcccagatg aagtgaaatt   360
gaagaagaaa taaattttta gcttgaaaaa aaaaaaaaaa aaaaaaaaaa aaaaaaaaa    420
aaaaaaaa                                                            428
```

<210> SEQ ID NO 55
<211> LENGTH: 572
<212> TYPE: PRT
<213> ORGANISM: Lutzomyia longipalpis

<400> SEQUENCE: 55

```
Met Leu Phe Phe Leu Asn Phe Phe Val Leu Val Phe Ser Ile Glu Leu
1               5                   10                  15

Ala Leu Leu Thr Ala Ser Ala Ala Glu Asp Gly Ser Tyr Glu Ile
            20                  25                  30

Ile Ile Leu His Thr Asn Asp Met His Ala Arg Phe Asp Gln Thr Asn
        35                  40                  45

Ala Gly Ser Asn Lys Cys Gln Glu Lys Asp Lys Ile Ala Ser Lys Cys
    50                  55                  60

Tyr Gly Gly Phe Ala Arg Val Ser Thr Met Val Lys Lys Phe Arg Glu
65                  70                  75                  80

Glu Asn Gly Ser Ser Val Leu Phe Leu Asn Ala Gly Asp Thr Tyr Thr
                85                  90                  95

Gly Thr Pro Trp Phe Thr Leu Tyr Lys Glu Thr Ile Ala Thr Glu Met
            100                 105                 110

Met Asn Ile Leu Arg Pro Asp Ala Ala Ser Leu Gly Asn His Glu Phe
        115                 120                 125

Asp Lys Gly Val Glu Gly Leu Val Pro Phe Leu Asn Gly Val Thr Phe
    130                 135                 140

Pro Ile Leu Thr Ala Asn Leu Asp Thr Ser Gln Glu Pro Thr Met Thr
145                 150                 155                 160

Asn Ala Lys Asn Leu Lys Arg Ser Met Ile Phe Thr Val Ser Gly His
                165                 170                 175

Arg Val Gly Val Ile Gly Tyr Leu Thr Pro Asp Thr Lys Phe Leu Ser
            180                 185                 190

Asp Val Gly Lys Val Asn Phe Ile Pro Glu Val Glu Ala Ile Asn Thr
        195                 200                 205

Glu Ala Gln Arg Leu Lys Lys Glu Asn Ala Glu Ile Ile Val
    210                 215                 220

Val Gly His Ser Gly Leu Ile Lys Asp Arg Glu Ile Ala Glu Lys Cys
225                 230                 235                 240

Pro Leu Val Asp Ile Ile Val Gly Gly His Ser His Thr Phe Leu Tyr
                245                 250                 255
```

Thr Gly Ser Gln Pro Asp Arg Glu Val Pro Val Asp Val Tyr Pro Val
                260                 265                 270

Val Val Thr Gln Ser Ser Gly Lys Lys Val Pro Ile Val Gln Ala Tyr
            275                 280                 285

Cys Phe Thr Lys Tyr Leu Gly Tyr Phe Lys Val Thr Ile Asn Gly Lys
        290                 295                 300

Gly Asn Val Val Gly Trp Thr Gly Gln Pro Ile Leu Leu Asn Asn Asn
305                 310                 315                 320

Ile Pro Gln Asp Gln Glu Val Leu Thr Ala Leu Glu Lys Tyr Arg Glu
                325                 330                 335

Arg Val Glu Asn Tyr Gly Asn Arg Val Ile Gly Val Ser Arg Val Ile
            340                 345                 350

Leu Asn Gly Gly His Thr Glu Cys Arg Phe His Glu Cys Asn Met Gly
        355                 360                 365

Asn Leu Ile Thr Asp Ala Phe Val Tyr Ala Asn Val Ile Ser Thr Pro
370                 375                 380

Met Ser Thr Asn Ala Trp Thr Asp Ala Ser Val Val Leu Tyr Gln Ser
385                 390                 395                 400

Gly Gly Ile Arg Ala Pro Ile Asp Pro Arg Thr Ala Ala Gly Ser Ile
                405                 410                 415

Thr Arg Leu Glu Leu Asp Asn Val Leu Pro Phe Gly Asn Ala Leu Tyr
            420                 425                 430

Val Val Lys Val Pro Gly Asn Val Leu Arg Lys Ala Leu Glu His Ser
        435                 440                 445

Val His Arg Tyr Ser Asn Thr Ser Gly Trp Gly Glu Phe Pro Gln Val
    450                 455                 460

Ser Gly Leu Lys Ile Arg Phe Asn Val Asn Glu Ile Gly Lys Arg
465                 470                 475                 480

Val Lys Ser Val Lys Val Leu Cys Ser Asn Cys Ser Gln Pro Glu Tyr
                485                 490                 495

Gln Pro Leu Arg Asn Lys Lys Thr Tyr Asn Val Ile Met Asp Ser Phe
            500                 505                 510

Met Lys Asp Gly Gly Asp Gly Tyr Ser Met Phe Lys Pro Leu Lys Ile
        515                 520                 525

Ile Lys Thr Leu Pro Leu Gly Asp Ile Glu Thr Val Glu Ala Tyr Ile
    530                 535                 540

Glu Lys Met Gly Pro Ile Phe Pro Ala Val Glu Gly Arg Ile Thr Val
545                 550                 555                 560

Leu Gly Gly Leu Gln Lys Ser Asp Glu Asp Trp His
                565                 570

<210> SEQ ID NO 56
<211> LENGTH: 1839
<212> TYPE: DNA
<213> ORGANISM: Lutzomyia longipalpis

<400> SEQUENCE: 56
agttgcaaga atttcttcat tgcgttaaga tgttgttttt ccttaacttt tttgtgctgg      60
tgttcagcat agaactggcg ttgttaacag catcagcagc agcagaagac ggcagctatg     120
agatcataat tcttcacacc aatgatatgc acgcgcgttt tgatcaaacc aatgctggaa     180
gcaacaaatg ccaagaaaaa gacaagattg cttccaaatg ctacggagga tttgcaagag     240 ttcaacaat ggtgaaaaaa ttccgagaag aaaatggcag cagtgtcttg ttcttgaatg     300
ctggtgacac gtatacaggt accccatggt ttaccctcta caaggagacc attgcaacgg     360

```
agatgatgaa catccttcgt ccagatgcag cctcactggg aaatcatgaa ttcgacaaag      420
gagtagaagg actcgtgcca ttcctcaatg gtgtcacctt ccctattta acagcgaatt      480 tggacacttc tcaagagcca acaatgacca atgctaaaaa tctcaaacgc tcaatgattt      540
ttacggtttc cgggcacaga gttggtgtaa ttggctacct aacgcctgat acaaaattcc      600
tctcggacgt tggtaaagtt aattttattc cggaagttga agccatcaat acggaagcac      660
agcgtctgaa gaaagaggaa aatgccgaaa taatcatcgt tgttggacat tcagggttga      720
taaaagatcg agaaattgca gagaaatgcc cactggttga cataattgtt ggaggacatt      780
cacacacatt cctctacaca ggaagtcagc ctgatcgtga ggttcctgta gacgtttatc      840
ctgttgttgt gacccaatcc agtgggaaga aagttccaat tgttcaagcc tattgcttta      900
caaagtattt ggggtacttt aaagtgacga tcaacgaaaa aggaaatgtt gtgggatgga      960
ctgggcagcc aattctcctt aataacaaca ttccccaaga tcaggaagtt ctcactgctc     1020
ttgaaaagta cagagaacgc gtggaaaact atggaaatcg cgtaattgga gtttcccgtg     1080
taattctcaa tgggggcat actgaatgtc gtttccatga atgcaatatg ggtaatctca      1140
tcacggacgc ttttgtgtat gccaatgtaa tcagtacacc aatgagtacg aatgcctgga     1200
cagatgcaag tgttgttctg tatcaaagtg gtggcattcg tgccccaatt gatcctcgta     1260
ccgcggcagg gagcatcaca cgcctcgagt tggacaatgt tctaccattt gggaatgcac     1320
tgtacgtcgt aaaagttcct gggaatgtct tacgcaaagc tttggaacat tcagttcatc     1380
gatactccaa cacttcggga tggggagaat ttccacaagt ttcggggcta aagattcgtt     1440
ttaacgtcaa tgaagaaatt ggaaaacgcg taaagtccgt taaagttctc tgtagcaatt     1500
gctctcaacc tgaataccaa ccactgagaa ataaaaaaac ttacaacgtt atcatggaca     1560
gttttatgaa ggatggaggt gatgggtata gcatgttcaa gcccttgaag atcatcaaga     1620
ccctcccact gggagatatt gaaacagtag aagcttatat tgagaaaatg gccccatttt     1680
tcccagcagt cgagggaagg atcactgttc ttgggggact tcaaaaatca gatgaggatt     1740
ggcattagaa acatcctgga cgttatggaa agaataaaag aaggatcata gaaaaaaaaa     1800 aaaaaaaat aaaaaaaaaa aaaaaaaaa aaaaaaaa                              1839
```

<210> SEQ ID NO 57
<211> LENGTH: 86
<212> TYPE: PRT
<213> ORGANISM: Lutzomyia longipalpis

<400> SEQUENCE: 57

```
Met Lys Gln Ile Leu Leu Ile Ser Leu Val Val Ile Leu Ala Val Leu
1               5                   10                  15

Ala Phe Asn Val Ala Glu Gly Cys Asp Ala Thr Cys Gln Phe Arg Lys
                20                  25                  30

Ala Ile Glu Asp Cys Lys Lys Ala Asp Asn Ser Asp Val Leu Gln
            35                  40                  45

Thr Ser Val Gln Thr Thr Ala Thr Phe Thr Ser Met Asp Thr Ser Gln
        50                  55                  60

Leu Pro Gly Asn Asn Val Phe Lys Ala Cys Met Lys Glu Lys Ala Lys
65                  70                  75                  80

Glu Phe Arg Ala Gly Lys
                85
```

<210> SEQ ID NO 58
<211> LENGTH: 419

```
<212> TYPE: DNA
<213> ORGANISM: Lutzomyia longipalpis

<400> SEQUENCE: 58
gtcagtgatc tgataagtta ttaaaatgaa gcaaatcctt ctaatctctt tggtggtgat      60
tcttgccgtg cttgccttca atgttgctga gggctgtgat gcaacatgcc aatttcgcaa     120
agccatagaa gactgcaaga agaaggcgga taatagcgat gttttgcaga cttctgtaca    180
aacaactgca acattcacat caatggatac atcccaacta cctggaaata atgtcttcaa    240
agcatgcatg aaggagaagg ctaaggaatt tagggcagga aagtaagaga ttgaggaaaa    300
ttgtagccga agagagaagg aaggaaagtc ccatattttg tttgttaatt gtaacgaatt    360
ttgcgaaaaa aataaaatat tatgcactcc aaaaaaaaaa aaaaaaaaaa aaaaaaaaa     419

<210> SEQ ID NO 59
<211> LENGTH: 84
<212> TYPE: PRT
<213> ORGANISM: Lutzomyia longipalpis

<400> SEQUENCE: 59

Met Asn Val Leu Phe Val Ser Phe Thr Leu Thr Ile Leu Leu Leu Cys
1               5                   10                  15

Val Lys Ala Arg Pro Glu Asp Phe Val Ala Leu Gln Asp Gln Ala Asn
            20                  25                  30

Phe Gln Lys Cys Leu Glu Gln Tyr Pro Glu Pro Asn Gln Ser Gly Glu
        35                  40                  45

Val Leu Ala Cys Leu Lys Lys Arg Glu Gly Ala Lys Asp Phe Arg Glu
    50                  55                  60

Lys Arg Ser Leu Asp Asp Ile Glu Gly Thr Phe Gln Glu Ser Gly Asn
65                  70                  75                  80

Leu Trp Gly Ala

<210> SEQ ID NO 60
<211> LENGTH: 429
<212> TYPE: DNA
<213> ORGANISM: Lutzomyia longipalpis

<400> SEQUENCE: 60
tatttttaat aattctgtgt aaaatgaacg ttcttttcgt gtctttcacg ctcacaattc      60
ttcttctctg tgttaaggca cggccagaag atttcgtagc tcttcaggat caagctaatt    120
tccagaaatg cctcgaacaa tatccagaac caaatcaatc tggagaagtt cttgcgtgcc    180
tcaagaagcg cgaaggtgcc aaagatttcc gggaaaagag gagcctggat gacatagaag    240
ggactttcca agagtctgga atctctgggg gtgcatagga agctcagagg acttctaatc    300
aatctgtgag aagagaaccc aacggctaga gaaaatttaa ggaaaataaa gaattaatg     360 aagcattaaa aaaaaaaaaa aaaaaaaaaa aaaaaaaaaa aaaaaaaaaa aaaaaaaaa     420 aaaaaaaaa                                                           429

<210> SEQ ID NO 61
<211> LENGTH: 626
<212> TYPE: PRT
<213> ORGANISM: Lutzomyia longipalpis

<400> SEQUENCE: 61

Met Lys Ile Thr Val Ile Leu Phe Thr Gly Phe Thr Ile Ala Leu Val
1               5                   10                  15

Ser Ser Ala Val Leu Lys Lys Asn Gly Glu Thr Ile Glu Glu Glu Glu
```

```
                    20                  25                  30
Val Arg Ala Glu Gln Arg Leu Arg Glu Ile Asn Glu Glu Leu Asp Arg
                35                  40                  45

Arg Lys Asn Ile Asn Thr Val Ala Ala Trp Ala Tyr Ala Ser Asn Ile
            50                  55                  60

Thr Glu Val Asn Leu Lys Asn Met Asn Asp Val Ser Val Glu Thr Ala
65                  70                  75                  80

Lys Tyr Tyr Lys Glu Leu Ala Ser Glu Leu Lys Gly Phe Asn Ala Lys
                85                  90                  95

Glu Tyr Lys Ser Glu Asp Leu Lys Arg Gln Ile Lys Lys Leu Ser Lys
            100                 105                 110

Leu Gly Tyr Ser Ala Leu Pro Ser Glu Lys Tyr Lys Glu Leu Leu Glu
            115                 120                 125

Ala Ile Thr Trp Met Glu Ser Asn Tyr Ala Lys Val Lys Val Cys Ser
            130                 135                 140

Tyr Lys Asp Pro Lys Lys Cys Asp Leu Ala Leu Glu Pro Glu Ile Thr
145                 150                 155                 160

Glu Ile Leu Ile Lys Ser Arg Asp Pro Glu Glu Leu Lys Tyr Tyr Trp
                165                 170                 175

Lys Gln Trp Tyr Asp Lys Ala Gly Thr Pro Thr Arg Glu Ser Phe Asn
            180                 185                 190

Lys Tyr Val Gln Leu Asn Arg Glu Ala Ala Lys Leu Asp Gly Phe Tyr
            195                 200                 205

Ser Gly Ala Glu Ser Trp Leu Asp Glu Tyr Asp Glu Thr Phe Glu
            210                 215                 220

Lys Gln Leu Glu Asp Ile Phe Ala Gln Ile Arg Pro Leu Tyr Glu Gln
225                 230                 235                 240

Leu His Ala Tyr Val Arg Phe Lys Leu Arg Glu Lys Tyr Gly Asn Asp
                245                 250                 255

Val Val Ser Glu Lys Gly Pro Ile Pro Met His Leu Leu Gly Asn Met
            260                 265                 270

Trp Gly Gln Thr Trp Ser Glu Val Ala Pro Ile Leu Val Pro Tyr Pro
            275                 280                 285

Glu Lys Lys Leu Leu Asp Val Thr Asp Glu Met Val Lys Gln Gly Tyr
            290                 295                 300

Thr Pro Ile Ser Met Phe Glu Lys Gly Asp Glu Phe Phe Gln Ser Leu
305                 310                 315                 320

Asn Met Thr Lys Leu Pro Lys Thr Phe Trp Glu Tyr Ser Ile Leu Glu
                325                 330                 335

Lys Pro Gln Asp Gly Arg Glu Leu Ile Cys His Ala Ser Ala Trp Asp
            340                 345                 350

Phe Tyr Thr Lys Asp Asp Val Arg Lys Gln Cys Thr Arg Val Thr Met
            355                 360                 365

Asp Gln Phe Phe Thr Ala His His Glu Leu Gly His Ile Gln Tyr Tyr
            370                 375                 380

Leu Gln Tyr Gln His Leu Pro Ser Val Tyr Arg Glu Gly Ala Asn Pro
385                 390                 395                 400

Gly Phe His Glu Ala Val Gly Asp Val Leu Ser Leu Ser Val Ser Ser
                405                 410                 415

Pro Lys His Leu Glu Lys Val Gly Leu Leu Lys Asp Phe Lys Phe Asp
            420                 425                 430

Glu Glu Ser Gln Ile Asn Gln Leu Leu Asn Leu Ala Leu Asp Lys Met
            435                 440                 445
```

```
Ala Phe Leu Pro Phe Ala Tyr Thr Ile Asp Lys Tyr Arg Trp Gly Val
    450                 455                 460

Phe Arg Gly Glu Ile Ser Pro Ser Glu Tyr Asn Cys Lys Phe Trp Glu
465                 470                 475                 480

Met Arg Ser Tyr Tyr Gly Gly Ile Glu Pro Pro Ile Ala Arg Ser Glu
                485                 490                 495

Ser Asp Phe Asp Pro Pro Ala Lys Tyr His Ile Ser Ser Asp Val Glu
            500                 505                 510

Tyr Leu Arg Tyr Leu Val Ser Phe Ile Ile Gln Phe Gln Phe His Gln
        515                 520                 525

Ala Val Cys Gln Lys Thr Gly Gln Phe Val Pro Asn Asp Pro Glu Lys
    530                 535                 540

Thr Leu Leu Asn Cys Asp Ile Tyr Gln Ser Ala Glu Ala Gly Asn Ala
545                 550                 555                 560

Phe Lys Glu Met Leu Lys Leu Gly Ser Ser Lys Pro Trp Pro Asp Ala
                565                 570                 575

Met Glu Ile Leu Thr Gly Gln Arg Lys Met Asp Ala Ser Ala Leu Ile
            580                 585                 590

Glu Tyr Phe Arg Pro Leu Ser Glu Trp Leu Gln Lys Lys Asn Lys Glu
        595                 600                 605

Leu Gly Ala Tyr Val Gly Trp Asp Lys Ser Thr Lys Cys Val Lys Asn
    610                 615                 620

Val Ser
625
```

<210> SEQ ID NO 62
<211> LENGTH: 2121
<212> TYPE: DNA
<213> ORGANISM: Lutzomyia longipalpis

<400> SEQUENCE: 62

```
gtatatcaag tatcattcaa gtgaatcatt ggctccgtaa tttgtacaaa agaaaaaaaa      60
agttgataaa atcatgaaaa tcactgtgat tttattcacg ggatttacaa ttgccctcgt     120
gagtagtgct gtgcttaaga aaacggtga aactattgaa gaagaagaag taagagctga     180
gcaacgactt agagagatca atgaggaact tgatcgtagg aagaatatca atactgtagc     240
cgcttgggct tatgcatcca atattactga ggtcaatctc aagaacatga atgatgtgtc     300
ggttgaaacc gcgaaatact acaaggaact tgcatctgaa ttgaagggat tcaatgccaa     360
ggaatacaag agtgaggatc tgaagagaca aattaagaag ctaagcaagt tgggatatag     420
tgctttacca tctgagaagt ataaggagct tttggaagct atcacatgga tggaatcgaa     480
ttatgcaaaa gtgaaagttt gctcatacaa ggatccaaag aaatgtgatt tagcacttga     540
acctgaaatt acggaaatcc ttattaaaag tcgagatcct gaggaactta atattattg     600
gaaacaatgg tacgacaaag ctggcacacc aactcgagag agtttttaata gtatgtaca     660
actaaatcgt gaagcagcga aattggatgg attttattcg ggtgcagaat cttggcttga     720
tgaatatgaa gatgagacat ttgagaaaca acttgaggat atcttcgccc aaattcgccc     780
actgtacgag caactccatg cttatgttag attcaagctg agggaaaagt atggaaatga     840
cgttgtttcg gagaaaggtc ccattccaat gcatctcttg gggaacatgt ggggtcaaac     900
gtggagtgaa gttgccccaa ttttagtccc ataccccgaa aagaagctcc tcgatgttac     960
cgatgagatg gttaagcagg gatacacacc aatttctatg tttgaaaaag gagacgaatt    1020
tttccaaagc ttgaatatga cgaaacttcc aaaaaacctt ctgggagtaca gtattttgga    1080
```

```
aaaacccccaa gatggtaggg aattgatctg ccatgcaagt gcatgggact tctatacaaa    1140
ggatgatgta aggattaaac agtgtaccag agttacaatg gatcaattct tcacggctca    1200
tcatgagctt ggtcacattc aatattattt gcaatatcaa catttgccga gtgtttacag    1260
agaaggtgcc aatccaggct ttcacgaggc tgttggggat gttctctctc tttcggtatc    1320
aagtcctaaa catttggaaa aagttggttt gcttaaagac ttcaaatttg atgaagaatc    1380
ccagataaat caacttctaa atttagctct ggataaaatg gcattcctcc catttgccta    1440
taccattgat aaatatcgct ggggtgtgtt tcggggtgaa atttcgccgt ctgagtacaa    1500
ttgcaaattt tgggaaatgc gttcctacta tggtggtata gaaccaccaa ttgcacgttc    1560
tgagagtgat tttgatccac cagcaaaata tcatatttca tcggatgttg agtacctcag    1620
gtatttggtt tccttcatta ttcagttcca attccatcaa gctgtgtgcc aaaagactgg    1680
tcagttcgta ccgaatgatc cggagaagac tcttctaaat tgtgacatct accagagtgc    1740
tgaggctggt aatgccttca agaaatgct caaattggga tcctcaaaac catggccaga    1800
tgcaatggaa attcttacgg ggcaaaggaa aatggatgct tctgcattaa ttgagtactt    1860
ccgtccactc agtgagtggt tgcagaagaa gaataaggaa ctaggagctt atgttggctg    1920
ggacaaatct actaagtgtg tcaaaaacgt cagttaattt tttgtgagcc ctaaaaaata    1980
ttcataacat ttcaatatga caaaatatat gattttcgtg aaaactaagc atgagtaagt    2040 ttttttttgtg aattttttagc agtttcattt cagaataaac gtcaaatttt taaaaaaaaa    2100
aaaaaaaaaa aaaaaaaaaa a                                              2121

<210> SEQ ID NO 63
<211> LENGTH: 42
<212> TYPE: PRT
<213> ORGANISM: Lutzomyia longipalpis

<400> SEQUENCE: 63

Met Lys Thr Phe Ala Leu Ile Phe Leu Ala Leu Ala Val Phe Val Leu
1               5                   10                  15

Cys Ile Asp Gly Ala Pro Thr Phe Val Asn Leu Leu Asp Asp Val Gln
            20                  25                  30

Glu Glu Val Glu Val Asn Thr Tyr Glu Pro
        35                  40

<210> SEQ ID NO 64
<211> LENGTH: 463
<212> TYPE: DNA
<213> ORGANISM: Lutzomyia longipalpis

<400> SEQUENCE: 64
tcagttagtt gactaacaaa ccacaataga gacactaaaa tgaagacatt cgccttaatc     60
ttcttggctc ttgctgtttt tgtgctctgc attgacggag ctccaacttt tgtgaattta    120
ctggacgacg tacaggaaga ggtagaagtt aatacgtatg agccttagga agaaaatgtt    180
tgaggagttt caggcagagg cagagctttc ccagagaggg agcttttgcc ttgctgtaga    240
tttttaaaaa tgaatcaatt tgattggagc aattacgcta tatttgtggg aatatttttg    300
aattaaaaac taattatgga aattaatata taattttcag aatttcaata aattcatcaa    360
aattgtatta attaaaaaat attgtatgaa attcccaata aaagctttca aattaaaaaa    420
aaaaaaaaaa aaaaaaaaaa aaaaaaaaaa aaaaaaaaaa aaa                      463

<210> SEQ ID NO 65
<211> LENGTH: 139
```

```
<212> TYPE: PRT
<213> ORGANISM: Lutzomyia longipalpis

<400> SEQUENCE: 65

Met Asn His Leu Cys Phe Ile Ile Ala Leu Phe Phe Leu Val Gln
1               5                   10                  15

Gln Ser Leu Ala Glu His Pro Glu Glu Lys Cys Ile Arg Glu Leu Ala
            20                  25                  30

Arg Thr Asp Glu Asn Cys Ile Leu His Cys Thr Tyr Ser Tyr Tyr Gly
        35                  40                  45

Phe Val Asp Lys Asn Phe Arg Ile Ala Lys Lys His Val Gln Lys Phe
    50                  55                  60

Lys Lys Ile Leu Val Thr Phe Gly Ala Val Pro Lys Lys Glu Lys Lys
65                  70                  75                  80

Lys Leu Leu Glu His Ile Glu Ala Cys Ala Asp Ser Ala Asn Ala Asp
                85                  90                  95

Gln Pro Gln Thr Lys Asp Glu Lys Cys Thr Lys Ile Asn Lys Tyr Tyr
            100                 105                 110

Arg Cys Val Val Asp Gly Lys Ile Leu Pro Trp Asn Ser Tyr Ala Asp
        115                 120                 125

Ala Ile Ile Lys Phe Asp Lys Thr Leu Asn Val
    130                 135

<210> SEQ ID NO 66
<211> LENGTH: 579
<212> TYPE: DNA
<213> ORGANISM: Lutzomyia longipalpis

<400> SEQUENCE: 66
ggccattatg gccggggata gaacttaatt gttgttaaaa tgaatcactt gtgctttatt      60
attattgctc tattctttt ggttcaacaa tctttggctg aacatccaga agaaaaatgt      120
attagagaat tggcgagaac tgatgaaaac tgcattcttc attgtacgta ttcgtactac     180
ggattcgttg ataaaattt caggatcgct aaaaaacatg ttcaaaaatt caaaaaaatc     240
ctagttacat tcggcgctgt tcctaagaaa gaaaaaaaga aacttttaga gcacattgag     300
gcttgtgcgg attctgcgaa tgctgatcaa cctcaaacta agatgaaaaa atgtacaaaa     360
ataaataagt actatcgttg tgttgtggat ggaaaaatat taccctggaa tagttatgct     420
gatgcaatca ttaagtttga taaaacccctt aacgtatgaa gcaagatat tcgaaaaaaa     480 aacatcaaga ttatgctgga agaaaaaaaa taaaaaaaaa ttgtgctaat caaattgaat     540
taacgcttaa tgctatatta aaaaaaaaaa aaaaaaaaa                            579

<210> SEQ ID NO 67
<211> LENGTH: 446
<212> TYPE: PRT
<213> ORGANISM: Lutzomyia longipalpis

<400> SEQUENCE: 67

Met Lys Ile Ile Phe Leu Ala Ala Phe Leu Leu Ala Asp Gly Ile Trp
1               5                   10                  15

Ala Ala Glu Glu Pro Ser Val Glu Ile Val Thr Pro Gln Ser Val Arg
            20                  25                  30

Arg His Ala Thr Pro Lys Ala Gln Asp Ala Arg Val Gly Ser Glu Ser
        35                  40                  45

Ala Thr Thr Ala Pro Arg Pro Ser Glu Ser Met Asp Tyr Trp Glu Asn
    50                  55                  60
```

Asp Asp Phe Val Pro Phe Glu Gly Pro Phe Lys Asp Ile Gly Glu Phe
65                  70                  75                  80

Asp Trp Asn Leu Ser Lys Ile Val Phe Glu Asn Lys Gly Asn Ala
            85                  90                  95

Ile Leu Ser Pro Leu Ser Val Lys Leu Leu Met Ser Leu Leu Phe Glu
            100                 105                 110

Ala Ser Ala Ser Gly Thr Leu Thr Gln His Gln Leu Arg Gln Ala Thr
            115                 120                 125

Pro Thr Ile Val Thr His Tyr Gln Ser Arg Glu Phe Tyr Lys Asn Ile
            130                 135                 140

Phe Asp Gly Leu Lys Lys Lys Ser Asn Asp Tyr Thr Val His Phe Gly
145                 150                 155                 160

Thr Arg Ile Tyr Val Asp Gln Phe Val Thr Pro Arg Gln Arg Tyr Ala
                165                 170                 175

Ala Ile Leu Glu Lys His Tyr Leu Thr Asp Leu Lys Val Glu Asp Phe
            180                 185                 190

Ser Lys Ala Lys Glu Thr Thr Gln Ala Ile Asn Ser Trp Val Ser Asn
            195                 200                 205

Ile Thr Asn Glu His Ile Lys Asp Leu Val Lys Glu Glu Asp Val Gln
210                 215                 220

Asn Ser Val Met Leu Met Leu Asn Ala Val Tyr Phe Arg Gly Leu Trp
225                 230                 235                 240

Arg Lys Pro Phe Asn Arg Thr Leu Pro Leu Pro Phe His Val Ser Ala
                245                 250                 255

Asp Glu Ser Lys Thr Thr Asp Phe Met Leu Thr Asp Gly Leu Tyr Tyr
            260                 265                 270

Phe Tyr Glu Ala Lys Glu Leu Asp Ala Lys Ile Leu Arg Ile Pro Tyr
275                 280                 285

Lys Gly Lys Gln Tyr Ala Met Thr Val Ile Leu Pro Asn Ser Lys Ser
290                 295                 300

Gly Ile Asp Ser Phe Val Arg Gln Ile Asn Thr Val Leu Leu His Arg
305                 310                 315                 320

Ile Lys Trp Leu Met Asp Glu Val Glu Cys Arg Val Ile Leu Pro Lys
            325                 330                 335

Phe His Phe Asp Met Thr Asn Glu Leu Lys Glu Ser Leu Val Lys Leu
            340                 345                 350

Gly Ile Ser Gln Ile Phe Thr Ser Glu Ala Ser Leu Pro Ser Leu Ala
            355                 360                 365

Arg Gly Gln Gly Val Gln Asn Arg Leu Gln Val Ser Asn Val Ile Gln
370                 375                 380

Lys Ala Gly Ile Ile Val Asp Lys Gly Ser Thr Ala Tyr Ala Ala
385                 390                 395                 400

Ser Glu Val Ser Leu Val Asn Lys Phe Gly Asp Glu Phe Val Met
            405                 410                 415

Phe Asn Ala Asn His Pro Phe Leu Phe Thr Ile Glu Asp Glu Thr Thr
            420                 425                 430

Gly Ala Ile Leu Phe Thr Gly Lys Val Val Asp Pro Thr Gln
435                 440                 445

<210> SEQ ID NO 68
<211> LENGTH: 1651
<212> TYPE: DNA
<213> ORGANISM: Lutzomyia longipalpis
<220> FEATURE:
<221> NAME/KEY: misc_feature
<222> LOCATION: (1636)..(1636)

<223> OTHER INFORMATION: n is a, c, g, or t

<400> SEQUENCE: 68

```
gtcggagatc gtctgccttg atgatcacat cgtgattgtg agttacaaga gtgaaacttt    60
ttaagtgtgt gtgtcttagc aaagtgattt ccacaatgaa gattatttt ttagccgctt    120
ttctactagc ggatggtatt tgggctgctg aagaaccttc agtggaaatt gtaacaccac    180
aatcagtgcg gagacacgct acgccaaaag cccaggacgc gagggtagga agtgaatccg    240
caacaacagc accaagacca gtgaatcaa tggattactg ggagaatgat gatttcgtcc     300
catttgaggg tccattcaag gatattggag aattcgactg gaacctttcg aagatcgttt    360
ttgaggaaaa caaaggtaat gccatcttgt cgccactctc tgtgaagcta ctaatgagtt    420
tgctcttcga ggccagtgcg tcaggtacct tgacccagca ccaactcaga caagccactc    480
ccaccatcgt cacccactat cagtctcgag aattttacaa gaatatcttt gacggtctca    540
agaaaaagag taacgactac acggttcact ttggtacgag aatctacgtg gatcagtttg    600
tgacgcctcg ccagagatat gctgccattt tggagaagca ttatctgact gatctcaaag    660
ttgaggactt ctcgaaggca aagaaacaa ctcaggcaat caatagttgg gtgtcaaaca     720
tcacaaatga gcacataaag gatctcgtga aggaggaaga tgttcagaat tcagttatgc    780
tcatgcttaa tgcagtctac ttccgcggac tctggcgcaa gcctttcaat cgtacactcc    840
cactgcccttt ccacgtgagc gctgatgagt ccaagacgac tgattttatg ctaaccgatg   900
ggctctacta cttctacgag gcaaaggaat tggatgctaa gatcctcaga attccttaca    960
aaggtaaaca atacgcaatg actgtgatct taccaaattc caagagtggc attgatagct   1020
ttgtgcgtca gattaacacg gtcctcctgc acaggattaa gtggttgatg gatgaagtgg   1080
agtgcagggt tattctaccc aagttccact ttgacatgac gaatgagctg aaggaatcgc   1140
tcgtaaagtt gggcatcagt cagattttca catcagaggc atctttgcca tcattagcac   1200
gaggacaggg cgtacagaat cgtctgcagg tgtctaatgt gattcagaag gcgggaataa   1260
ttgtggatga aagggcagc acagcctatg ctgcgtcaga agtgagccta gtcaacaagt    1320
ttggagatga tgagttcgtc atgttcaacg ctaatcatcc attcctcttt acaattgagg   1380
acgaaaccac cggcgcaatc ctatttacgg gaaaagtcgt cgatcccacg caatagggaa   1440
tgaaaagcat ttcatcgtat acaacttttt ttttaattaa ttattcctca ttgaaggaca   1500
ttaatagagc atcttctcag gaaggcactc ctgacttatt tttactaaat gtgatccttg   1560
gacacataaa aaaacagct gtactttcta cttttatata tatacgacca tatttgtgag   1620
gaaaaaaaaa aaaanaaaa aaaaaaaaa a                                     1651
```

<210> SEQ ID NO 69
<211> LENGTH: 166
<212> TYPE: PRT
<213> ORGANISM: Lutzomyia longipalpis

<400> SEQUENCE: 69

```
Met Arg Phe Leu Leu Leu Ala Phe Ser Val Ala Leu Val Leu Ser Pro
  1               5                  10                  15

Thr Phe Ala Lys Pro Gly Leu Trp Asp Ile Val Thr Gly Ile Asn Asp
             20                  25                  30

Met Val Lys Asn Thr Ala Asn Ala Leu Lys Asn Arg Leu Thr Thr Ser
         35                  40                  45

Val Thr Leu Phe Thr Asn Thr Ile Thr Glu Ala Ile Lys Asn Ala Asn
     50                  55                  60
```

```
Ser Ser Val Ser Glu Leu Leu Gln Gln Val Asn Glu Thr Leu Thr Asp
 65                  70                  75                  80

Ile Ile Asn Gly Val Gly Gln Val Gln Ser Ala Phe Val Asn Ser Ala
                 85                  90                  95

Gly Asn Val Val Val Gln Ile Val Asp Ala Ala Gly Asn Val Leu Glu
            100                 105                 110

Val Val Val Asp Glu Ala Gly Asn Ile Val Glu Val Ala Gly Thr Ala
        115                 120                 125

Leu Glu Thr Ile Ile Pro Leu Pro Gly Val Val Ile Gln Lys Ile Ile
    130                 135                 140

Asp Ala Leu Gln Gly Asn Ala Gly Thr Thr Ser Asp Ser Ala Ser Ser
145                 150                 155                 160

Thr Val Pro Gln Gln Ser
                165

<210> SEQ ID NO 70
<211> LENGTH: 739
<212> TYPE: DNA
<213> ORGANISM: Lutzomyia longipalpis

<400> SEQUENCE: 70
tcagttaagc agattttcaa gctaaagaaa cttaactaag atgcgattcc ttcttttggc     60
cttctccgtt gctttggtgc tttcaccaac attcgccaaa ccaggtcttt gggacattgt    120
aactggtatt aatgatatgg taaaaaatac tgcgaatgca ctcaaaaatc gtctaacaac    180
ttctgtgaca ttattcacaa ataccatcac cgaagctata aaaaatgcaa attcttctgt    240
ttcggaactc cttcagcaag tcaatgaaac ccttacggat attattaatg gtgtaggaca    300
agtgcagagt gcctttgtga attcagctgg aaatgttgtt gtgcaaattg ttgatgccgc    360
tggaaatgtt ttggaagttg ttgttgatga ggctggaaat atcgtggagg tagctggaac    420
agcattggaa actatcattc cactgcccgg tgtagtgatt cagaagataa ttgatgctct    480
ccaaggaaat gcagggacta catcggattc agcttcatca actgtgcccc aacaatctta    540
actacaaccg caatgatgtt gtctttaacg gagaattttt aaatttgaat atcaaaatcc    600
aagatgaaat attcagattt ttcaatcaat atgatacgaa attttgaaat tattttttccg    660 actaaagcaa tttgtaaaag gaaaaccaaa taaatatttg aaattgtaaa gaaaaaaaaa    720
aaaaaaaaaa aaaaaaaaa                                                 739

<210> SEQ ID NO 71
<211> LENGTH: 109
<212> TYPE: PRT
<213> ORGANISM: Lutzomyia longipalpis

<400> SEQUENCE: 71

Met Val Lys Tyr Ser Cys Leu Val Leu Val Ala Ile Phe Leu Leu Ala
1               5                  10                  15

Gly Pro Tyr Gly Val Val Gly Ser Cys Glu Asn Asp Leu Thr Glu Ala
             20                  25                  30

Ala Lys Tyr Leu Gln Asp Glu Cys Asn Ala Gly Glu Ile Ala Asp Glu
         35                  40                  45

Phe Leu Pro Phe Ser Glu Glu Val Gly Glu Ala Leu Ser Asp Lys
     50                  55                  60

Pro Glu Asn Val Gln Glu Val Thr Asn Ile Val Arg Gly Cys Phe Glu
65                  70                  75                  80

Ala Glu Gln Ala Lys Glu His Gly Lys Cys Glu Arg Phe Ser Ala Leu
                85                  90                  95
```

Ser Gln Cys Tyr Ile Glu Lys Asn Leu Cys Gln Phe Phe
            100                 105

<210> SEQ ID NO 72
<211> LENGTH: 447
<212> TYPE: DNA
<213> ORGANISM: Lutzomyia longipalpis

<400> SEQUENCE: 72
atatcaattt tatcatcatg gtgaagtact cgtgtcttgt tcttgttgca attttcttc      60 tggccggacc ctacggcgtt gtaggttctt gtgagaatga cctgacagag gccgccaagt    120
atcttcaaga tgaatgcaat gcaggtgaaa ttgcagatga atttctaccc ttctctgaag    180
aagaagtggg tgaagcattg agcgacaaac cagaaaacgt gcaggaagtc accaacatcg    240
tgagaggatg ctttgaagct gaacaagcca agagcatgg aaaatgtgaa agattttccg     300
ctttgagtca atgctacatt gaaaagaatt tatgtcaatt cttctaaaat attttgaaga    360
aaagttatga atgaaaattt tctgaaattt tgttgcaaaa atatataaat tgcccaatta    420
aaaaaaaaaa aaaaaaaaaa aaaaaaa                                        447

<210> SEQ ID NO 73
<211> LENGTH: 115
<212> TYPE: PRT
<213> ORGANISM: Lutzomyia longipalpis

<400> SEQUENCE: 73

Met Lys Phe Phe Tyr Leu Ile Phe Ser Ala Ile Phe Phe Leu Ala Asp
1               5                   10                  15

Pro Ala Leu Val Lys Cys Ser Glu Asp Cys Glu Asn Ile Phe His Asp
            20                  25                  30

Asn Ala Tyr Leu Leu Lys Leu Asp Cys Glu Ala Gly Arg Val Asp Pro
        35                  40                  45

Val Glu Tyr Asp Asp Ile Ser Asp Glu Ile Tyr Glu Ile Thr Val
    50                  55                  60

Asp Val Gly Val Ser Ser Glu Asp Gln Glu Lys Val Ala Lys Ile Ile
65                  70                  75                  80

Arg Glu Cys Ile Ala Gln Val Ser Thr Gln Asp Cys Thr Lys Phe Ser
                85                  90                  95

Glu Ile Tyr Asp Cys Tyr Met Lys Lys Lys Ile Cys Asn Tyr Tyr Pro
            100                 105                 110

Glu Asn Met
        115

<210> SEQ ID NO 74
<211> LENGTH: 496
<212> TYPE: DNA
<213> ORGANISM: Lutzomyia longipalpis

<400> SEQUENCE: 74
agtttaattt tcatcatgaa gttcttctac ttgattttct ctgcaatttt ctttctggct      60
gatcctgctt tggtcaagtg ttcagaggat tgtgagaata ttttcatga caatgcgtac      120 ctccttaaat tggattgtga agcaggaagg gttgatcctg ttgaatacga cgatatttcg     180
gatgaagaaa tatatgaaat aacggtcgat gttggagttt catctgagga ccaggagaaa     240
gttgcgaaaa taataaggga gtgcattgca caagtttcaa cgcaagattg cacgaaattt     300
tcagaaattt atgattgtta catgaagaag aaaatctgta attattatcc tgaaaatatg     360

```
taaaaaaaaa ttatttattt atataaaaaa atataaggat taaaatctct tattgattgt    420
aaaaatggcc taatattgaa gcaaaaatta aagcatgaaa caagaccaaa aaaaaaaaaa    480
aaaaaaaaaa aaaaaa                                                    496

<210> SEQ ID NO 75
<211> LENGTH: 409
<212> TYPE: PRT
<213> ORGANISM: Lutzomyia longipalpis

<400> SEQUENCE: 75

Met His Leu Gln Leu Asn Leu Cys Ala Ile Leu Leu Ser Val Leu Asn
1               5                   10                  15

Gly Ile Gln Gly Ala Pro Lys Ser Ile Asn Ser Lys Ser Cys Ala Ile
            20                  25                  30

Ser Phe Pro Glu Asn Val Thr Ala Lys Lys Glu Pro Val Tyr Leu Lys
        35                  40                  45

Pro Ser Asn Asp Gly Ser Leu Ser Thr Pro Leu Gln Pro Ser Gly Pro
    50                  55                  60

Phe Val Ser Leu Lys Ile Gly Glu Ser Leu Ala Ile Phe Cys Pro Gly
65                  70                  75                  80

Asp Gly Lys Asp Val Glu Thr Ile Thr Cys Asn Thr Asn Phe Asp Leu
                85                  90                  95

Ala Ser Tyr Ser Cys Asn Lys Ser Thr Ser Thr Asp Thr Ile Glu Thr
            100                 105                 110

Glu Glu Val Cys Gly Gly Ser Gly Lys Val Tyr Lys Val Gly Phe Pro
        115                 120                 125

Leu Pro Ser Gly Asn Phe His Ser Ile Tyr Gln Thr Cys Phe Asp Lys
    130                 135                 140

Lys Asn Leu Thr Pro Leu Tyr Ser Ile His Ile Leu Asn Gly Gln Ala
145                 150                 155                 160

Val Gly Tyr His Leu Lys His Thr Arg Gly Ser Phe Arg Thr Asn Gly
                165                 170                 175

Ile Tyr Gly Lys Val Asn Ile Asp Lys Leu Tyr Lys Thr Gln Ile Glu
            180                 185                 190

Lys Phe Asn Lys Leu Phe Gly Pro Lys Gln Thr Phe Phe Arg Arg Pro
        195                 200                 205

Leu Asn Phe Leu Ser Arg Gly His Leu Ser Pro Glu Val Asp Phe Thr
    210                 215                 220

Phe Arg Arg Glu Gln His Ala Thr Glu Met Tyr Ile Asn Thr Ala Pro
225                 230                 235                 240

Gln Tyr Gln Ser Ile Asn Gln Gly Asn Trp Leu Arg Val Glu Asn His
                245                 250                 255

Val Arg Asp Leu Ala Lys Val Leu Gln Lys Asp Ile Thr Val Val Thr
            260                 265                 270

Gly Ile Leu Gly Ile Leu Arg Leu Lys Ser Lys Lys Ile Glu Lys Glu
        275                 280                 285

Ile Tyr Leu Gly Asp Asp Val Ile Ala Val Pro Ala Met Phe Trp Lys
    290                 295                 300

Ala Val Phe Asp Pro Gln Lys Gln Glu Ala Ile Val Phe Val Ser Ser
305                 310                 315                 320

Asn Asn Pro His Val Lys Thr Phe Asn Pro Asn Cys Lys Asp Val Cys
                325                 330                 335

Ala Gln Ala Gly Phe Gly Asn Asp Asn Leu Glu Tyr Phe Ser Asn Tyr
            340                 345                 350
```

```
Ser Ile Gly Leu Thr Ile Cys Cys Lys Leu Glu Glu Phe Val Lys Arg
        355                 360                 365

Asn Lys Ile Ile Leu Pro Lys Glu Val Asn Asn Lys Asn Tyr Thr Lys
    370                 375                 380

Lys Leu Leu Lys Phe Pro Lys Thr Arg Asn Lys Glu Gly Asp Lys Lys
385                 390                 395                 400

Val Val Arg Lys Arg Ala Lys Gly Ala
                405
```

<210> SEQ ID NO 76
<211> LENGTH: 1281
<212> TYPE: DNA
<213> ORGANISM: Lutzomyia longipalpis

<400> SEQUENCE: 76

```
tcaatctaac aatgcacctg caattgaatt tgtgcgctat tctcctttcg gtactaaatg     60
gaattcaggg cgctcccaaa agtattaatt caaaatcctg cgcaatctcc tttccggaga    120
atgtaacggc taagaaggag ccagtgtact tgaaaccatc aaatgatggc tcattgagta    180
ccccccctaca gccaagtggg ccatttgtaa gtctcaaaat tggagaatct cttgcaatct    240
tctgtccagg tgatggaaag gacgtagaga caattacgtg caatacaaat ttcgatttag    300
cttcatattc gtgcaacaag agcacatcaa cggataccat tgaaacggaa gaagtttgcg    360
gaggaagtgg aaaagtgtac aaagttggtt ttccgctgcc ctctgggaat ttccattcaa    420
tctaccaaac gtgttttgat aagaaaaatc tcacacctct ctactcaatt cacattctca    480
atggtcaagc tgttggatat caccttaagc acacaagagg aagctttcgt accaatggta    540
tctacgggaa agtcaacatt gataaactct acaagacgca aattgagaaa ttcaacaaac    600
ttttcggccc taaacaaaca ttttccgta  gaccctcaa ttttctatca cgtggacact    660
taagccccga gtggactttt acattccgta gggaacaaca tgcaacggaa atgtacatta    720
acacagcacc acagtaccaa tcaattaatc aaggaaattg gctacgtgtt gaaaatcacg    780
tgagggatct cgcaaaagtt ctgcagaagg acataacagt cgttacggga attttgggga    840
tacttcggtt gaagagtaag aaaatagaga agaaatcta tttaggagat gacgtaattg    900
ccgtaccagc aatgttctgg aaggctgttt ttgaccctca aaaacaagaa gcaattgtct    960
ttgtttcctc aaataatccc cacgtgaaga cctttaatcc caactgcaag gatgtatgcg   1020
ctcaagctgg atttgggaat gataatcttg aatatttctc caattattct attggtctga   1080
ctatttgttg caaacttgag gaatttgtta aagaaataa aataattcta cccaaagaag   1140
taaataacaa aaactacacc aaaaaactcc ttaagtttcc taaaacaaga acaaggagg    1200
gagataagaa ggtggtacgt aagcgcgcca aaggagcata aatattaaac gaaaaaaaaa   1260
aaaaaaaaaa aaaaaaaaa a                                              1281
```

<210> SEQ ID NO 77
<211> LENGTH: 160
<212> TYPE: PRT
<213> ORGANISM: Lutzomyia longipalpis

<400> SEQUENCE: 77

```
Met Asn Leu His Leu Ala Ile Ile Leu Phe Val Ser Tyr Phe Thr Leu
1               5                   10                  15

Ile Thr Ala Thr Asp Leu Ile Glu Lys Glu Leu Ser Asp Cys Lys Lys
            20                  25                  30

Ile Phe Ile Ser Lys Ala Glu Leu Thr Trp Phe Gln Ala Leu Asp Phe
        35                  40                  45
```

Cys Thr Glu Gln Asn Leu Thr Leu Leu Ser Ile Lys Ser Ala Arg Glu
    50                  55                  60

Asn Asp Glu Val Thr Lys Ala Val Arg Ala Glu Val His Leu Pro Asp
65                  70                  75                  80

Thr Lys Lys Ser His Ile Trp Leu Gly Gly Ile Arg Tyr Asp Gln Asp
                85                  90                  95

Lys Asp Phe Arg Trp Ile Ser Asp Gly Thr Thr Val Thr Lys Thr Val
            100                 105                 110

Tyr Ile Asn Trp Tyr Gln Gly Glu Pro Asn Gly Gly Arg Tyr Gln Lys
        115                 120                 125

Glu Phe Cys Met Glu Leu Tyr Phe Lys Thr Pro Ala Gly Gln Trp Asn
    130                 135                 140

Asp Asp Ile Cys Thr Ala Lys His His Phe Ile Cys Gln Glu Lys Lys
145                 150                 155                 160

<210> SEQ ID NO 78
<211> LENGTH: 671
<212> TYPE: DNA
<213> ORGANISM: Lutzomyia longipalpis

<400> SEQUENCE: 78
gttctacgat aaaattttct tttcaaactt ttcttttaaa gaaaaatctt caaaaagtta      60
aaatgaattt gcaccttgcg attatcctct ttgtgagtta cttcacactg atcactgcta     120
cggatctaat tgaaaaggaa ctttctgatt gcaaaaagat cttcatctcc aaggctgagc     180
taacttggtt ccaagctctc gatttctgta ccgaacaaaa cctaactttg ctctcaatta     240
aatccgcccg ggaaaatgat gaggtgacta aagcagttcg agctgaggtt catcttccag     300
acacaaagaa gtctcacatt tggctcggag gtattcgtta tgatcaagac aaggatttcc     360
gttggataag cgatggaaca actgttacga agacagtcta catcaattgg taccaaggag     420
aaccaaatgg tgggaggtac caaaaggaat tttgtatgga attgtacttt aaaactccag     480
ctggtcaatg gaatgatgat atttgtacag caaagcatca ttttatatgt caggagaaaa     540
aataaattga attgttcatg tgtctttggc ggtgcgaagg tataattcag gttgacgaca     600
taaattgatt tttctttcat taagaaaata aaggcttgaa tttataaaaa aaaaaaaaa     660
aaaaaaaaa a                                                          671

<210> SEQ ID NO 79
<211> LENGTH: 160
<212> TYPE: PRT
<213> ORGANISM: Lutzomyia longipalpis

<400> SEQUENCE: 79

Met Asn Leu Pro Leu Ala Ile Ile Leu Phe Val Ser Tyr Phe Thr Leu
1               5                   10                  15

Ile Thr Ala Ala Asp Leu Thr Glu Lys Glu Leu Ser Asp Gly Lys Lys
            20                  25                  30

Ile Phe Ile Ser Lys Ala Glu Leu Ser Trp Phe Asp Ala Leu Asp Ala
        35                  40                  45

Cys Thr Glu Lys Asp Leu Thr Leu Leu Thr Ile Lys Ser Ala Arg Glu
    50                  55                  60

Asn Glu Glu Val Thr Lys Ala Val Arg Ala Glu Val His Leu Pro Asp
65                  70                  75                  80

Thr Lys Lys Ser His Ile Trp Leu Gly Gly Ile Arg Tyr Asp Gln Asp
                85                  90                  95

```
Lys Asp Phe Arg Trp Ile Ser Asp Gly Thr Thr Val Thr Lys Thr Val
            100                 105                 110

Tyr Ile Asn Trp Tyr Gln Gly Glu Pro Asn Gly Gly Arg Tyr Gln Lys
            115                 120                 125

Glu Phe Cys Met Glu Leu Tyr Phe Lys Thr Pro Ala Gly Gln Trp Asn
130                 135                 140

Asp Asp Ile Cys Thr Ala Lys His His Phe Ile Cys Gln Glu Lys Lys
145                 150                 155                 160

<210> SEQ ID NO 80
<211> LENGTH: 672
<212> TYPE: DNA
<213> ORGANISM: Lutzomyia longipalpis

<400> SEQUENCE: 80
gttctacgat aaaattttct tttcaaactt tccttttaaa gaaaaatctt caaaaagtta      60
aaatgaattt gccccttgcg attatcctct ttgtgagtta cttcacactg atcactgctg     120
cggatctaac tgaaaaggaa ctttctgatg caaaaagat cttcatctcc aaggctgagc     180
taagttggtt cgatgctctc gatgcctgta ccgaaaaaga cctaactttg ctcacaatta     240
aatccgcccg ggaaaatgag gaagtgacta aagcagttcg agctgaggtt catcttccag     300
acacaaagaa gtctcacatt tggctcggag gtattcgtta tgatcaagac aaggatttcc     360
gttggataag cgatggaaca actgttacga agacagtcta catcaattgg taccaaggag     420
aaccaaatgg tgggaggtac caaaggaat tttgtatgga attgtacttt aaaactccag     480
ctggtcaatg gaatgatgat atttgtacag caaagcatca ttttatatgt caggagaaaa     540
aataaattga attgttcatg tgtctttggc ggtgcgaagg tataattcag gttgacgaca     600
taaattgatt tttctttcat taagaaaata aaggcttgaa tttagcaaaa aaaaaaaaaa     660
aaaaaaaaaa aa                                                         672

<210> SEQ ID NO 81
<211> LENGTH: 399
<212> TYPE: PRT
<213> ORGANISM: Lutzomyia longipalpis

<400> SEQUENCE: 81

Met Lys Val Phe Phe Ser Ile Phe Thr Leu Val Leu Phe Gln Gly Thr
1               5                   10                  15

Leu Gly Ala Asp Thr Gln Gly Tyr Lys Trp Lys Gln Leu Leu Tyr Asn
            20                  25                  30

Asn Val Thr Pro Gly Ser Tyr Asn Pro Asp Asn Met Ile Ser Thr Ala
        35                  40                  45

Phe Ala Tyr Asp Ala Glu Gly Glu Lys Leu Phe Leu Ala Val Pro Arg
    50                  55                  60

Lys Leu Pro Arg Val Pro Tyr Thr Leu Ala Glu Val Asp Thr Lys Asn
65                  70                  75                  80

Ser Leu Gly Val Lys Gly Lys His Ser Pro Leu Leu Asn Lys Phe Ser
            85                  90                  95

Gly His Lys Thr Gly Lys Glu Leu Thr Ser Ile Tyr Gln Pro Val Ile
            100                 105                 110

Asp Asp Cys Arg Arg Leu Trp Val Val Asp Ile Gly Ser Val Glu Tyr
            115                 120                 125

Arg Ser Arg Gly Ala Lys Asp Tyr Pro Ser His Arg Pro Ala Ile Val
130                 135                 140

Ala Tyr Asp Leu Lys Gln Pro Asn Tyr Pro Glu Val Val Arg Tyr Tyr
```

```
                145                 150                 155                 160
Phe Pro Thr Arg Leu Val Glu Lys Pro Thr Tyr Phe Gly Gly Phe Ala
                    165                 170                 175
Val Asp Val Ala Asn Pro Lys Gly Asp Cys Ser Glu Thr Phe Val Tyr
                180                 185                 190
Ile Thr Asn Phe Leu Arg Gly Ala Leu Phe Ile Tyr Asp His Lys Lys
            195                 200                 205
Gln Asp Ser Trp Asn Val Thr His Pro Thr Phe Lys Ala Glu Arg Pro
    210                 215                 220
Thr Lys Phe Asp Tyr Gly Gly Lys Glu Tyr Glu Phe Lys Ala Gly Ile
225                 230                 235                 240
Phe Gly Ile Thr Leu Gly Asp Arg Asp Ser Glu Gly Asn Arg Pro Ala
                245                 250                 255
Tyr Tyr Leu Ala Gly Ser Ala Ile Lys Val Tyr Ser Val Asn Thr Lys
                260                 265                 270
Glu Leu Lys Gln Lys Gly Gly Lys Leu Asn Pro Glu Leu Leu Gly Asn
            275                 280                 285
Arg Gly Lys Tyr Asn Asp Ala Ile Ala Leu Ala Tyr Asp Pro Lys Thr
    290                 295                 300
Lys Val Ile Phe Phe Ala Glu Ala Asn Thr Lys Gln Val Ser Cys Trp
305                 310                 315                 320
Asn Thr Gln Lys Met Pro Leu Arg Met Lys Asn Thr Asp Val Val Tyr
                325                 330                 335
Thr Ser Ser Arg Phe Val Phe Gly Thr Asp Ile Ser Val Asp Ser Lys
                340                 345                 350
Gly Gly Leu Trp Phe Met Ser Asn Gly Phe Pro Pro Ile Arg Lys Ser
            355                 360                 365
Glu Lys Phe Lys Tyr Asp Phe Pro Arg Tyr Arg Leu Met Arg Ile Met
    370                 375                 380
Asp Thr Gln Glu Ala Ile Ala Gly Thr Ala Cys Asp Met Asn Ala
385                 390                 395

<210> SEQ ID NO 82
<211> LENGTH: 1429
<212> TYPE: DNA
<213> ORGANISM: Lutzomyia longipalpis

<400> SEQUENCE: 82
ttgaattgaa gcagcagcaa tgaaagtgtt tttctcaatt tttacgctcg tcctcttcca      60
agggacccct ggagcggata ctcaaggata taaatggaag caattgctct acaataatgt     120
tacaccagga tcctacaatc cggataatat gatcagtacg gcttttgcct acgatgctga     180
gggtgaaaaa ctcttcctag ctgtcccaag gaagttaccc agagttccgt atacattggc     240
ggaagtggat acaaagaata gtcttggtgt taagggaaaa cattcaccgt tacttaacaa     300
attcagtggg cacaaaactg gaaggaact aacatcaatc tatcagccag ttattgatga     360
ttgtcgtcgc ctttgggtgg ttgatattgg ttccgtggaa tatcgctcaa gaggtgccaa     420
agactacccg agtcatcgtc ctgcaattgt tgcgtacgac ctaaagcaac caaactaccc     480
cgaagttgtt cgatactatt tccccacaag attagtggag aagccaacat atttcggtgg     540
atttgccgtt gatgttgcaa acccaaaggg ggattgtagt gaaactttg tctacattac     600
aaacttcctc aggggagctc tctttatata cgatcataag aagcaggatt cgtggaatgt     660
aactcatccc accttcaaag cagaacgacc cactaaattt gattacggcg aaaggaata     720
tgaattcaaa gccggaattt tcggaattac tctcggagat cgagacagtg aaggcaatcg     780
```

-continued

```
tccagcttac tacttagccg gaagtgccat caaagtctac agcgtcaaca cgaaagaact      840
taagcagaag ggtggaaagc tgaatccgga gcttcttgga accgcggga agtacaacga      900 tgccattgcc ctagcttacg atcccaaaac taaagttatc ttctttgctg aggccaacac      960
aaagcaagta tcctgctgga acacacagaa aatgccactg aggatgaaga ataccgacgt     1020
agtctacact agttctcgct tgtctttgg aacggacatt tcggttgata gcaagggcgg     1080
cctctggttc atgtctaacg gctttccgcc tataaggaaa tcagaaaaat tcaaatatga     1140
cttcccacgc taccgtctaa tgaggatcat ggacacacag gaagcaattg ccggaactgc     1200
ttgcgatatg aatgcataaa agttaatttt caacccaaga agaagaccta aagaggcttt     1260
tccaggcttt gatgcaggag aggtggttat caacgcaaaa tcagctattg ttgtatgagg     1320
aggagaaatt attgattctg aattctataa aaaaaattta atttgtgaaa tatttggcaa     1380
taataaatta attgaattac aaaaaaaaaa aaaaaaaaaa aaaaaaaa                  1429
```

<210> SEQ ID NO 83
<211> LENGTH: 170
<212> TYPE: PRT
<213> ORGANISM: Lutzomyia longipalpis

<400> SEQUENCE: 83

```
Met Gln Ser Lys Ile Leu Ser Phe Val Leu Phe Thr Leu Ser Leu Gly
1               5                   10                  15

Tyr Val Leu Gly Glu Thr Cys Ser Asn Ala Lys Val Lys Gly Ala Thr
            20                  25                  30

Ser Tyr Ser Thr Thr Asp Ala Thr Ile Val Ser Gln Ile Ala Phe Val
        35                  40                  45

Thr Glu Phe Ser Leu Glu Cys Ser Asn Pro Gly Ser Glu Lys Ile Ser
    50                  55                  60

Leu Phe Ala Glu Val Asp Gly Lys Ile Thr Pro Val Ala Met Ile Gly
65                  70                  75                  80

Asp Thr Thr Tyr Gln Val Ser Trp Asn Glu Glu Val Asn Lys Ala Arg
                85                  90                  95

Ser Gly Asp Tyr Ser Val Lys Leu Tyr Asp Glu Glu Gly Tyr Gly Ala
            100                 105                 110

Val Arg Lys Ala Gln Arg Ser Gly Glu Glu Asn Lys Val Lys Pro Leu
        115                 120                 125

Ala Thr Val Val Arg His Pro Gly Thr Tyr Thr Gly Pro Trp Phe
    130                 135                 140

Asn Ser Glu Ile Leu Ala Ala Gly Leu Ile Ala Val Val Ala Tyr Phe
145                 150                 155                 160

Ala Phe Ser Thr Arg Ser Lys Ile Leu Ser
                165                 170
```

<210> SEQ ID NO 84
<211> LENGTH: 712
<212> TYPE: DNA
<213> ORGANISM: Lutzomyia longipalpis

<400> SEQUENCE: 84

```
tctctttggt taacattgtg aagttatcgg acgtggccgg tttctatttc ttttgcaaaa       60
atgcagtcaa aaattctttc tttcgtcctt ttcacctat ccttgggcta tgttttgggt     120
gaaacatgct caaatgctaa ggttaaggga gctacctctt attccacaac ggatgccaca    180
attgtaagcc aaattgcctt tgtgactgaa ttctccttgg aatgctcaaa tcctggatcc     240
```

```
gagaaaatct ccctatttgc tgaagtcgat ggcaaaatta ctcctgttgc catgatcggg      300
gataccacct accaggtgag ctggaatgaa gaggttaata aggctagaag tggtgactac      360
agtgtgaagc tgtacgatga agaaggatac ggagcagtac gcaaagctca gagatcaggt      420
gaagagaaca aggtcaaacc actagcaacc gttgttgttc gacatccagg aacatacact      480
ggaccatggt tcaattccga atcctcgca gctggtctca ttgctgttgt tgcctacttt      540
gctttctcaa cgcgaagcaa aattcttttcc taaagacacg cagcatgaaa tttcacaaaa      600
aaataaaaac aaattcaagt catcaaccat gtctctttgg cactcagact gtttctgtga      660
aatacaaact attatttaac aaaaaaaaaa aaaaaaaaaa aaaaaaaaaa aa              712
```

<210> SEQ ID NO 85  
<211> LENGTH: 73  
<212> TYPE: PRT  
<213> ORGANISM: Lutzomyia longipalpis

<400> SEQUENCE: 85

```
Met Val Ser Ile Leu Leu Ile Ser Leu Ile Leu Asn Leu Leu Val Phe
1               5                   10                  15

Tyr Ala Lys Ala Arg Pro Leu Glu Asp Ile Ser Ser Asp Leu Ser Pro
            20                  25                  30

Asp Tyr Tyr Ile Thr Glu Gly Tyr Asp Gly Val Lys Glu Lys Arg Glu
        35                  40                  45

Ile Glu Leu Val Pro Val Thr Phe Gly Ile Phe Asn Ile His Thr Thr
    50                  55                  60

Pro Ala Pro Arg Ile Thr Phe Glu Trp
65                  70
```

<210> SEQ ID NO 86  
<211> LENGTH: 379  
<212> TYPE: DNA  
<213> ORGANISM: Lutzomyia longipalpis

<400> SEQUENCE: 86

```
attcccacaa gaagctgcta aaatggtgtc aattctgtta atctccttga ttcttaattt       60
gttggttttc tatgctaaag ctagaccact agaagacatc tcgtcagatc tttcccctga      120
ttattacatc actgaaggct atgacggtgt gaaggagaag agagagatcg aacttgtacc      180
tgtgacattt ggaatattta atatacatac aacacctgct cccagaatta cctttgaatg      240
gtaaaaaatc caagaagaat ttatgatttt attcttcctt ccattgggat ggattgtaag      300
tcagcataaa acgccgttaa aaatgaattt ttaataaaaa aaaattattc caaaaaaaa      360 aaaaaaaaaa aaaaaaaaa                                                  379
```

<210> SEQ ID NO 87  
<211> LENGTH: 76  
<212> TYPE: PRT  
<213> ORGANISM: Lutzomyia longipalpis

<400> SEQUENCE: 87

```
Met Lys Leu Phe Cys Leu Ile Phe Val Val Phe Val Ala Leu Glu Val
1               5                   10                  15

Cys Ile Glu Thr Val Lys Ala Met Glu Ala Thr Glu Glu Ile Ser Val
            20                  25                  30

Lys Leu Gln Asp Asp Ala Asn Glu Pro Asp Asp Ser Leu Asp Leu Asp
        35                  40                  45

Glu Gly Leu Pro Asp Ala Phe Asp Glu Asp Tyr Asn Asn Gln Ala Glu
    50                  55                  60
```

Tyr Lys Pro Asn Pro Arg Gly Asp Tyr Arg Arg Arg
65                  70                  75

<210> SEQ ID NO 88
<211> LENGTH: 526
<212> TYPE: DNA
<213> ORGANISM: Lutzomyia longipalpis

<400> SEQUENCE: 88

| | | | | | |
|---|---|---|---|---|---|
| cactattcat | tggaagattt | attaacttca | agatgaaatt | attttgttta | attttgttg | 60 |
| tgtttgttgc | tttagaagtc | tgtatagaga | ccgtgaaagc | tatggaagca | acggaggaga | 120 |
| tatctgtaaa | attgcaagat | gatgcgaatg | aacctgatga | ctctctggat | ttagacgaag | 180 |
| gtcttcctga | tgcattcgat | gaggactata | ataatcaggc | tgagtacaag | ccgaatccta | 240 |
| gaggggacta | cagaagacga | taattaatat | aaattcagga | aaacactcta | aaaatttcca | 300 |
| attgactcta | ctttaaacga | tttaatacct | acctacacta | ataccatat | gcaataatta | 360 |
| tgttttaatt | atttagtgca | agatctacta | gtttcagttc | atattttggg | actttcccgc | 420 |
| ctttctctcg | atggaaaaat | gattttacgg | attcttaatt | ttcattgtac | agagttaata | 480 |
| aaacaattga | aagcaattaa | aaaaaaaaaa | aaaaaaaaaa | aaaaaa | | 526 |

<210> SEQ ID NO 89
<211> LENGTH: 1021
<212> TYPE: DNA
<213> ORGANISM: Lutzomyia longipalpis

<400> SEQUENCE: 89

| | | | | | |
|---|---|---|---|---|---|
| cttctttgga | tttattgagt | gattaacagg | aaattagctg | aagaaatgaa | ttcgattaat | 60 |
| ttcctatcaa | tagttggttt | aatcagtttt | ggattcattg | ttgcagtaaa | gtgtgatggt | 120 |
| gatgaatatt | tcattggaaa | atacaaagaa | aaagatgaga | cactgttttt | tgcaagctac | 180 |
| ggcctaaaga | gggatccttg | ccaaattgtc | ttaggctaca | aatgctcaaa | caatcaaacc | 240 |
| cactttgtgc | ttaattttaa | accaataag | aaatcctgca | tatcagcaat | taagctgact | 300 |
| tcttacccaa | aaatcaatca | aaactcggat | ttaactaaaa | atctctactg | ccaaactgga | 360 |
| ggaataggaa | cagataactg | caaacttgtc | ttcaagaaac | gtaaaagaca | aatagcagct | 420 |
| aatattgaaa | tctacggcat | tccagcgaag | aaatgttcct | tcaaggatcg | ttacattgga | 480 |
| gctgatccac | tccacgtcga | ttcctatggg | cttccgtatc | agtttgatca | ggaacatgga | 540 |
| tggaatgtgg | aacgatataa | cattttcaaa | gacacaagat | tttccacaga | agttttctac | 600 |
| cacaaaaatg | gtttatttaa | cacccaaata | acttatttgg | ctgaagaaga | ttccttctct | 660 |
| gaagctcgag | agattactgc | gaaggatatt | aagaagaagt | tttcaattat | tttgcccaat | 720 |
| gaagagtata | agaggattag | tttcttggac | gtttattggt | tccaggagac | tatgcgaaaa | 780 |
| aagcctaaat | atccctacat | tcactacaat | ggagaatgca | gcaatgagaa | taaaacttgt | 840 |
| gaacttgtct | ttgacaccga | tgaactaatg | acctacgccc | ttgttaaagt | ctttactaat | 900 |
| cctgagagtg | atggatctag | gctcaaagaa | gaggatttgg | gaagaggata | aatcttctta | 960 |
| ataaaaaaaa | gttctgtaag | aaaatattgt | tcaataaatt | aaaaaaaaaa | aaaaaaaaa | 1020 |
| a | | | | | | 1021 |

<210> SEQ ID NO 90
<211> LENGTH: 1409
<212> TYPE: DNA
<213> ORGANISM: Lutzomyia longipalpis

```
<400> SEQUENCE: 90
agtcagtgtt aatgaagaaa ttgcaattat gaggttcttc tttgtttcc ttgccatcgt      60 cctttttcaa gggatccacg gagcttatgt ggaaatagga tattctctga gaaatattac    120
attcgatgga ttggatacag atgactacaa tccaaagttc aacattccaa cgggtttggc    180
agttgatccc gaaggatata ggctcttcat agccatccca aggagaaagc caaaggttcc    240
ctacactgtg gctgaactga atatggtcat gaatcccgga tttcccgtcg agagagctcc    300
gagctttgag aaattcaaaa aattcaatgg cgagggcaaa aaggatcttg ttaatgtgta    360
tcagccagtc attgatgatt gtcgtcgtct tgggtgctt gacattggga aggtggaata     420
caccggtggt gatgctgatc aatatcccaa aggaaagcct accctaattg cctacgacct    480
caagaaggat catactccgg aaattcatcg atttgaaatt ccagacgatc tctatagctc    540
acaagttgaa tttggtggat tgccgttga tgttgttaac acgaaggag actgtacgga      600 gtcatttgtc tacctgacca atttcaagga taactctcta attgtctacg atgagacaca    660
aaagaaagct tggaaattca cagataaaac atttgaagct gataaggaat ccacgttctc    720
ctactcggga gaggaacaaa tgaagtacaa agtcggtctt tttgggatag ctctgggtga    780
tagggatgaa atggggcatc gtcctgcctg ctacatcgct gggagtagca ccaaagtcta    840
cagtgttaac actaaagaac tcaaaacaga gaatggtcag ttaaatcctc agcttcacgg    900
tgatcgtgga aagtacacag atgcaattgc cctagcctac gatcctgagc ataaagtcct    960
ctactttgct gaatccgaca gcaggcaggt gtcctgttgg aatgtaaata tggagctaaa   1020
accagacaat acgatgtga tcttctctag tgcccgtttt acttttggaa cggatatttt    1080
ggttgatagc aagggaatgc tgtggataat ggctaatgga catccaccag tagaggatca   1140
agagaagatt tggaagatga gattcgtaaa ccggaagatc cgtattatga aagtggatac   1200
ggaacgtgtt ttcaaatatt cacgctgcaa tccaaattat aagcccccaa aggaaattga   1260
agtttgagac acaggaaaaa gctcaatttt caacaagaat ttgatcttaa tctgaatacc   1320
ctaaagtctg tcaaagaatt tcatattatt tgaaaaccaa taaattgatt aattttccga   1380
aaaaaaaaaa aaaaaaaaa aaaaaaaaa                                       1409

<210> SEQ ID NO 91
<211> LENGTH: 1239
<212> TYPE: DNA
<213> ORGANISM: Lutzomyia longipalpis

<400> SEQUENCE: 91
atgcggttct tcttcgtgtt cctggccatc gtgctgttcc agggcatcca cggcgcctac     60
gtggagatcg gctacagcct gcggaacatc accttcgacg gcctggacac cgacgactac   120
aaccccaagt tcaacatccc caccggcctg ccgtggaccc cgagggcta ccggctgttc    180 atcgccatcc ccaggcggaa gcccaaggtg ccctacaccg tggccgagct gaacatggtg   240
atgaaccccg gcttccccgt ggagagggcc cccagcttcg agaagttcaa gaagtttaac   300
ggcgagggca agaagacct ggtgaacgtg taccagcccg tgatcgacga ctgcaggcgg    360
ctgtgggtgc tggacatcgg caaggtggag tacacaggcg gcgacgccga ccagtacccc   420
aagggcaagc ccaccctgat cgcctacgac ctgaagaagg accacacccc cgagatccac   480
cggttcgaga tccccgacga cctgtacagc agccaggtgg agttcggcgg ctttgccgtg   540
gacgtggtga acaccaaggg cgactgcacc gagagcttcg tgtacctgac caacttcaag   600
gacaacagcc tgatcgtgta cgacgagacc cagaagaagg cctggaagtt caccgacaag   660
```

| | |
|---|---|
| accttcgagg ccgacaaaga gagcaccttc agctacagcg gcgaggaaca gatgaagtac | 720 |
| aaagtgggcc tgttcggcat cgccctgggc gaccgggacg agatgggcca caggcccgcc | 780 |
| tgctacatcg ccggcagcag caccaaggtg tacagcgtga ataccaaaga gctgaaaacc | 840 |
| gagaacggca agctgaaccc ccagctgcac ggcgaccggg caagtacac cgacgccatt | 900 |
| gccctggcct acgaccccga gcacaaggtg ctgtacttcg ccgagagcga cagccggcag | 960 |
| gtgtcctgct ggaacgtgaa catggaactg aagcccgaca caccgacgt gatcttcagc | 1020 |
| agcgcccggt tcaccttcgg caccgacatc ctggtggaca gcaagggcat gctgtggatc | 1080 |
| atggccaacg gccaccccc cgtggaggac caggaaaaga tctggaagat gcggttcgtg | 1140 |
| aaccggaaga tccggatcat gaaggtggac accgagcggg tgttcaagta cagccggtgc | 1200 |
| aaccccaact acaagccccc caaagaaatc gaagtgtga | 1239 |

<210> SEQ ID NO 92
<211> LENGTH: 4995
<212> TYPE: DNA
<213> ORGANISM: Lutzomyia longipalpis

<400> SEQUENCE: 92

| | |
|---|---|
| tcagatatat tagatgcatt gttagttctg tagatcagta acgtatagca tacgagtata | 60 |
| attatcgtag gtagtaggta tcctaaaata aatctgatac agataataac tttgtaaatc | 120 |
| aattcagcaa tttctctatt atcatgataa tgattaatac acagcgtgtc gttatttttt | 180 |
| gttacgatag tatttctaaa gtaaagagca ggaatcccta gtataataga aataatccat | 240 |
| atgaaaaata tagtaatgta catatttcta atgttaacat atttataggt aaatccagga | 300 |
| agggtaattt ttacatatct atatacgctt attacagtta ttaaaaatat acttgcaaac | 360 |
| atgttagaag taaaaagaa agaactaatt ttacaaagtg ctttaccaaa atgccaatgg | 420 |
| aaattactta gtatgtatat aatgtataaa ggtatgaata tcacaaacag caaatcggct | 480 |
| attcccaagt tgagaaacgg tataatagat atatttctag ataccattaa taaccttata | 540 |
| agcttgacgt ttcctataat gcctactaag aaaactagaa gatacataca tactaacgcc | 600 |
| atacgagagt aactactcat cgtataacta ctgttgctaa cagtgacact gatgttataa | 660 |
| ctcatctttg atgtggtata aatgtataat aactatatta cactggtatt ttatttcagt | 720 |
| tatatactat atagtattaa aaattatatt tgtataatta tattattata ttcagtgtag | 780 |
| aaagtaaaat actataaata tgtatctctt atttataact tattagtaaa gtatgtacta | 840 |
| ttcagttata ttgtttttata aaagctaaat gctactagat tgatataaat gaatatgtaa | 900 |
| taaattagta atgtagtata ctaatattaa ctcacatttg actaattagc tataaaaacc | 960 |
| cctagtcaat aaaaactcga gtcatcacac ttcgatttct ttgggggggct tgtagttggg | 1020 |
| gttgcaccgg ctgtacttga acacccgctc ggtgtccacc ttcatgatcc ggatcttccg | 1080 |
| gttcacgaac cgcatcttcc agatctttc ctggtcctcc acgggggggt ggccgttggc | 1140 |
| catgatccac agcatgccct tgctgtccac caggatgtcg gtgccgaagg tgaaccgggc | 1200 |
| gctgctgaag atcacgtcgg tgttgtcggg cttcagttcc atgttcacgt tccagcagga | 1260 |
| cacctgccgg ctgtcgctct cggcgaagta cagcaccttg tgctcggggt cgtaggccag | 1320 |
| ggcaatggcg tcggtgtact tgccccggtc gccgtgcagc tggggggttca gctggccgtt | 1380 |
| ctcggttttc agctctttgg tattcacgct gtacaccttg gtgctgctgc cggcgatgta | 1440 |
| gcaggcgggc ctgtggccca tctcgtcccg gtcgcccagg gcgatgccga acaggcccac | 1500 |
| tttgtacttc atctgttcct cgccgctgta gctgaaggtg ctctctttgt cggcctcgaa | 1560 |

```
ggtcttgtcg gtgaacttcc aggccttctt ctgggtctcg tcgtacacga tcaggctgtt    1620
gtccttgaag ttggtcaggt acacgaagct ctcggtgcag tcgcccttgg tgttcaccac    1680
gtccacggca aagccgccga actccacctg gctgctgtac aggtcgtcgg ggatctcgaa    1740
ccggtggatc tcgggggtgt ggtccttctt caggtcgtag gcgatcaggg tgggcttgcc    1800
cttggggtac tggtcggcgt cgccgcctgt gtactccacc ttgccgatgt ccagcaccca    1860
cagccgcctg cagtcgtcga tcacgggctg gtacacgttc accaggtctt tcttgccctc    1920
gccgttaaac ttcttgaact tctcgaagct gggggccctc tccacgggga agccggggtt    1980
catcaccatg ttcagctcgg ccacggtgta gggcaccttg ggcttccgcc tgggatggc     2040 gatgaacagc cggtagccct cggggtccac ggccaggccg gtggggatgt tgaacttggg    2100
gttgtagtcg tcggtgtcca ggccgtcgaa ggtgatgttc cgcaggctgt agccgatctc    2160
cacgtaggcg ccgtggatgc cctggaacag cacgatggcc aggaacacga agaagaaccg    2220
cattacgata caaacttaac ggatatcgcg ataatgaaat aatttatgat tatttctcgc    2280
tttcaattta acacaaccct caagaacctt tgtatttatt ttcactttt aagtatagaa     2340 taaagaagct ctaattaatt aacgagcaga tagtctcgtt ctcgccctgc ctgatgacta    2400
attaattaac ccctagttaa tcaaataaaa agcatacaag ctattgcttc gctatcgtta    2460
caaaatggca ggaattttgt gtaaactaag ccacatactt gccaatgaaa aaaatagtag    2520
aaaggatact attttaatgg gattagatgt taaggttcct tgggattata gtaactgggc    2580
atctgttaac ttttacgacg ttaggttaga tactgatgtt acagattata ataatgttac    2640
aataaaatac atgacaggat gtgatatttt tcctcatata actcttggaa tagcaaatat    2700
ggatcaatgt gatagatttg aaaatttcaa aaagcaaata actgatcaag atttacagac    2760
tatttctata gtctgtaaag aagagatgtg ttttcctcag agtaacgcct ctaaacagtt    2820
gggagcgaaa ggatgcgctg tagttatgaa actggaggta tctgatgaac ttagagccct    2880
aagaaatgtt ctgctgaatg cggtaccctg ttcgaaggac gtgtttggtg atatcacagt    2940
agataatccg tggaatcctc acataacagt aggatatgtt aaggaggacg atgtcgaaaa    3000
caagaaacgc ctaatggagt gcatgtccaa gtttaggggg caagaaatac aagttctagg    3060
atggtattaa taagtatcta agtatttggt ataatttatt aaatagtata attataacaa    3120
ataataaata acatgataac ggttttatt agaataaaat agagataata tcataatgat     3180
atataatact tcattaccag aaatgagtaa tggaagactt taaatgaac tgcataaagc      3240 tataaggtat agagatataa atttagtaag gtatatactt aaaaaatgca aatcaataa     3300 cgtaaatata ctatcaacgt ctttgtattt agccgtaagt atttctgata tagaaatggt    3360
aaaattatta ctagaacacg gtgccgatat tttaaaatgt aaaaatcctc ctcttcataa    3420
agctgctagt ttagataata cagaaattgc taaactacta atagattctg gcgctgacat    3480
agaacagata cattctggaa atagtccgtt atatatttct gtatatagaa acaataagtc    3540
attaactaga tatttattaa aaaaggtgt taattgtaat agattctttc taaattatta    3600
cgatgtactg tatgataaga tatctgatga tatgtataaa atatttatag attttaatat    3660
tgatcttaat atacaaacta gaaattttga aactccgtta cattacgcta taagtataa     3720 gaatatagat ttaattagga tattgttaga taatagtatt aaaatagata aaagtttatt    3780
tttgcataaa cagtatctca taaaggcact taaaaataat tgtagttacg atataatagc    3840
gttacttata aatcacggag tgcctataaa cgaacaagat gatttaggta aaacccccatt   3900 acatcattcg gtaattaata gaagaaaaga tgtaacagca cttctgttaa atctaggagc    3960
```

```
tgatataaac gtaatagatg actgtatggg cagtcccctta cattacgctg tttcacgtaa   4020
cgatatcgaa acaacaaaga cacttttaga aagaggatct aatgttaatg tggttaataa   4080
tcatatagat accgttctaa atatagctgt tgcatctaaa aacaaaacta tagtaaactt   4140
attactgaag tacggtactg atacaaagtt ggtaggatta gataaacatg ttattcacat   4200
agctatagaa atgaaagata ttaatatact gaatgcgatc ttattatatg gttgctatgt   4260
aaacgtctat aatcataaag gtttcactcc tctatacatg gcagttagtt ctatgaaaac   4320
agaatttgtt aaactcttac ttgaccacgg tgcttacgta aatgctaaag ctaagttatc   4380
tggaaatact cctttacata aagctatgtt atctaatagt tttaataata taaaattact   4440
tttatcttat aacgccgact ataattctct aaataatcac ggtaatacgc ctctaacttg   4500
tgttagcttt ttagatgaca agatagctat tatgataata tctaaaatga tgttagaaat   4560
atctaaaaat cctgaaatag ctaattcaga aggttttata gtaaacatgg aacatataaa   4620
cagtaataaa agactactat ctataaaaga atcatgcgaa aaagaactag atgttataac   4680
acatataaag ttaaattcta tatattcttt taatatcttt cttgacaata acatagatct   4740
tatggtaaag ttcgtaacta atcctagagt taataagata cctgcatgta tacgtatata   4800
tagggaatta atacggaaaa ataaatcatt agcttttcat agacatcagc taatagttaa   4860
agctgtaaaa gagagtaaga atctaggaat aataggtagg ttacctatag atatcaaaca   4920
tataataatg gaactattaa gtaataatga tttacattct gttatcacca gctgttgtaa   4980
cccagtagta taaag                                                    4995

<210> SEQ ID NO 93
<211> LENGTH: 4995
<212> TYPE: DNA
<213> ORGANISM: Lutzomyia longipalpis

<400> SEQUENCE: 93
ctttatacta ctgggttaca acagctggtg ataacagaat gtaaatcatt attacttaat     60
agttccatta ttatatgttt gatatctata ggtaacctac ctattattcc tagattctta    120
ctctctttta cagctttaac tattagctga tgtctatgaa aagctaatga tttattttc    180
cgtattaatt ccctatatat acgtatacat gcaggtatct tattaactct aggattagtt    240
acgaacttta ccataagatc tatgttattg tcaagaaaga tattaaaaga atatatagaa    300
tttaacttta tatgtgttat aacatctagt tctttttcgc atgattcttt tatagatagt    360
agtcttttat tactgtttat atgttccatg tttactataa aaccttctga attagctatt    420
tcaggatttt tagatatttc aacatcatt ttagatatta tcataatagc tatcttgtca    480
tctaaaaagc taacacaagt tagaggcgta ttaccgtgat tatttagaga attatagtcg    540
gcgttataag ataaaagtaa ttttatatta ttaaaactat tagataacat agctttatgt    600
aaaggagtat ttccagataa cttagcttta gcatttacgt aagcaccgtg gtcaagtaag    660
agtttaacaa attctgtttt catagaacta actgccatgt atagaggagt gaaaccttta    720
tgattataga cgtttacata gcaaccatat aataagatcg cattcagtat attaatatct    780
ttcatttcta tagctatgtg aataacatgt ttatctaatc ctaccaactt tgtatcagta    840
ccgtacttca gtaataagtt tactatagtt ttgtttttag atgcaacagc tatatttaga    900
acggtatcta tatgattatt aaccacatta acattagatc ctctttctaa aagtgtcttt    960
gttgtttcga tatcgttacg tgaaacagcg taatgtaagg gactgcccat acagtcatct   1020
attacgttta tatcagctcc tagatttaac agaagtgctg ttacatcttt tcttctatta   1080
```

```
attaccgaat gatgtaatgg ggttttacct aaatcatctt gttcgtttat aggcactccg    1140
tgatttataa gtaacgctat tatatcgtaa ctacaattat ttttaagtgc ctttatgaga    1200
tactgtttat gcaaaaataa acttttatct atttttaatac tattatctaa caatatccta    1260
attaaatcta tattcttata ctttatagcg taatgtaacg gagtttcaaa atttctagtt    1320
tgtatattaa gatcaatatt aaaatctata aatatttat acatatcatc agatatctta     1380
tcatacagta catcgtaata attttagaaag aatctattac aattaacacc ttttttttaat  1440 aaatatctag ttaatgactt attgtttcta tatacagaaa tatataacgg actatttcca    1500
gaatgtatct gttctatgtc agcgccagaa tctattagta gtttagcaat ttctgtatta    1560
tctaaactag cagctttatg aagaggagga ttttacatt ttaaaatatc ggcaccgtgt     1620
tctagtaata attttaccat ttctatatca gaaatactta cggctaaata caaagacgtt    1680
gatagtatat ttacgttatt gtatttgcat tttttaagta tataccttac taaatttata   1740
tctctatacc ttatagcttt atgcagttca tttataagtc ttccattact catttctggt   1800
aatgaagtat tatatatcat tatgatatta tctctatttt attctaataa aaaccgttat   1860
catgttattt attatttgtt ataattatac tatttaataa attataccaa atacttagat   1920
acttattaat accatcctag aacttgtatt tcttgccccc taaacttgga catgcactcc   1980
attaggcgtt tcttgttttc gacatcgtcc tccttaacat atcctactgt tatgtgagga   2040
ttccacggat tatctactgt gatatcacca aacacgtcct tcgaacaggg taccgcattc   2100
agcagaacat ttcttagggc tctaagttca tcagatacct ccagtttcat aactacagcg   2160
catcctttcg ctcccaactg tttagaggcg ttactctgag gaaaacacat ctcttcttta   2220
cagactatag aaaatagtctg taaatcttga tcagttattt gctttttgaa attttcaaat   2280
ctatcacatt gatccatatt tgctattcca agagttatat gaggaaaaat atcacatcct   2340
gtcatgtatt ttattgtaac attattataa tctgtaacat cagtatctaa cctaacgtcg   2400
taaaagttaa cagatgccca gttactataa tcccaaggaa ccttaacatc taatcccatt   2460
aaaatagtat cctttctact attttttttca ttggcaagta tgtggcttag tttacacaaa  2520
attcctgcca ttttgtaacg atagcgaagc aatagcttgt atgcttttta tttgattaac   2580
taggggttaa ttaattagtc atcaggcagg gcgagaacga gactatctgc tcgttaatta   2640
attagagctt ctttattcta tacttaaaaa gtgaaaataa atacaaaggt tcttgagggt   2700
tgtgttaaat tgaaagcgag aaataatcat aaattatttc attatcgcga tatccgttaa   2760
gtttgtatcg taatgcggtt cttcttcgtg ttcctggcca tcgtgctgtt ccagggcatc   2820
cacggcgcct acgtggagat cggctacagc ctgcggaaca tcaccttcga cggcctggac   2880
accgacgact acaaccccaa gttcaacatc cccaccggcc tggccgtgga ccccgagggc   2940
taccggctgt tcatcgccat ccccaggcgg aagcccaagg tgccctacac cgtggccgag   3000
ctgaacatgg tgatgaaccc cggcttcccc gtggagaggg cccccagctt cgagaagttc   3060
aagaagttta acggcgaggg caagaaagac ctggtgaacg tgtaccagcc cgtgatcgac   3120
gactgcaggc ggctgtgggt gctggacatc ggcaaggtgg agtacacagg cggcgacgcc   3180
gaccagtacc ccaagggcaa gcccacccctg atcgcctacg acctgaagaa ggaccacacc   3240
cccgagatcc accggttcga gatccccgac gacctgtaca gcagccaggt ggagttcggc   3300
ggctttgccg tggacgtggt gaacaccaag ggcgactgca ccgagagctt cgtgtacctg   3360
accaacttca aggacaacag cctgatcgtg tacgacgaga cccagaagaa ggcctggaag   3420
ttcaccgaca agaccttcga ggccgacaaa gagagcacct tcagctacag cggcgaggaa   3480
```

```
cagatgaagt acaaagtggg cctgttcggc atcgccctgg gcgaccggga cgagatgggc    3540
cacaggcccg cctgctacat cgccggcagc agcaccaagg tgtacagcgt gaataccaaa    3600
gagctgaaaa ccgagaacgg ccagctgaac ccccagctgc acggcgaccg gggcaagtac    3660
accgacgcca ttgccctggc ctacgacccc gagcacaagg tgctgtactt cgccgagagc    3720
gacagccggc aggtgtcctg ctggaacgtg aacatggaac tgaagcccga caacaccgac    3780
gtgatcttca gcagcgcccg gttcaccttc ggcaccgaca tcctggtgga cagcaagggc    3840
atgctgtgga tcatggccaa cggccacccc ccgtggagg accaggaaaa gatctggaag    3900
atgcggttcg tgaaccggaa gatccggatc atgaaggtgg acaccgagcg ggtgttcaag    3960
tacagccggt gcaaccccaa ctacaagccc cccaagaaaa tcgaagtgtg atgactcgag    4020
tttttattga ctaggggttt ttatagctaa ttagtcaaat gtgagttaat attagtatac    4080
tacattacta atttattaca tattcattta tatcaatcta gtagcattta gcttttataa    4140
aacaatataa ctgaatagta catactttac taataagtta taaataagag atacatattt    4200
atagtatttt actttctaca ctgaatataa taatataatt atacaaatat aatttttaat    4260
actatatagt atataactga aataaaatac cagtgtaata tagttattat acatttatac    4320
cacatcaaag atgagttata acatcagtgt cactgttagc aacagtagtt atacgatgag    4380
tagttactct cgtatggcgt tagtatgtat gtatcttcta gttttcttag taggcattat    4440
aggaaacgtc aagcttataa ggttattaat ggtatctaga aatatatcta ttataccgtt    4500
tctcaacttg ggaatagccg atttgctgtt tgtgatattc atacctttat acattatata    4560
catactaagt aatttccatt ggcattttgg taaagcactt tgtaaaatta gttctttctt    4620
ttttacttct aacatgtttg caagtatatt tttaataact gtaataagcg tatatagata    4680
tgtaaaaatt acccttcctg gatttaccta taaatatgtt aacattagaa atatgtacat    4740
tactatattt ttcatatgga ttatttctat tatactaggg attcctgctc tttactttag    4800
aaatactatc gtaacaaaaa ataacgacac gctgtgtatt aatcattatc atgataatag    4860
agaaattgct gaattgattt acaaagttat tatctgtatc agatttattt taggatacct    4920
actacctacg ataattatac tcgtatgcta tacgttactg atctacagaa ctaacaatgc    4980
atctaatata tctga                                                    4995
```

<210> SEQ ID NO 94
<211> LENGTH: 5040
<212> TYPE: DNA
<213> ORGANISM: Lutzomyia longipalpis

<400> SEQUENCE: 94

```
cgagtccttc taacactgtg gtttattggc tggaataaaa ggataaagac acctatactg      60
attcattttc atctgtcaac gtttctctaa gagattcata ggtattatta ttacatcgat     120
ctagaagtct aataactgct aagtatatta ttggatttaa cgcgctataa acgcatccaa     180
aacctacaaa tataggagaa gcttctctta tgaaacttct taaagcttta ctcttactat     240
tactactcaa aagagatatt acattaatta tgtgatgagg catccaacat ataaagaaga     300
ctaaagctgt agaagctgtt atgaagaata tcttatcaga tatattagat gcattgttag     360
ttctgtagat cagtaacgta tagcatacga gtataattat cgtaggtagt aggtatccta     420
aaataaatct gatacagata ataactttgt aaatcaattc agcaatttct ctattatcat     480
gataatgatt aatacacagc gtgtcgttat tttttgttac gatagtatttt ctaaagtaaa     540 gagcaggaat ccctagtata atagaaataa tccatatgaa aaatatagta atgtacatat    600
```

```
ttctaatgtt aacatattta taggtaaatc caggaagggt aattttttaca tatctatata    660
cgcttattac agttattaaa aatatacttg caaacatgtt agaagtaaaa aagaaagaac    720
taattttaca aagtgcttta ccaaaatgcc aatggaaatt acttagtatg tatataatgt    780
ataaaggtat gaatatcaca aacagcaaat cggctattcc caagttgaga acggtataa    840
tagatatatt tctagatacc attaataacc ttataagctt gacgtttcct ataatgccta    900
ctaagaaaac tagaagatac atacatacta acgccatacg agagtaacta ctcatcgtat    960
aactactgtt gctaacagtg acactgatgt tataactcat ctttgatgtg gtataaatgt   1020
ataataacta tattacactg gtatttttatt tcagttatat actatatagt attaaaaatt   1080
atatttgtat aattatatta ttatattcag tgtagaaagt aaaatactat aaatatgtat   1140
ctcttattta taacttatta gtaaagtatg tactattcag ttatattgtt ttataaaagc   1200
taaatgctac tagattgata taaatgaata tgtaataaat tagtaatgta gtatactaat   1260
attaactcac atttgactaa ttagctataa aaacccgggt taattaatta gtcatcaggc   1320
agggcgagaa cgagactatc tgctcgttaa ttaattagag cttctttatt ctatacttaa   1380
aaagtgaaaa taaatacaaa ggttcttgag ggttgtgtta aattgaaagc gagaaataat   1440
cataaattat ttcattatcg cgatatccgt taagtttgta tcgtaatgaa cagcatcaac   1500
tttctgagca tcgtgggcct gatcagcttc ggcttcatcg tggccgtgaa gtgcgacggc   1560
gacgagtact tcatcggcaa gtacaaagag aaggacgaga ccctgttctt cgccagctac   1620
ggcctgaagc gggacccctg ccagatcgtg ctgggctaca gtgcagcaa caaccagacc   1680
cacttcgtgc tgaacttcaa gaccaacaag aagagctgca tcagcgccat caagctgacc   1740
agctacccca agatcaacca gaacagcgac ctgaccaaga acctgtactg ccagaccggc   1800
ggcatcggca ccgacaactg caagctggtg ttcaagaagc ggaagcggca gatcgccgcc   1860
aacatcgaga tctacggcat ccccgccaag aagtgcagct tcaaggaccg gtacatcggc   1920
gccgaccccc tgcacgtgga ctcctacggc ctgccctacc agttcgacca ggaacacggc   1980
tggaacgtcg agcggtacaa catcttcaag gacacccggt tcagcaccga ggtgttctac   2040
cacaagaacg gcctgttcaa cacccagatc acctacctgg ccgaagagga cagcttcagc   2100
gaggcccggg agatcaccgc caaggacatc aagaagaagt tcagcatcat cctgcccaac   2160
gaggaataca gcggatcag cttcctggac gtgtactggt ccaggaaaac catgcggaag   2220
aagcccaagt accccctacat ccactacaac ggcgagtgct ccaacgagaa caagacctgc   2280
gaactggtgt cgacaccga cgagctgatg acctacgccc tggtgaaggt gttcaccaac   2340
cccgagagcg acggcagccg gctgaaagaa gaggacctgg gcagggggctg atgactcgag   2400
tttttattga ctagttaatc aaataaaaag catacaagct attgcttcgc tatcgttaca   2460
aaatggcagg aattttgtgt aaactaagcc acatacttgc caatgaaaaa aatagtagaa   2520
aggatactat tttaatggga ttagatgtta aggttccttg ggattatagt aactgggcat   2580
ctgttaactt ttacgacgtt aggttagata ctgatgttac agattataat aatgttacaa   2640
taaaatacat gacaggatgt gatatttttc ctcatataac tcttggaata gcaaatatgg   2700
atcaatgtga tagatttgaa aatttcaaaa agcaaataac tgatcaagat ttacagacta   2760
tttctatagt ctgtaaagaa gagatgtgtt ttcctcagag taacgcctct aaacagttgg   2820
gagcgaaagg atgcgctgta gttatgaaac tggaggtatc tgatgaactt agagccctaa   2880
gaaatgttct gctgaatgcg gtaccctgtt cgaggacgt gtttggtgat atcacagtag   2940
ataatccgtg gaatcctcac ataacagtag gatatgttaa ggaggacgat gtcgaaaaca   3000
```

```
agaaacgcct aatggagtgc atgtccaagt ttaggggca agaaatacaa gttctaggat    3060
ggtattaata agtatctaag tatttggtat aatttattaa atagtataat tataacaaat    3120
aataaataac atgataacgg tttttattag aataaaatag agataatatc ataatgatat    3180
ataatacttc attaccagaa atgagtaatg gaagacttat aaatgaactg cataaagcta    3240
taaggtatag agatataaat ttagtaaggt atatacttaa aaaatgcaaa tacaataacg    3300
taaatatact atcaacgtct ttgtatttag ccgtaagtat ttctgatata gaaatggtaa    3360
aattattact agaacacggt gccgatattt taaaatgtaa aaatcctcct cttcataaag    3420
ctgctagttt agataataca gaaattgcta aactactaat agattctggc gctgacatag    3480
aacagataca ttctggaaat agtccgttat atatttctgt atatagaaac aataagtcat    3540
taactagata tttattaaaa aaaggtgtta attgtaatag attctttcta aattattacg    3600
atgtactgta tgataagata tctgatgata tgtataaaat atttatagat tttaatattg    3660
atcttaatat acaaactaga aattttgaaa ctccgttaca ttacgctata aagtataaga    3720
atatagattt aattaggata ttgttagata atagtattaa aatagataaa agtttatttt    3780
tgcataaaca gtatctcata aaggcactta aaaataattg tagttacgat ataatagcgt    3840
tacttataaa tcacggagtg cctataaacg aacaagatga tttaggtaaa accccattac    3900
atcattcggt aattaataga agaaaagatg taacagcact tctgttaaat ctaggagctg    3960
atataaacgt aatagatgac tgtatgggca gtcccttaca ttacgctgtt tcacgtaacg    4020
atatcgaaac aacaaagaca cttttagaaa gaggatctaa tgttaatgtg gttaataatc    4080
atatagatac cgttctaaat atagctgttg catctaaaaa caaaactata gtaaacttat    4140
tactgaagta cggtactgat acaaagttgg taggattaga taaacatgtt attcacatag    4200
ctatagaaat gaaagatatt aatatactga atgcgatctt attatatggt tgctatgtaa    4260
acgtctataa tcataaaggt ttcactcctc tatacatggc agttagttct atgaaaacag    4320
aatttgttaa actcttactt gaccacggtg cttacgtaaa tgctaaagct aagttatctg    4380
gaaatactcc tttacataaa gctatgttat ctaatagttt taataatata aaattacttt    4440
tatcttataa cgccgactat aattctctaa ataatcacgg taatacgcct ctaacttgtg    4500
ttagcttttt agatgacaag atagctatta tgataatatc taaaatgatg ttagaaatat    4560
ctaaaaatcc tgaaatagct aattcagaag gttttatagt aaacatggaa catataaaca    4620
gtaataaaag actactatct ataaaagaat catgcgaaaa agaactagat gttataacac    4680
atataaagtt aaattctata tattcttta atatctttct tgacaataac atagatctta    4740
tggtaaagtt cgtaactaat cctagagtta ataagatacc tgcatgtata cgtatatata    4800
gggaattaat acgaaaaat aaatcattag cttttcatag acatcagcta atagttaaag    4860
ctgtaaaaga gagtaagaat ctaggaataa taggtaggtt acctatagat atcaaacata    4920
taataatgga actattaagt aataatgatt tacattctgt tatcaccagc tgttgtaacc    4980
cagtagtata aagtgatttt attcaattac gaagataaac attaaatttg ttaacagata    5040
```

LEISHMANIA VACCINE USING SAND FLY SALIVARY IMMUNOGEN

INCORPORATION BY REFERENCE

This application claims benefit of U.S. provisional application Ser. No. 61/051,635 filed May 8, 2008, and of U.S. provisional application Ser. No. 61/101,345 filed Sep. 30, 2008, which make reference to International Application No. PCT/US2003/034453 entitled *Lutzomyia Longipalpis* Polypeptides and Methods of Use filed Oct. 29, 2003, which claims priority to provisional application No. 60/422,303 filed Oct. 29, 2002.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to formulations for combating *Leishmania* infections in animals or humans. Specifically, the present invention provides vectors that contain and express in vivo or in vitro sand fly *Lu. longipalpis* salivary antigens that elicit an immune response in animal or human against *Leishmania*, including compositions comprising said vectors, methods of vaccination against *Leishmania*, and kits for use with such methods and compositions.

BACKGROUND OF THE INVENTION

Leishmaniasis is a major and severe parasitic disease that affects humans, canines (dogs, wolves, foxes, coyotes, jackals), and to a lesser degree, felines (lions, tigers, domestic cats, wild cats, other big cats, and other felines including cheetahs and lynx).

*Leishmania* and *Viannia* subgenera are grouped into complexes of species and subspecies based upon molecular, biochemical and immunological similarities. There are several forms of the disease named by their clinical presentation including cutaneous, mucocutaneous or visceral leishmaniasis. Each of these forms of disease is caused by different species of sand flies found in different regions of the world. Cutaneous leishmaniasis of humans is associated with members of *L. aethiopica, L. major*, and *L. tropica* complexes in the Old World and *L. mexicana* and *L. braziliensis* complexes in the New World. Visceral leishmaniasis is caused by *L. donovani* and *L. infantum* in Old World regions while *L. chagasi* is primarily responsible for visceral disease in the New World. Because *L. infantum* is the primary agent associated with canine leishmaniasis, infections in dogs often are regarded as visceral even though they tend to cause both visceral and cutaneous disease.

The agent of visceral leishmaniasis is a protozoan parasite and belongs to the *leishmania donovani* complex. This parasite is widely distributed in temperate and subtropical countries of Southern Europe, Africa, Asia, South America and Central America (Desjeux P. et al.). *Leishmania donovani infantum* (*L. infantum*) is responsible for the feline and canine disease in Southern Europe, Africa, and Asia. In South America and Central America, the agent is *Leishmania donovani chagasi* (*L. chagasi*), which is closely related to *L. infantum*. In humans, the agent is *Leishmania donovani donovani* (*L. donovani*), which is also related to *L. infantum* and *L. chagasi.*

Sand flies of the genus *Phlebotomus* (Old World) and *Lutzomyia* (New World) are the primary vectors responsible for disease transmission. Currently these are the only known vectors capable of spread; fleas, ticks and other arthropods have not been shown to be competent vectors. However, rare cases of leishmaniasis have been contracted through exchange of blood or body fluids, direct contact and at least one case of congenital transmission. The importance of native sand flies is yet undetermined but could be related to infectious dose of the organism. Still, in recent years, and in the absence of known vectors, there has been an overwhelming incidence of leishmaniasis in Foxhound kennels across the United States. It is still not known how transmission of disease occurred or how this disease is maintained in these dogs because infected sand flies have not been reported in the United States. However, certain species of *Lutzomyia* (*L. shannoni*), found along the eastern United States and as far north as New Jersey, are considered a potentially competent vector for *L. mexicana. Phlebotomus ariasi* (*P. ariasi*) and *Phlebotomus perniciosus* (*P. perniciosus*), *Phlebotomus neglectus* (*P. neglectus*) are the most common carriers in Southern Europe, Africa, and Asia, whereas *Lutzomyia longipalpis* (*Lu. longipalpis*) is the most common carrier in Southern and Central America.

Leishmaniasis is a slowly progressive disease that can take up to 7 years to become clinically apparent (McConkey S E et al.; Slappendel R J et al.). Even then, signs are frequently nonspecific and a diagnosis of *Leishmania* is seldom considered. Dogs are most commonly infected with *L. infantum* (*L. donovani* complex) which is responsible for viscerotropic disease in people. However, up to 90% of infected dogs present with both visceral and cutaneous lesions (Slappendel R J et al.). On the other hand, many dogs appear naturally resistant to this parasite and may remain asymptomatic despite known infection (Grosjean N L et al.). It is estimated that only 10% of dogs residing in endemic areas actually develop clinical disease (Lindsay D S et al.). This lower incidence of clinical disease is attributed to a genetic predisposition of certain dogs to mount a more protective cell-mediated immune response than a humoral response (Lindsay D S et al., McConkey S E et al., Slappendel R J, et al.). Furthermore, it has been reported that up to 20% of infected dogs may mount an adequate immune response and spontaneously recover from clinical illness (McConkey S E et al.). In animals that mount a humoral response, IgG1 appears to correlate with clinical disease while asymptomatic dogs have higher IgG2 antibody levels (Lindsay et al.).

Some of the more frequently reported clinical signs of leishmaniasis include listlessness, fatigue and exercise intolerance coupled with anorexia and weight loss that eventually culminate as wasting disease (McConkey S E et al.). These signs may or may not be accompanied by fever, local or generalized lymphadenopathy (90%) and/or hepatosplenomegaly (Grosjean N L et al., Lindsay D S et al., McConkey S E et al., Martinez-Subiela S et al.). Articular involvement is also fairly common and may present as lameness with swollen joints or simply as a stiff gait. Less common findings include ocular lesions (<5%), chronic diarrhea (30%) and long, deformed brittle nails (20%) referred to as onychogryphosis (Lindsay D S et al., Slappendel R J et al.). Cutaneous lesions are present in up to 89% of infected dogs, with or without overt signs of visceral involvement. Lesions of cutaneous leishmaniasis may occur anywhere on the body but the most common sites are those which are exposed to the environment and are therefore more susceptible to bites from the sand flies. The initial papule rapidly gives rise to an ulcer. Viseral leishmaniasis is invariably fatal if not treated promptly. Viseral leishmaniasis affects the internal body organs, specifically the spleen and the liver.

Dogs are considered the major reservoir of Leishmaniasis. The disease is characterized by chronic evolution of viscerocutaneous signs occurring in less than 50% of infected animals (Lanotte G. et al.). Both asymptomatic and symptomatic dogs with detectable antibodies may be infectious (Molina R. et al.; Courtenay O. et al.). Cats may also be carriers of the protozoan parasites and are thus considered secondary potential reservoirs.

Due to a number of factors, treatment options for leishmaniasis in dogs and response to therapy are limited at best. For some undefined reason, visceral leishmaniasis is more difficult to treat in dogs than in humans. No treatment option is 100% effective in clearing parasitic infection and clinical disease often reappears with cessation of therapy (Lindsay D S et al.). In endemic areas, the most common treatment regimen has been a combination of allopurinol with a pentavalent antimonial such as meglumine antimonite or sodium stibogluconate (Lindsay D S et al., Slappendel R J et al.). However, in recent years this protocol has fallen out of favor due to increasing resistance of the parasite to the drug as well as adverse side effects associated with these compounds (Lindsay D S et al.). To further limit treatment options, Pentostam® (sodium stibogluconate) is the only available antimonial in the United States and its distribution is regulated by the Centers for Disease Control and Prevention (CDC) in Atlanta, Ga. (Lindsay D S et al.).

Other protocols have been tried but have proven no more efficacious at clearing parasitic infection or at preventing clinical relapse. In addition, each protocol is associated with potential adverse effects. Amphotericin B binds sterols and disrupts cell membrane permeability but is nephrotoxic (Lindsay D S et al.). When given parenterally, Paramomycin acts synergistically with antimonials causing higher levels of the antimonial for longer periods of time but is also nephrotoxic and is not currently recommended for clinical use (Lindsay D S et al.). Pentamidine isethionate is effective against leishmaniasis but requires at least 15 intramuscular injections and is quite painful (Lindsay D S et al.). Ketaconazole, miconazole, fluconazole and itraconazole are oral drugs that may be useful in containing the disease but are cost prohibitive and carry the risk of drug resistance when treating patients symptomatically. In summary, the various treatment regimens for leishmaniasis in dogs have been investigated but are not 100% efficacious; relapses are the rule rather than the exception. Ultimately, the veterinary practitioner is faced with the dilemma of treating symptomatic outbreaks of leishmaniasis in dogs at the risk of developing drug resistant strains of this parasite within the United States.

Mass detection of seropositive dogs followed by culling and/or drug treatment, or the mass application of deltamethrin-impregnated collars, was shown to have an impact in reducing human and canine Leishmaniasis prevalence in endemic areas of Southern Europe, Africa, and Asia (Maroli M. et al. Mazloumi Gavgani A. S. et al.), although the efficacy of eliminating seropositive canines has been debated (Dietze R. et al.; Moreira Jr. E. D. et al.). These control measures are either considered unacceptable, expensive or not effective (Gradoni L. et al.). Mathematical models used to compare the effectiveness of various tools for controlling Leishmaniasis suggest that a canine vaccine may be the most practical and effective method (Dye C.). Therefore, the development of vaccines able to protect canines from Leishmaniasis and/or to prevent disease progression in infected animals is highly desirable for the implementation of Leishmaniasis control programs as well for the veterinary community (Gradoni L. et al.).

Previous investigations have sought to identify methods of diagnosing and treating *Leishmania* through, for example, administration of antigenic polypeptides (see, for example, WO 2004/039958 which is hereby incorporated herein by reference in its entirety). However, to date, no vaccine is available for the treatment of *Leishmania*. The vectors and vaccine formulations of the present invention fulfill this long-felt need in the art.

Citation or identification of any document in this application is not an admission that such document is available as prior art to the present invention.

SUMMARY OF THE INVENTION

An object of this invention can be any one or all of providing recombinant vectors or viruses as well as methods for making such viruses, and providing compositions and/or vaccines as well as methods for treatment and prophylaxis of infection by *Leishmania*.

The invention provides a recombinant vector, such as a recombinant virus, e.g., a recombinant poxvirus, that contains and expresses at least one exogenous nucleic acid molecule and, the at least one exogenous nucleic acid molecule may comprise a nucleic acid molecule encoding an immunogen or epitope of interest from salivary proteins from sand fly vectors of *Lu. longipalpis*.

In particular, the present invention provides a recombinant vector, such as a recombinant virus, e.g., a recombinant poxvirus, that contains and expresses at least one exogenous nucleic acid molecule and, the at least one exogenous nucleic acid molecule may comprise salivary *Lu. longipalpis* polypeptides and/or variants or fragments thereof.

These vaccines may prevent diffusion and/or replication of the parasite in a host.

The invention further provides immunological (or immunogenic), or vaccine compositions comprising such an expression vector or the expression product(s) of such an expression vector.

The invention further provides methods for inducing an immunological (or immunogenic) or protective response against *Leishmania*, as well as methods for preventing or treating *Leishmania* or disease state(s) caused by *Leishmania*, comprising administering the expression vector or an expression product of the expression vector, or a composition comprising the expression vector, or a composition comprising an expression product of the expression vector.

The invention also relates to expression products from the virus as well as antibodies generated from the expression products or the expression thereof in vivo and uses for such products and antibodies, e.g., in diagnostic applications.

These and other embodiments are disclosed or are obvious from and encompassed by, the following Detailed Description.

BRIEF DESCRIPTION OF DRAWINGS

The following detailed description, given by way of example, and which is not intended to limit the invention to specific embodiments described, may be understood in conjunction with the accompanying figures, incorporated herein by reference, in which:

FIG. 1 shows the nucleic acid sequence of one strand of the plasmid pVR2001 LJM17 (SEQ ID NO:9), wherein the two BamHI restriction sites are in bold, the sequence encoding the tPA signal peptide is underlined and the sequence encoding the LJM17 is in bold capital letters.

Figure 4:
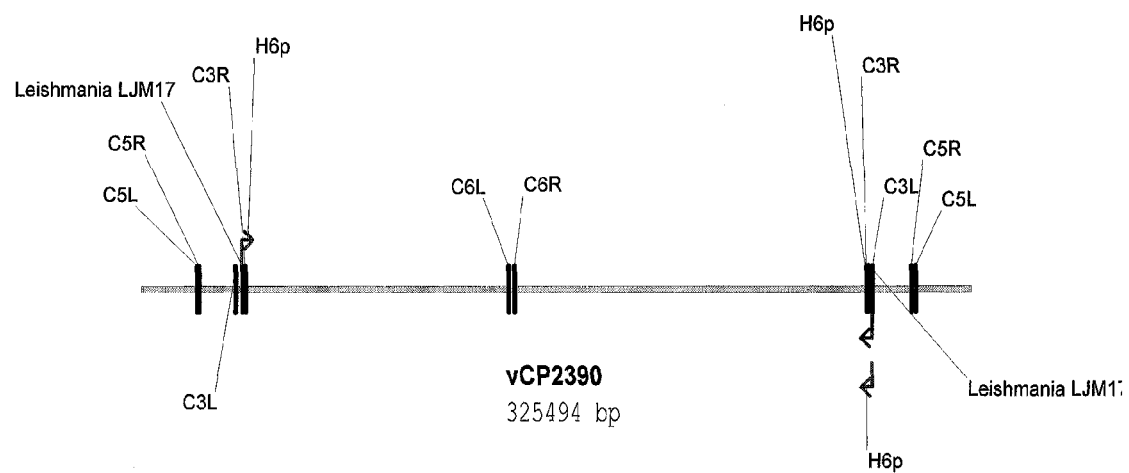

FIG. 4 illustrates the vCP2390 canarypox expression vector, for both forward and reverse complementary strands (SEQ ID NO:93 and SEQ ID NO:92). SEQ ID NO:93 represents the vCP2390 vector strand which contains the codon-optimized LJM17 polynucleotide in the direction that encodes the LJM17 polypeptide (SEQ ID NO:5).

FIG. 5 shows a map of the donor vector, pALVAC C3 H6p-LJL143, having 5400 base pairs.

FIG. 6 illustrates the vCP2389 canarypox expression vector with its insert encoding LJL143, and provides the nucleotide sequence of one strand of the expression vector (SEQ ID NO:94).

FIG. 7 illustrates anti-IgG antibodies to both LJM17 and LJL143, absorbance measured at 405 nm, in vaccinated and control dogs, from one day before V1 administration to two weeks after V5 administration.

FIG. 8 illustrates interferon-gamma secretion (pg/mL) from dogs PBMC corresponding to the 5 groups, 2 weeks after the $5^{th}$ immunization (V5 administration). PBMC were stimulated by SGH (2 pairs), LJL143 (4 μg), LJM17 (4 μg), ConA (4 μg) or non-stimulated by medium (med).

FIG. 9 shows a scheme of an in vitro killing assay including results, expressed in percentage of infected macrophages (NT: no treatment, LPS: lipopolysaccharide, conA: concavaline A).

FIG. 10 shows biopsies of vaccinated and control dogs, at the sand flies bite sites, stained with hematoxylin/eosin (H & E), Luna's, Toludine blue and immunohistochemical procedures for CD3 and macrophage/monocyte markers (Mac).

FIG. 11 shows the nucleic acid sequence of one strand of the plasmid pNBO002 (SEQ ID NO:19), wherein the two BamHI restriction sites are in bold, the sequence encoding the tPA signal peptide is underlined and the sequence encoding the LJM17 is in bold capital letters.

FIG. 12 shows a map of the pNBO002 plasmid vector with its insert encoding LJM17, having 6247 base pairs.

FIG. 13 shows the nucleic acid sequence of one strand of the plasmid pNBO003 (SEQ ID NO:20), wherein the two BamHI restriction sites are in bold, the sequence encoding the tPA signal peptide is underlined and the sequence encoding the LJL143 is in bold capital letters.

FIG. 14 shows a map of the pNBO003 plasmid vector with its insert encoding LJL143, having 5899 base pairs.

FIG. 15 shows the protein sequences of LJL143 and LJM17 from *L. longipalpis.*

FIG. 16 shows the DNA sequences of LJL143 and LJM17 from *L. longipalpis.*

FIG. 17 shows the sequence identity tables.

FIG. 18 shows the SEQ ID NO assigned to each DNA and polypeptide.

FIG. 19 is a set of graphs and images demonstrating anti-saliva immunity in dogs exposed to the bites of the *Lu. longipalpis* sand fly. FIG. 19A is a set of graphs demonstrating the early kinetics of anti-*Lu. longipalpis* IgG, IgG2, and IgG1 antibody titers in exposed dogs. FIG. 19B is a graph of a delayed-type hypersensitivity reaction on a representative dog throughout exposure experiments. FIG. 19C is a set of images of an H/E histological analysis performed on skin punch biopsies before exposure (E0), 47 h after first exposure (E1), 48 h after second exposure (E2) and 48 h after third exposure (E3) to sand fly bites. FIG. 19D is a set of images characterizing the inflammatory population at 48 h after third exposure (E3) to sand fly bites with immunohistochemistry for CD3+ T lymphocytes and macrophages and Luna's stain for eosinophils.

FIG. 20 is a set of graphs and images demonstrating a cDNA reverse antigen screening assay in dogs.

FIG. 21 is a set of graphs and images demonstrating a protein reverse antigen screening assay in dogs.

FIG. 22 is a set of two graphs demonstrating interferon γ production of peripheral blood mononuclear cells (PBMCs) from vaccinated dogs after stimulation with recombinant salivary protein.

FIG. 23 is a set of four bar graphs demonstrating an in vitro killing assay for *Leishmania chagasi* by PBMCs from immunized dogs (NT, no treatment; Ly, lymphocytes).

DETAILED DESCRIPTION

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

It is noted in this disclosure and the appended claims and/or paragraphs, the term "salivary *Lu. longipalpis* polypeptide", "*Lu. longipalpis* polypeptide", or "salivary polypeptide" is used interchangeably, the term "salivary *Lu. longipalpis* polynucleotide", "*Lu. longipalpis* polynucleotide", or "salivary polynucleotide" is used interchangeably.

The terms "polypeptide" and "protein" are used interchangeably herein to refer to a polymer of consecutive amino acid residues.

The term "nucleic acid", "nucleotide", and "polynucleotide" refers to RNA or DNA and derivatives thereof, such as those containing modified backbones. It should be appreciated that the invention provides polynucleotides comprising sequences complementary to those described herein. Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al; Pandher K et al.; Chung J Y et al), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "immunogenic polypeptide" or "immunogenic fragment" as used herein refers to a polypeptide or a fragment of a polypeptide which comprises an allele-specific motif, an epitope or other sequence such that the polypeptide or the fragment will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

By definition, an epitope is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. Specific, non-limiting examples of an epitope include a tetra- to penta-peptide sequence in a polypeptide, a tri- to penta-glycoside sequence in a polysaccharide. In the animal most antigens will present several or even many antigenic determinants simultaneously. Such a polypeptide may also be qualified as an immunogenic polypeptide and the epitope may be identified as described further.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. A polypeptide preparation is substantially purified such that the polypeptide represents several embodiments at least 60%, at least 70%, at least 80%, at least 90%, at least 95%, or at least 98%, of the total polypeptide content of the preparation. The same applies to polynucleotides. The polypeptides disclosed herein can be purified by any of the means known in the art.

A recombinant polynucleotide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In one embodiment, a recombinant polynucleotide encodes a fusion protein.

In one aspect, the present invention provides polypeptides from sand fly species *Lu. longipalpis*. In another aspect, the present invention provides a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87, and variant or fragment thereof.

Moreover, homologs of polypeptides from sand fly species *Lu. longipalpis* are intended to be within the scope of the present invention. As used herein, the term "homologs" includes orthologs, analogs and paralogs. The term "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type salivary polypeptide can differ from the wild-type salivary polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type salivary polypeptide or polynucleotide sequences, and will exhibit a similar function.

In another aspect, the present invention provides a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87.

In yet another aspect, the present invention provides fragments and variants of the *L. longipalpis* polypeptides identified above (SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87) which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene if interest, are intended to be within the scope of the invention.

A variant is any secreted polypeptide from *Lu. longipalpis* saliva, capable of inducing in animals, such as dogs, vaccinated with this polypeptide a specific cell-based immune response characterized by secretion of interferon gamma (IFN-gamma) upon stimulation by *Lu. longipalpis* salivary gland extract compounds. Such IFN-gamma secretion may be demonstrated using in vitro methodology (i.e. Quantikine® immunoassay from R&D Systems Inc. (catalog number# CAIF00); Djoba Siawaya J F et al.).

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the *Lu. longipalpis* polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An immunogenic fragment of a *Lu. longipalpis* polypeptide includes at least 8, 10, 15, or consecutive amino acids, at least 21 amino acids, at least 23 amino acids, at least 25 amino acids, or at least 30 amino acids of a *L. longipalpis* polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87, or variants thereof. In another embodiment, a fragment of a *Lu. longipalpis* polypeptide includes a specific antigenic epitope found on a full-length *Lu. longipalpis* polypeptide.

Procedures to determine fragments of polypeptide and epitope such as, generating overlapping peptide libraries (Hemmer B. et al.), Pepscan (Geysen H. M. et al., 1984; Geysen H. M. et al., 1985; Van der Zee R. et al.; Geysen H. M.) and algorithms (De Groot A. et al.; Hoop T. et al.; Parker K. et al.), can be used in the practice of the invention, without undue experimentation. Generally, antibodies specifically bind a particular antigenic epitope. Specific, non-limiting examples of epitopes include a tetra- to penta-peptide sequence in a polypeptide, a tri- to penta glycoside sequence in a polysaccharide. In animals most antigens will present several or even many antigenic determinants simultaneously. Preferably wherein the epitope is a protein fragment of a larger molecule it will have substantially the same immunological activity as the total protein.

In another aspect, the present invention provides a polynucleotide encoding a polypeptide from *Lu. longipalpis* sand fly, such as a polynucleotide encoding a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or a conservative variant, an allelic variant, a homolog or an immunogenic fragment comprising at least eight or at east ten consecutive amino acids of one of these polypeptides, or a combination of these polypeptides.

In another aspect, the present invention provides a polynucleotide having a nucleotide sequence as set forth in SEQ ID NO: 2, 4, 6, 8, 12, 14, 16, 18, 21, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 89, 90, or 91, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 2, 4, 6, 8, 12, 14, 16, 18, 21, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 89, 90, or 91, or a variant thereof.

These polynucleotides may include DNA, cDNA, and RNA sequences that encode a *Lu. longipalpis* polypeptide. It is understood that all polynucleotides encoding a *Lu. longipalpis* polypeptide are also included herein, as long as they encode a polypeptide with the recognized activity, such as the binding to an antibody that recognizes the polypeptide, the induction of an immune response to the polypeptide, or an effect on survival of *Leishmania* when administered to a subject exposed to the parasite or who undergoes a decrease in a sign or a symptom of *Leishmania* infection.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for salivary polypeptides, the DNA sequence of the salivary protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of salivary protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the *Lu. longipalpis* salivary polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

Sequence identity between two nucleotide sequences also may be determined using the "Align" program of Myers and Miller, ("Optimal Alignments in Linear Space", CABIOS 4, 11-17, 1988) and available at NCBI, as well as the same or other programs available via the Internet at sites thereon such as the NCBI site.

Alternatively or additionally, the term "identity", for instance, with respect to a nucleotide or amino acid sequence, may indicate a quantitative measure of homology between two sequences. The percent sequence homology may be calculated as: $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

Advantageously, sequence identity or homology such as amino acid sequence identity or homology can be determined using the BlastP program (Altschul et al.) and available at NCBI, as well as the same or other programs available via the Internet at sites thereon such as the NCBI site.

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

The *Lu. longipalpis* polynucleotides may include a recombinant DNA which is incorporated into a vector, into an autonomously replicating plasmid or virus, or into the genomic DNA of a prokaryote or eukaryote, or which exists as a separate molecule (for example, a cDNA) independent of other sequences.

Recombinant vectors disclosed herein may include a polynucleotide encoding a polypeptide, a variant thereof or a fragment thereof. Recombinant vectors may include plasmids and viral vectors and may be used for in vitro or in vivo expression. Recombinant vectors may include further a signal peptide. Signal peptides are short peptide chain (3-60 amino acids long) that direct the post-translational transport of a protein (which are synthesized in the cytosol) to certain organelles such as the nucleus, mitochondrial matrix, endoplasmic reticulum, chloroplast, apoplast and peroxisome. Typically, the naturally occurring salivary *Lu. longipalpis* polypeptides, such as LJM17 and LJL143 proteins, may be translated as precursors, having an N-terminal signal peptide sequence and a "mature" protein domain. The signal peptide may be cleaved off rapidly upon translation. The signal sequence may be the natural sequence from the salivary protein or a peptide signal from a secreted protein e.g. the signal peptide from the tissue plasminogen activator protein (tPA), in particular the human tPA (S. Friezner Degen et al.; R. Rickles et al.; D. Berg. et al.), or the signal peptide from the Insulin-like growth factor 1 (IGF1), in particular the equine IGF1 (K. Otte et al.), the canine IGF1 (P. Delafontaine et al.), the feline IGF1 (WO03/022886), the bovine IGF1 (S. Lien et al.), the porcine IGF1 (M. Muller et al.), the chicken IGF1 (Y. Kajimoto et al.), the turkey IGF1 (GenBank accession number AF074980). The signal peptide from IGF1 may be natural or optimized which may be achieved by removing cryptic splice sites and/or by adapting the codon usage. Upon translation, the unprocessed polypeptide may be cleaved at a cleavage site to lead to the mature polypeptide. The cleavage site may be predicted using the method of Von Heijne (1986).

A plasmid may include a DNA transcription unit, for instance a nucleic acid sequence that permits it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

In a further aspect, the present invention relates to an in vivo expression vector comprising a polynucleotide sequence, which contains and expresses in vivo in a host the salivary *Lu. longipalpis* polypeptides and/or variants or fragments thereof.

The in vivo expression vector may include any transcription unit containing a polynucleotide or a gene of interest and those essential elements for its in vivo expression. These expression vectors may be plasmids or recombinant viral vectors. For in vivo expression, the promoter may be of viral or cellular origin. In one embodiment, the promoter may be the cytomegalovirus (CMV) early promoter (CMV-IE promoter), the SV40 virus early or late promoter or the Rous Sarcoma virus LTR promoter, a promoter of a cytoskeleton gene, such as the desmin promoter (Kwissa M. et al.), or the actin promoter (Miyazaki J. et al.). When several genes are present in the same plasmid, they may be provided in the same transcription unit or in different units.

As used herein, the term "plasmid" may include any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. The plasmids may also comprise other transcription-regulating elements such as, for example, stabilizing sequences of the intron type. In several embodiments, the plasmids may include the first intron of CMV-IE (WO 89/01036), the intron II of the rabbit beta-globin gene (van Ooyen et al.), the signal sequence of the protein encoded by the tissue plasminogen activator (tPA; Montgomery et al.), and/or a polyadenylation signal (polyA), in particular the polyA of the bovine growth hormone (bGH) gene (U.S. Pat. No. 5,122,458) or the polyA of the rabbit beta-globin gene or of SV40 virus.

In a further aspect, the present invention relates to a vaccine composition comprising: a) an in vivo expression vector, wherein the vector comprises a polynucleotide encoding one or more polypeptide selected from the group consisting of a salivary *Lu. longipalpis* polypeptide, a variant or fragment of the salivary *Lu. longipalpis* polypeptide, and a mixture thereof, and b) a pharmaceutically or veterinary acceptable vehicle, diluent or excipient.

In another aspect, the present invention relates to a vaccine composition comprising: a) a first in vivo expression vector, wherein the vector comprises a polynucleotide encoding one or more polypeptide selected from the group consisting of a salivary *Lu. longipalpis* polypeptide, a variant or fragment of the salivary *Lu. longipalpis* polypeptide, and a mixture thereof, b) a second in vivo expression vector, wherein the vector comprises a polynucleotide encoding one or more polypeptide selected from the group consisting of a salivary *Lu. longipalpis* polypeptide, a variant or fragment of the salivary *Lu. longipalpis* polypeptide, and a mixture thereof, and c) a pharmaceutically or veterinary acceptable vehicle, diluent or excipient.

Figures 1, 20:
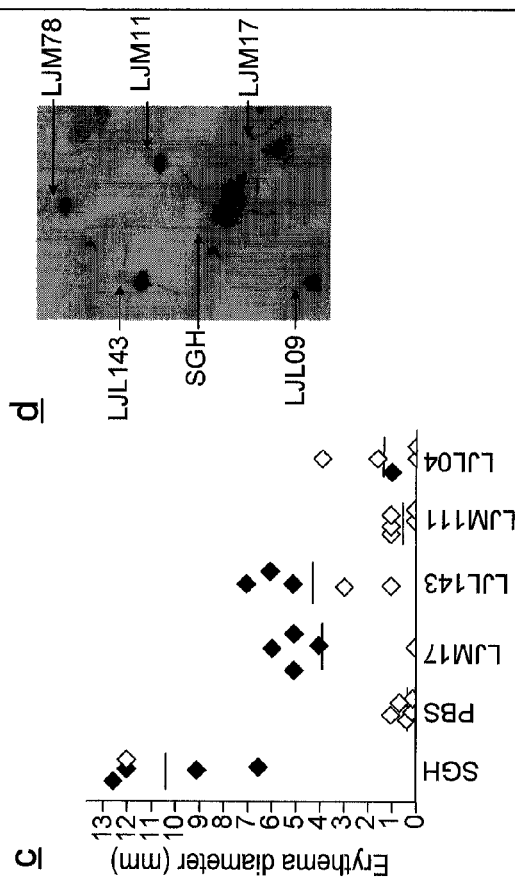

The term "vaccine composition" or "vaccine" comprises any composition, once it has been injected to a host, including canines, felines and humans, that protects the host from cutaneous leishmaniasis and/or visceral leishmaniasis, and/or which may prevent implantation of the parasite, and/or which may prevent disease progression in infected subjects, and/or which may limit the diffusion of runaway parasites to internal organs, and/or which may avoid or limit parasite uptake by a sand fly during a blood meal on a vaccinated dog. This may be accomplished upon vaccination according to the present invention through the induction of cytokine secretion, notably IFN-gamma secretion (as example of a method of measurement of IFN-gamma secretion, the Quantikine® immunoassay from R&D Systems Inc. (catalog number# CAIF00) could be used (Djoba Siawaya J F et al.)).

The pharmaceutically acceptable vehicles or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides, plasmids, viral vectors herein disclosed. In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, freeze-dried pastille, powder, pill, tablet, or capsule forms), conventional non-toxic solid vehicles or excipients can include, for example, pharmaceutical grades of mannitol, lactose, starch, or magnesium stearate. In addition to biologically neutral vehicles or excipients, immunogenic compositions to be administered can contain minor amounts of non-toxic auxiliary substances, such as wetting or emulsifying agents, preservatives, and pH buffering agents and the like, for example sodium acetate or sorbitan monolaurate.

The vaccines according to the instant invention may include vectors encoding any polynucleotide according to the present invention as described above.

Multiple insertions may be done in the same vector using different insertion sites or using the same insertion site. When the same insertion site is used, each polynucleotide insert, which may be any polynucleotide of the present invention aforementioned, may be inserted under the control of the same and/or different promoters. The insertion can be done tail-to-tail, head-to-head, tail-to-head, or head-to-tail. IRES elements (Internal Ribosome Entry Site, see EP 0803573) can also be used to separate and to express multiple inserts operably linked to the same and/or different promoters.

In one embodiment, the present invention relates to an expression vector comprising a polynucleotide aforementioned. The expression vector may be an in vivo expression vector, or an in vitro expression vector.

More generally, the present invention encompasses in vivo expression vectors including any plasmid (EP-A2-1001025; Chaudhuri P.) containing and expressing in vivo in a host the polynucleotide or gene of *Lu. longipalpis* salivary polypeptide, variant thereof or fragment thereof and elements necessary for its in vivo expression.

In a specific, non-limiting example, the pVR1020 or pVR1012 plasmid (VICAL Inc.; Luke C. et al.; Hartikka J. et al.), pVR2001-TOPA (or pVR2001-TOPO) (Oliveira F. et al.) or pAB 110 (U.S. Pat. No. 6,852,705) can be utilized as a vector for the insertion of a polynucleotide sequence. The pVR1020 plasmid is derived from pVR1012 and contains the human tPA signal sequence. The pVR1020 is a plasmid backbone available from Vical, Inc., (San Diego, Calif.) which has been previously used, see, e.g., U.S. Pat. Nos. 6,451,769 and 7,078,507. As described in Oliveira et al, plasmid pVR2001-TOPO (or pVR2001-TOPA) is pVR1020 modified by the addition of topoisomerases flanking the cloning site and containing coding for and expressing a signal secretory peptide, for example, tissue plasminogen activator signal peptide (tPA), that increases the likelihood of producing a secreted protein, (see FIG. 1 in Oliveira F. et al.).

Each plasmid may comprise or contain or consist essentially of, the polynucleotide according to the present invention, operably linked to a promoter or under the control of a promoter or dependent upon a promoter, wherein the promoter may be advantageously adjacent to the polynucleotide for which expression is desired. In general, it is advantageous to employ a strong promoter that is functional in eukaryotic cells. One example of a useful promoter may be the immediate early cytomegalovirus promoter (CMV-IE) of human or murine origin, or it may optionally have another origin such as from rat or guinea pig. The CMV-IE promoter may comprise the actual promoter part, which may or may not be associated with the enhancer part. Reference can be made to EP 260 148, EP 323 597, U.S. Pat. Nos. 5,168,062, 5,385,839, and 4,968,615, as well as to WO 87/03905. The CMV-IE promoter may advantageously be a human CMV-IE (Boshart M. et al.) or murine CMV-IE. In more general terms, the promoter may have either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as the desmin promoter (Kwissa M. et al.), or the actin promoter (Miyazaki J. et al.). Functional sub fragments of these promoters, i.e., portions of these promoters that maintain adequate promoter activity, are included within the present invention, e.g. truncated CMV-IE promoters according to WO 98/00166 or U.S. Pat. No. 6,156,567 and may be used in the practice of the invention. A promoter useful in the practice of the invention consequently may include derivatives and/or sub fragments of a full-length promoter that maintain adequate promoter activity and hence function as a promoter, and which may advantageously have promoter activity that is substantially similar to that of the actual or full-length promoter from which the derivative or sub fragment is derived, e.g., akin to the activity of the truncated CMV-IE promoters of U.S. Pat. No. 6,156,567 in comparison to the activity of full-length CMV-IE promoters. Thus, a CMV-IE promoter in the practice of the invention may comprise or consist essentially of or consist of the promoter portion of the full-length promoter and/or the enhancer portion of the full-length promoter, as well as derivatives and/or sub fragments thereof.

Advantageously, the plasmids comprise or consist essentially of other expression control elements. It is especially advantageous to incorporate stabilizing sequence(s), e.g., intron sequence(s), for example, the first intron of the hCMV-IE (WO 89/01036), the intron II of the rabbit β-globin gene (van Ooyen et al.). As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

In one embodiment of the present invention, the plasmid vector is pVR2001 comprising LJM17 polynucleotide, as described in example 1 herein.

In another embodiment of the present invention, the plasmid vector is pVR2001 comprising LJL143 polynucleotide, as described in example 2 herein.

In another embodiment of the present invention, the plasmid vector is pNBO002, as described in example 9 herein.

In yet another embodiment of the present invention, the plasmid vector is pNBO003, as described in example 10 herein.

More generally, the present invention encompasses in vivo expression vectors including any recombinant viral vector containing a polynucleotide or gene encoding one or more salivary *Lu. longipalpis* immunogens and/or variants or fragments thereof, including any elements necessary for its in vivo expression.

Said recombinant viral vectors could be selected from, for example, the poxviruses, especially avipox viruses, such as fowlpox viruses or canarypox viruses. In one embodiment, the fowlpox virus is a TROVAC (see WO 96/40241). In another embodiment, the canarypox vector is an ALVAC. The use of these recombinant viral vectors and the insertion of polynucleotides or genes of interest are fully described in U.S. Pat. No. 5,174,993; U.S. Pat. No. 5,505,941 and U.S. Pat. No. 5,766,599 for fowlpox, and in U.S. Pat. No. 5,756,103 for canarypox. More than one insertion site inside the viral genome could be used for the insertion of multiple genes of interest.

In one embodiment the viral vector is an adenovirus, such as a human adenovirus (HAV) or a canine adenovirus (CAV).

In another embodiment the viral vector is a human adenovirus, specifically a serotype 5 adenovirus, rendered incompetent for replication by a deletion in the E1 region of the viral genome, especially from about nucleotide 459 to about nucleotide 3510 by reference to the sequence of the hAd5 disclosed in Genbank under the accession number M73260 and in the referenced publication Chroboczek et al, 1992. The deleted adenovirus is propagated in E1-expressing 293 (Graham et al., 1977) or PER cells, especially PER.C6 (Falloux et al., 1998). The human adenovirus can additionally or alternatively be deleted in the E3 region, especially from about nucleotide 28592 to about nucleotide 30470. The deletion in the E1 region can be done in combination with a deletion in the E3 region (see, e.g. Shriver et al.; Graham et al.; Ilan et al.; U.S. Pat. Nos. 6,133,028 and 6,692,956; Tripathy et al.; Tapnell; Danthinne et al.; Berkner; Berkner et al.; Chavier et al.). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, advantageously a cytomegalovirus immediate-early gene promoter (CMV-IE promoter), especially the enhancer/promoter region from about nucleotide −734 to about nucleotide +7 in Boshart et al., or the enhancer/promoter region from the pCI vector from Promega Corp. The CMV-IE promoter is advantageously of murine or human origin. The promoter of the elongation factor Ia can also be used. A muscle specific promoter can also be used (Li et al.). Strong promoters are also discussed herein in relation to plasmid vectors. In one embodiment, a splicing sequence can be located downstream of the enhancer/promoter region. For example, the intron 1 isolated from the CMV-IE gene (Stenberg et al.), the intron isolated from the rabbit or human β-globin gene, especially the intron 2 from the β-globin gene, the intron isolated from the immunoglobulin gene, a splicing sequence from the SV40 early gene or the chimeric intron sequence isolated from the pCI vector from Promege Corp. A poly(A) sequence and terminator sequence can be inserted downstream the polynucleotide to be expressed, e.g. a bovine growth hormone gene, especially from about nucleotide 2339 to about nucleotide 2550 in Genbank under the accession number BOVGHRH, a rabbit β-globin gene or a SV40 late gene polyadenylation signal.

In another embodiment the viral vector is a canine adenovirus, especially a CAV-2 (see, e.g. Fischer et al.; U.S. Pat. Nos. 5,529,780 and 5,688,920; WO 95/14102). For CAV, the insertion sites can be in the E3 region and/or in the region located between the E4 region and the right ITR region (see U.S. Pat. Nos. 6,090,393 and 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another embodiment, the viral vector is a herpesvirus such as a canine herpesvirus (CHV) or a feline herpesvirus (FHV). For CHV, the insertion sites may be in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

For recombinant vectors based on a poxvirus vector, a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel; Sutter et al; available as ATCC VR-1508; or NYVAC, see U.S. Pat. No. 5,494,807, and U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO 96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807) can be used. Attenuated canarypox viruses are described in U.S. Pat. No. 5,756,103 (ALVAC) and WO 01/05934. Reference is also made to U.S. Pat. No. 5,766,599 which pertains to the attenuated fowlpox strain TROVAC. Reference is made to the canarypox available from the ATCC under access number VR-111. Numerous fowlpox virus vaccination strains are also available, e.g. the DIFTOSEC CT strain marketed by MERIAL and the NOBILIS VARIOLE vaccine marketed by INTERVET. For information on the method used to generate recombinants thereof and how to administer recombinants thereof, the skilled artisan can refer documents cited herein and to WO 90/12882, e.g., as to vaccinia virus, mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and 5,766,599 inter alia; as to canarypox, mention is made of U.S. Pat. No. 5,756,103 inter alia. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus are advantageously as in various publications, including Carroll M. W. et al.; Stittelaar K. J. et al.; Sutter G. et al; and, in this regard it is also noted that the complete MVA genome is described in Antoine G., Virology, which enables the skilled artisan to use other insertion sites or other promoters. Advantageously, the polynucleotide to be expressed is inserted under the control of a specific poxvirus promoter, e.g., the vaccinia promoter 7.5 kDa (Cochran et al.), the vaccinia promoter I3L (Riviere et al.), the vaccinia promoter HA (Shida), the cowpox promoter ATI (Funahashi et al.), the vaccinia promoter H6 (Taylor J. et al.; Guo P. et al. J.; Perkus M. et al.), inter alia.

In a further embodiment, the recombinant viral vector is the recombinant ALVAC canarypox virus vCP2390-SEQ ID NO:6, expressing the *Lu. longipalpis* salivary LJM17 polypeptide, as described in example 3.

In a further embodiment, the recombinant viral vector is the recombinant ALVAC canarypox virus vCP2390, expressing the *Lu. longipalpis* salivary LJM17 polypeptide, as described in example 11.

In a further embodiment, the recombinant viral vector is the recombinant ALVAC canarypox virus vCP2389-SEQ ID NO:2, expressing the *Lu. longipalpis* salivary LJL143 polypeptide, as described in example 4.

In a further embodiment, the recombinant viral vector is the recombinant ALVAC canarypox virus vCP2389, expressing the *Lu. longipalpis* salivary LJL143 polypeptide, as described in the example 12.

In a further embodiment, the recombinant viral vector is the recombinant MVA virus MVA-LJM17, expressing the *Lu. longipalpis* salivary LJM17 polypeptide, as described in example 5.

In a further embodiment, the recombinant viral vector is the recombinant MVA virus MVA-LJL143, expressing the *Lu. longipalpis* salivary LJL143 polypeptide, as described in the example 6.

Any of the polynucleotides disclosed here may be expressed in vitro by DNA transfer or expression vectors into a suitable host cell. The host cell may be prokaryotic or eukaryotic. The term "host cell" also includes any progeny of the subject host cell. Methods of stable transfer, meaning that the foreign polynucleotide is continuously maintained in the host cell, are known in the art. Host cells may include bacteria (for example, *Escherichia coli*), yeast, insect cells, and vertebrate cells. Methods of expressing DNA sequences in eukaryotic cells are well known in the art. As a method for in vitro expression, recombinant Baculovirus vectors (for example, Autographa California Nuclear Polyhedrosis Virus (AcNPV)) may be used with the nucleic acids disclosed herein. For example, polyhedrin promoters may be utilized with insect cells (for example, *Spodoptera frugiperda* cells, like Sf9 cells available at the ATCC under the Accession number CRL 1711, or Sf21 cells) (see for example, Smith et al.; Pennock et al.; Vialard et al.; Verne A.; O'Reilly et al.; Kidd I. M. & Emery V. C.; EP 0370573; EP 0265785; U.S. Pat. No. 4,745,051). For expression, the BaculoGold Starter Package (Cat #21001K) from Pharmingen (Becton Dickinson) may be used. As a method for in vitro expression, recombinant *E. coli* may be used with a vector. For example, when cloning in bacterial systems, inducible promoters such as arabinose promoter, pL of bacteriophage lambda, plac, ptrp, ptac (ptrp-lac hybrid promoter), and the like may be used. Transformation of a host cell with recombinant DNA may be carried out by conventional techniques are well known to those skilled in the art. Where the host is prokaryotic, such as *E. coli*, competent cells which are capable of DNA uptake can be prepared from cells harvested after exponential growth phase and subsequently treated by the CaCl2 method using procedures well known in the art. Alternatively, MgCl2 or RbCl can be used. Transformation can also be performed by electroporation. When the host is a eukaryote, such methods of transduction of DNA as calcium phosphate coprecipitates, conventional mechanical procedures such as microinjection, electroporation, insertion of a plasmid encased in liposomes, or virus vectors may be used. Eukaryotic cells may also be cotransformed with *L. longipalpis* polynucleotide sequences, and a second foreign DNA molecule encoding a selectable phenotype, such as the herpes simplex thymidine kinase gene. Another method is to use a eukaryotic viral vector (see above), such as a herpes virus or adenovirus (for example, canine adenovirus 2), to transiently transduce eukaryotic cells and express the protein (Gluzman EA). In addition, a transfection agent can be utilized, such as dioleoyl-phosphatidyl-ethanolamme (DOPE).

Isolation and purification of recombinantly expressed polypeptide may be carried out by conventional means including preparative chromatography (for example, size exclusion, ion exchange, affinity), selective precipitation and ultra-filtration. Examples of state of the art techniques that can be used, but not limited to, may be found in "Protein Purification Applications", Second Edition, Edited by Simon Roe and available at Oxford University Press. Such a recombinantly expressed polypeptide is part of the present disclosure. The methods for production of any polypeptide according to the present invention as described above are also encompassed, in particular the use of a recombinant expression vector comprising a polynucleotide according to the disclosure and of a host cell.

The vaccines containing recombinant viral vectors according to the invention may be freeze-dried, advantageously with a stabilizer. Freeze-drying can be done according to well-known standard freeze-drying procedures. The pharmaceutically or veterinary acceptable stabilizers may be carbohydrates (e.g. sorbitol, mannitol, lactose, sucrose, glucose, dextran, trehalose), sodium glutamate (Tsvetkov T et al; Israeli E et al.), proteins such as peptone, albumin, lactalbumin or casein, protein containing agents such as skimmed milk (Mills C K et al.; Wolff E et al), and buffers (e.g. phosphate buffer, alkaline metal phosphate buffer). An adjuvant may be used to make soluble the freeze-dried preparations.

Any vaccine composition according to the invention can also advantageously contain one or more adjuvant.

The plasmid-based vaccines may be formulated with cationic lipids, advantageously with DMRIE (N-(2-hydroxyethyl)-N,N-dimethyl-2,3-bis(tetradecyloxy)-1-propanammonium; WO96/34109), and advantageously in association with a neutral lipid, for example DOPE (dioleoyl-phosphatidyl-ethanolamine; Behr J. P.), in order to form DMRIE-DOPE. In one embodiment, the mixture is made extemporaneously, and before its administration it is advantageous to wait about 10 min to about 60 min, for example, about 30 min, for the appropriate complexation of the mixture. When DOPE is used, the molar ratio of DMRIE/DOPE can be from 95/5 to 5/95 and is advantageously 1/1. The weight ratio plasmid/DMRIE or DMRIE-DOPE adjuvant is, for example, from 50/1 to 1/10, from 10/1 to 1/5 or from 1/1 to 1/2.

Optionally a cytokine may be added to the composition, especially GM-CSF or cytokines inducing Th1 (e.g. IL12). These cytokines can be added to the composition as a plasmid encoding the cytokine protein. In one embodiment, the cytokines are from canine origin, e.g. canine GM-CSF which gene sequence has been deposited at the GenBank database (accession number S49738). This sequence can be used to create said plasmid in a manner similar to what was made in WO 00/77210.

The recombinant viral vector-based vaccine may be combined with fMLP (N-formyl-methionyl-leucyl-phenylalanine; U.S. Pat. No. 6,017,537) and/or Carbomer adjuvant (Phameuropa Vol. 8, No. 2, June 1996). Persons skilled in the art can also refer to U.S. Pat. No. 2,909,462, which describes such acrylic polymers cross-linked with a polyhydroxylated compound having at least 3 hydroxyl groups, advantageously not more than 8, the hydrogen atoms of at least three hydroxyls being replaced by unsaturated aliphatic radicals having at least 2 carbon atoms. For example, the radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (BF Goodrich, Ohio, USA) are appropriate. The products are cross-linked with an allyl sucrose or with allyl pentaerythritol. Among them, there may be advantageously mentioned CARBOPOL® 974P, 934P and 971P.

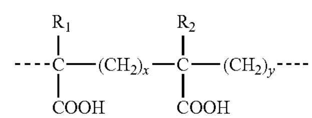

Among the copolymers of maleic anhydride and alkenyl derivative, the copolymers EMA® (Monsanto) which are copolymers of maleic anhydride and ethylene, linear or cross-linked, for example cross-linked with divinyl ether, are advantageous. Reference may be made to J. Fields et al.

The polymers of acrylic or methacrylic acid and the copolymers EMA® are formed, for example, of basic units of the following formula in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution, which is neutralized, advantageously to physiological pH, in order to provide the adjuvant solution into which the vaccine itself is incorporated. The carboxyl groups of the polymer are then partly in $COO^-$ form.

In one embodiment, a solution of adjuvant, especially of carbomer (*Pharmeuropa*, vol. 8, No. 2, June 1996), is prepared in distilled water, advantageously in the presence of sodium chloride, the solution obtained being at an acidic pH. This stock solution is diluted by adding it to the desired quantity (for obtaining the desired final concentration), or a substantial part thereof, of water charged with NaCl, advantageously physiological saline (NaCl 9 g/l) all at once in several portions with concomitant or subsequent neutralization (pH 7.3 to 7.4), advantageously with NaOH. This solution at physiological pH is used for mixing with the vaccine, which may be especially stored in freeze-dried, liquid or frozen form.

The polymer concentration in the final vaccine composition can be from 0.01% to 2% w/v, from 0.06 to 1% w/v, or from 0.1 to 0.6% w/v.

The sub-unit vaccine may be combined with adjuvants, like oil-in-water, water-in-oil-in-water emulsions based on mineral oil and/or vegetable oil and non ionic surfactants such as block copolymers, TWEEN®, SPAN®. Such emulsions are notably those described in page 147 of "Vaccine Design—The Subunit and Adjuvant Approach", Pharmaceutical Biotechnology, 1995, or TS emulsions, notably the TS6 emulsion, and LF emulsions, notably LF2 emulsion (for both TS and LF emulsions, see WO 04/024027). Other suitable adjuvants are for example vitamin E, saponins, and CARBOPOL® (Noveon; see WO 99/51269; WO 99/44633), aluminium hydroxide or aluminium phosphate ("Vaccine Design, The subunit and adjuvant approach", Pharmaceutical Biotechnology, vol. 6, 1995), biological adjuvants (i.e. C4b, notably murine C4b (Ogata R T et al.) or equine C4b, GM-CSF, notably equine GM-CSF (U.S. Pat. No. 6,645,740)), toxins (i.e. cholera toxins CTA or CTB, *Escherichia coli* heat-labile toxins LTA or LTB (Olsen C W et al.; Fingerut E et al.; Zurbriggen R et al. Peppoloni S et al.), and CpG (i.e. CpG #2395 (see Jurk M et al.), CpG #2142 (see SEQ. ID. NO: 890 in EP 1,221,955)).

The vaccine may also may also contain or comprise one or more *Leishmania* antigens, for example, kinetoplastid membrane protein 11 (KMP11).

*Leishmania* KMP11 antigens are derived from, for example, *L. infantum* or *L. chagasi*. KMP11 is a highly conserved surface membrane protein present in all members of the family Kinetoplastidae, and is differentially expressed both in amastigote and promastigote forms of *Leishmania* (Jardim A. et al.; Jardim A. et al.; Berberich C. et al.). The nucleic acid sequence of the gene and the amino acid sequence of the protein KMP11 of *Leishmania* are available in public databases, notably as *L. infantum* in the GenBank database under the accession numbers 95627 and X95626. The nucleic acid sequence of *L. donovani* is also available from the GenBank database, notably under the accession number S77039.

The state of the art regarding KMP11, vectors expressing KMP11 and vaccines are best summarized in patent application WO 08/064,181. A plasmid-based vaccine comprising pVR1020KMP11 is described in example 1 and the canarypox virus vector-based vaccine comprising vCP2350 is described in example 3. WO 08/064,181 also gives information regarding adjuvants, formulation, doses and route of administration.

KMP11 polypeptides and variants or fragments thereof may be produced, isolated and purified in the same manner set forth for in vitro expression of sand fly salivary polypeptides.

In one embodiment, the vaccine comprises *Lu. longipalpis* salivary polypeptides and/or variants or fragments thereof, and/or vectors comprising a polynucleotide encoding the *Lu. longipalpis* polypeptides and/or variants or fragments thereof, and/or vectors comprising the KMP11 polynucleotide encoding the KMP11 polypeptide and/or fragments or variants thereof from *Leishmania*. In one specific, non-limiting example of this embodiment, the *Lu. longipalpis* salivary polypeptide includes a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87. In another specific, non-limiting example of this embodiment, the polynucleotide encodes a *Lu. longipalpis* salivary polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87. In yet another specific, non-limiting example, the polynucleotide has at least 70%, at least 75%, at least 80%, at least 85%, at least 90%, at least 95%, 96%, 97%, 98% or 99% to a polynucleotide having a sequence as set forth in SEQ ID NO: 2, 4, 6, 8, 12, 14, 16, 18, 21, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 89, 90, or 91.

In a particular embodiment, the vaccine comprises *Lu. longipalpis* salivary LJM17 polypeptides and/or variants or fragments thereof, and/or vectors comprising the polynucleotide encoding the *Lu. longipalpis* LJM17 polypeptide and/or variants or fragments thereof, and/or vectors comprising the KMP11 polynucleotide encoding the KMP11 polypeptide and/or fragments or variants thereof from *Leishmania*. For example, the vectors for LJM17 may be selected from the group consisting of pVR2001 LJM17, pNBO002, vCP2390, vCP2390-SEQ ID NO:6 and MVA-LJM17. The vectors for KMP11 may be selected from the group consisting of pVR1020 KMP11 and vCP2350. In one embodiment, the vaccine comprises plasmids pVR2001 LJM17 and pVR1020KMP11. In another embodiment, the vaccine comprises vectors vCP2390 and vCP2350. In yet another embodiment, the vaccine comprises plasmids pNBO002 and pVR1020 KMP11. In yet another embodiment, the vaccine comprises vCP2390-SEQ ID NO:6 and vCP2350.

In another particular embodiment, the vaccine comprises *Lu. longipalpis* salivary LJL143 polypeptides and/or variants or fragments thereof, and/or vectors comprising the polynucleotide encoding the *Lu. longipalpis* LJL143 polypeptide and/or variants or fragments thereof, and/or vectors comprising the polynucleotide encoding *Leishmania* KMP11 polypeptides and/or variants or fragments thereof. For example, the vectors for LJL143 may be selected from the group consisting of pVR2001 LJL143, pNBO003, vCP2389, vCP2389-SEQ ID NO:2 and MVA-LJL143. The vectors for KMP11 may be selected from the group consisting of pVR1020 KMP11 and vCP2350. In one embodiment, the vaccine comprises plasmids pVR2001 LJL143 and pVR1020 KMP11. In another embodiment, the vaccine comprises vectors vCP2389 and vCP2350. In yet another embodiment, the vaccine comprises plasmids pNBO003 and pVR1020 KMP11. In yet another embodiment, the vaccine comprises vectors vCP2389-SEQ ID NO:2 and vCP2350.

In another particular embodiment, the vaccine comprises *Lu. longipalpis* salivary LJL143 polypeptides, variants thereof, fragments thereof, and/or vectors comprising the polynucleotide encoding the *Lu. longipalpis* LJL143 polypeptide and/or variants or fragments thereof, and/or *Lu. longipalpis* salivary LJM17 polypeptides and/or variants or fragments thereof, and/or vectors comprising the LJM17 polynucleotide encoding the *Lu. Longipalpis* LJM17 polypeptide and/or variants or fragments thereof, and/or *Leishmania* KMP11 polypeptides and/or variants or fragments thereof, and/or vectors comprising the KMP11 polynucleotide or gene. For example, the vectors for LJL143 may be selected from the group consisting of pVR2001 LJL143, pNBO003, vCP2389, vCP2389-SEQ ID NO:2 and MVA-LJL143. The vectors for LJM17 may be selected from the group consisting of pVR2001 LJM17, pNBO002, vCP2390, vCP2390-SEQ ID NO:6 and MVA-LJM17. The vectors for KMP11 may be selected from the group consisting of pVR1020 KMP11 and vCP2350. In one embodiment, the vaccine comprises plasmids pVR2001 LJL143, pVR2001 LJM17 and pVR1020 KMP11. In another embodiment, the vaccine comprises vectors vCP2389, vCP2390 and vCP2350. In yet another embodiment, the vaccine comprises plasmids pNBO003, pNBO002 and pVR1020KMP11. In another embodiment, the vaccine comprises vCP2389-SEQ ID NO:2, vCP2390-SEQ ID NO:6 and vCP2350 vectors.

The vaccine may also be associated with at least one *Leishmania* antigen, for example inactivated *Leishmania*.

In a particular embodiment, the *Leishmania* strain may be *Leishmania infantum*, and/or *Leishmania braziliensis*. In a preferred embodiment, the *Leishmania* strain may be *Leishmania braziliensis*.

These strains of *Leishmania* may be inactivated by chemical or physical methods. The chemical methods are notably BPL, formaldehyde. The physical methods may notably be sonication. One method for inactivating *Leishmania* for use in a vaccine is described in R. Cordeiro Giunchetti et al., Vaccine, 2007. The promastigotes are cultivated in NNN/LIT medium for 6 to 14 days, but more preferably 10 days, until the differentiation between promastigote procyclic form into promastigote metacyclic form is achieved on the basis of a microscopic observation. The culture can then be harvested by centrifugation (2000×g, 20 minutes, 4° C.). When applicable, the supernatant is discarded and the biomass is washed three times in saline buffer. Whether the culture is clarified or not, the promastigote suspension (i.e. crude culture or promastigote resuspended in saline buffer after centrifugation) is subsequently disrupted by ultrasound treatment using a power from 10 to 375 W, but more preferably 40 W, for 1 minute, at 0° C. The batch volume for this treatment is between 5 and 150 mL, preferably 30 mL. After treatment the lysate can be stored at −80° C.

The vaccine formulation may be prepared from the protein concentrate that is obtained following cell lysis. The cell lysate protein quantity that may be used for vaccination of a canine is from about 50 µg to about 2000 µg, preferably from about 50 µg to about 600 µg. Protein concentration is determined according to the method of Lowry.

The inactivated *Leishmania* vaccine may be combined with adjuvants, like those described previously for sub-unit vaccines.

In one embodiment, the vaccine comprises *Lu. longipalpis* salivary polypeptides and/or variants or fragments thereof, and/or vectors comprising the *Lu. longipalpis* salivary polynucleotide and/or variants or fragments thereof, and/or inactivated *Leishmania*. In one specific, non-limiting example of this embodiment, the *Lu. longipalpis* salivary polypeptide includes a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87. In another specific, non-limiting example of this embodiment, the polynucleotide encodes a *Lu. longipalpis* salivary polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87. In yet another specific, non-limiting example, the polynucleotide has at least 70%, at least 75%, at least 80%, at least 85%, at least 90%, at least 95%, 96%, 97%, 98% or 99% to a polynucleotide having a sequence as set forth in SEQ ID NO: 2, 4, 6, 8, 12, 14, 16, 18, 21, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 89, 90, or 91.

In a particular embodiment, the vaccine comprises *Lu. longipalpis* salivary LJM17 polypeptides and/or variants or fragments thereof, and/or vectors comprising the LJM17 polynucleotide and/or variants or fragments thereof, and/or inactivated *Leishmania*. For example, the vectors for LJM17 may be selected among the group consisting of pVR2001 LJM17, pNBO002, vCP2390, vCP2390-SEQ ID NO:6 and MVA-LJM17, and may be combined with inactivated *Leishmania* selected from the group consisting of sonicated inactivated *Leishmania infantum*, and/or *Leishmania braziliensis*. For example, in one embodiment, the vaccine comprises the vCP2390 vector and sonicated inactivated *Leishmania braziliensis*. In another embodiment, the vaccine comprises the vCP2390-SEQ ID NO:6 vector and sonicated inactivated *Leishmania braziliensis*.

In another particular embodiment, the vaccine comprises *Lu. longipalpis* salivary LJL143 polypeptides and/or variants or fragments thereof, and/or vectors comprising the LJL143 polynucleotide and/or variants or fragments thereof, and/or inactivated *Leishmania*. For example, the vectors for LJL143 may be selected from the group consisting of pVR2001 LJL143, pNBO003, vCP2389, vCP2389-SEQ ID NO:2 and MVA-LJL143. The inactivated *Leishmania* may be selected from the group consisting of sonicated inactivated *Leishmania infantum*, and/or *Leishmania braziliensis*. For example, in one embodiment, the vaccine comprises the vCP2389 vector and sonicated inactivated *Leishmania braziliensis*. In another embodiment, the vaccine comprises the vCP2389-SEQ ID NO:2 vector and sonicated inactivated *Leishmania braziliensis*.

In another particular embodiment, the vaccine comprises *Lu. longipalpis* salivary LJL143 polypeptides and/or variants or fragments thereof, and/or vectors comprising the LJL143 polynucleotide and/or variants or fragments thereof, and/or *Lu. longipalpis* salivary LJM17 polypeptides and/or variants or fragments thereof, and/or vectors comprising the LJM17 polynucleotide and/or variants or fragments thereof, and/or inactivated *Leishmania*. For example, the vectors could be selected for LJL143 from the group consisting of pVR2001 LJL143, pNBO003, vCP2389, vCP2389-SEQ ID NO:2 and MVA-LJL143. For LJM17, the vectors may be selected from the group consisting of pVR2001 LJM17, pNBO002, vCP2390, vCP2390-SEQ ID NO:6 and MVA-LJM17. The inactivated *Leishmania* may be selected from the group consisting of sonicated inactivated *Leishmania infantum*, and/or *Leishmania braziliensis*. In one embodiment, the vaccine comprises vCP2389 and vCP2390 vectors and sonicated inactivated *Leishmania braziliensis*. In another embodiment, the vaccine comprises vCP2389-SEQ ID NO:2 and vCP2390-SEQ ID NO:6 vectors and sonicated inactivated *Leishmania braziliensis*.

Another aspect of the present invention relates to methods of vaccinating a host against *Leishmania* using the vaccine compositions disclosed herein.

The host may be any one or all of humans, felines (for example, domesticated cats, kittens, big cats and wild cats) and canines (for example, dogs, bitchs, puppies, foxes, jackals, and wolves). In one embodiment, the host is a canine.

The routes of administration may be, for example, intramuscular (IM) or intradermal (ID) or transdermal (TD) or subcutaneous (SC). The means of administration may be, for example, a syringe with a needle, or needle free apparatus, or a syringe with a needle coupled to electrotransfer (ET) treatment, or needle free apparatus coupled to ET treatment.

Another aspect of the invention relates to the use of a plasmid-based vaccine according to the present invention for administration to *Leishmania*, a host, wherein this administration is coupled to ET treatment. The administration of a plasmid-based vaccine is advantageously intramuscular. The means of administration is, for example, a syringe and a needle. One or several injections may be administered successively. In the case of several injections, they may be carried out 2 to 6 weeks apart, for example, about 3 weeks apart. In one embodiment, a semi-annual booster or an annual booster is further administered.

For plasmid-based vaccines, advantageous routes of administration may be ID or IM. This administration may be through use of a syringe with a needle or with a needle free apparatus like Dermojet or Biojector (Bioject, Oregon, USA) or VETJET™ (Merial) or VITAJET™ (Bioject Inc.), see US 2006/0034867. The dosage may be from 50 µg to 500 µg per plasmid. When DMRIE-DOPE is added, 100 µg per plasmid may be utilized. When canine GM-CSF or other cytokines are used, the plasmid encoding this protein may be present at a dosage of from about 200 µg to about 500 µg and may advantageously be 200 µg. The volume of doses can be between 0.01 ml and 0.5 ml, for example, 0.25 ml. Administration may be provided with multiple points of injection.

Alternatively, plasmid-based vaccines may be administered via the IM route coupled to electrotransfer (ET) treatment. The ET treatment may be performed using an apparatus for electrotransfer and the specifications of the manufacturer (i.e. Sphergen G250 generator (Sphergen SARL, Evry Genopole, France); MedPulser® DNA electroporation system (Innovio Biomedical Corporation, San Diego, Calif., USA)). In one embodiment, the apparatus for electrotransfer has a unipolar field. The field intensity may be from about 50 to about 250 V/cm, from about 50 to about 200 V/cm, or from about 50 to about 175 V/cm. The pulse duration may be from about 1 to about 50 msec, or from about 15 to about 25 msec. The frequency may be from about 1 to about 50 Hz, or from about 5 to about 15 Hz. The interpulse interval may be from about 1 to 1000 msec, or from about 1 to about 200 msec. The number of pulses may be from 1 to 20, or from 5 to 10. The intra tissular intensity may advantageously be up to about 2 A. The distance between electrodes may be from about 0.2 to about 1 cm, or from about 0.2 to about 0.5 cm.

For recombinant viral vector-based vaccines, the routes of administration may advantageously be SC or IM or TD or ID. This administration may be made by a syringe with a needle or with a needle free apparatus like Dermojet or Biojector (Bioject, Oregon, USA) or VETJET™ (Merial) or VITAJET™ (Bioject Inc.). The dosage may be from about $10^3$ pfu to about $10^9$ pfu per recombinant poxvirus vector. When the vector is a canarypox virus, the dosage may be, for example, from about $10^5$ pfu to about $10^9$ pfu, or from about $10^6$ pfu to about $10^8$ pfu. The volume of doses may be from about 0.01 ml to 0.2 ml, and is advantageously 0.1 ml. Administration may comprise multiple points of injection.

For the IM route the volume of the vaccine provided may be from 0.2 to 2 ml, in particular from about 0.5 to 1 ml. The same dosages are utilized for any of the vectors of the present invention.

For sub-unit vaccines, the route of administration may advantageously be via SC or IM or TD or ID. This administration may be made by a syringe with a needle or with a needle free apparatus like Dermojet or Biojector (Bioject, Oregon, USA) or VETJET™ (Merial) or VITAJET™ (Bioject Inc.). The dosage may be from about 50 to about 500 µg, in particular from about 50 to about 150 µg, and more particularly from about 50 to about 100 µg. The volume of the sub-unit vaccine provided is from 0.2 to 2 ml, in particular from about 0.5 to 1 ml.

In another aspect, the present invention relates to a vaccine strategy, which is based on a prime-boost administration regimen, where the primo-administration and the boost administration(s) utilize a composition comprising a pharmaceutically or veterinary acceptable excipient, diluent or vehicle and an in vivo expression vector comprising a polynucleotide sequence, that contains and expresses the *Lu. longipalpis* salivary polypeptide and/or variants or fragments thereof.

The present invention relates to the use of in vivo expression vectors in a prime-boost administration regimen, comprising a primo-administration of a vaccine comprising a pharmaceutically or veterinary acceptable vehicle, diluent or excipient, an in vivo expression vector containing a polynucleotide sequence for expressing, in vivo, *Lu. longipalpis* salivary polypeptides and/or variants or fragments thereof, followed by a boost administration of a vaccine comprising a pharmaceutically or veterinary acceptable vehicle or excipient, an in vivo expression vector containing a polynucleotide sequence for expressing, in vivo, sand fly *Lu. longipalpis* polypeptides and/or variants or fragments thereof as described above, to protect a host from leishmaniasis and/or to prevent disease progression in infected hosts.

A prime-boost regimen comprises at least one primo-administration and at least one boost administration using at least one common polypeptide and/or variants or fragments thereof. The vaccine used in primo-administration may be different in nature from those used as a later booster vaccine. The primo-administration may comprise one or more administrations. Similarly, the boost administration may comprise one or more administrations.

The routes of administration, doses and volumes are as previously disclosed herein.

The prime-boost administrations may be advantageously carried out 2 to 6 weeks apart, for example, about 3 weeks apart. According to one embodiment, a semi-annual booster or an annual booster, advantageously using the viral vector-based vaccine, is also envisaged. The animals are advantageously at least 6 to 8 weeks old at the time of the first administration.

In a particular embodiment, the prime-boost administration regimen comprises at least one primo-administration of a plasmid-based vaccine according to the present invention and at least one boost-administration of a recombinant viral vector-based vaccine according to the present invention.

In another particular embodiment, the prime-boost administration regimen comprises at least one primo-administration of a recombinant viral vector-based vaccine according to the present invention and at least one boost-administration of a sub-unit vaccine according to the present invention.

In another particular embodiment, the prime-boost administration regimen comprises at least one primo-administration of a recombinant viral vector-based vaccine according to the present invention and at least one boost-administration of a plasmid-based vaccine according to the present invention.

In one embodiment, the present invention relates to a method of vaccinating a subject susceptible to *Leishmania* comprising a prime-boost administration regimen wherein said regiment comprises a primo-administration of a vaccine comprising, in a pharmaceutically or veterinary acceptable vehicle, diluent or excipient, a plasmid containing a polynucleotide for expressing, in vivo, a salivary *Lu. longipalpis* polypeptide, a variant or fragment of the salivary *Lu. longipalpis* polypeptide, or a mixture thereof, followed by a boost administration of a vaccine comprising, in a pharmaceutically or veterinary acceptable vehicle or excipient, a recombinant viral vector comprising a polynucleotide for expressing, in vivo, the same salivary *Lu. longipalpis* polypeptide(s), variant thereof, fragment thereof, to protect the subject from leishmaniasis and/or to prevent disease progression in infected subject.

In another embodiment, the present invention relates to a method vaccinating a subject susceptible to *Leishmania* comprising a prime-boost administration regimen wherein said regiment comprises a primo-administration of a vaccine comprising, in a pharmaceutically or veterinary acceptable vehicle, diluent or excipient, a recombinant viral vector comprising a polynucleotide for expressing, in vivo, a salivary *Lu. longipalpis* polypeptide, a variant or fragment of the salivary *Lu. longipalpis* polypeptide, or a mixture thereof, followed by a boost administration of a vaccine comprising, in a pharmaceutically or veterinary acceptable vehicle or excipient, a plasmid containing a polynucleotide for expressing, in vivo, the same salivary *Lu. longipalpis* polypeptide(s), variant thereof, fragment thereof, to protect the subject from leishmaniasis and/or to prevent disease progression in infected subject.

In yet another embodiment, the present invention related to a method of vaccinating a subject susceptible to *Leishmania* comprising a prime-boost administration regimen wherein said regiment comprises a primo-administration of a vaccine comprising, in a pharmaceutically or veterinary acceptable vehicle, diluent or excipient, a recombinant viral vector comprising a polynucleotide for expressing, in vivo, a salivary *Lu. longipalpis* polypeptide, a variant or fragment of the salivary *Lu. longipalpis* polypeptide, or a mixture thereof, followed by a boost administration of a vaccine comprising, in a pharmaceutically or veterinary acceptable vehicle or excipient, the same salivary *Lu. longipalpis* polypeptide(s), variant thereof, fragment thereof, to protect the subject from leishmaniasis and/or to prevent disease progression in infected subject.

In another embodiment, the prime-boost administration regimen comprises at least one primo-administration of a pVR2001 LJM17 or pNBO002 plasmid-based vaccine, and at least one boost-administration of a vCP2390 or vCP2390-SEQ ID NO:6 vector-based vaccine.

In another embodiment, the prime-boost administration regimen comprises at least one primo-administration of a pVR2001 LJL143 or pNBO003 plasmid-based vaccine, and at least one boost-administration of a vCP2389 or vCP2389-SEQ ID NO:2 vector-based vaccine.

In another embodiment, the prime-boost administration regimen comprises at least one primo-administration of a pVR2001 LJL143 and pVR2001 LJM17 plasmid-based vaccine, and at least one boost-administration of a vCP2389 and vCP2390 vector-based vaccine.

In another embodiment, the prime-boost administration regimen comprises at least one primo-administration of a pNBO003 and pNBO002 plasmid-based vaccine, and at least one boost-administration of a vCP2389-SEQ ID NO:2 and vCP2390-SEQ ID NO:6 vector-based vaccine.

In yet another embodiment, the prime-boost administration regimen comprises at least one primo-administration of a pVR2001 LJM17 or pNBO002 plasmid-based vaccine, and at least one boost-administration of a MVA-LJM17 vector-based vaccine.

In another embodiment, the prime-boost administration regimen comprises at least one primo-administration of a pVR2001 LJL143 or pNBO003 plasmid-based vaccine, and at least one boost-administration of a MVA-LJL143 vector-based vaccine.

In another embodiment, the prime-boost administration regimen comprises at least one primo-administration of a pVR2001 LJL143 and pVR2001 LJM17 plasmid-based vaccine, and at least one boost-administration of a MVA-LJL143 and MVA-LJM17 vector-based vaccine.

In yet another embodiment, the prime-boost administration regimen comprises at least one primo-administration of a pNBO003 and pNBO002 plasmid-based vaccine, and at least one boost-administration of a MVA-LJL143 and MVA-LJM17 vector-based vaccine.

In another embodiment, the prime-boost administration regimen comprises at least one primo-administration of a vCP2390 or vCP2390-SEQ ID NO:6 vector-based vaccine, and at least one boost-administration of a LJM17 polypeptide sub-unit vaccine.

In another embodiment, the prime-boost administration regimen comprises at least one primo-administration of a vCP2389 or vCP2389-SEQ ID NO:2 vector-based vaccine, and at least one boost-administration of a LJL143 polypeptide sub-unit vaccine.

In another embodiment, the prime-boost administration regimen comprises at least one primo-administration of a vCP2389 or vCP2389-SEQ ID NO:2 and vCP2390 or vCP2390-SEQ ID NO:6 vector-based vaccine, and at least one boost-administration of a LJL143 polypeptide and LJM17 polypeptide sub-unit vaccine.

In yet another embodiment, the prime-boost administration regimen comprises at least one primo-administration of a MVA-LJM17 vector-based vaccine, and at least one boost-administration of a LJM17 polypeptide sub-unit vaccine.

In another embodiment, the prime-boost administration regimen comprises at least one primo-administration of a MVA-LJL143 vector-based vaccine, and at least one boost-administration of a LJL143 polypeptide sub-unit vaccine.

In another embodiment, the prime-boost administration regimen comprises at least one primo-administration of a MVA-LJL143 and MVA-LJM17 vector-based vaccine, and at least one boost-administration of a LJL143 polypeptide and LJM17 polypeptide sub-unit vaccine.

In another embodiment, the prime-boost administration regimen comprises at least one primo-administration of a vCP2390 or vCP2390-SEQ ID NO:6 vector-based vaccine, and at least one boost-administration of a pVR2001 LJM17 or pNBO002 plasmid-based vaccine.

In another embodiment, the prime-boost administration regimen comprises at least one primo-administration of a vCP2389 or vCP2389-SEQ ID NO:2 vector-based vaccine, and at least one boost-administration of a pVR2001 LJL143 or pNBO003 plasmid-based vaccine.

In another embodiment, the prime-boost administration regimen comprises at least one primo-administration of a vCP2389 and vCP2390 vector-based vaccine, and at least one boost-administration of a pVR2001 LJL143 and pVR2001 LJM17 plasmid-based vaccine.

In another embodiment, the prime-boost administration regimen comprises at least one primo-administration of a vCP2389-SEQ ID NO:2 and vCP2390-SEQ ID NO:6 vector-based vaccine, and at least one boost-administration of a pNBO003 and pNBO002 plasmid-based vaccine.

In another embodiment, the prime-boost administration regimen comprises at least one primo-administration of a MVA-LJM17 vector-based vaccine, and at least one boost-administration of a pVR2001 LJM17 or pNBO002 plasmid-based vaccine.

In another embodiment, the prime-boost administration regimen comprises at least one primo-administration of a MVA-LJL143 vector-based vaccine, and at least one boost-administration of a pVR2001 LJL143 or pNBO003 plasmid-based vaccine.

In another embodiment, the prime-boost administration regimen comprises at least one primo-administration of a MVA-LJL143 and MVA-LJM17 vector-based vaccine, and at least one boost-administration of a pNBO003 and pNBO002 plasmid-based vaccine.

Another aspect of the present invention relates to a kit for prime-boost vaccination according to the present invention. The kit may comprise at least two vials: a first vial containing a vaccine for the primo-vaccination according to the present invention, and a second vial containing a vaccine for the boost-vaccination according to the present invention. The kit may advantageously contain additional first or second vials for additional primo-vaccinations or additional boost-vaccinations.

In one embodiment, the kit may comprise two vials, one containing a plasmid-based vaccine for the primo-vaccination according to the present invention, the other vial containing a recombinant viral vector-based vaccine for the boost-vaccination according to the present invention.

In another embodiment, the kit may comprise two vials, one containing a recombinant viral vector-based vaccine for the primo-vaccination according to the present invention, the other vial containing a sub-unit vaccine for the boost-vaccination according to the present invention.

In another embodiment, the kit may comprise two vials, one containing a recombinant viral vector-based vaccine for the primo-vaccination according to the present invention, the other vial containing a plasmid-based vaccine for the boost-vaccination according to the present invention.

It is disclosed herein that individuals who experience an anti-*Leishmania* DTH response conversion also have an increase in antibodies against *Lu. longipalpis* salivary proteins. Thus, the presence or absence of antibodies to *Lu. longipalpis* salivary proteins can be used to ascertain if a subject has a *Leishmania* infection.

A method is disclosed herein for diagnosing infection with *Leishmania* by detecting the presence of antibodies that specifically bind one or more polypeptides having an amino acid sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87, or a polypeptide having at least 80%, at least 90%, at least 95%, or at least 99% homologous to one of these polypeptides, a conservative variant, a homolog or an immunogenic fragment of one of these polypeptides. The method can utilize a single *Lu. longipalpis* polypeptide or a combination of these polypeptides. In certain examples, the method of diagnosis detects antibodies that specifically bind at least 3, 6, or 10 of these polypeptides, or immunogenic fragments thereof.

In one embodiment, one or more *Lu. longipalpis* polypeptide can be bound to a solid substrate. For example, the *Lu. longipalpis* polypeptide having an amino acid sequence as set forth in SEQ ID NO: 1, 3, 5, 7, 11, 13, 15, 17, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, or 87 can be bound to the substrate. One of more of these polypeptides can be bound to the substrate, for example at least 3, 6, or 10 of these polypeptides, or an immunogenic fragment thereof. In one example, one or more polypeptides having a sequence as set forth in SEQ ID NO: 1, 3, 5, 7, 11, 13, 15, 17, 25, 33, 39, 47, or 77 can be bound to the substrate. In another example, one or more *Lu. longipalpis* polypeptides having a sequence as set forth in SEQ ID NO: 1, 3, 5, 7, 11, 13, 15, 17, or 57 can be bound to the substrate. In one specific, non-limiting example, at least six *Lu. longipalpis* polypeptides are bound to a solid substrate, wherein each of the polypeptides comprises an amino acid sequence as set forth in SEQ ID NO: 25, SEQ ID NO: 1 (or 3, or 11, or 13), SEQ ID NO: 5 (or 7, or 15, or 17), SEQ ID NO: 47, SEQ ID NO: 73, or SEQ ID NO: 77, or an immunogenic fragment thereof. In another specific, non-limiting example, at least three *Lu. Longipalpis* polypeptides are bound to a solid substrate, wherein each of the polypeptides comprises an amino acid sequence as set forth in SEQ ID NO: 1 (or 3, or 11, or 13), SEQ ID NO: (or 7, or 15, or 17), or SEQ ID NO: 57, or an immunogenic fragment thereof.

In one embodiment, two or more (for example at least 3, 6, or 10) *Lu. longipalpis* polypeptides (or immunogenic fragments thereof) are applied to a solid substrate, for example as a series of "dots," such as in a "dot blot" assay. In another embodiment, two or more *Lu. longipalpis* polypeptides are applied to a substrate such as in a linear array. In a further embodiment, *Lu. longipalpis* polypeptides are applied to a membrane in a two-dimensional array. In this manner, the presence of antibodies to more than one *Lu. longipalpis* polypeptide is assessed. Each *Lu. longipalpis* polypeptide can be applied directly to the surface of a membrane in a single location or in a combination of locations.

The solid substrate can be a polystyrene bead, a membrane, a chip or a plate. A plastic or glass substrate can be utilized. In other embodiments, a membrane is utilized that is composed of porous materials such as nylon, nitrocellulose, cellulose acetate, glass fibers, and other porous polymers. The surface of a solid support may be activated by chemical processes that cause covalent linkage of polypeptide to the support. However, any other suitable method may be used for immobilizing a polypeptide to a solid support including, without limitation, ionic interactions, hydrophobic interactions, covalent interactions and the like. Once the polypeptide is applied to the substrate, the substrate can be contacted with a substance, such as protein-containing solution, which non-specifically saturates the binding sites thereon. Specific, non-limiting examples of a protein-containing solution include a solution made from powdered milk or serum albumin, such as bovine serum albumin.

A specimen (for example, sera, blood, plasma, urine, semen, saliva, sputum, lacrimal fluid, lymph fluid) is then added to the substrate, and the combined specimen and substrate are incubated for a sufficient time to allow specific binding. Specific binding of antibodies to the *Lu. longipalpis* polypeptides disclosed herein, are then detected using any means known to one of skill in the art. In one embodiment, a labeled secondary antibody is used to detect the antibodies that specifically bind the *Lu. longipalpis* polypeptides. The label can be a radiolabel (for example, $^{125}$I), an enzymatic label (for example, alkaline phosphatase or horseradish peroxidase), or a fluorescent label (for example, fluoroscein isothiocyanate). Detection systems for these labels are known to one of skill in the art. Binding of the specimen, or a component of the specimen, to the *Lu. longipalpis* polypeptide, as indicated by the presence of the marker, indicates infection with *Leishmania*.

In another embodiment, the specimen is adsorbed onto a solid substrate containing binding sites for polypeptides, such as antibody molecules. In one embodiment, the solid substrate is a polystyrene bead, a chip, a membrane or a plate. The substrate is thereafter contacted with a substance, such as a protein-containing solution that non-specifically saturates the binding sites thereon. The substrate is then washed with a buffer. A solution of one or more *Lu. longipalpis* polypeptides is then added to the bound specimens. In one embodiment, the *Lu. longipalpis* polypeptide is directly labeled. The labeling of the *Lu. longipalpis* polypeptide can be brought about by use of any marker, such as by incorporation of a radioactive isotope or group, or by coupling this component to an enzyme, a dyestuff, for example a chromophoric moiety or a fluorescent group. The enzymes of use are those which can be colorimetrically, spectrophotometrically, or fluorimetrically determined. Non-limiting examples of enzymes for use in the present invention include enzymes from the group of oxidoreductases, such as catalase, peroxidase, glucose oxidase, beta-glucuronidase, beta-D-glucosidase, beta-D-galactosidase, urease and galactose oxidase. After the labeled *Lu. longipalpis* polypeptide is incubated with the solid substrate, any unbound labeled *Lu. longipalpis* polypeptide is removed by washing. Bound labeled *Lu. longipalpis* polypeptide is then detected by an appropriate assay. Binding of the labeled *Lu. longipalpis* polypeptide to the specimen, or to a component of the specimen, is indicative of infection with *Leishmania*.

In general, the incubation steps utilized in carrying out the procedures can be performed in a known manner, such as by incubating at temperatures between about 4° C. and about 25° C., for about 30 minutes to about 48 hours. Washings can be included with an aqueous solution such as a buffer, wherein the buffer is from about pH 6 to about pH 8, such as by using an isotonic saline solution of a pH of about 7.

Competitive binding assays are also of use in detecting infection with *Leishmania*. One of skill in the art, given the *Lu. longipalpis* polypeptides disclosed herein, will readily be able to design additional assays, such as competitive binding assays, of use in detecting *Leishmania* infection.

In another embodiment, the *Lu. longipalpis* polypeptides disclosed herein can be included in a diagnostic test kit. For example, a diagnostic test kit for detecting a *Leishmania* infection includes a solid substrate having applied thereon one or more *Lu. longipalpis* polypeptide disclosed herein. In other embodiments, the kit includes written instructions and/or a container including a specified amount of labeled antibodies to immunoglobulins, such as IgG or IgM, or labeled secondary antibodies that bind antibodies from a species of interest. For example labeled antibodies can be provided that specifically detect dog or human immunoglobulins. The labeled antibodies can be fluorescently labeled, enzymatically labeled, or radiolabeled. Labeled antibodies used in the above-described test kits can be packaged in either solution or lyophilized form suitable for reconstitution.

In another embodiment the test kit includes a specified amount of one or more *Lu. longipalpis* polypeptide described herein in a container, and written instructions. In one example, the *Lu. longipalpis* polypeptide is directly labeled. In another example, the one or more *Lu. longipalpis* polypeptide is unlabeled. If the *Lu. longipalpis* polypeptide is unlabeled, a container can also be included with a detection reagent that specifically binds the *Lu. longipalpis* polypeptide, such as a labeled monoclonal antibody. The kit can also optionally include a solid substrate for binding the specimen.

The above described process and test kit for detection of antibodies to the *Lu. longipalpis* polypeptides disclosed herein can be utilized in many applications, including, but not limited to detecting *Leishmania* infection in a subject using the methods disclosed herein. The tests and kits disclosed herein can be used to detect the efficacy of a therapeutic treatment in a subject. In yet another embodiment, the tests and kits disclosed herein can also be used to assess a primary infection with *Leishmania* or to predict recovery from *Leishmania* infection by taking a body fluid from an infected subject, for example at various times following infection, and applying the above described detection procedures.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 1

Construction of the pVR2001 LJM17 Plasmid Expressing the *Lu. longipalpis* Salivary LJM17 Polypeptide The polynucleotide encoding the *Lu. longipalpis* LJM17 polypeptide is synthesized and has the sequence described in SEQ ID NO: 8 which contains poly(A) tail. The LJM17 fragment is amplified by PCR and cloned into the TOPO cloning site of the pVR2001-TOPA donor plasmid (also referred to as pVR2001-TOPO).

The resultant plasmid, pVR2001 LJM17 therefore contains and expresses a nucleotide encoding a promoter capable of driving expression in a mammalian cell, a leader peptide for facilitating secretion/release of a prokaryotic protein sequence from a mammalian cell, LJM17, topoisomerases flanking the DNA encoding LJM17, as well as a termination sequence.

The nucleic acid sequence of one strand of the plasmid pVR2001 LJM17 is described in SEQ ID NO: 9 and in FIG. 1, wherein BamHI sites are in positions [4-9] and [5051-5056], the nucleotide sequence encoding the tPA signal peptide is in position [4976-5062] and the nucleotide sequence encoding LJM17 is in position [5063-6247].

Example 2

Construction of the pVR2001 LJL143 Plasmid Expressing the *Lu. longipalpis* Salivary LJL143 Polypeptide The polynucleotide encoding the *Lu. longipalpis* LJL143 polypeptide is synthesized and has the sequence described in SEQ ID NO: 4 which contains poly(A) tail. The LJL143 fragment is amplified by PCR and cloned into the TOPO cloning site of the pVR2001-TOPA plasmid as described in example 1, to generate the plasmid pVR2001 LJL143.

Figures 2, 20:
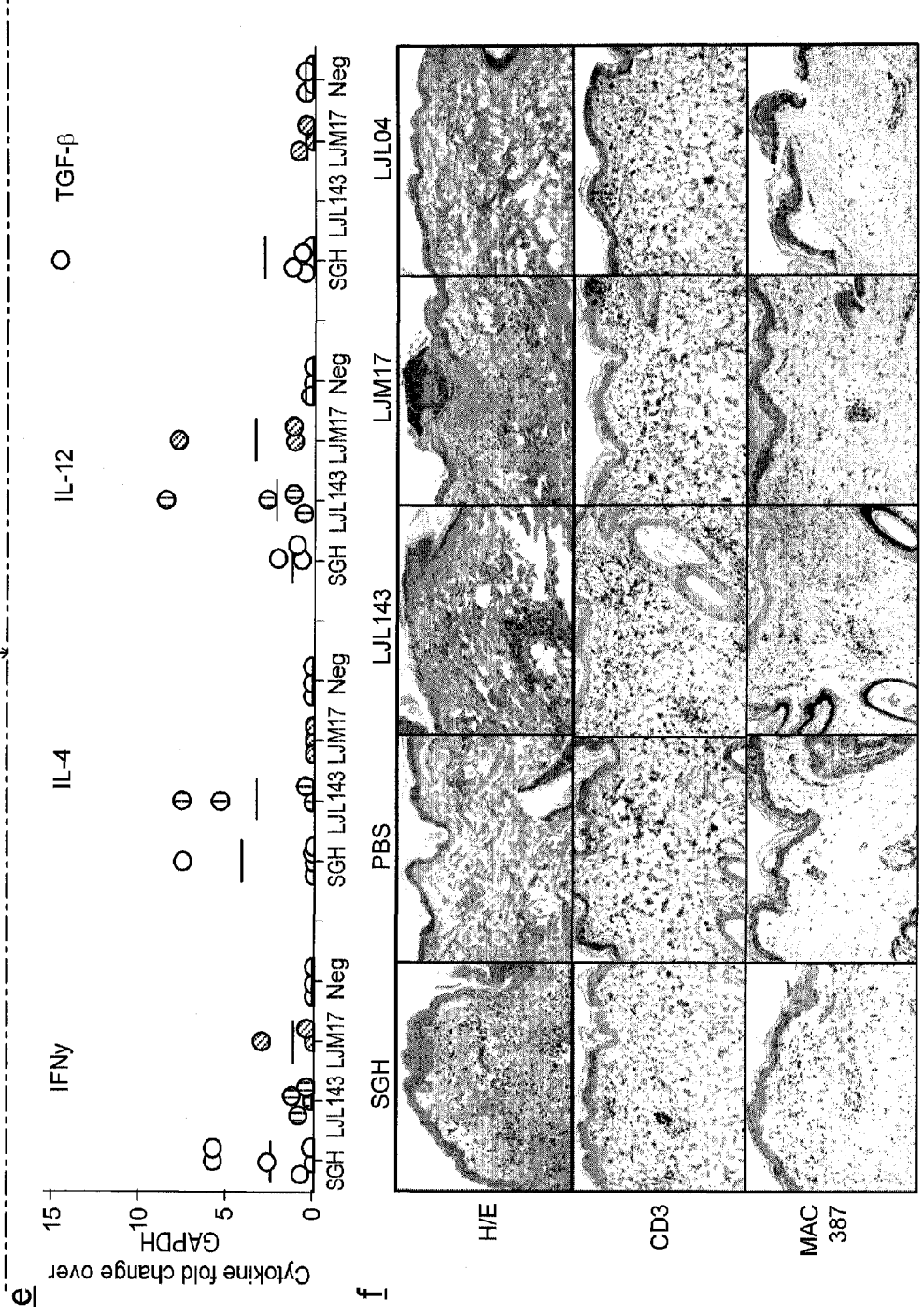
FIG. 2 shows the nucleic acid sequence of one strand of the plasmid pVR2001 LJL143 (SEQ ID NO:10), wherein the two BamHI restriction sites are in bold, the sequence encoding the tPA signal peptide is underlined and the sequence encoding the LJL143 is in bold capital letters.

The nucleic acid sequence of one strand of the plasmid pVR2001 LJL143 is described in SEQ ID NO: 10 and in FIG. 2, wherein BamHI sites are in positions [4-9] and [5051-5056], the nucleotide sequence encoding the tPA signal peptide is in position [4976-5062] and the nucleotide sequence encoding LJL143 is in position [5063-5899].

Example 3

Construction of an ALVAC Canarypox Virus Vector Expressing the *Lu. longipalpis* Salivary LJM17 Polypeptide For a discussion and examples of the plasmid pALVAC, and the C3 locus, see e.g., U.S. Pat. Nos. 5,756,103; 5,833, 975; and 6,780,407. The sequence of the vaccinia virus H6 promoter has been previously described (see e.g., Taylor et al.; Taylor et al.; Guo et al.).

Figure 3:
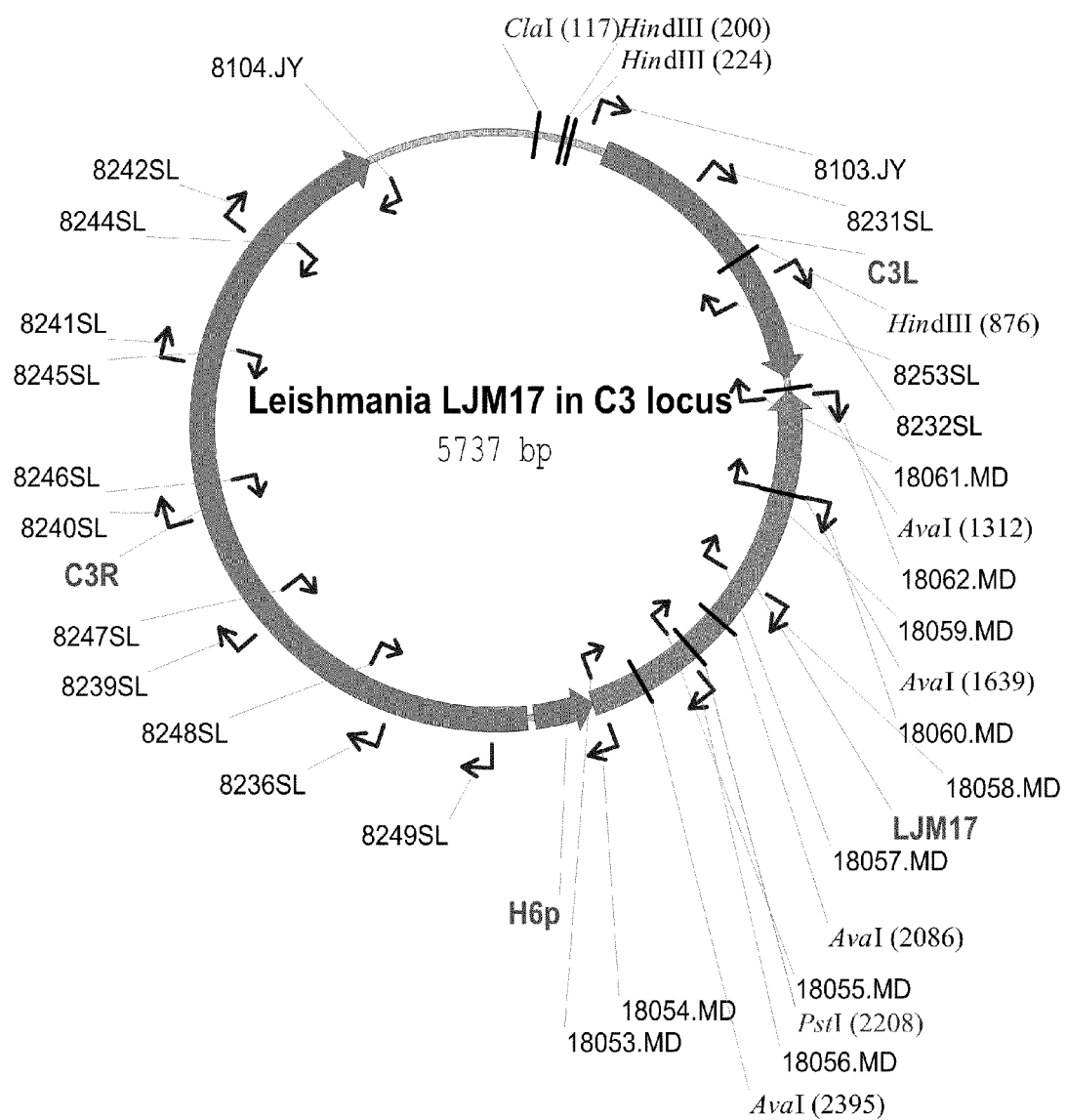
FIG. 3 shows a map of the donor vector, pALVAC C3 H6p-LJM17, having 5737 base pairs.

The polynucleotide encoding the *Lu. longipalpis* LJM17 polypeptide is synthesized and has the sequence described in SEQ ID NO:6. This polynucleotide is then ligated to the pALVAC C3 H6p donor plasmid resulting in pALVAC C3 H6p-LJM17 containing 5737 base pairs (FIG. 3).

To generate vCP2390-SEQ ID NO:6, the pALVAC C3 H6p-LJM17 plasmid is linearized with NotI restriction enzyme. The linearized fragments were individually transfected into ALVAC-infected primary CEF cells using the calcium phosphate precipitation method (see, Panicali et al.; Piccini et al.). After 24 h, the transfected cells are harvested, sonicated and used for recombinant virus screening.

Recombinant plaques are screened based on the plaque lift hybridization method using a *Lu. longipalpis* LJM17-specific probe which is labeled with horse radish peroxidase according to the manufacturer's protocol (Amersham Cat# RPN-3001). After three sequential rounds of plaque purification, the recombinants are generated by hybridization confirmation as 100% positive for the *Lu. longipalpis* LJM17 insert and 100% negative for the C3 ORF.

A single plaque is selected from the third round of plaque purification and expanded to obtain P1 (60 mm), P2 (T75 flasks), and P3 (roller bottles) stocks to amplify vCP2390-SEQ ID NO:6. The infected cell culture fluid from the roller bottles is harvested and concentrated to produce virus stock.

The construct is sequenced to confirm the sequences of the *Lutzomyia longipalpis* LJM17 insert and the C3 left and right arms around the *Lutzomyia longipalpis* LJM17 insert in vCP2390-SEQ ID NO:6.

Example 4

Figure 5:
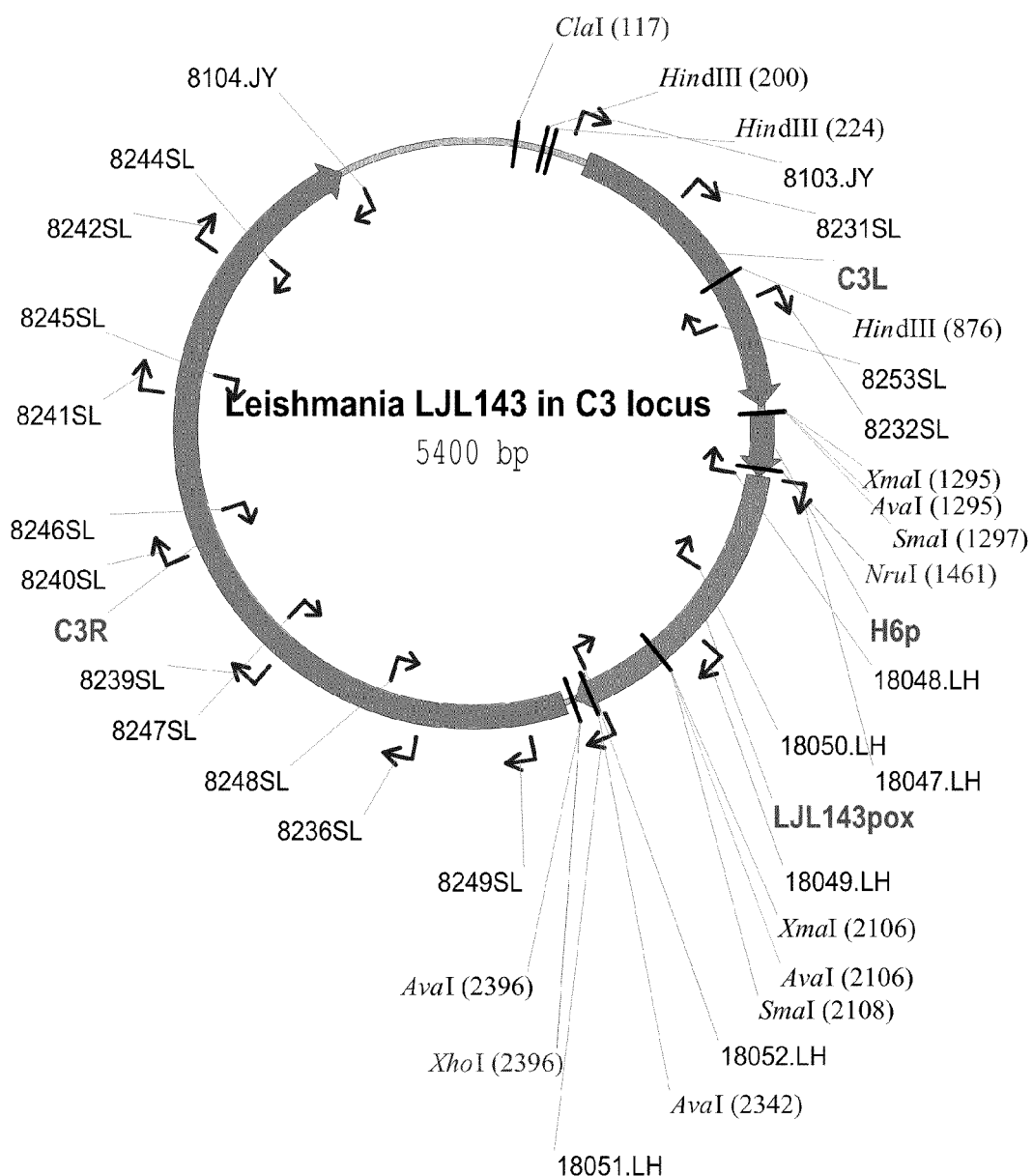

Construction of an ALVAC Canarypox Virus Vector Expressing the *Lu. longipalpis* Salivary LJL143 Polypeptide The polynucleotide encoding the *Lu. longipalpis* LJL143 polypeptide is synthesized and has the sequence described in SEQ ID NO:2. This sequence is then ligated to a pALVAC C₃H6p donor plasmid. The resulting plasmid, pALVAC C3 H6p-LJL143 comprises 5400 base pairs (FIG. 5), and is sequenced to confirm the nucleic acid sequence (SEQ ID NO: 2) of the LJL143 gene.

To generate vCP2389-SEQ ID NO:2, the pALVAC C3 H6p-LJL143 plasmid is linearized with NotI restriction enzyme. The linearized fragments are individually transfected into ALVAC-infected primary CEF cells by using the calcium phosphate precipitation method (see, Panicali et al.; Piccini et al.). After 24 h, the transfected cells are harvested, sonicated and used for recombinant virus screening.

Recombinant plaques are screened based on the plaque lift hybridization method using a *Lu. longipalpis* LJL143-specific probe which is labeled with horse radish peroxidase according to the manufacturer's protocol (Amersham Cat# RPN-3001). After three sequential rounds of plaque purification, the recombinants are generated by hybridization confirmation as 100% positive for the *Lu. longipalpis* LJL143 insert and 100% negative for the C3 ORF.

A single plaque is selected from the third round of plaque purification and expanded to obtain P1 (60 mm), P2 (T75 flasks), P3 (roller bottles) stocks to amplify vCP2389-SEQ ID NO:2. The infected cell culture fluid from the roller bottles are harvested and concentrated to produce virus stock.

The construct is sequenced to confirm the sequences of the *Lutzomyia longipalpis* LJL143 insert and the C3 left and right arms around the *Lutzomyia longipalpis* LJL143 insert in vCP2389-SEQ ID NO:2.

Example 5

Construction of a MVA Vector Expressing the *Lu. longipalpis* Salivary LJM17 Polypeptide MVA is a modified Ankara strain obtained after more than 570 passages of the Ankara vaccine strain on chicken embryo fibroblasts (see Stickl & Hochstein-Mintzel; Sutter et al.) available as ATCC VR-1508. Its adaptation to these cells caused the excision of 6 regions which are nonessential for its development and its infectious cycle on this type of cells (disappearance of about 15% of the viral genome; Meyer et al.). Exogenous genetic material may be inserted into any of these excision regions. In the context of the present invention, foreign genetic material is inserted into excisions II and III which are located using the HindIII restriction fragments N and A respectively (Altenburger et al).

Engineering of the recombinant MVA virus expressing LJM17 is performed as previously described in Staib C. et al., with the exception that the 723-base pairs DNA fragment containing the gfp ORF is replaced by the 1239 base pairs DNA fragment encoding LJM17 antigen (SEQ ID NO: 6), generating MVA-LJM17.

Example 6

Construction of a MVA Vector Expressing the *Lu. longipalpis* Salivary LJL143 Polypeptide Construction of the recombinant MVA virus expressing LJL143 is performed as previously described in Staib C. et al., with the exception that the 723-base pairs DNA fragment containing the gfp ORF is replaced by the 906 base pairs DNA fragment encoding LJL143 antigen (SEQ ID NO: 2), generating MVA-LJL143.

Example 7

Expression of *Lu. longipalpis* Salivary Protein In Vitro

Expression plasmids containing His-tagged *Lu. longipalpis* salivary antigens encoded by cDNA derived from the plasmids pVR2001 LJM17 (see example 1) and pVR2001 LJL143 (see example 2) are constructed and transfected in HEK-293F cells. Supernatants collected at 72 h are analyzed by HPLC chromatography using Nickel column and imidazole gradient. HPLC fractions positive for the recombinant salivary protein with 6xHis motif at their C-terminus are tested with polyclonal sera of mice previously immunized with the corresponding original cDNA plasmids. Recombinant proteins are tested by SDS-PAGE and Western blotting, aliquoted in PBS and stored at −70° C.

The sub-unit vaccine comprising LJM17 is referred to herein as rLJM17. The vaccine is prepared by combining 100 µg of purified recombinant protein LJM17 with 300 µg of the adjuvant CpG #2142 in 20% EMULSIGEN® (MVP laboratories) (for CpG #2142, see SEQ. ID. NO: 890 in EP-B1-1, 221,955).

The sub-unit vaccine comprising LJL143 is referred to herein as rLJL143. The vaccine is prepared by combining 100

μg of purified recombinant protein LJL143 with 300 μg of the adjuvant CpG #2142 in 20% Emulsigen®.

Example 8

Vaccination of Dogs Against Leishmaniasis 25 dogs (1-2 years old female beagles) are randomly divided into 5 groups of 5 dogs each. All dogs from groups 1 to 4 are vaccinated at D0 (V1) by the intradermal (ID) route into the ear pinnea using a syringe and a needle with 500 μg of purified pVR2001 LJM17 plasmid (example 1) expressing LJM17 (groups 1 and 2) or pVR2001 LJL143 plasmid (example 2) expressing LJL143 (groups 3 and 4).

Dogs from group 1 and group 3 are boosted at D14 (V2) and D28 (V3) with 500 μg of the same plasmids used for V1 by the transdermal (TD) route in the inner upper part of both hind legs using the VETJET™ (Merial) needle-free delivery device. Dogs from group 1 and group 3 were further boosted at D42 (V4) with 500 μg of the same plasmids by the intramuscular route coupled to electroporation (ET/IM) in the external side of both thighs using the Sphergen devise and technology (parameters: 88V, T1=20, T2=80, N=10).

Dogs from groups 2 and 4 are boosted at D14 (V2) and D28 (V3) with 500 μg of the same plasmids used for V1 by the IM route coupled to electroporation (ET/IM) as described above. Dogs from groups 2 and 4 are further boosted at D42 (V4) by the ID route into the ear pinnea as described above with sub-unit vaccines (see example 7) rLJM17 (group 2) or rLJL143 (group 4), respectively.

All dogs from groups 1 and 2 receive a final vaccine booster at D192 (V5) by the IM route in the left quadriceps using $10^8$ pfu of a recombinant canarypox virus vCP2390 (example 3) expressing LJM17. All dogs from groups 3 and 4 receive a final vaccine booster at D192 (V5) by the IM route in the left quadriceps using $10^8$ pfu of a recombinant canarypox virus vCP2389 (example 4) expressing LJL143.

Dogs from group 5 are vaccinated with 500 μg of the purified parental plasmid pVR2001 which expresses no antigen at D0 by ID, D14 by TD, D28 by TD and D42 by ET/IM and receive a final booster at D192 by the IM route using $10^8$ pfu of a control recombinant canarypox virus (PUREVAX™).

Example 9

Construction of the pNBO002 Plasmid Expressing the *Lu. longipalpis* Salivary LJM17 Polypeptide The nucleic acid sequence encoding the *Lu. longipalpis* LJM17 polypeptide was synthesized and has the sequence described in SEQ ID NO: 18 which contains poly(A) tail. The LJM17 fragment was amplified by PCR and cloned into the TOPO cloning site of the pVR2001-TOPA donor plasmid as described in example 1, to generate the plasmid pNBO002.

Figure 12:
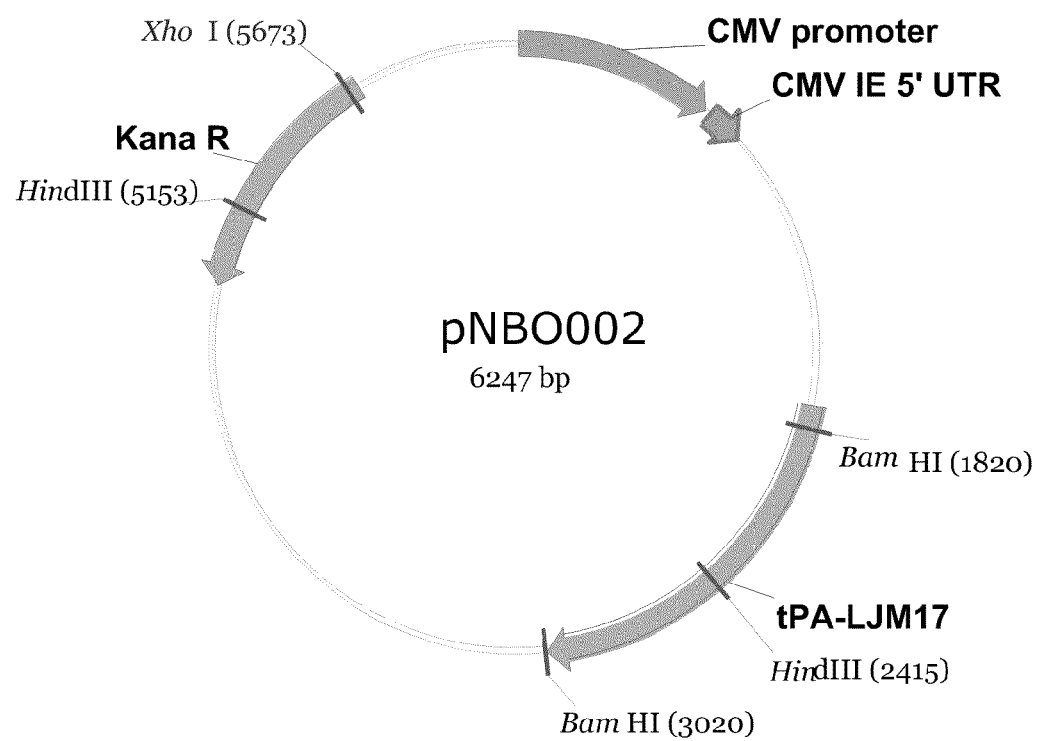

The nucleic acid sequence of one strand of the plasmid pNBO002 is described in SEQ ID NO: 19 and in FIG. 11, wherein BamHI sites are in positions [1819-1824] and [3019-3024], the nucleotide sequence encoding the tPA signal peptide is in position [1744-1830] and the nucleotide sequence encoding LJM17 is in position [1831-3015]. The map of the pNBO002 plasmid is shown in FIG. 12.

pNBO002 is analogous to pVR2001 LJM17. In this case, this construct and the construct of example 1 are identifiable by the nucleic acid sequence of their inserts, SEQ ID NO: 18 and SEQ ID NO: 8, respectively.

Example 10

Construction of the pNBO003 Plasmid Expressing the *Lu. longipalpis* Salivary LJL143 Polypeptide The nucleic acid sequence encoding the *Lu. longipalpis* LJL143 was synthesized and has the sequence described in SEQ ID NO: 14, which contains poly(A) tail. The LJL143 fragment was amplified by PCR and cloned into the TOPO cloning site of the pVR2001-TOPA plasmid, as described in example 1, to generate the plasmid pNBO003.

Figure 14:
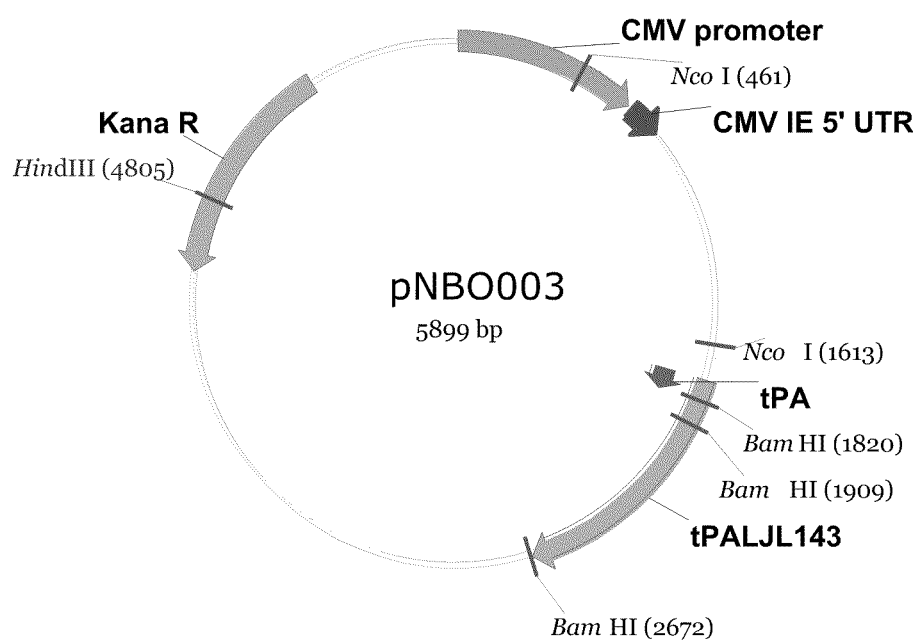

The nucleic acid sequence of one strand of the plasmid pNBO003 is described in SEQ ID NO: 20 and in FIG. 13, wherein BamHI sites are in positions [1819-1824] and [2671-2676], the nucleotide sequence encoding the tPA signal peptide is in position [1744-1830] and the nucleotide sequence encoding LJL143 is in position [1831-2667]. The map of the pNBO003 plasmid is shown in FIG. 14.

pNBO003 is analogous to pVR2001 LJL143. In this case, this construct and the construct of example 2 are identifiable by the nucleic acid sequence of their inserts, SEQ ID NO: 14 and SEQ ID NO: 4, respectively.

Example 11

Construction of an ALVAC Canarypox Virus Vector Expressing the *Lu. longipalpis* Salivary LJM17 Polypeptide For discussion and examples of the plasmid pALVAC and the C3 locus, see e.g., U.S. Pat. Nos. 5,756,103; 5,833,975; and 6,780,407. The sequence of the vaccinia virus H6 promoter has been previously described (see e.g., Taylor et al.; Taylor et al.; Guo et al.).

The nucleic acid sequence encoding the *Lu. longipalpis* LJM17 polypeptide was synthesized and has the sequence described in SEQ ID NO:6. This sequence was codon-optimized for mammalian expression by Geneart GmbH (Regensburg, Germany), resulting in the sequence described in SEQ ID NO:91, which encodes the LJM15 polypeptide (SEQ ID NO:5).

This codon-optimized sequence was then ligated to the pALVAC C3 H6p donor plasmid to generate pALVAC C3 H6p-LJM17 containing 5737 base pairs (FIG. 3). The resulting plasmid, pALVAC C3 H6p-LJM17, was sequenced and confirmed to contain the nucleic acid sequence (SEQ ID NO:91) of the LJM17 gene.

To generate vCP2390, the pALVAC C3 H6p-LJM17 plasmid was linearized with NotI restriction enzyme. The linearized fragments were individually transfected into ALVAC-infected primary CEF cells by using the calcium phosphate precipitation method described previously (Panicali et al.; Piccini et al.). After 24 h, the transfected cells were harvested, sonicated and used for recombinant virus screening.

Recombinant plaques were screened based on the plaque lift hybridization method using a *Lu. longipalpis* synthetic LJM17-specific probe which was labeled with horse radish peroxidase according to the manufacturer's protocol (Amersham Cat# RPN-3001). After three sequential rounds of plaque purification, the recombinants were generated and confirmed by hybridization as 100% positive for the synthetic LJM17 insert and 100% negative for the C3 ORF.

A single plaque was selected from the third round of plaque purification and expanded to obtain P1 (60 mm), P2 (T75 flasks), P3 (roller bottles) stocks to amplify vCP2390. The infected cell culture fluid from the roller bottles was harvested and concentrated to produce virus stock.

The construct was sequenced to confirm the sequences of the condon-optimized LJM17 insert and the C3 left and right arms around the codon-optimized LJM17 insert in vCP2390.

The vCP2390 vector is illustrated in FIG. 4. The nucleic acid sequences for both vCP2390 strands are described in FIG. 4.

Example 12

Construction of an ALVAC Canarypox Virus Vector Expressing the *Lu. longipalpis* Salivary LJL143 Polypeptide The nucleic acid sequence encoding the *Lu. longipalpis* LJL143 was synthesized and has the sequence described in SEQ ID NO:2. This sequence was codon-optimized for mammalian expression by Geneart GmbH (Regensburg, Germany), resulting in the sequence described in SEQ ID NO:22, which encodes the LJL143 protein (SEQ ID NO: 1).

This codon-optimized sequence was then ligated to the pALVAC C3 H6p donor plasmid resulting in pALVAC C3 H6p-LJL143 containing 5400 base pairs (FIG. 5), which was sequenced and confirmed to contain the nucleic acid sequence (SEQ ID NO:22) of the LJL143 gene.

To generate vCP2389, the plasmid pALVAC C3 H6p-LJL143 plasmid was linearized with NotI restriction enzyme. The linearized fragments were individually transfected into ALVAC-infected primary CEF cells by using the calcium phosphate precipitation method (see, Panicali et al.; Piccini et al.). After 24 h, the transfected cells were harvested, sonicated and used for recombinant virus screening.

Recombinant plaques were screened based on the plaque lift hybridization method using a *Lu. longipalpis* synthetic LJL143-specific probe which was labeled with horse radish peroxidase according to the manufacturer's protocol (Amersham Cat# RPN-3001). After three sequential rounds of plaque purification, the recombinants were generated and confirmed by hybridization as 100% positive for the synthetic LJL143 insert and 100% negative for the C3 ORF.

A single plaque was selected from the third round of plaque purification and expanded to obtain P1 (60 mm), P2 (T75 flasks), P3 (roller bottles) stocks to amplify vCP2389. The infected cell culture fluid from the roller bottles was harvested and concentrated to produce virus stock.

After sequencing, the results showed that the sequence of the synthetic LJL143 insert and the C3 left and right arms around the synthetic LJL143 insert in vCP2389 were correct.

Figure 6:
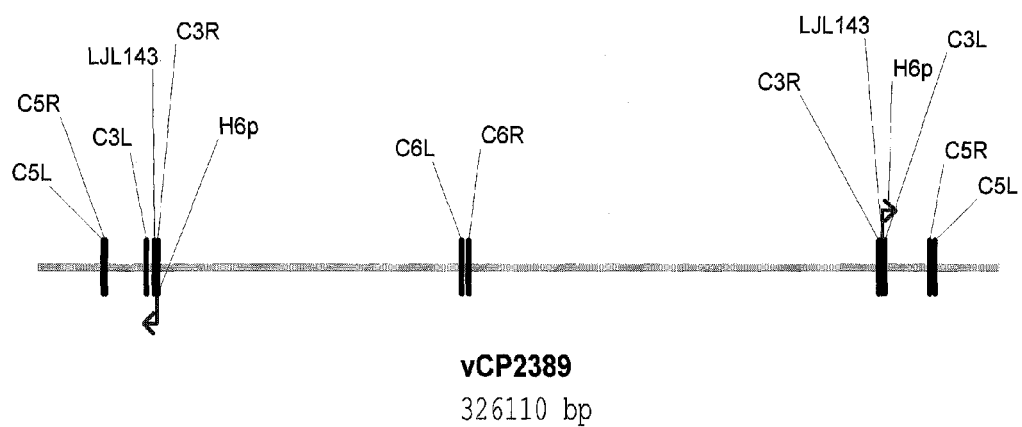

The vCP2389 vector is illustrated in FIG. 6.

Example 13

Expression of *Lu. longipalpis* Salivary Protein In Vitro

Expression plasmids containing His-tagged *Lu. longipalpis* salivary antigens encoded by cDNA derived from plasmids pNBO002 (see example 9) and pNBO003 (see example 10) were constructed and transfected into HEK-293F cells. Supernatants collected at 72 h were analyzed by HPLC chromatography using Nickel column and imidazole gradient. HPLC fractions positive for the recombinant salivary protein with 6×His motif at their C-terminus were tested with polyclonal sera of mice previously immunized with the corresponding original cDNA plasmids. Recombinant proteins were tested by SDS-PAGE and Western blotting, aliquoted in PBS and stored at −70° C.

The sub-unit vaccine comprising LJM17 is referred to herein as rLJM17. The vaccine is prepared by combining 100 µg of purified recombinant protein LJM17 with 300 µg of the adjuvant CpG #2142 in 20% EMULSIGEN® (MVP laboratories) (for CpG #2142, see SEQ. ID. NO: 890 in EP 1,221,955).

The sub-unit vaccine comprising LJL143 is referred to herein as rLJL143. The vaccine is prepared by combining 100 µg of purified recombinant protein LJL143 with 300 µg of the adjuvant CpG #2142 in 20% EMULSIGEN®.

Example 14

Vaccination of Dogs Against Leishmaniasis 25 dogs (1-2 years old female beagles) were randomly divided into 5 groups of 5 dogs each. All dogs from groups 1 to 4 were vaccinated at D0 (V1) by the intradermal (ID) route into the ear pinnea using a syringe and a needle with 500 µg of purified pNBO002 plasmid (example 9) expressing LJM17 (groups 1 and 2) or pNBO003 plasmid (example 10) expressing LJL143 (groups 3 and 4) antigens, respectively.

Dogs from group 1 and group 3 were boosted at D14 (V2) and D28 (V3) with 500 µg of the same plasmids used for V1 by the transdermal (TD) route in the inner upper part of both hind legs using the VetJet™ (Merial) needle-free delivery device. Dogs from group 1 and group 3 were further boosted at D42 (V4) with 500 µg of the same plasmids by the intramuscular route coupled to electroporation (ET/IM) in the external side of both thighs using the Sphergen devise and technology (parameters: 88V, T1=20, T2=80, N=10).

Dogs from groups 2 and 4 were boosted at D14 (V2) and D28 (V3) with 500 µg of the same plasmids used for V1 by the IM route coupled to electroporation (ET/IM) as described above. Dogs from groups 2 and 4 were further boosted at D42 (V4) by the ID route into the ear pinnea as described above with sub-unit vaccines (see example 13) rLJM17 (group 2) or rLJL143 (group 4), respectively.

All dogs from groups 1 and 2 received a final vaccine booster at D192 (V5) by the IM route in the left quadriceps using $10^8$ pfu of a recombinant canarypox virus vCP2390 (example 11, having SEQ ID NO: 21 as insert) expressing LJM17. All dogs from groups 3 and 4 received a final vaccine booster at D192 (V5) by the IM route in the left quadriceps using $10^8$ pfu of a recombinant canarypox virus vCP2389 (example 12, having SEQ ID NO: 22 as insert) expressing LJL143.

Dogs from group 5 were vaccinated with 500 µg of the purified parental plasmid VR2001 which expresses no antigen at D0 by ID, D14 by TD, D28 by TD and D42 by ET/IM and received a final booster at D192 by the IM route using $10^8$ pfu of a control recombinant canarypox virus (PUREVAX™).

Figure 7:
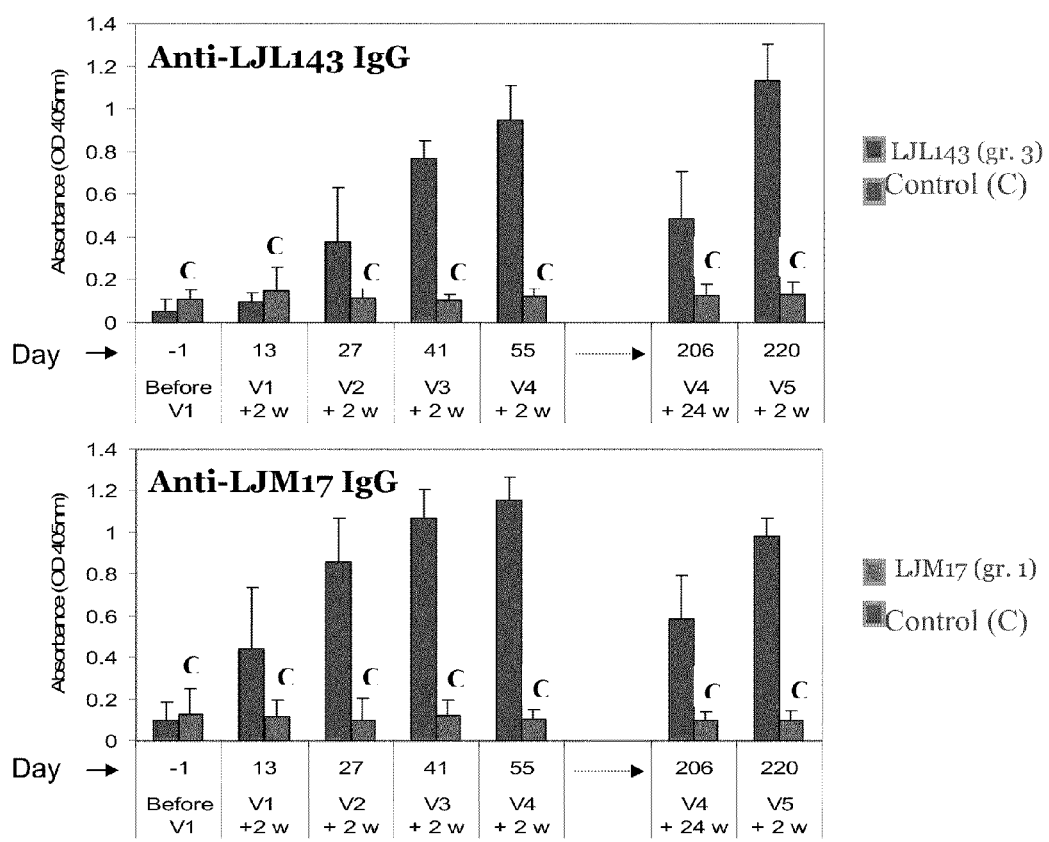
Figure 8:
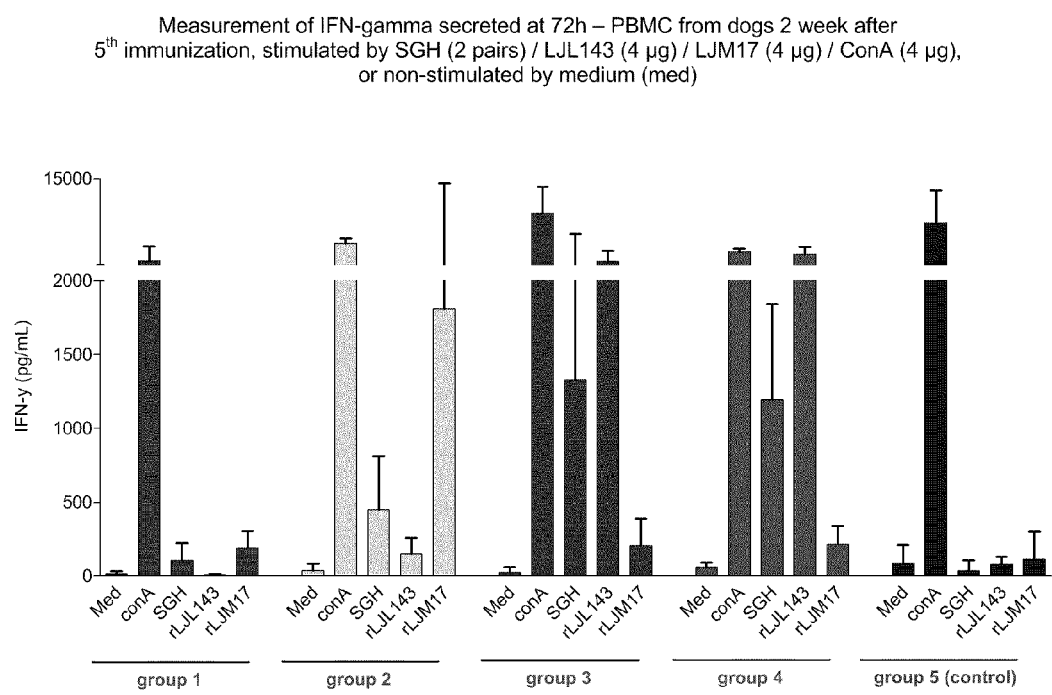
Figure 10:
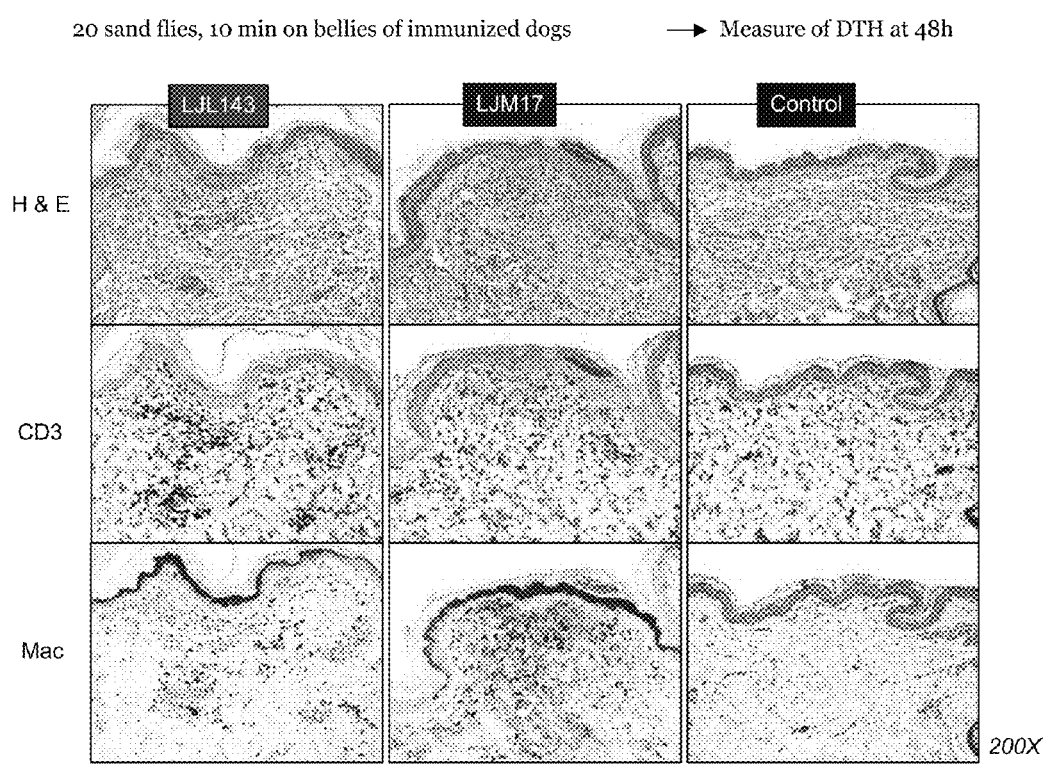

Specific and significant humoral immunity to both LJM17 and LJL143 was evidenced by ELISA in vaccinated dogs (see FIG. 7). 96-well plates (Maxisorp™, Nunc) were coated overnight at 4° C. with rLJM17 protein (2 µg/mL) or rLJL143 (2 µg/mL). Dog serum was successively added to the plates in triplicate at a dilution of 1/50 with alkaline phosphatase-conjugated AffiniPure rabbit anti-dog IgG (Jackson ImmunoResearch) at 1/5000 and p-nitrophenylphosphate (Sigma). Absorbance was measured at 405 nm using a Spectramax Plus (Molecular Devices).

Significant antibody titers persisted up to 6 months after V4 administration. The vCP booster (V5) recalled specific antibody responses in vaccinated dogs efficiently. Post vCP anamnestic responses established the expression of LJL143 and LJM17 from vCP2389 and vCP2390 respectively, and the ability of the vectors to boost humoral immune responses in vivo.

PBMC from dogs taken 2 weeks after the V5 administration were stimulated by 2 pairs of salivary gland homogenate (SGH), LJL143 (4 μg), and LJM17 (4 μg), or by ConA (4 μg). PBMCs that were non-stimulated by medium (med) served as controls. IFN-gamma production was evaluated by measuring the levels of IFN-gamma secretion in the medium at 72 hours (Quantikine ELISA; R&D Systems).

The results are illustrated in FIG. 8. Addition of purified recombinant LJM17 or LJL143 proteins caused PBMCs from LJM17- or LJL143-vaccinated dogs to increase secretion of IFN-gamma. No increased secretion of IFN-gamma was evidenced when PBMCs were in the presence of control medium (med).

The addition of ConA or SGH to PBMCs from LJM17- or LJL143-vaccinated dogs also caused an increased secretion of IFN-gamma. Notably, the LJM17 antigen caused very strong INF-gamma responses in animals of group 2 (1800 pg/mL), and also caused a strong response in animals of group 1 (200 pg/mL). The LJL143 antigen also caused very strong INF-gamma responses in animals of groups 3 and 4, with more than 2000 pg/mL, which were comparable to results seen when PBMCs were stimulated by ConA.

2 weeks after the V5 administration, PBMCs were isolated from two dogs that had been vaccinated with LJM17 and LJL143. Autologous T cells lymphocytes ($5.10^6$ cells) were stimulated with either 25 μg of recombinant LJM17, 25 μg of recombinant LJL143, or 4 μg of ConA. Cells were then incubated in the presence of macrophages infected by *Leishmania* chagasi amastigotes (infected at a 5:1 ratio). Lipopolysaccharides (LPS) and non-stimulated T cells (NT, no treatment) served as controls. Cells were evaluated for efficiency of killing which was measured by a significant reduction in the percent of infected macrophages (FIG. 9).

Lymphocytes stimulated with recombinant LJM17 or recombinant LJL143 were as cytototic to macrophages as lymphocytes that had been stimulated by the non-specific mitogen ConA.

LJL143- and LJM 7-vaccinated and control dogs were fitted with a Velcro collar device. The Velcro collar device was prepared by disposing twenty uninfected 6 day old female *Lu. longipalpis* were in a 10 mm-thin Plexiglas device which contained a secured screw and a nylon mesh on one of its sides so that sand flies were able to probe through the mesh. The device was kept at 25° C. before exposure to limit condensation and was then firmly attached to a Velcro collar for 10 minutes on the shaved belly of LJL143- and LJM17-vaccinated and control dogs. Dogs were unrestrained throughout the time of exposure. 4 mm or 6 mm-skin punches biopsies (Acuderm) were taken from the belly of anesthetized dogs 48 hours after the sand fly bites.

Biopsies were stored in neutral-buffered formaldehyde (10% formalin) and were then routinely processed for staining with hematoxylin/eosin (H & E), Luna's, Toludine blue and immunohistochemical procedures for CD3 and macrophage/monocyte markers (Mac). FIG. 10 provides the immunohistochemical results of sand fly bite sites. Specific immune cellular infiltration (darker spots on the pictures) is observed on vaccinated dogs whereas no infiltration was observed on control dogs.

Example 15

Vaccination of Dogs with LJL143 and LJM17 Salivary Proteins Produce a Protective Immune Response that Killed *Leishmania chagasi* Amastigotes In Vitro In this study, *Lu. longipalpis* salivary proteins were tested to determine if they are immunogenic in dogs. In addition, *Lu. longipalpis* salivary proteins were identified that can produce a protective cellular immune response and kill *Leishmania infantum* in an in vitro assay.

To identify these salivary components, an in vivo high-throughput DNA-based reverse antigen-screening assay was developed. This screening identified two strong DTH-inducing antigens out of the 35 most abundant proteins in the salivary glands of *Lu. longipalpis*. These data were further validated with recombinant proteins, resulting in the confirmation of DTH-inducing potential for the *Lu. longipalpis* salivary proteins LJM17 (SEQ ID NO:5) and LJL143 (SEQ ID NO:1). Furthermore, peripheral blood mononuclear cells of dogs vaccinated with LJL143 and LJM17 produced interferon (IFN)-γ upon stimulation with the salivary recombinant proteins and, more importantly, stimulation of these cells with the recombinant proteins resulted in the killing of *Leishmania infantu* in vitro. These molecules represent therefore strong candidates to be used as a vaccine to control *Leishmania infantum* in dogs.

Material and Methods

Dogs:

1-2 year old female beagles (Marshall Farms) were housed at the animal facility of NIH, Bethesda, USA, following the Animal Care and User Committee guidelines. They were well-fed animals under constant scrutiny for health problems by a veterinarian and had all received routine vaccinations. No ectoparasitic treatments were administrated during the last four months before sand fly exposure experiments.

Sand Flies:

*Lutzomyia longipalpis*, Jacobina strain, were reared using as larval food a mixture of fermented rabbit feces and rabbit food. Adult sand flies were offered a cotton swab containing 20% sucrose but were starved from sugar 24 hours before exposure experiments. Some females were used for dissection of salivary glands at 4-7 days following emergence and salivary gland homogenates (SGH) were prepared as described above.

Exposure to Sand Fly Bites:

Six day old female *Lu. longipalpis* were placed in a 10 mm-thin Plexiglas device. The device contained a secured screw and a nylon mesh on one of its sides for sand fly probing through it. The device was kept at 25° C. before exposure to limit condensation and was firmly attached with a Velcro collar on the shaved neck of dogs for 20 minutes. Dogs were unrestrained throughout the time of exposure.

Reverse Antigen-Screening (RAS):

Dogs pre-exposed to sand fly bites were anesthetized and injected intradermally with DNA plasmids or recombinant proteins. Injection sites were separated from each other by 15 mm. For DNA plasmids, the molecules were coded and randomly regrouped for each dog prior to injection on the belly. The code was broken only after induration and erythema measurements were completed. For DNA-RAS, 38 samples were injected in a total volume of 40 μL, including PBS, 1 pair of *Lu. longipalpis* SGH diluted in PBS, and 20 μg of control vector and the 35 recombinant DNA plasmids, diluted in PBS, encoding *Lu. longipalpis* individual salivary proteins. For protein-RAS, 5 samples were injected in duplicates (40

μL) including PBS, 1 pair of *Lu. longipalpis* SGH diluted in PBS, and 3 *Lu. longipalpis* salivary recombinant proteins (300 ng). Measure of induration and erythema diameters were performed 48 hours after intradermal injection of the samples.

Histology and Real-Time PCR on Skin Punch Biopsies:

4 mm or 6 mm-skin punches biopsies (Acuderm) were taken from the neck or belly of anesthetized dogs and split into two equal halves. One half was stored in neutral-buffered formaldehyde (10% formalin) then routinely processed for staining with hematoxylin/eosin, Luna's, Toludine blue and immunohistochemical procedures for CD3 and macrophage/monocyte markers. The other half, stored in RNAlater (Sigma), was used for RNA extraction (AGENCOURT® RNADVANCE™ Tissue, Beckman Coulter). RNA were reverse-transcribed (Transcriptor first strand cDNA synthesis, Roche) and used for Real-time PCR using the LightCycler 480 (Roche), primer set (0.2 μM final concentration) and FAM/TAMRA dual-labeled probes to a total of 15 μl per reaction in triplicates. Primers and probes for canine IL4, IL12, TGF-β, IFN-γ and GAPDH were described previously (Breathnach et al.). Amplification conditions, acquisition, melting curve analysis and standard curve were performed as described previously (Breathnach et al.). Expression levels of the interested gene were normalized to endogenous GAPDH levels to control for RNA quantity.

Recombinant cDNA:

From a cDNA library (see above), the 35 most abundant molecules from *Lu. longipalpis* salivary glands were selected and their cDNA cloned in the pVR2001-TOPO vector by standard cloning techniques. Plasmids were prepared using GENELUTE™ endotoxin-Free Plasmid Megaprep (Sigma), cleaned with ultrapure water using CENTRICON® Plus-20 (Millipore) and eluted in PBS. Quality control of the 35 purified plasmids included endotoxin measurements, restriction profile analyses and sequencing. Purified salivary DNA plasmids were sterilely filtered and stored at −70° C.

Recombinant Proteins:

Expression plasmids containing His-tagged *Lu. longipalpis* salivary antigens encoding cDNA derived from the parental salivary DNA plasmids were constructed as described (Oliveira et al.) and transfected in HEK-293F cells. Supernatants collected at 72 h were submitted to HPLC chromatography using Nickel column and imidazole gradient. HPLC fractions positive for the recombinant salivary protein with 6×His motif at their C-terminus were tested with polyclonal sera of mice previously immunized with the corresponding original cDNA plasmids. Recombinant proteins were tested by SDS-PAGE and Western blotting, aliquoted in PBS and stored at −70° C.

Recombinant Canarypox Viruses:

Two canarypox viruses derived from ALVAC vectors expressing respectively the LJL143 (vCP2389) or LJM17 (vCP2390) antigens were generated using standard methods and validated by sequencing of viral DNA, RT-PCR on mRNA of infected cells and Western Blotting of supernatants of infected cells. PUREVAX™ ferret distemper vaccine (Merial) was used as control of canarypox virus injections.

Immunization of Dogs with Salivary Vaccines:

25 dogs were randomly divided in 5 groups of 5 dogs each. All dogs from groups 1 to 4 were vaccinated at D0 (V1) by the intradermal (ID) route into the ear pinnea using a syringe and a needle with 500 μg of purified plasmid expressing LJM17 (groups 1 and 2) or LJL143 (groups 3 and 4) antigens, respectively. Dogs from group 1 and group 3 were boosted at D14 (V2) and D28 (V3) with 500 μg of the same plasmids used for V1 by the transdermal (TD) route in the inner upper part of both hind legs using the VETJET™ (Merial) needle-free delivery device. Dogs from group 1 and group 3 were further boosted at D42 (V4) with 500 μg of the same plasmids by the intramuscular (IM) route coupled to electroporation in the external side of both thighs using the Sphergen devise and technology (parameters: 88V, T1=20, T2=80, N=10). Dogs from groups 2 and 4 were boosted at D14 (V2) and D28 (V3) with 500 μg of the same plasmids used for V1 by the IM route coupled to electroporation as described above. Dogs from groups 2 and 4 were further boosted at D42 (V4) with 100 μg of aforementioned purified recombinant protein LJM17 (rLJM17) (group 2) or LJL143 (rLJL143) (group 4) in association with 300 μg CpG ODN in 20% EMULSIGEN® (MVP laboratories) by the ID route into the ear pinnea as described above. All dogs from groups 1 to 4 received a final vaccine booster at D192 (V5) by the IM route in the left quadriceps using $10^8$ pfu of a recombinant canarypoxvirus vCP2390 and vCP2389 expressing respectively LJM17 (groups 1 and 2) or LJL143 (groups 3 and 4) antigens. Dogs from group 5 were vaccinated at D0, D14, D28 and D42 with 500 μg of the purified parental plasmid VR2001 which expresses no antigen and received a final booster at D192 by the IM route using $10^8$ pfu of a control recombinant canarypoxvirus (PUREVAX™).

ELISA:

96-well plates (MAXISORP™, Nunc) were coated overnight at 4° C. with *Lu. longipalpis* SGH (5 pairs/ml), rLJM17 protein (2 μg/mL) or rLJL143 (2 μg/mL). Dog serum in triplicate at 1/50 dilution, alkaline phosphatase-conjugated AffiniPure rabbit anti-dog IgG (Jackson ImmunoResearch) at 1/5000 and p-nitrophenylphosphate (Sigma) were successively added to the plates. 405 nm absorbance was measured using a Spectramax Plus (Molecular Devices). IFN-γ production in cell supernatants was measured after 72 h (Quantikine ELISA; R&D Systems) after stimulation with SGH (1 or 2 pairs), conA (4 μg), rLJM17 (2 or 10 μg) or rLJL143 (2 or 10 μg).

Anti-Leishmanial Activity:

Canine monocyte-derived macrophages were prepared as using standard methods. Autologous T cells ($5 \times 10^6$ cells) were taken from the culture after 1 week, stimulated with *Lu. longipalpis* SGH (2 pairs), conA (4 μg), rLJM17 (25 μg) or rLJL143 (25 μg), and put back in presence of macrophages infected by *L. infantum* infected at a 5:1 ratio. Anti-leishmanial activity was assessed by changes in the percentages of infected cells and number of amastigotes per macrophage after microscopic examination of Giemsa-stained preparations.

Bites of *Lutzomyia longipalpis* Sand flies Induce a Strong Delayed Type Hypersensitivity Response in Dogs In rodent models, cellular immunity characterized by a Th1 delayed type hypersensitivity (DTH) response to sand fly salivary proteins, protect animals from cutaneous and visceral leishmaniasis. There is no information pertaining to the presence and nature of cellular immunity to sand fly saliva in dogs, the main reservoirs of visceral leishmaniasis caused by *Leishmania infantum* (chagasi) in Europe and Latin America. Thus, the early kinetics of anti-saliva immunity in dogs following exposure to bites of *Lutzomyia longipalpis*, the vector of *Leishmania infantum* chagasi in Latin America, was investigated. Seven of nine beagles showed specific anti-saliva antibodies one week after the third exposure to bites (FIG. 19A). Apart from a single dog, these animals showed a strong IgG2 antibody response in the absence of IgG1 (FIG. 19A). One dog showed a mixed IgG2/IgG1 antibody response. To investigate whether dogs exposed to sand fly bites develop a DTH response, the skin induration at the bite site up to 96 hours following each exposure was measured. Following the second exposure to sand fly bites, a small induration was observed in the 7 dogs that produced significant levels of *Lu. longipalpis* IgG antibodies (FIG. 19B). This was characterized by a localized erythema, swelling and eventually thickening of the skin. The intensity and duration of the observed induration was significantly increased following the third exposure lasting up to 96 hours following sand fly bites (FIG. 19B). This induration was not observed after the first exposure in naive animals (FIG. 19B). Histological analyses of the induration site show minimal inflammation characterized by scattered perivascular lymphocytes and rare neutrophils within the superficial dermis 48 hours following the first and second exposure (FIG. 19C). A dramatic increase in the cellular infiltrate was noted 48 hours following the third exposure. This was characterized by a prominent thickening of the epidermis and the presence of multifocal infiltrates of inflammatory cells consisting of lymphocytes, macrophages and eosinophils (FIG. 19D). Based on the timing of the reaction as well as the nature of the infiltrate, it was concluded that sand fly saliva induces a delayed-type hypersensitivity reaction in the skin of dogs after repeated exposures.

*Lutzomyia longipalpis* Salivary Proteins that Induce a DTH in Dogs

Figures 1, 21:
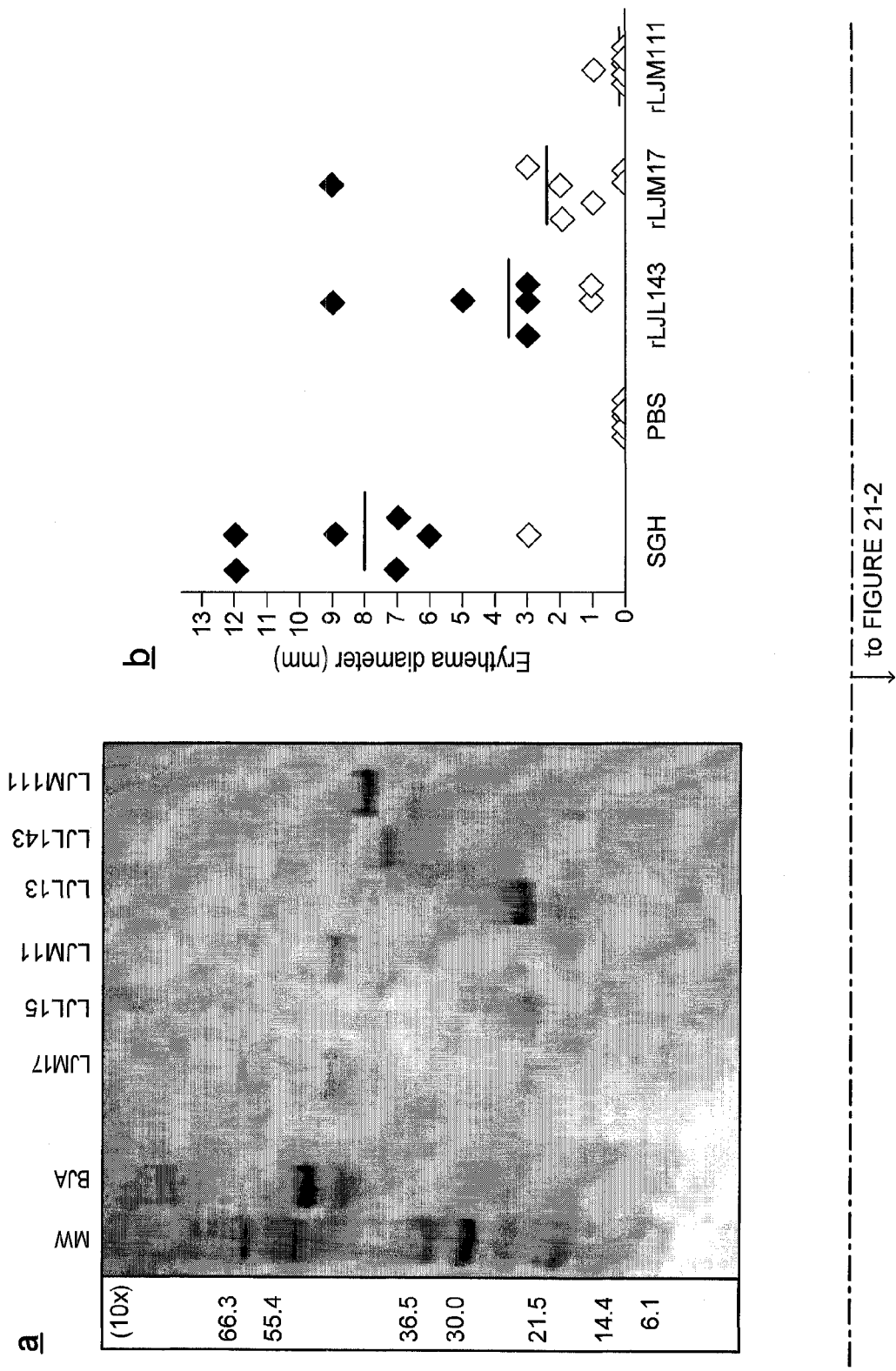
Figures 3, 21:
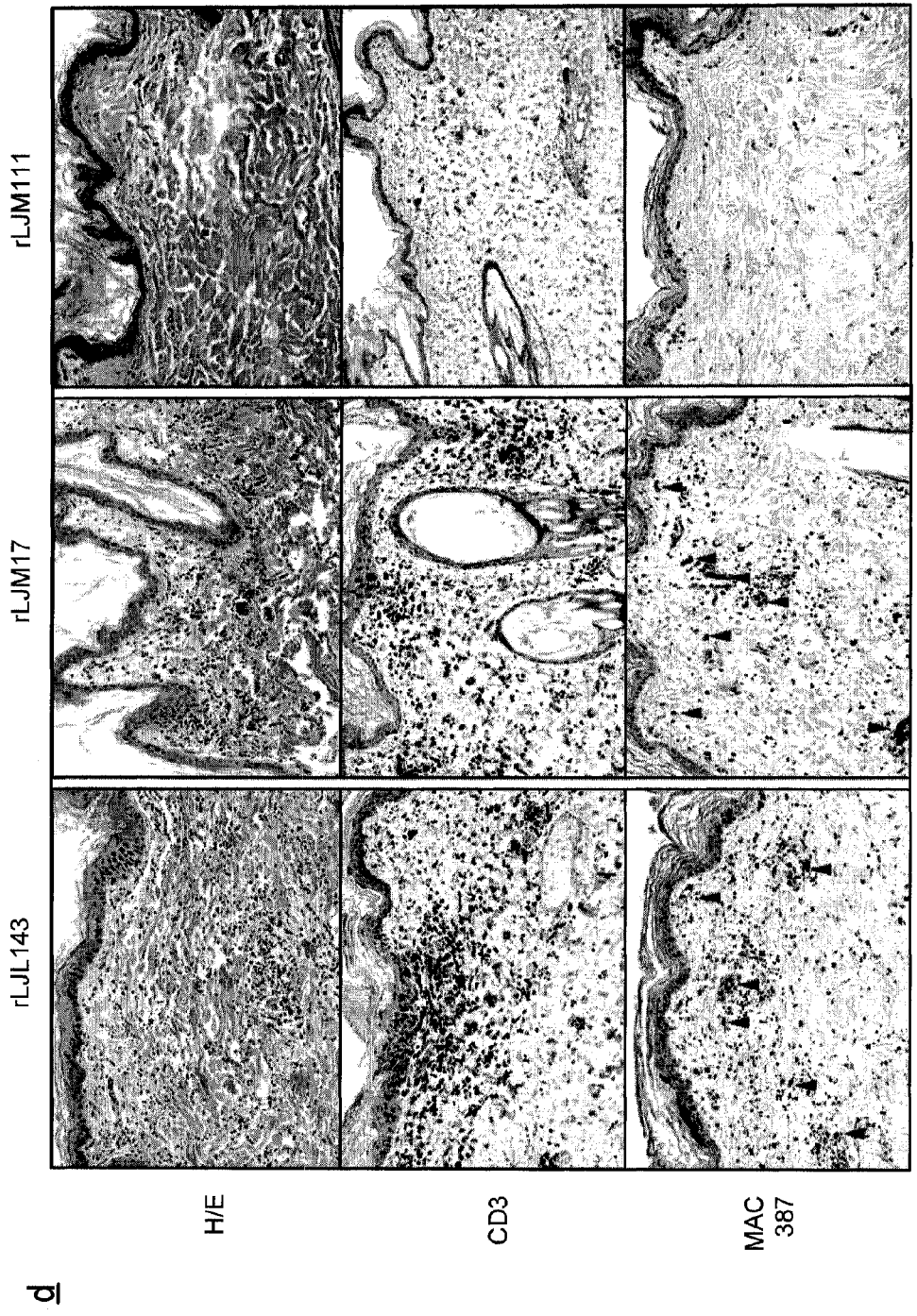

Salivary molecules of *Lu. longipalpis* which are responsible for the generation of a DTH response in dogs was investigated. Transcripts coding for the 35 most abundant secreted proteins from the salivary glands of this species were identified above. Identifying candidates capable of inducing a cellular immune response from a large pool of antigens in large animals such as dogs is prohibitive in terms of cost and space. To overcome this obstacle, a reverse antigen screening approach was developed that consisted of exposing a minimal number of dogs (five) to sand fly bites and injecting each animal with up to 38 samples (35 DNA plasmids encoding for salivary proteins and three controls) (FIG. 20A). Out of the 35 injected DNA plasmids only 4 (LJM17, LJM11, LJL143 and LJL138) induced a significant erythema in more than 3 dogs, 48 hours after challenge (FIG. 20B) and only 2 DNA plasmids (LJL143 and LJM17) produced a strong induration in 3 dogs, 48 hours after challenge (FIG. 20B). The majority of the injected plasmids did not produce a significant erythema or induration (FIG. 20B) and the injection of PBS and empty vector control induced minimal erythema at the site of injection compared to LJM17 and LJL143 (FIG. 20C). The specificity and reactivity of injected DNA plasmids is shown in FIG. 20D. Based upon these results LJM17 and LJL143 were chosen for further analysis. LJL143 and LJM17 induced the production of cytokines indicative of a Th1 environment at the injection site, including IL-12 and IFN-γ (FIG. 20E). Histological sections taken 48 hours after challenge show that LJL143 and LJM17 recruit lymphocytes and macrophages at the site of injection indicative of a classical delayed type hypersensitivity (DTH) response (FIG. 20F). To validate the specificity of this approach soluble highly purified LJL143, LJM17 and LJM111, among several other salivary recombinant proteins, was prepared (FIG. 21A). LJL143 and LJM17 recombinant proteins reproduced the DTH response observed upon injection of their respective DNA plasmids (FIGS. 21B and 21C) including the recruitment of lymphocytes and macrophages to the site of injection (FIG. 21D).

Dogs Immunized with LJL143 and LJM17 Produce IFN-γ Specific to Recombinant Salivary Proteins.

Figure 22:
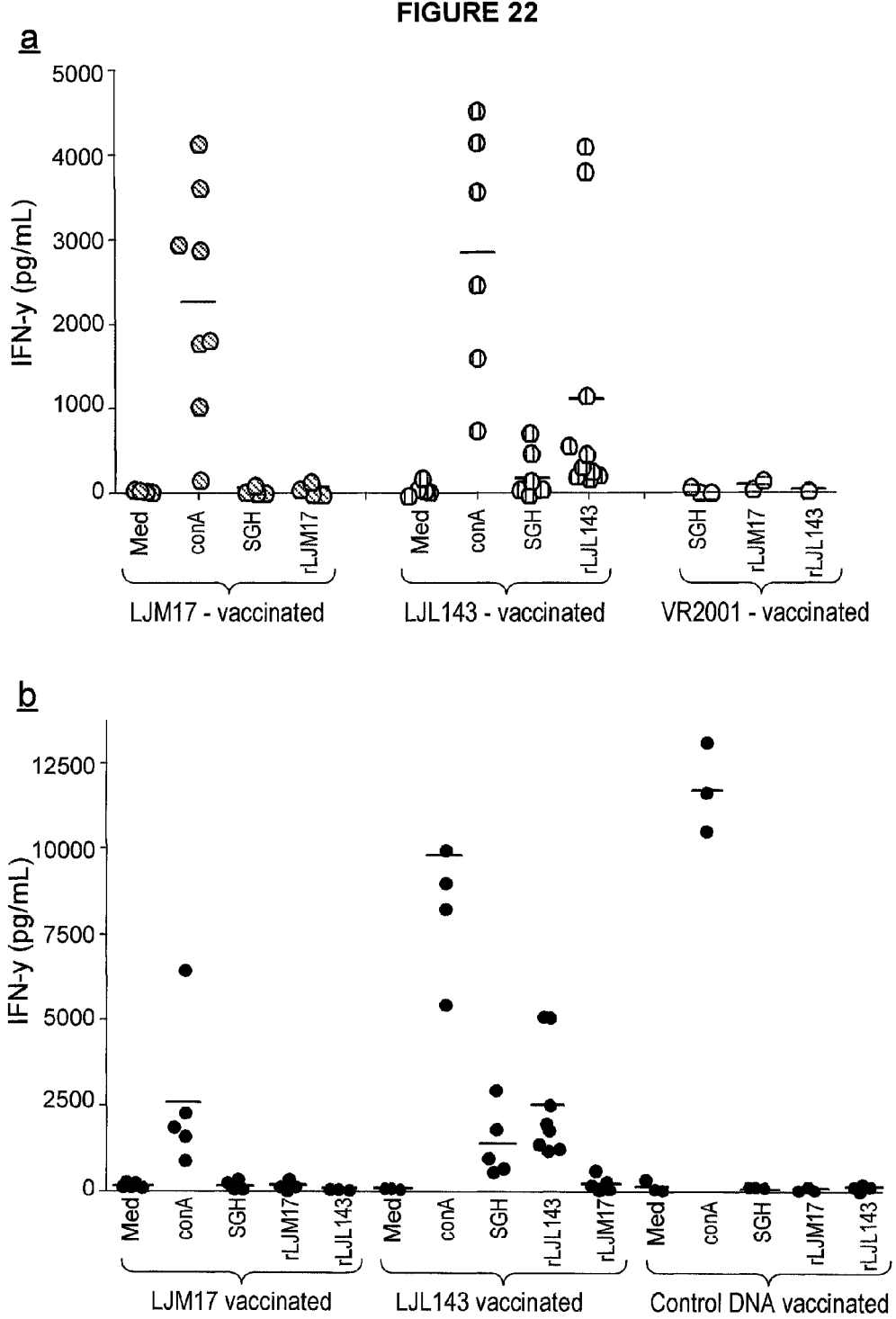

Dogs (5 per group) were immunized with DNA plasmids coding for LJL143, LJM17 or control DNA plasmid, a prime boost with the respective recombinant salivary proteins and a final immunization with canarypox virus expressing the respective salivary proteins (Table 1). PBMCs from immunized dogs were stimulated with up to 4 ug of their respective recombinant protein, ConA and 1 pair of salivary gland homogenate (SGH). LJL143 vaccinated dogs produced significant levels of IFN-γ five weeks post-fourth vaccination and before canarypox injection (FIG. 22A). More importantly, the native LJL143 protein present in 1 pair of salivary gland homogenate was able to generate a similar response in LJL143 vaccinated dogs (FIG. 22A). LJM17 vaccinated dogs produced a considerable lower levels of IFN-γ compared to LJL143 vaccinated dogs (FIG. 22A). A similar profile was observed two weeks after canarypox vaccination, where PBMCs from dogs vaccinated with LJL143 produced two fold higher IFN-γ compared to their pre-pox status (FIG. 22B).

TABLE 1

| Group | Antigen | D0 (V1) | D14 (V2) | D28 (V3) | D42 (V4) | D192 (V5) |
|---|---|---|---|---|---|---|
| 1 | LJM17 | ID-cDNA | TD-cDNA | TD-cDNA | IM/ET-cDNA | IM-vCP |
| 2 | LJM17 | ID-cDNA | IM/ET-cDNA | IM/ET-cDNA | ID-protein | IM-vCP |
| 3 | LJL143 | ID-cDNA | TD-cDNA | TD-cDNA | IM/ET-cDNA | IM-vCP |
| 4 | LJL143 | ID-cDNA | IM/ET-cDNA | IM/ET-cDNA | ID-protein | IM-vCP |
| 5 | Control | ID-cDNA | TD-cDNA | TD-cDNA | IM/ET-cDNA | IM-vCP |

Vaccination with LJL143 and LJM17 Generates a Protective Immune Response that Kills *Leishmania chagasi* Amastigotes In Vitro.

Figure 23:
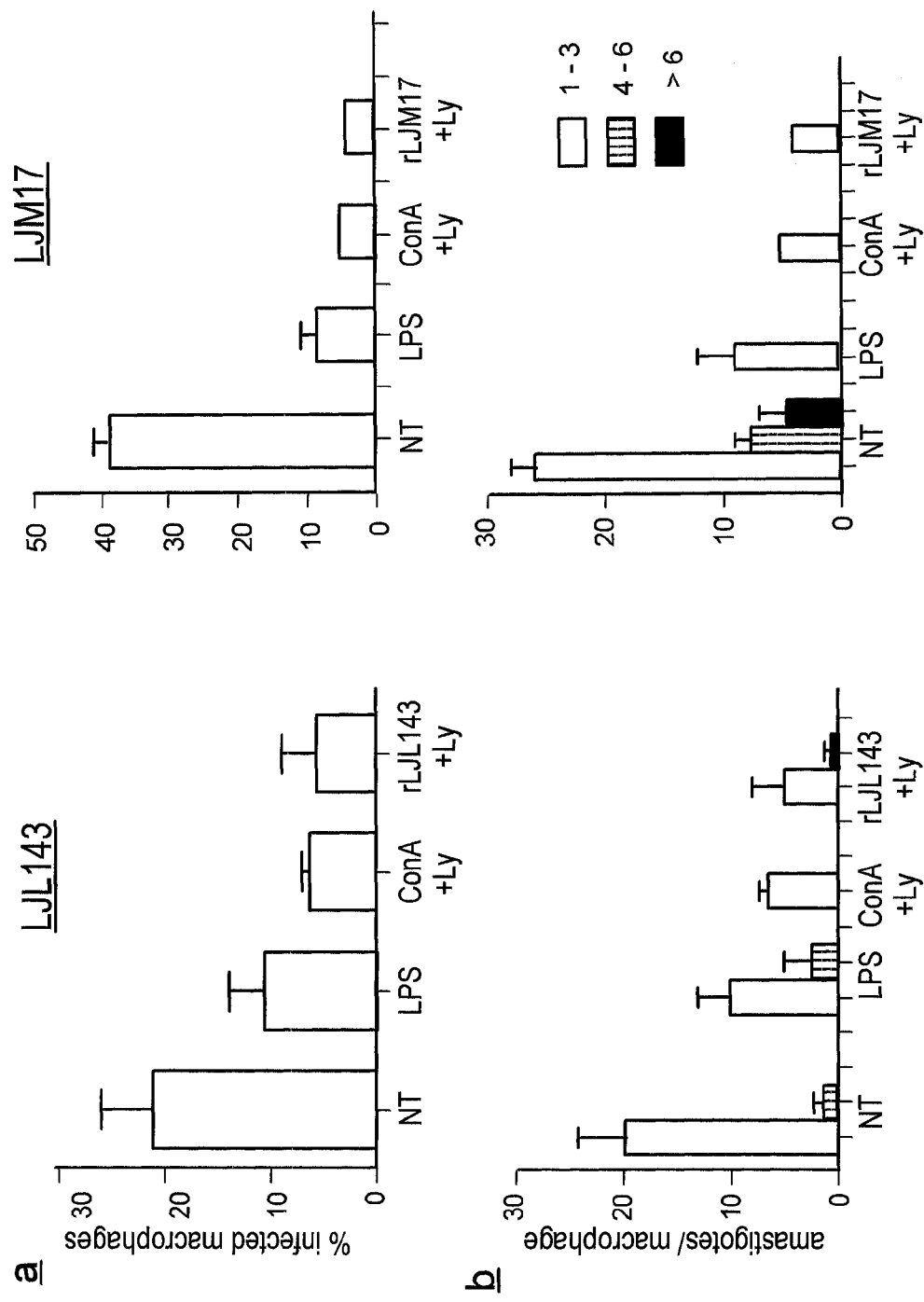

Infected macrophages from PBMCs of two dogs vaccinated with LJM17 and LJL143 efficiently killed *Leishmania chagasi* amastigotes following the addition of autologous lymphocytes stimulated with LJM17 and LJL143 recombinant proteins respectively (FIG. 23). The efficiency of killing was measured by a significant reduction in the percent of infected macrophages (FIG. 23A) as well as in the number of amastigotes per macrophages (FIG. 23B). This killing effect was comparable to that observed upon the addition of the non-specific mitogen ConA (FIG. 23).

Example 16

Production of an Immune Response in Dogs

Twelve dogs approximately three years old with natural immunity against Leishmaniasis are injected via an intradermal route (ID) in the back after shaving, with 100 μg of each individual plasmid suspended in 100 μl of PBS. Each plasmid is injected at a different point. The points are separated by at least 3 cm to avoid interference between DTH responses. The negative control (100 μl of buffer) is also inoculated by ID route.

The DTH response is assessed 72 hours after injection by measuring the larger diameter of the skin tumefaction area. The results are expressed as the mean value of the tumefaction area for all the dogs and as a percentage of dogs having a positive DTH response. A positive DTH is a tumefaction area diameter greater than or equal to 4 mm at 72 hours after injection.

In a second study, 10 naïve dogs 4 to 6 months old are immunized by ID injection in 10 points (100 µl per point) in the right ear with a pool of the plasmids encoding a *Lu. longipalpis* polypeptide, 100 µg for each one suspended in 1000 µl of PBS. On day 21, dogs are injected in 10 points (100 µl per point) in the left ear and in 10 points (100 µl per point) in the belly with a pool of the plasmids, 100 µg for each one suspended in 2000 µl of PBS. All dogs are challenged on day 35 by inoculation by ID route in the back (after shaving), with 100 µg of each individual plasmid suspended in 100 µl of PBS. Each plasmid is injected at a different point. The points are separated by at least 3 cm to avoid interference. As a negative control, 100 µl of buffer is inoculated intradermally. The DTH response is assessed 72 hours after challenge, by measuring the larger diameter of the skin tumefaction area. The results are expressed as the mean value of the tumefaction area for all the dogs and as a percentage of dogs having a positive DTH response. A positive DTH is a tumefaction area diameter higher or equal of 4 mm at 72 hours after injection.

The results of this study show that plasmids can induce a cellular immunity in dogs after injection, a cellular immunity reveled by a DTH response. The variation of the DTH response level can be by the variation of the expression of the insert.

It will be apparent that the precise details of the methods described may be varied or modified without departing from the spirit of the described disclosure. We claim all such modifications and variations that fall within the scope and spirit of the claims below.

REFERENCES

1. Adler and Theodor, *Ann. Trop. Med. Parasitol.* 20:109, 1926
2. Altenburger et al., 1989, *Arch. Virol.* 105, 15-27
3. Altschul et al. J. Mol. Biol. 1990. 215. 403-410
4. Altschul et al., Nucl. Acids Res. 25, 3389-3402
5. Antoine G., Virology, 1998, 244, 365-396
6. Bairoch, *Nucleic Acids Res.* 19 (Suppl.):2241, 1991
7. Barral et al., Am J Trop Med Hyg 62:740-5, 200
8. Behr J. P., Bioconjugate Chemistry, 1994: 5: 382-389
9. Berberich C. et al., Biochim. Biophys. Acta, 1998, 1442: 230-7
10. Boshart M. et al., Cell, 1985, 41, 521-530
11. Boshart M. et al., Cen 41:521-530, 1985
12. Breathnach et al., *Vet Dermatol* 2006, 17:313-21
13. Carroll M. W. et al., Vaccine, 1997, 15 (4), 387-394
14. Charlab et al., *Proc Natl Acad Sci USA* 96:15155-60, 1999
15. Chaudhuri P Res. Vet. Sci. 2001, 70(3), 255-6
16. Chung J Y et al., FEMS Microbiol letters 1998, 166: 289-296
17. Cochran et al., J. Virology, 1985, 54, 30-35
18. D. Berg. et al Biochem. Biophys. Res. Commun. 1991, 179, 1289-1296
19. De Groot A. et al., Nature Biotechnology, 1999, 17, 533-561
20. Desjeux P., Trans. R. Soc. Trop. Med. Hyg., 2001, 95: 239-43
21. Devereux J, Haeberlie P and Smithies O, "A comprehensive set of sequence analysis program for the VAX," Nucl. Acids Res., 12: 387-395 (1984)
22. Dietze R. et al., Clin. Infect. Dis., 1997, 25: 1240-2
23. Djoba Siawaya J F et al., PLoS ONE, 2008, 3(7), e2535
24. Doree S M et al., J. Bacteriol. 2001, 183(6): 1983-9
25. Dye C., Am. J. Trop. Med. Hyg., 1996, 55: 125-30
26. Feng D F and Dolittle R F, "Progressive sequence alignment as a prerequisite to correct phylogenetic trees," J. of Molec. Evol., 25:351-360 (1987)
27. Fingerut E et al., Vaccine, 2005, 23(38): 4685-4696
28. Funahashi et al., J. Gen. Virol., 1988, 69, 35-47
29. Geysen H. M. et al., Proc. Nat. Acad. Sci. USA, 1984, 81 (13), 3998-4002
30. Geysen H. M. et al., Proc. Nat. Acad. Sci. USA, 1985, 82 (1), 178-182
31. Geysen H. M., Southeast Asian J. Trop. Med. Public Health, 1990, 21 (4), 523-533
32. Gradoni L. et al., Vaccine, 2005, 23: 5245-51
33. Grosjean N L et al., Lindsay D S et al., McConkey S E et al., Martínez-Subiela S, Tecles F, Eckersall P D, Cerón J J: Serum concentrations of acute phase proteins in dogs with leishmaniasis. Vet Rec 150:241-244, 2002
34. Grosjean N L, Vrable R A, Murphy A J, Mansfield L S: Seroprevalence of antibodies against *Leishmania* spp among dogs in the United States. J Am Vet Med Assoc 222:603-606, 2003
35. Guo P. et al. J. Virol., 1989, 63, 4189-4198
36. Hartikka J. et al., Human Gene Therapy, 1996, 7, 1205-1217
37. Hemmer B. et al., Immunology Today, 1998, 19 (4), 163-168
38. Henikoff et al., *Bioinformatics* 15:471, 1999
39. Higgins D G and Sharp P M, "Fast and sensitive multiple sequence alignment on a microcomputer," CABIOS, 5: 151-153 (1989)
40. Hoop T. et al., Mol. Immunol. 1983, 20(4), 483-489
41. Immonogenicity of a killed *Leishmania* vaccine with Saponin adjuvant in dogs", R. Cordeiro Giunchetti et al., Vaccine, 2007, 25: 7674-7686
42. Israeli E et al., Cryobiology 1993, 30(5): 519-23
43. J. Fields et al., Nature, 186: 778-780, 4 Jun. 1960
44. J. Mol. Biol. 48:444-453 (1970)
45. J. Sambrook et al (Molecular Cloning: A Laboratory Manual, 2nd Edition, Cold Spring Harbor Laboratory, Cold Spring Harbor, N.Y., 1989
46. Jardim A. et al., Biochem. J., 1995, 305: 307-13
47. Jardim A. et al., Biochem. J., 1995, 305: 315-20
48. Jeanmougin et al., *Trends Biochem. Sci.* 23:403, 1998
49. Jurk M et al., Immunobiology 2004, 209(1-2): 141-154
50. K. Otte et al. Gen. Comp. Endocrinol. 1996, 102(1), 11-15
51. Kidd I. M. & Emery V. C., "The use of baculoviruses as expression; vectors," Applied Biochemistry and Biotechnology 42:37-159, 1993
52. Kwissa M. et al., Vaccine, 2000, 18, 2337-2344
53. Lanotte G. et al., Ann. Parasitol. Hum. Comp., 1979, 54: 277-95
54. Lindsay D S, Zajac A M, Barr S C: Leishmaniasis in American Foxhounds: An Emerging Zoonosis? Compend Cont Educ Pract Vet 24:304-312, 2002
55. Luke C. et al., Journal of Infectious Diseases, 1997, 175, 91-97
56. Muller M. et al. Nucleic Acids Res. 1990, 18(2), 364
57. Maniatis et al., Molecular Cloning: a Laboratory Manuel, Cold Spring Harbor Laboratory, 1982
58. Maroli M. et al., Med. Vet. Entomol., 2001, 15: 358-63
59. Martinez-Subiela S, Tecles F, Eckersall P D, Cerón J J: Serum concentrations of acute phase proteins in dogs with leishmaniasis. Vet Rec 150:241-244, 2002
60. Mazloumi Gavgani A. S. et al., Lancet, 2002, 360: 374-9
61. McConkey S E, López A, Shaw D, Calder J: Leishmanial polyarthritis in a dog. Canine Vet J 43:607-609, 2002
62. Melanby, *Nature.* 158, 554-555.13, 1946

63. Meyer et al., 1991, J. Gen. Virol. 72, 1031-1038
64. Mills C K et al., Cryobiology 1988, 25(2): 148-52
65. Miyazaki J. et al., Gene, 1989, 79, 269-277
66. Molina R. et al., Trans. R. Soc. Trop. Med. Hyg., 1994, 88: 491-3; Courtenay O. et al., J. Infect. Dis., 2002, 186: 1314-20
67. Montgomery et al., Cell. Mol. Biol. 43:285-292, 1997
68. Moreira Jr. E. D. et al., Vet. Parasitol., 2004, 122: 245-52
69. Nielsen et al., *Protein Eng.* 10:1, 1997
70. Ogata R T et al., J. Biol. Chem. 1989, 264(28): 16565-16572
71. Oliveira F. et al. Vaccine (2006) 24: 374-90
72. Olsen C W et al., Vaccine, 1997, 15(10): 1149-1156
73. Optimal Alignments in Linear Space", CABIOS 4, 11-17, 1988
74. O'Reilly et al., "Baculovirus expression vectors, A laboratory manual," New York Oxford, Oxford University Press, 1994
75. P. Delafontaine et al. Gene 1993, 130, 305-306
76. Pandher K et al., Infect. Imm. 1998, 66(12): 5613-9
77. Panicali et al., Proc. Natl. Acad Sci USA, 1982, 79: 4927-4931
78. Parker K. et al., Immunol. Res. 1995, 14(1), 34-57
79. Piccini et al., Methods Enzymol., 1987, 153: 545-563
80. Pasleau et al., Gene 38:227-232, 1985
81. Pennock et al., Mol. Cell. Biol. 4: 399-406, 1994
82. Peppoloni S et al., Expert Rev Vaccines, 2003, 2(2): 285-293
83. Perkus M. et al., J. Virol., 1989, 63, 3829-3836
84. Phameuropa Vol. 8, No. 2, June 1996
85. Pharmaceutical Biotechnology, 1995, volume 6, edited by Michael F. Powell and Mark J. Newman, Plenum Press, New York and London
86. Piccini et al., Methods Enzymol., 1987, 153: 545-563
87. Ribeiro et al., *Insect Biochem.* 19:409-412, 1989
88. Rickles R. et al J. Biol. Chem. 1988, 263, 1563-1569
89. Riviere et al., J. Virology, 1992, 66, 3424-3434
90. S. Friezner Degen et al J. Biol. Chem. 1996, 261, 6972-6985
91. S. Lien et al. Mamm. Genome 2000, 11(10), 877-882
92. Shida, Virology, 1986, 150, 451-457
93. Slappendel R J, Ferrer L. In: Greene C E: Infectious Diseases of the Dog and Cat. WB Saunders Co, Philadelphia, 1998, pp. 450-458
94. Smith et al., Mol. Cell Biol. 3:2156-2165, 1983
95. Smith T F and Waterman M S, "Comparison of Biosequences," Advances in Applied Mathematics 2:482-489 (1981)
96. Smith T F, Waterman M S and Sadler J R, "Statistical characterization of nucleic acid sequence functional domains," Nucleic Acids Res., 11:2205-2220 (1983)
97. Soares et al., *J. Immunol.* 160:1811-6, 1998
98. Staib C. et al., Biotechniques, 2000, 28(6): 1137-42, 1144-6, 1148
99. Stickl & Hochstein-Mintzel, Munch. Med. Wschr., 1971, 113, 1149-1153
100. Stittelaar K. J. et al., J. Virol., 2000, 74 (9), 4236-4243;
101. Sutter et al., Proc. Natl. Acad. Sci. U.S.A., 1992, 89, 10847-10851
102. Sutter G. et al., 1994, Vaccine, 12 (11), 1032-1040
103. Taylor et al. Vaccine. 6: 497-503, 1988a
104. Taylor et al. Vaccine. 6: 504-508, 1988b
105. Taylor J. et al., Vaccine, 1988, 6, 504-508
106. Thompson J D, Higgins D G and Gibson T J, "ClusterW: improving the sensitivity of progressive multiple sequence alignment through sequence weighing, positions-specific gap penalties and weight matrix choice," Nucleic Acid Res., 22:4673-480, 1994
107. Titus and Ribeiro, *Parasitol Today* 6:157-159, 1990
108. Tsvetkov T et al., Cryobiology 1983, 20(3): 318-23
109. Vaccine Design, The subunit and adjuvant approach", Pharmaceutical Biotechnology, vol. 6, Edited by Michael F. Powell and Mark J. Newman, 1995, Plenum Press New York
110. Valenzuela et al., *J. Exp. Med.* 194:331-42, 2001
111. Van der Zee R. et al., Eur. J. Immunol., 1989, 19 (1), 43-47
112. van Ooyen et al., Science, 1979, 206, 337-344
113. Verne A., Virology-167:5671, 1988
114. Vialard et al., J. Virol. 64:37-50, 1990
115. VICAL Inc.; Luke C. et al., Journal of Infectious Diseases, 1997, 175, 91-97
116. Von Heijne (1986), Nucleic Acid Research, 14; 4683-4691
117. Ward C K et al., Infect. Imm. 1998, 66(7): 3326-36
118. Wilbur and Lipman, 1983 PNAS USA 80:726
119. Wolff E et al., Cryobiology 1990, 27(5): 569-75
120. Y. Kajimoto et al. Mol. Endocrinol. 1989, 3(12), 1907-1913
121. Zurbriggen R et al., Expert Rev Vaccines, 2003, 2(2): 295-304

What we claim is:

1. A vaccine composition comprising an ALVAC vector, wherein the vector is vCP2389 comprising a polynucleotide having the sequence as set forth in SEQ ID NO:94.

2. A method of vaccinating a subject susceptible to *Leishmania* comprising at least one administration of the vaccine according to claim 1.

3. The method of claim 2, wherein the subject is human, canine, or feline.

4. An isolated polynucleotide, wherein the polynucleotide comprises a nucleotide sequence having at least 80% sequence identity to a polynucleotide having the sequence as set forth in SEQ ID NO: 22.

5. The polynucleotide of claim 4, wherein the polynucleotide comprises a nucleotide sequence having at least 90% sequence identity to a polynucleotide having the sequence as set forth in SEQ ID NO:22.

6. The polynucleotide of claim 4, wherein the polynucleotide comprises a nucleotide sequence having at least 95% sequence identity to a polynucleotide having the sequence as set forth in SEQ ID NO:22.

7. The polynucleotide of claim 4, wherein the polynucleotide comprises a nucleotide sequence having the sequence as set forth in SEQ ID NO:22.

8. An ALVAC vector comprising a polynucleotide of claim 4.

9. A host cell transformed with the vector of claim 8.

10. The ALVAC vector of claim 8, wherein the ALVAC vector comprises a nucleotide sequence having at least 90% sequence identity to a polynucleotide having the sequence as set forth in SEQ ID NO:22.

11. The ALVAC vector of claim 8, wherein the ALVAC vector comprises a nucleotide sequence having at least 95% sequence identity to a polynucleotide having the sequence as set forth in SEQ ID NO:22.

12. The ALVAC vector of claim 8, wherein the polynucleotide has the sequence as set forth in SEQ ID NO: 22.

* * * * *